United States Patent
Niu et al.

(10) Patent No.: US 11,505,568 B1
(45) Date of Patent: Nov. 22, 2022

(54) COMPOSITIONS AND METHODS FOR SULFATION OF CARBOHYDRATES

(71) Applicant: Trustees of Boston College, Chestnut Hill, MA (US)

(72) Inventors: Jia Niu, Lexington, MA (US); Chao Liu, Newton, MA (US); Cangjie Yang, Brighton, MA (US)

(73) Assignee: The Trustees of Boston College, Chesnut Hill, MA (US)

( * ) Notice: Subject to any disclaimer, the term of this patent is extended or adjusted under 35 U.S.C. 154(b) by 0 days.

(21) Appl. No.: 16/869,848

(22) Filed: May 8, 2020

Related U.S. Application Data

(63) Continuation of application No. 16/851,024, filed on Apr. 16, 2020, now abandoned.

(60) Provisional application No. 62/834,523, filed on Apr. 16, 2019.

(51) Int. Cl.
| | |
|---|---|
| *C07H 13/00* | (2006.01) |
| *C07H 11/00* | (2006.01) |
| *C07C 303/26* | (2006.01) |
| *C07H 1/00* | (2006.01) |
| *C07J 41/00* | (2006.01) |

(52) U.S. Cl.
CPC ............ *C07H 13/00* (2013.01); *C07C 303/26* (2013.01); *C07H 1/00* (2013.01); *C07H 11/00* (2013.01); *C07J 41/0072* (2013.01)

(58) Field of Classification Search
CPC . C07H 1/00; C07H 11/00; C07H 13/00; C07J 41/00; C07C 303/26
See application file for complete search history.

(56) References Cited

PUBLICATIONS

Dong et al., Angewandte Chem. Int. Ed., 2014, 53, p. 9430-9448. (Year: 2014).*
Wuts, et al. ed., Greene's Protective Groups in Organic Synthesis, 4th ed, 2007, John Wiley & Sons, p. 16-366. (Year: 2007).*
Desoky et al., Tetrahedron, 2011, 67, p. 1281-1287. (Year: 2011).*
Dondoni et al., Org. Biomol. Chem., 2017, 15, p. 1549-1553. (Year: 2017).*

* cited by examiner

*Primary Examiner* — Jonathan S Lau
(74) *Attorney, Agent, or Firm* — Lei Fang, Esq.; Smith Tempel Blaha LLC

(57) ABSTRACT

In one aspect, the disclosure relates to a facile strategy to introduce electron-deficient aryl sulfate diesters to silylated hydroxyl groups of carbohydrates and amino acids, among other substrates, wherein selective hydrolysis and the removal of an electron-deficient aromatic group allows for the efficient generation of sulfated carbohydrates, peptides, and other compounds. The incorporation of electron-deficient aryl sulfate diesters in the early stage of the synthesis of glycans, peptides, and the like, disclosed herein avoids time-consuming protecting group manipulations, simplifies the purification of sulfated products, and improves the overall yield and efficiency. This abstract is intended as a scanning tool for purposes of searching in the particular art and is not intended to be limiting of the present disclosure.

9 Claims, 22 Drawing Sheets

Direct O-Sulfation Reagents

| Reagents | Solvents | Temp. & Time |
| --- | --- | --- |
| $SO_3 \cdot$Pyridine | DMF | rt, >3 h |
| $SO_3 \cdot NMe_3$ | DMF | 55 °C, 24 h |
| $SO_3 \cdot NEt_3$ | DMF | 55 °C, 24 h |
| $HOSO_2Cl$ | DMF/Pyridine | rt, 8 h |

Direct N-Sulfation Reagents

| Reagents | Solvents | Temp. & Time |
| --- | --- | --- |
| $SO_3 \cdot$Pyridine, $Et_3N$ | Pyridine | rt, 24-48 h |
| $SO_3 \cdot NEt_3$, $Et_3N$, 0.1 M NaOH | MeOH | 0 °C to rt, 5~24 h |

| $R^1$ | Reagents[a] | Conditions | Deprotection |
|---|---|---|---|
| H |  | THF, NaH, 21 h | $PtO_2$, $H_2$, 20 h |
| $SO_3^-$ | $CF_3CHN_2$ | Citric acid, $CH_3CN$, rt, 24 h | $^tBuOH$, $^tBuOK$, 1-2 h |
| H | $ClSO_2OnP$ or $ClSO_2OiBu$ | NHMDS, THF, −75 °C to rt | NaI, acetone, 55 °C, 5 h |
| H |  | THF, N-methyl imidazole, 0 °C, 24 h | Zn dust, $NH_4HCO_3$, MeOH, 6 h |

[a] TCE:

solvent: polar aprotic ($CH_3CN$, DMF, NMP)
$SiR_3 = SiMe_3$ (< 4 h, rt); $SiR_3 = SiMe_2tBu$ (4-18 h, rt to 80 °C)

For sugar O-sulfation and alkyl sulfate amino acid (like L-threonine)

For sugar N-sulfation

For aryl sulfate amino acid (L-tyrosine)

| Solvent | Equiv. Ratio | Temp. and Time | Yield[a] β | α |
|---|---|---|---|---|
| DCM | 1.0:1.2 | -78 °C, 7 h; rt, 6 h | 7% | ~2% |
| PhMe | 1.0:1.5 | -78 °C, 2h; -42 °C, 2 h; rt, 10 h | 18% | 8% |
| PhMe | 1.0:2.0 | 0 °C, 6.5 h | 32% | 7% |

[a] Isolated yield.

| Conditions | Yield |
|---|---|
| 0 °C, 3 h | 79% |
| -78 °C (3 h), -41 °C (2 h), rt (2 h) | 47% |

| Conditions | Solvent | Concentration of SM | Stability |
| --- | --- | --- | --- |
| Benzylamine (2.0 equiv) + Et$_3$N (1.0 equiv) | DMF | 96 mM | After 24 hours, recyled yield: 92% |
| Benzylamine (2.0 equiv) + DIPEA (1.0 equiv) | DMF | 79 mM | After 24 hours, recyled yield: 86% |
| Trifluoroacetic acid | - | 71 mM | After 4 days, de-Boc yield quantitative |
| 20% (v/v) Piperidine in DMF | DMF | 148 mM | 1 hour later, recycled yield 54% |

DIPEA: N,N-Diisopropylethylamine

UDP sugar with masked sulfate for enzymatic synthesis

Photocaging

Sulfated Polysaccharide synthesis

Chondroitin Sulfate
Brain Development
Learning and Memory
Cancer

Dermatan Sulfate

Keratan Sulfate
Macular Corneal Dystrophy $R = SO_3^-$ or H
$R' = SO_3^-$ or Ac
n = 20-200

Heparin/Heparan Sulfate
Brain Development
Blood Clotting
Cancer

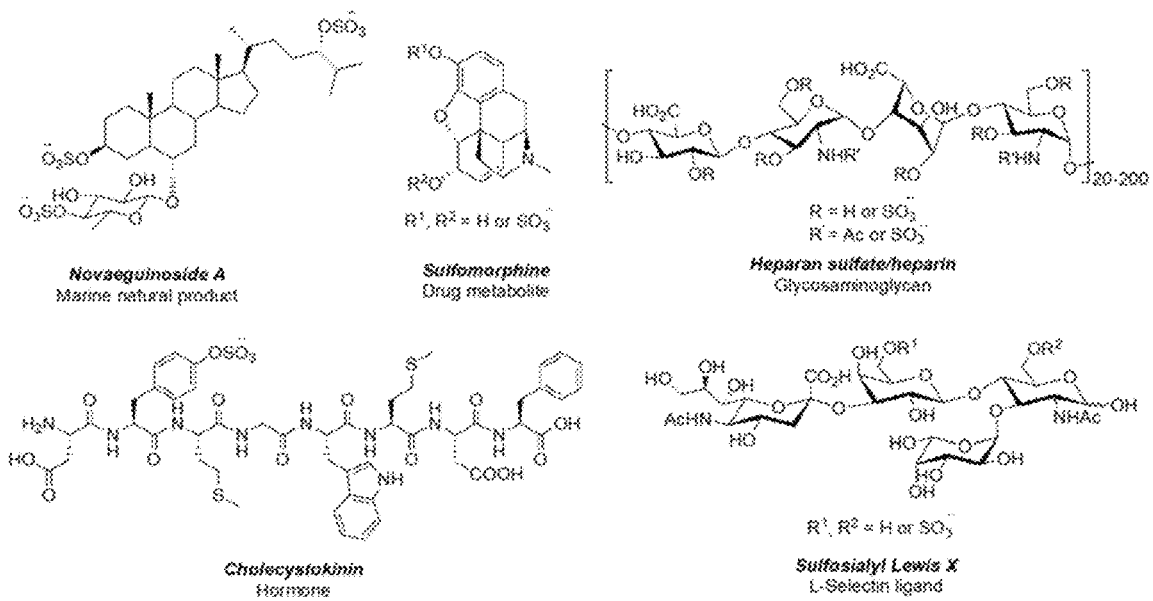
A. Diverse bioactive natural products consist of O-sulfation
B. Existing chemical O-sulfation strategies
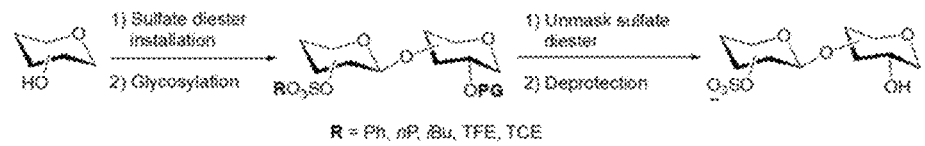
C. Enzymatic O-sulfation
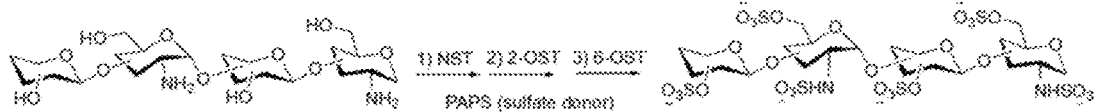
FIGs. 15A-15C

COMPOSITIONS AND METHODS FOR SULFATION OF CARBOHYDRATES

CROSS-REFERENCE TO RELATED APPLICATIONS

This application is a continuation of, and claims priority to, U.S. application Ser. No. 16/851,024, filed Apr. 16, 2020, which claims the benefit of U.S. Provisional Application No. 62/834,523, filed on Apr. 16, 2019, each of which is incorporated herein by reference in its entirety.

STATEMENT REGARDING FEDERALLY SPONSORED RESEARCH OR DEVELOPMENT

This invention was made with U.S. Government support under grant number 1DP2HG011027-01, awarded by the National Institutes of Health. The U.S. government has certain rights in the invention.

FIELD OF INVENTION

The present invention is directed to facile sulfation of carbohydrates and peptides via electron deficient aryl sulfate diesters.

BACKGROUND

O-sulfation widely exists in polysaccharides, liposaccharides, peptides, proteins, marine natural products, and drug metabolites in nature (FIGS. 1A-E and 15A). The spatiotemporal distribution of the O-sulfate modifications in these molecules plays important roles in a variety of biological activities such as telomerase inhibition, cell signaling, anticoagulation, drug detoxification, and cancer metastasis (FIG. 14). However, the lack of synthetic tools for efficient and scalable O-sulfation imposes a significant constraint on our abilities to access bioactive molecules carrying complex sulfation patterns and use them to study the structure-function relationships of the sulfate modifications in biology.

To date, sulfur trioxide-nitrogen base remains the most common chemical reagent to introduce O-sulfation to a variety of substrates (FIG. 15B). O-sulfation using this reagent can only be performed at the late stage of synthesis, as the purification and further chemical manipulation are often challenging due to the high polarity of the sulfated compounds and their sensitivity to acidic conditions. These limitations are frequently exacerbated by the modest yield, poor scalability, and limited regioselectivity of the sulfur trioxide-nitrogen base reagents when polysulfated products are targeted. Efforts to address these deficiencies have led to the development of the so-called "early-stage" sulfation strategies, in which targeted hydroxyl groups were converted to sulfate diesters at the early stage of synthesis. The sulfate diesters were subsequently deprotected to generate the desired O-sulfated product at the end of the synthetic routes (FIG. 15B).

Several sulfate diesters have been demonstrated to enable early stage O-sulfation, including those with phenyl (Ph), neopentyl (nP), isobutyl (iBu), trifluoroethylene (TFE), and 2, 2, 2-trichloroethylene (TCE) groups (FIGS. 3 and 15B). While the installation of Ph, nP and iBu sulfate diesters via chlorosulfates and chlorosulfites suffer from harsh reaction conditions and poor functional group compatibility, sulfuryl imidazole salts, in particular the TCE derivatives, offered promising efficiencies in the installation and unmasking of the corresponding sulfate diesters. However, the need for high excess (2-10 equiv.) of sulfuryl imidazole salts and long reaction time (16-72 hours) can result in undesired side reactions. More importantly, the strong electron-withdrawing effect of the TCE group leads to an increased sensitivity of the TCE sulfate diester to nucleophiles and bases and also deactivate the modified carbohydrate substrates in glycosylation, limiting its utility in the synthesis of polysulfated complex carbohydrates.

In contrast, enzymatic O-sulfation by sulfotransferases has recently emerged as a promising strategy for the efficient synthesis of sulfated oligosaccharides, achieving excellent yields and regioselectivity (FIG. 15C). However, due to the stringent specificity of existing sulfotransferase enzymes, the order of the hydroxyl groups being sulfated is inflexible in enzymatic O-sulfation reactions. For example, in the chemoenzymatic synthesis of heparin oligosaccharides, N-sulfation of the glucosamine residue is required for 2-O-sulfation of the iduronic acid residue, which is then required for 6-O- or 3-O-sulfation of the glucosamine residue. While enabling excellent regioselectivity, such an inflexible order of sulfation creates challenges for sequence-specific and saccharide residue-specific O-sulfation in oligosaccharides and polysaccharides. Substrate scope is also restricted: examples of synthetically useful enzymatic O-sulfation strategies for substrates beyond glycosaminoglycans are very rare. Finally, the purification of the sulfated carbohydrates obtained from the enzymatic reaction requires carbohydrate- and sulfation-specific HPLC techniques (e.g., Q-Sepharose column), further affecting their practicality and scalability.

Despite advances in sulfation of various substrates, difficulties still exist, including sulfation of different functional groups on the same molecule in any desired order, lack of enzymes for achieving sulfation of some functional groups in biomolecules, excessive amounts of reagents required for some reactions, lengthy reaction times required as well as potential side reactions, modest yields, poor scalability, limited regioselectivity, and other problems. What is needed is an approach that provides and efficient and scalable synthesis of sulfate diesters as protected O-sulfation for both carbohydrate and non-carbohydrate substrates, that offers balance between stability and reactivity of the modified substrates, and that allows for mild and quantitative unmasking (FIG. 15D). These needs and other needs are satisfied by the present disclosure.

SUMMARY

In accordance with the purpose(s) of the present disclosure, as embodied and broadly described herein, the disclosure, in one aspect, relates to a facile strategy to introduce electron-deficient aryl sulfate diesters to silylated hydroxyl groups of carbohydrates and amino acids, among other substrates, wherein selective hydrolysis and the removal of an electron-deficient aromatic group allows for the efficient generation of sulfated carbohydrates, peptides, and other compounds. The incorporation of electron-deficient aryl sulfate diesters in the early stage of the synthesis of glycans, peptides, and the like, disclosed herein avoids time-consuming protecting group manipulations, simplifies the purification of sulfated products, and improves the overall yield and efficiency.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A, tyrosine in peptides and proteins; FIG. 1B, sulfation of alkyl amino acids; FIG. 1C, sulfated glycopeptides, FIG. 1D, sulfated lipopeptides, FIG. 1E sulfated glycosaminoglycan families.

FIGS. 15A-15D show the significance of O-sulfation and approaches to O-sulfation for carbohydrates and other substrates: FIG. 15A, representative examples of O-sulfated bioactive natural products; FIG. 15B, existing chemical O-sulfation strategies, FIG. 15C, an enzymatic O-sulfation strategy, where NST and 6-OST are, respectively the N- and 6-O sulfotransferases of the iduronic residues (PAPS: 3'-phosphoadenosine-5'-phosphosulfate); FIG. 15D, proposed early stage O-sulfation strategy as disclosed herein.

Figures 1A, 1B, 1C, 1D, 1E:
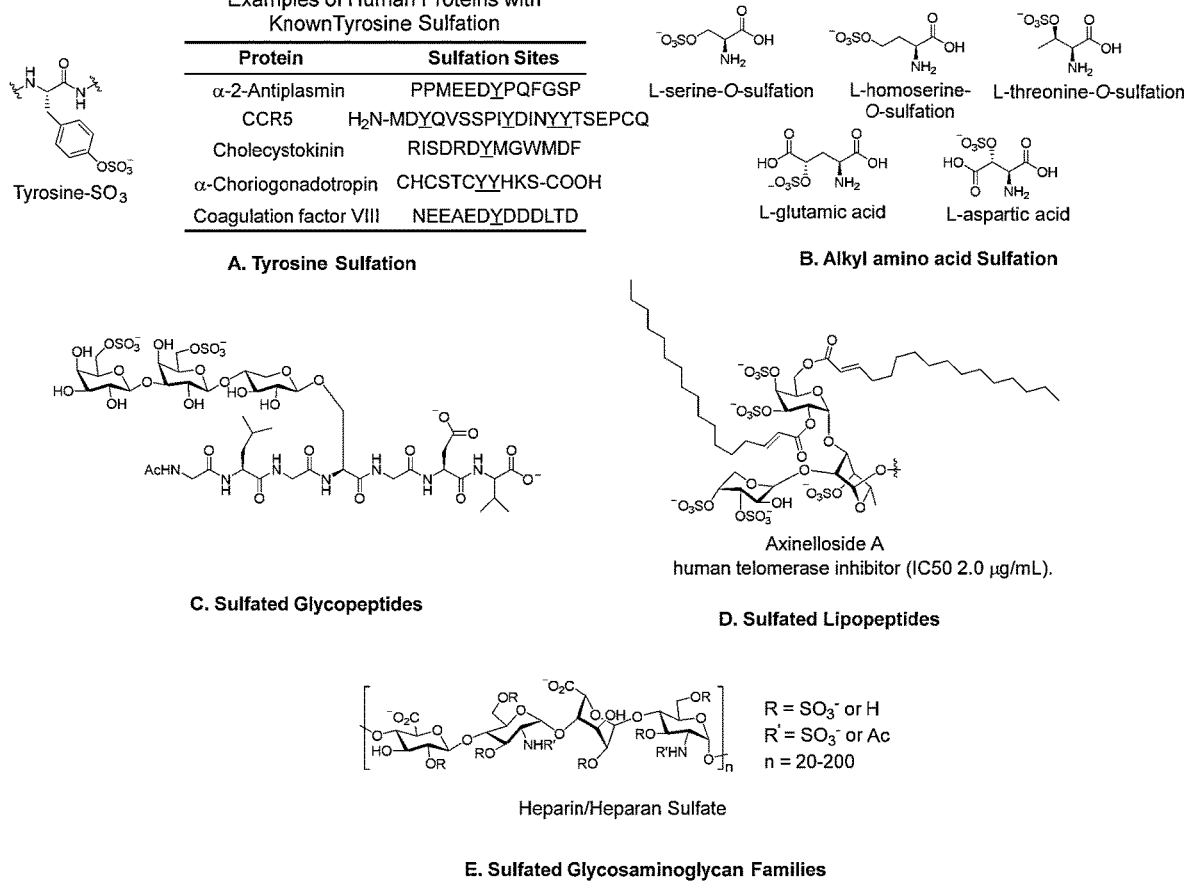
FIGS. 1A-1E show sulfation of various biomolecules in nature.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a substituent," "a catalyst," or "a sulfate ester," includes, but is not limited to, mixtures of two or more such substituents, catalysts, or sulfate esters, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a base refers to an amount that is sufficient to achieve the desired improvement in the property modulated by the formulation component, e.g. achieving the desired level of modulus. The specific level in terms of wt % in a composition required as an effective amount will depend upon a variety of factors including the amount and type of substrate; desired position of sulfation, hydrolysis, or hydrogenolysis; reaction time and temperature; solvent system; and any intended purification methods.

As used herein, the terms "optional" or "optionally" means that the subsequently described event or circumstance can or cannot occur, and that the description includes instances where said event or circumstance occurs and instances where it does not.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "alkanediyl" as used herein, refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, —$CH_2C(CH_3)_2CH_2$—, and —$CH_2CH_2CH_2$— are non-limiting examples of alkanediyl groups.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C$=$C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) and —N(-alkyl)$_2$, where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," . . . "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^{\circ}$; —$(CH_2)_{0-4}OR^{\circ}$; —O$(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH═CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}$; —$OC(O)R^{\circ}$; —$OC(O)(CH_2)_{0-4}SR$—, $SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ}_2$; $SiR^{\circ}_3$; —$(C_{1-4}$ straight or branched alkylene)O—$N(R^{\circ})_2$; or —$(C_{1-4}$ straight or branched)alkylene)C(O)O—$N(R^{\circ})_2$, wherein each $R^{\circ}$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R˙, -(haloR˙), —(CH$_2$)$_{0-2}$OH, —(CH$_2$)$_{0-20}$R˙, —(CH$_2$)$_{0-2}$CH(OR˙)$_2$; —O(haloR˙), —CN, —N$_3$, —(CH$_2$)$_{0-2}$C(O)R˙, —(CH$_2$)$_{0-2}$C(O)OH, —(CH$_2$)$_{0-2}$C(O)OR˙, —(CH$_2$)$_{0-2}$SR˙, —(CH$_2$)$_{0-2}$SH, —(CH$_2$)$_{0-2}$NH$_2$, —(CH$_2$)$_{0-2}$NHR˙, —(CH$_2$)$_{0-2}$NR˙$_2$, —NO$_2$, —SiR˙$_3$, —OSiR˙$_3$, —C(O)SR˙, —(C$_{1-4}$ straight or branched alkylene)C(O)OR˙, or —SSR˙ wherein each R˙ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

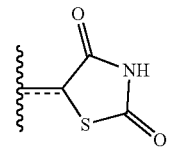

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2$H, $^3$H, $^{13}$O, $^{14}$O, $^{15}$N, $^{18}$O, $^{17}$O, $^{35}$S, $^{18}$F, and $^{36}$Cl, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

It is also appreciated that certain compounds described herein can be present as an equilibrium of tautomers. For example, ketones with an α-hydrogen can exist in an equilibrium of the keto form and the enol form.

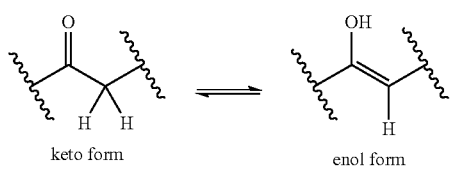

keto form          enol form

-continued

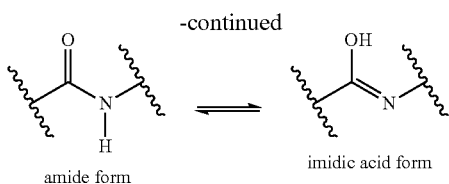

amide form       imidic acid form

Likewise, amides with an N-hydrogen can exist in an equilibrium of the amide form and the imidic acid form. Unless stated to the contrary, the invention includes all such possible tautomers.

In some aspects, a structure of a compound can be represented by a formula:

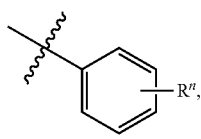

which is understood to be equivalent to a formula:

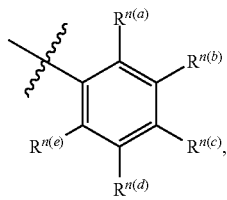

wherein n is typically an integer. That is, $R^n$ is understood to represent five independent substituents, $R^{n(a)}$, $R^{n(b)}$, $R^{n(c)}$, $R^{n(d)}$ and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

Unless otherwise specified, temperatures referred to herein are based on atmospheric pressure (i.e. one atmosphere).

SulFEx Reaction Procedure

Two-Step Procedure

In one aspect, provided herein is a two-step procedure for synthesizing a sulfate diester starting with a hydroxyl-exposed substrate. In one aspect, in the first step of the two-step procedure, the hydroxyl-exposed substrate is silylated using TMSCI. Further in this aspect, TMSCI is used to contact the substrate bearing a free hydroxyl group in an amount of from 1.0 to 5.0 equivalents per free hydroxyl group, or at about 1, 1.5, 2, 2.5, 3, 3.5, 4, 4.5, or about 5 equivalents per free hydroxyl group, or a combination of any of the foregoing values, or a range encompassing any of the foregoing values. In one aspect, 1.2 equivalents of TMSCl are used per free hydroxyl group on the substrate.

In an alternative aspect, in the first step of the two-step procedure, the hydroxyl-exposed substrate is silylated using HMDS. Further in this aspect, HMDS is sued to contact the substrate bearing a free hydroxyl group in an amount of from 0.5 to 5.0 equivalents per free hydroxyl group, or at about 0.5, 1, 1.5, 2, 2.5, 3, 3.5, 4, 4.5, or about 5 equivalents per free hydroxyl group, or a combination of any of the foregoing values, or a range encompassing any of the foregoing values. In one aspect, 1.1 equivalents of HMDS are used per free hydroxyl group on the substrate.

In either of these aspects, non-limiting examples of the substrate include

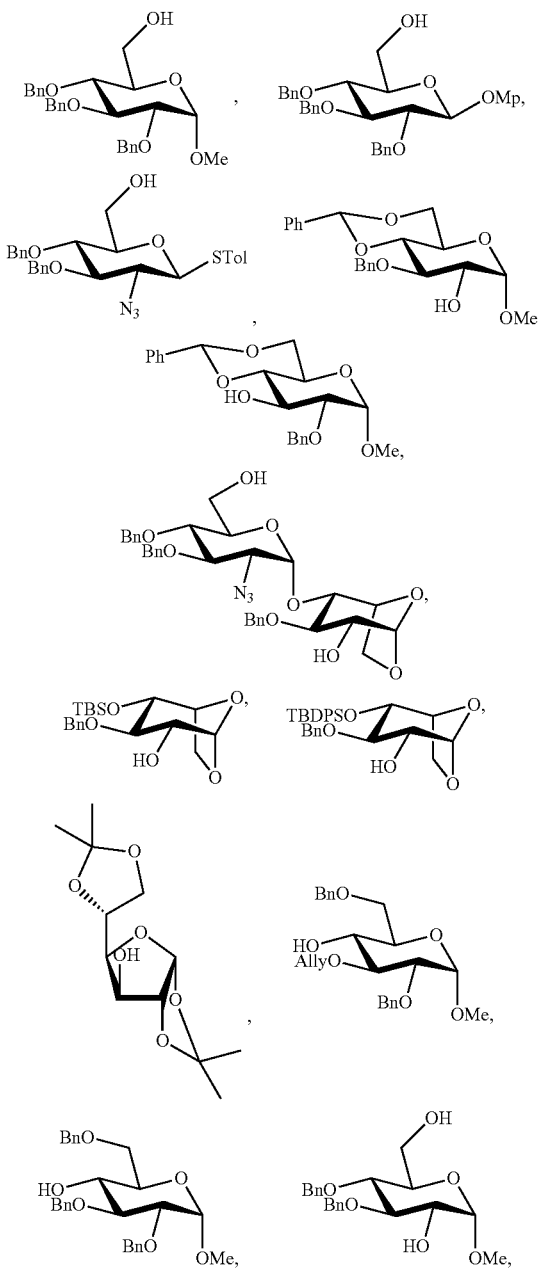

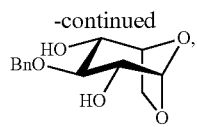

or a combination thereof.

In another aspect, in the second step of the two-step procedure, the silylated substrate is contacted with an aryl fluorosulfate. In one aspect, from 1 to 10 equivalents of aryl fluorosulfate are used per silylated hydroxyl group, or about 1, 1.5, 2, 2.5, 3, 3.5, 4, 4.5, 5, 5.5, 6, 6.5, 7, 7.5, 8, 8.5, 9, 9.5, or about 10 equivalents are used per silylated hydroxyl group, or a combination of any of the foregoing values, or a range encompassing any of the foregoing values. In one aspect, about 1.1 equivalents of the aryl fluorosulfate are used.

Further in this aspect, non-limiting examples of the aryl fluorosulfate include

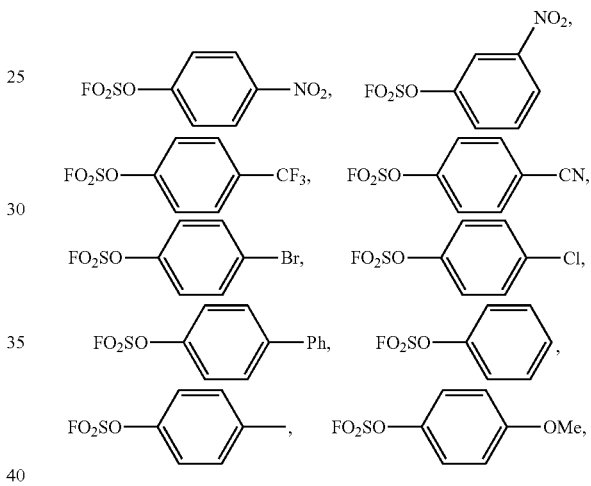

or a combination thereof.

In another aspect, in addition to an aryl fluorosulfate, the silylated substrate is additionally contacted with a catalyst. In a further aspect, from about 0.05 to 1.0 equivalents of catalyst are used per silylated hydroxyl group on the substrate, or about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or about 1 equivalent of catalyst are used per silylated hydroxyl group on the substrate, or a combination of any of the foregoing values, or a range encompassing any of the foregoing values. In one aspect, 0.2 equivalents of the catalyst are used.

Further in this aspect, non-limiting examples of the catalyst include 1,8-diazabicyclo[5.4.0]undec-7-ene (DBU, 1,5-diazabicyclo[4.3.0]non-5-ene (DBN), tert-butylamino-tri (pyrrolidino)phosphorane (BTPP), 2-tert-butylimino-2-diethylamino-1,3-dimethylperhydro-1,3,2-diazaphorphorine (BEMP), potassium bifluoride (KHF$_2$), 7-methyl-1,5,7-triazabicyclo[4.4.0]dec-5-ene (MTBD), tri-azabicyclodecene (TBD), imidazole, or a combination thereof.

In another aspect, for the second step of the two-step procedure, the concentration of the silylated hydroxyl group (i.e., the TMS ether) in the reaction solvent can be from about 0.05 to about 1 M, or can be about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or about 1 M, or a combination of any of the foregoing values, or a range encompassing any of the foregoing values. In one aspect, the concentration of TMS ether is about 0.3 M. In one aspect, the solvent can be selected from acetonitrile, N-methyl-2-pyrrolidone (NMP), dimethylformamide (DMF), tetrahydrofuran (THF), or combinations thereof. In another aspect, the solvent is acetonitrile.

In any of these aspects, the reactions can be conducted for from about 1 to about 10 hours, or for about 1, 1.5, 2, 2.5, 3, 3.5, 4, 4.5, 5, 5.5, 6, 6.5, 7, 7.5, 8, 8.5, 9, 9.5, or about 10 hours, or a combination of any of the foregoing values, or a range encompassing any of the foregoing values. In one aspect, the reaction is conducted for about 2 hours.

In another aspect, the reaction temperature can be from about 0° C. to about 50° C., or can be about 0, 5, 10, 15, 20, 25, 30, 35, 40, 45, or about 50° C., or a combination of any of the foregoing values, or a range encompassing any of the foregoing values. In one aspect, the reaction temperature is about 25° C. or is about room temperature.

One-Pot Procedure

In another aspect, disclosed herein is a one-pot reaction for forming sulfate diesters. Further in this aspect, the reactants, substrates, concentrations, ratios, temperatures, solvents, and the like, are essentially the same as for the two-step synthesis disclosed herein, but are added to the reaction vessel initially rather than sequentially, and without any workup between steps.

Deprotection by Hydrolysis

In some aspects, the aryl group can be removed from the sulfate diesters disclosed herein to form a sulfated substrate in a hydrolysis reaction. In a further aspect, the hydrolysis reaction involves contacting the sulfate diesters disclosed herein with a base. In a further aspect, the base can be sodium methoxide, potassium hydroxide, sodium hydroxide, lithium methoxide, or a combination thereof. In one aspect, the base is sodium methoxide.

In another aspect, the base concentration is from about 3 to about 30 M, or is about 3, 4, 5, 6, 7, 8, 9, 10, 11, 12, 13, 14, 15, 16, 17, 18, 19, 20, 21, 22, 23, 24, 25, 26, 27, 28, 29, or about 30 M, or a combination of any of the foregoing values, or a range encompassing any of the foregoing values. In one aspect, the base concentration is about 3 M.

In still another aspect, the hydrolysis reaction can be performed at temperatures ranging from about 20° C. to about 60° C., or at about 20, 25, 30, 35, 40, 45, 50, 55, or about 60° C., or a combination of any of the foregoing values, or a range encompassing any of the foregoing values. In one aspect, the hydrolysis reaction is performed at about 25° C., or at about room temperature.

Deprotection by Hydrogenolysis

In other aspects, the aryl group can be removed from the sulfate diesters disclosed herein to form a sulfated substrate in a hydrogenolysis reaction. In a further aspect, the hydrogenolysis reaction involves contacting the substrate in a solvent with a catalyst and a reducing agent.

In one aspect, the catalyst can be Pd(OH)$_2$/C or PtO$_2$/C. In another aspect, the reducing agent can be ammonium formate or hydrogen gas.

In another aspect, the catalyst is present in an amount of from about 1 gram to about 10 grams per gram of substrate, or at about 1 gram catalyst per 1, 2, 3, 4, 5, 6, 7, 8, 9, or about 10 grams per gram of substrate, or a combination of any of the foregoing values, or a range encompassing any of the foregoing values. In one aspect, about 5 grams of catalyst per 1 gram of substrate are used.

In another aspect, the solvent can be a combination of acetonitrile, methanol, and phosphate buffered saline (PBS) in a ratio of from about 1:1:1 to about 9:9:2, or a range encompassing any of the foregoing values. In one aspect, the ratio of acetonitrile to methanol to PBS is about 2:2:1. In another aspect, the concentration of the PBS can be from about 0.01 to about 0.1 M, or can be about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, or about 0.1 M, or a combination of any of the foregoing values, or a range encompassing any of the foregoing values. In one aspect, the PBS concentration is about 0.018 M. In still another aspect, the pH of the PBS can be from about 5 to about 9, or can be about 5, 5.5, 6, 6.5, 7, 7.5, 8, 8.5, or about 9, or a combination of any of the foregoing values, or a range encompassing any of the foregoing values. In one aspect, the pH of the pBS is 7.4.

General Considerations

In one aspect, performing the two-step or one-pot SulFEx reactions disclosed herein on two adjacent hydroxyl groups can generate a cyclic sulfate diester linkage as shown, for example, in compound A of the scheme below:

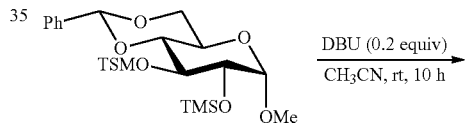

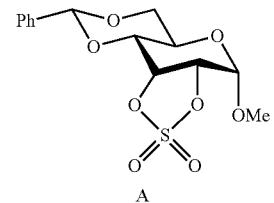

A

In another aspect, the reactions disclosed herein can install 1, 2, or 3 sulfate diesters on a given pyranose sugar molecule, as shown, for example, in compound B of the scheme below:

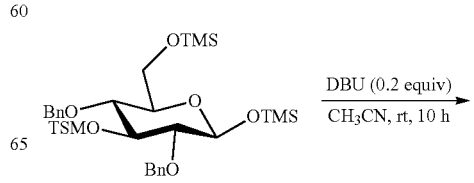

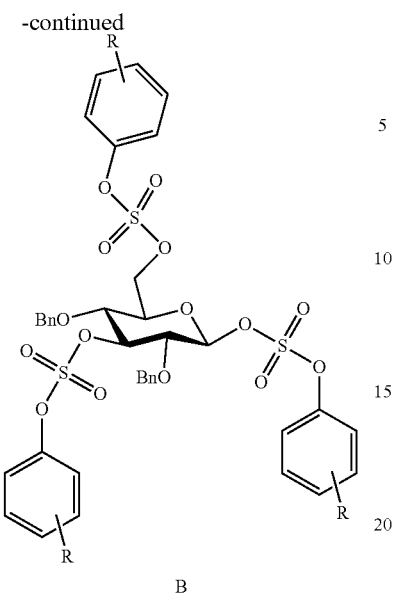

B

In still another aspect, the number of sulfate diesters that can be installed on a polypeptide or polysaccharide substrate can be higher. Without wishing to be bound by theory, the hydroxyl groups available for silylation on such a substrate are maintained at a greater distance from one another so as to prevent steric hindrance and cyclic sulfate diester formation.

Aspects

The following listing of exemplary aspects supports and is supported by the disclosure provided herein.

Aspect 1. A method for synthesis of sulfate diesters, the method comprising: (a) contacting a substrate having at least one hydroxyl group with a silylating reagent in a first solvent to form a silyl-protected substrate; and (b) contacting the protected substrate with an aryl fluorosulfate and a catalyst in a second solvent to produce a product sulfate diester.

Aspect 2. The method of aspect 1, wherein the substrate comprises a sugar, a sugar comprising at least one protected hydroxyl group, an amino acid, a polysaccharide, a glycopeptide, a polypeptide, a glycosaminoglycan, a lipopeptide, a sterol, or a combination thereof.

Aspect 3. The method of aspect 2, wherein the sugar comprising at least one protected hydroxyl group comprises 1,2:3,4-di-O-isopropylidene-α-D-galactopyranose.

Aspect 4. The method of aspect 2, wherein the amino acid comprises serine, threonine, tyrosine, or a combination thereof.

Aspect 5. The method of aspect 2, wherein the glycosaminoglycan comprises heparin, chondroitin, keratan, hyaluronic acid, or a combination thereof.

Aspect 6. The method of aspect 1, wherein the substrate comprises

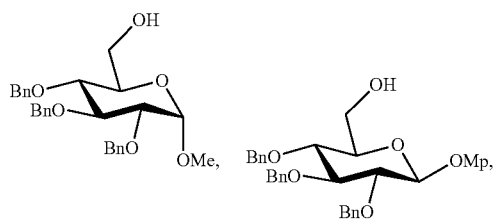

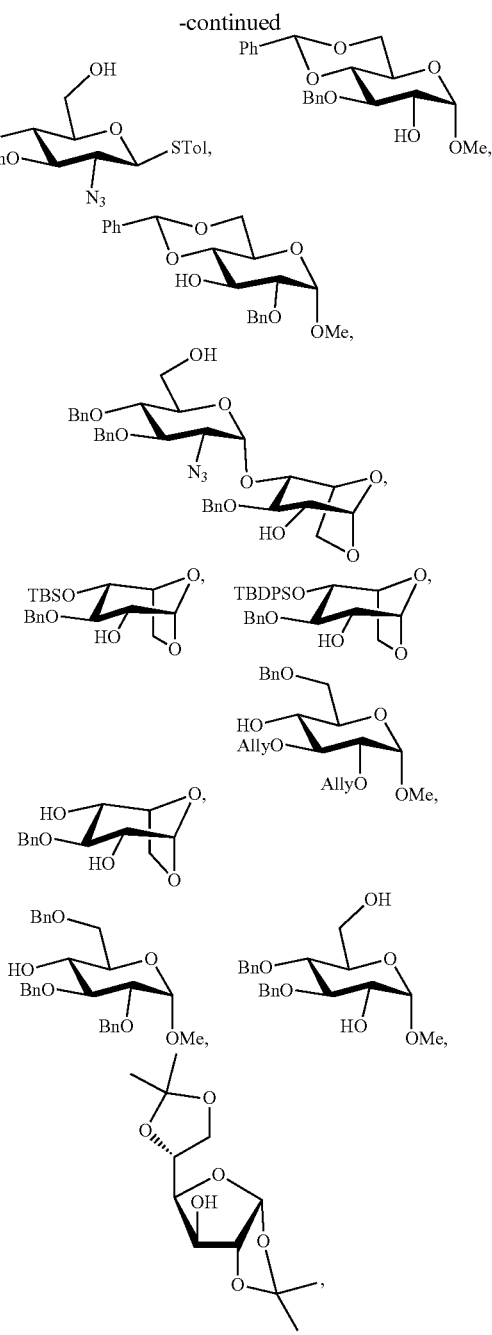

or a combination thereof.

Aspect 7. The method of any of aspects 1-6, wherein the silylating reagent comprises trimethylsilyl chloride (TMSCl), bis(trimethylsilyl)amine (HMDS), or a combination thereof.

Aspect 8. The method of any of aspects 1-7, wherein the aryl fluorosulfate comprises

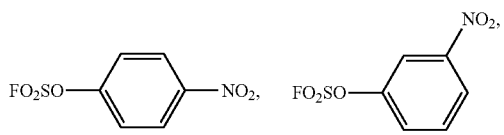

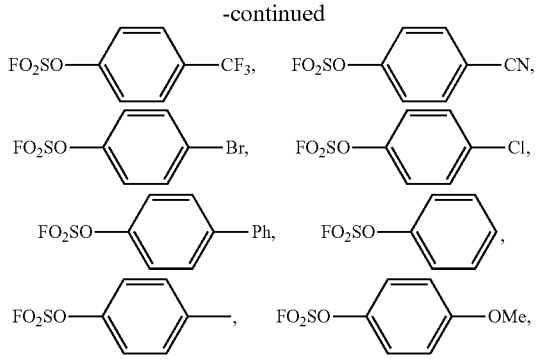

or a combination thereof.

Aspect 9. The method of any of aspects 1-8, wherein the catalyst comprises 1,8-diazabicyclo[5.4.0]undec-7-ene (DBU, 1,5-diazabicyclo[4.3.0]non-5-ene (DBN), tert-butylamino-tri(pyrrolidino)phosphorane (BTPP), 2-tert-butylimino-2-diethylamino-1,3-dimethylperhydro-1,3,2-diazaphorphorine (BEMP), potassium bifluoride ($KHF_2$), 7-methyl-1,5,7-triazabicyclo[4.4.0]dec-5-ene (MTBD), triazabicyclodecene (TBD), imidazole, or a combination thereof.

Aspect 10. The method of any of aspects 1-9, wherein the first solvent comprises pyridine, acetonitrile, N-methyl-2-pyrrolidone, dimethylformamide, tetrahydrofuran, or a combination thereof.

Aspect 11. The method of any of aspects 1-9, wherein the second solvent comprises acetonitrile.

Aspect 12. The method of any of aspects 1-11, wherein step (a), step (b), or both are carried out under an inert atmosphere.

Aspect 13. The method of aspect 12, wherein the inert atmosphere comprises nitrogen.

Aspect 14. The method of any of aspects 1-13, wherein in step (a) the substrate is contacted with the silylating reagent at 0° C.

Aspect 15. The method of aspect 14, wherein step (a) is carried out for from about 1 to about 10 h.

Aspect 16. The method of any of aspects 1-13, wherein step (a) is carried out at room temperature.

Aspect 17. The method of aspect 16, wherein step (a) is carried out for from about 2 to about 3 h.

Aspect 18. The method of any of aspects 1-17, wherein step (b) is carried out at room temperature.

Aspect 19. The method of aspect 18, wherein step (b) is carried out for about 2 h.

Aspect 20. The method of any of aspects 1-19, wherein in step (a), from about 1 to about 1.5 equivalents of silylating reagent is used to contact 1 equivalent of hydroxyl group.

Aspect 21. The method of aspect 20, wherein 1.2 equivalent of silylating reagent is used to contact 1 equivalent of hydroxyl group.

Aspect 22. The method of aspect 20, wherein 1.1 equivalent of silylating reagent is used to contact 1 equivalent of hydroxyl group.

Aspect 23. The method of any of aspects 1-22, wherein in step (b), 1.1 equivalent of aryl fluorosulfate is used to contact 1 equivalent of silyl-protected substrate.

Aspect 24. The method of any of aspects 1-23, wherein in step (b), 0.2 equivalent of catalyst is used to contact 1 equivalent of silyl-protected substrate.

Aspect 25. The method of any of aspects 1-24, wherein the sulfate diester comprises from about 1 to about 3 sulfate diester linkages.

Aspect 26. The method of aspect 25, wherein the sulfate diester comprises one sulfate diester linkage.

Aspect 27. The method of aspect 25, wherein the sulfate diester comprises 2 sulfate diester linkages.

Aspect 28. The method of any of aspects 1-27, wherein the sulfate diester comprises

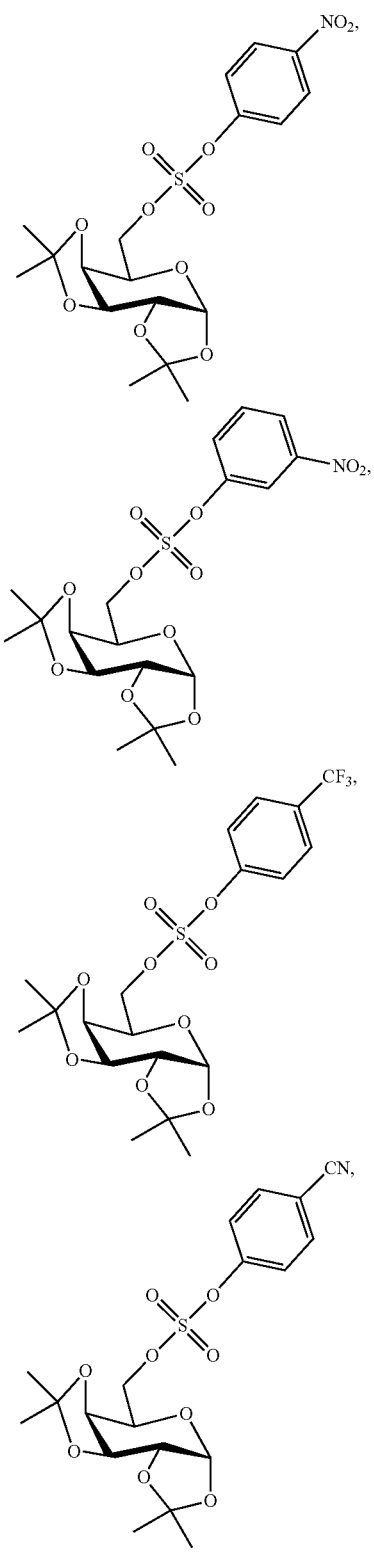

-continued

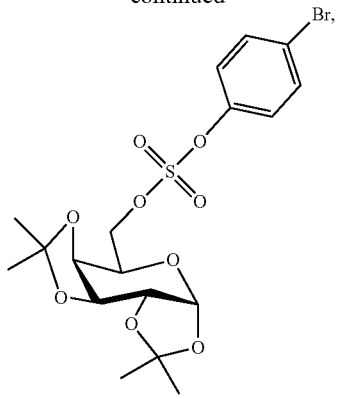

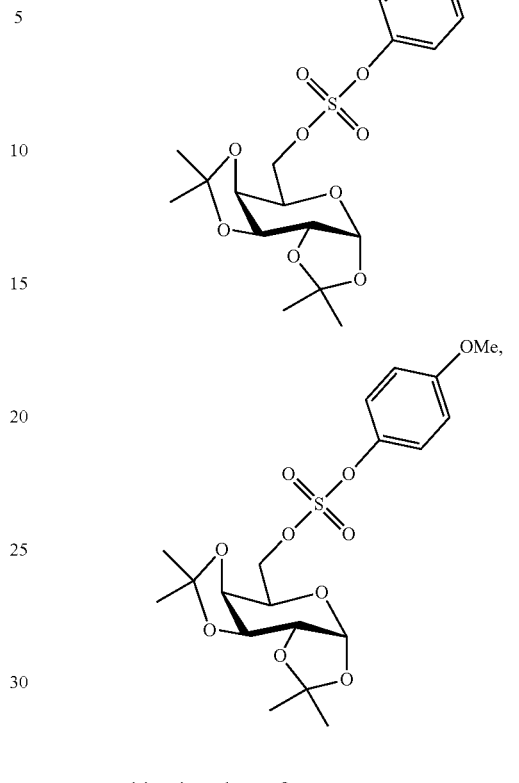

or a combination thereof.

Aspect 29. A method for synthesis of sulfate diesters, the method comprising contacting a substrate having at least one hydroxyl group with an aryl fluorosulfate, a silylating reagent, and a catalyst in a solvent to produce a product sulfate diester.

Aspect 30. The method of aspect 29, wherein the substrate comprises a sugar, a sugar comprising at least one protected hydroxyl group, an amino acid, a polysaccharide, a glycopeptide, a polypeptide, a glycosaminoglycan, a lipopeptide, a sterol, or a combination thereof.

Aspect 31. The method of aspect 30, wherein the sugar comprising at least one protected hydroxyl group comprises 1,2:3,4-di-O-isopropylidene-α-D-galactopyranose.

Aspect 32. The method of aspect 30, wherein the amino acid comprises serine, threonine, tyrosine, or a combination thereof.

Aspect 33. The method of aspect 30, wherein the glycosaminoglycan comprises heparin, chondroitin, keratan, hyaluronic acid, or a combination thereof.

Aspect 34. The method of aspect 29, wherein the substrate comprises

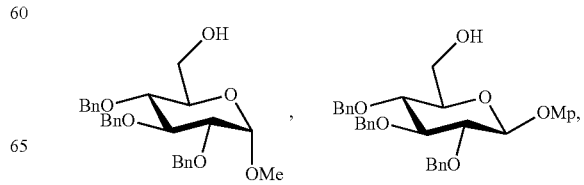

31
-continued

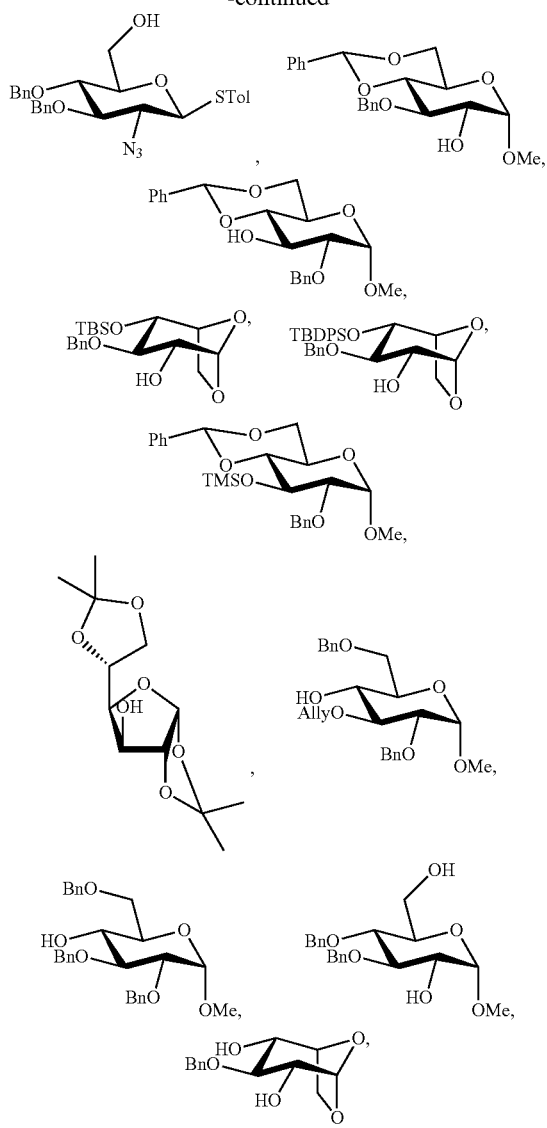

or a combination thereof.

Aspect 35. The method of any of aspects 29-34, wherein the silylating reagent comprises trimethylsilyl chloride (TMSCl), bis(trimethylsilyl)amine (HMDS), or a combination thereof.

Aspect 36. The method of any of aspects 29-35, wherein the aryl fluorosulfate comprises

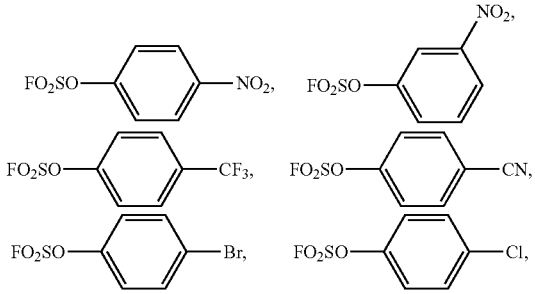

32
-continued

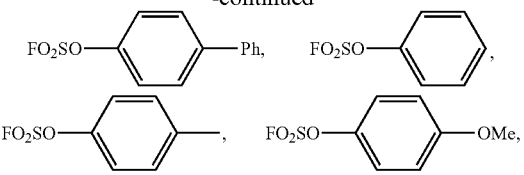

or a combination thereof.

Aspect 37. The method of any of aspects 29-36, wherein the catalyst comprises 1,8-diazabicyclo[5.4.0]undec-7-ene (DBU, 1,5-diazabicyclo[4.3.0]non-5-ene (DBN), tert-butylamino-tri(pyrrolidino)phosphorane (BTPP), 2-tert-butylimino-2-diethylamino-1,3-dimethylperhydro-1,3,2-diazaphosphorine (BEMP), potassium bifluoride (KHF$_2$), 7-methyl-1,5,7-triazabicyclo[4.4.0]dec-5-ene (MTBD), triazabicyclodecene (TBD), imidazole, or a combination thereof.

Aspect 38. The method of any of aspects 29-37, wherein the solvent comprises acetonitrile.

Aspect 39. The method of any of aspects 29-38, the method is carried out under an inert atmosphere.

Aspect 40. The method of aspect 39, wherein the inert atmosphere comprises nitrogen.

Aspect 41. The method of any of aspects 29-40, wherein the method is carried out at room temperature.

Aspect 42. The method of any of aspects 29-41, wherein the silylating agent is bis(trimethylsilyl)amine (HMDS) and wherein about 0.6 equivalents of silylating reagent are used to contact 1 equivalent of hydroxyl group.

Aspect 43. The method of any of aspects 29-42, wherein about 1.1 equivalents of aryl fluorosulfate are used to contact 1 equivalent of hydroxyl group.

Aspect 44. The method of any of aspects 29-43, wherein about 0.1 equivalents of catalyst are used to contact 1 equivalent of hydroxyl group.

Aspect 45. The method of any of aspects 29-44, wherein the sulfate diester comprises from about 1 to about 3 sulfate diester linkages.

Aspect 46. The method of aspect 45, wherein the sulfate diester comprises one sulfate diester linkage.

Aspect 47. The method of aspect 45, wherein the sulfate diester comprises 2 sulfate diester linkages.

Aspect 48. The method of any of aspects 29-47, wherein the sulfate diester comprises

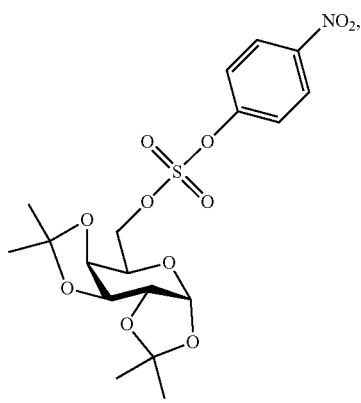

33
-continued
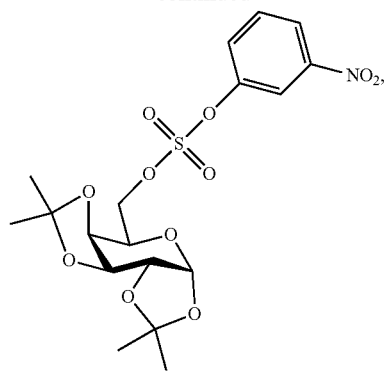
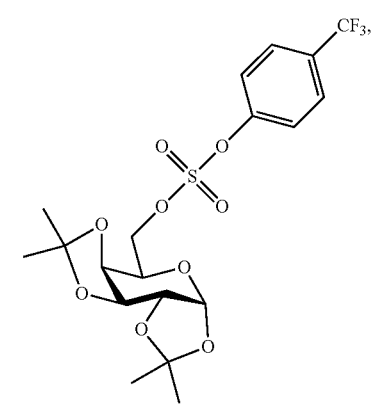
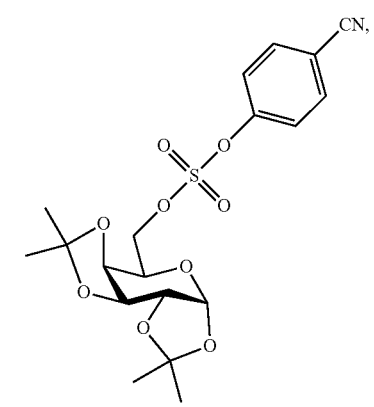
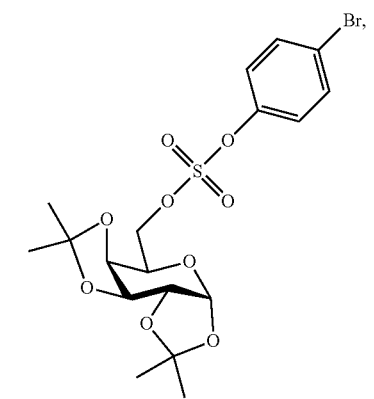
34
-continued
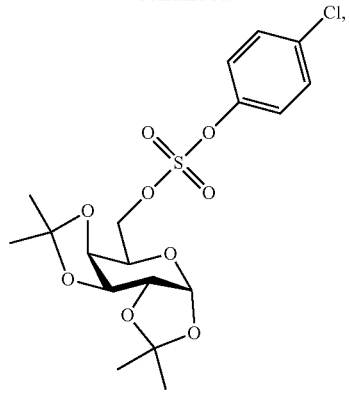
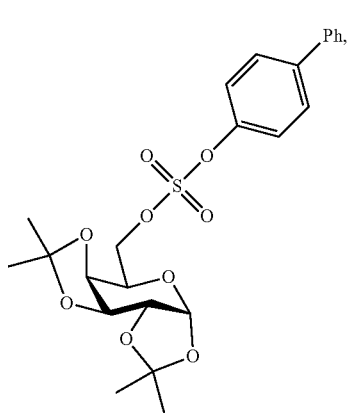
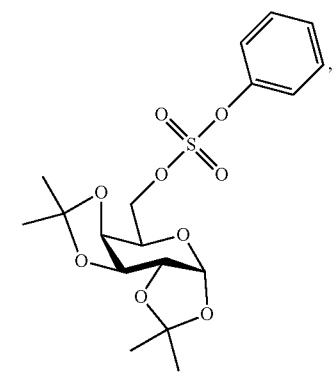
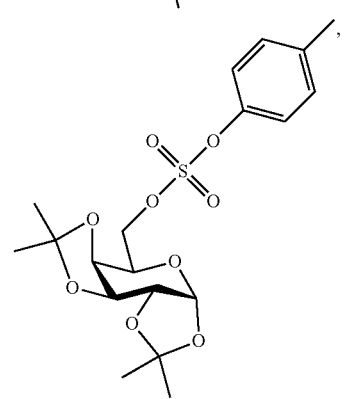

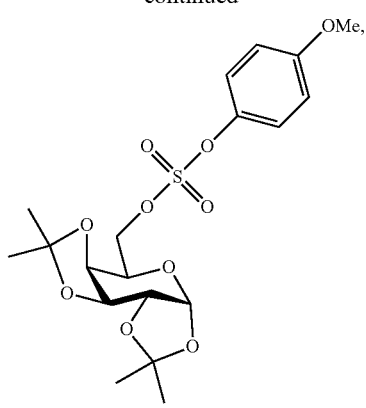

or a combination thereof.

Aspect 49. The method of any of aspects 29-48, wherein the substrate is contacted with the aryl fluorosulfate and the silylating reagent sequentially.

Aspect 50. The method of any of aspects 29-48, wherein the substrate is contacted with the aryl fluorosulfate and the silylating reagent simultaneously.

Aspect 51. A method for deprotecting a masked sulfate diester to form a sulfated product, the method comprising contacting the masked sulfate diester in a solvent with a strong base.

Aspect 52. The method of aspect 51, wherein the masked sulfate diester comprises

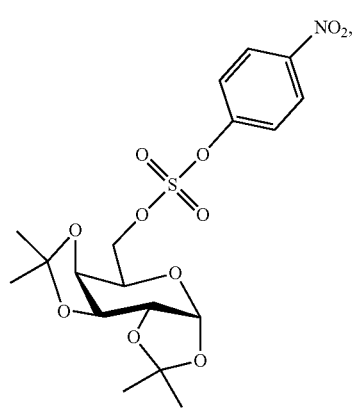

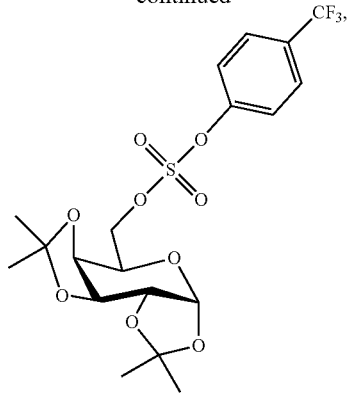

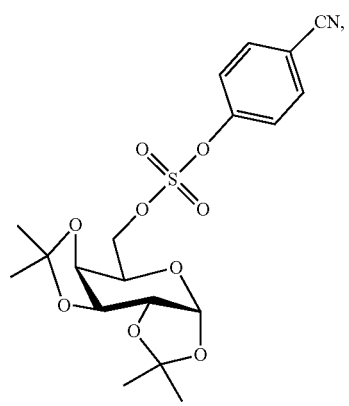

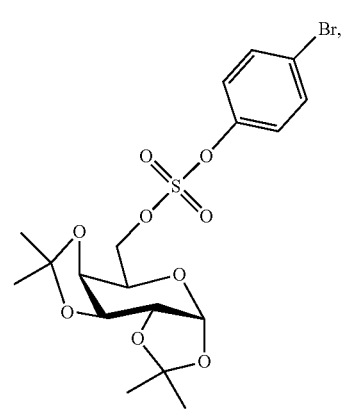

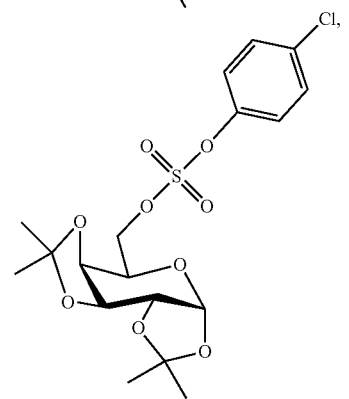

-continued

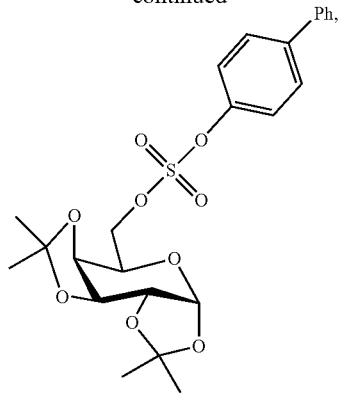

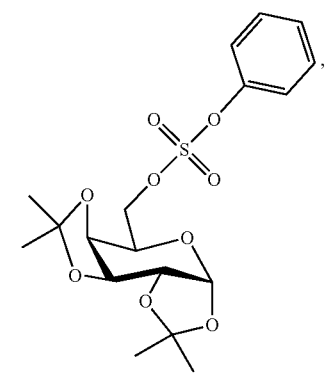

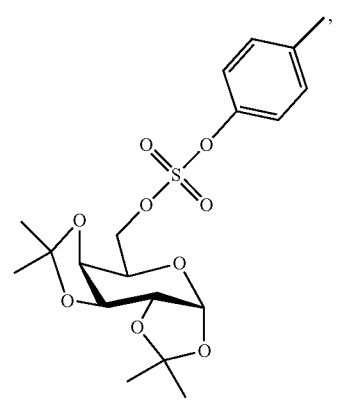

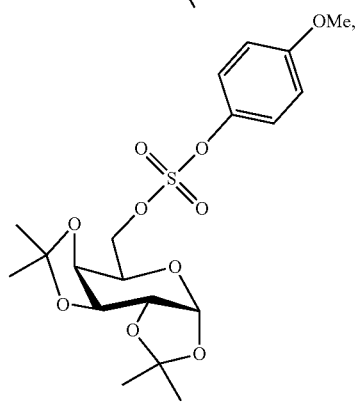

or a combination thereof.

Aspect 53. The method of aspect 51 or 52, wherein the sulfated product comprises a sulfated sugar, a sulfated sugar comprising at least one protected hydroxyl group, a sulfated amino acid, a sulfated polysaccharide, a sulfated glycopeptide, a sulfated polypeptide, a sulfated glycosaminoglycan, a sulfated lipopeptide, a sulfated sterol, or a combination thereof.

Aspect 54. The method of aspect 53, wherein the sulfated product comprises

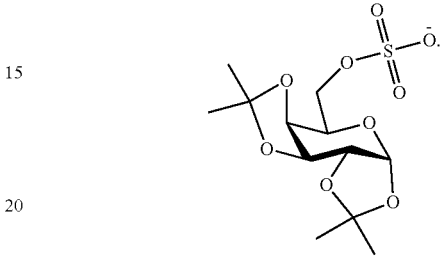

Aspect 55. The method of aspect 53, wherein the sulfated amino acid comprises sulfated serine, sulfated threonine, sulfated tyrosine, or a combination thereof.

Aspect 56. The method of aspect 53, wherein the sulfated glycosaminoglycan comprises heparan sulfate, dermatan sulfate, keratan sulfate, sulfated hyaluronic acid, or a combination thereof.

Aspect 57. The method of any of aspects 51-56, wherein the solvent comprises methanol, acetonitrile, or a combination thereof.

Aspect 58. The method of any of aspects 51-57, wherein the base comprises sodium methoxide, potassium hydroxide, sodium hydroxide, lithium methoxide, or a combination thereof.

Aspect 59. The method of any of aspects 51-58, wherein the masked sulfate diester is contacted with about 100 equivalents of base to 1 equivalent of sulfate diester.

Aspect 60. A method for deprotecting a masked sulfate diester to form a sulfated product, the method comprising contacting the masked sulfate diester with a catalyst in a solvent in the presence of a reducing agent.

Aspect 61. The method of aspect 60, wherein the masked sulfate diester comprises

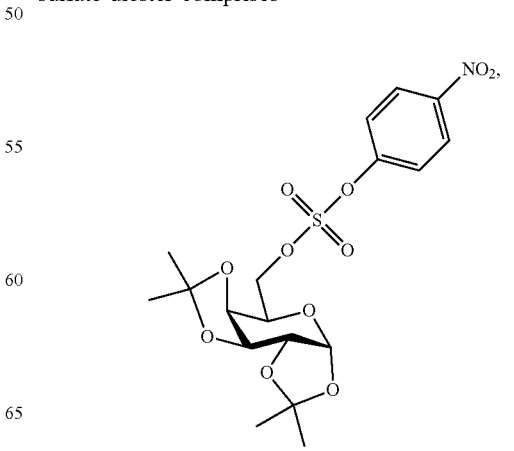

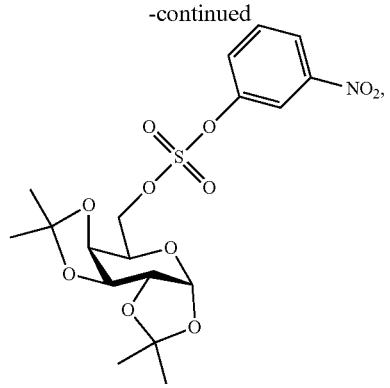
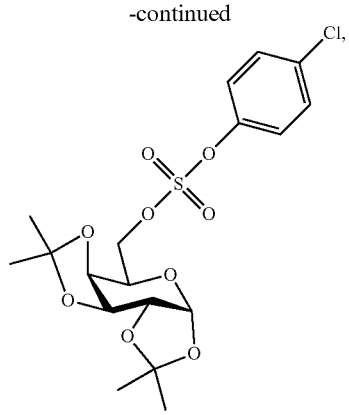
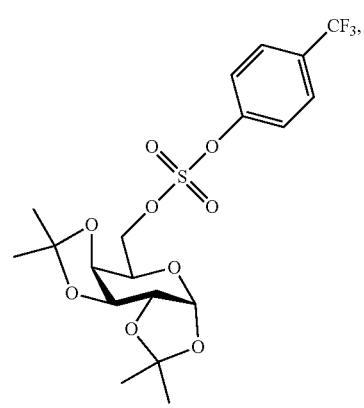
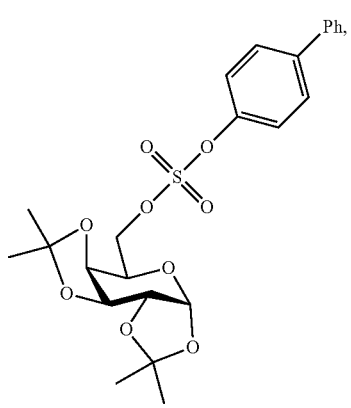
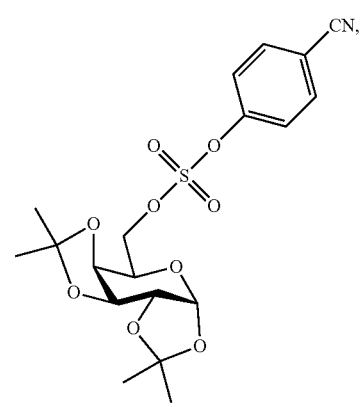
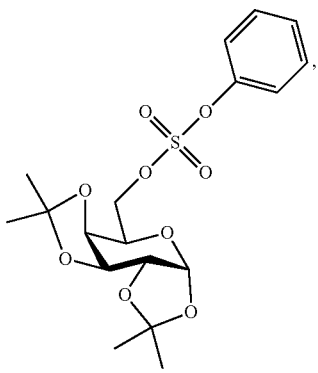
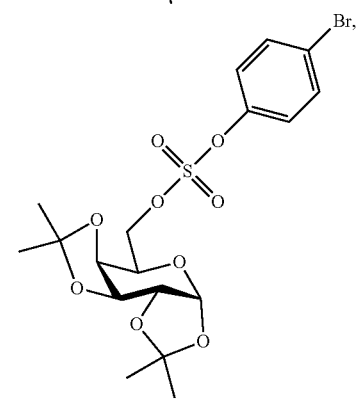
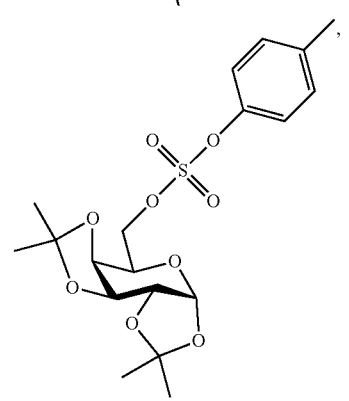

-continued

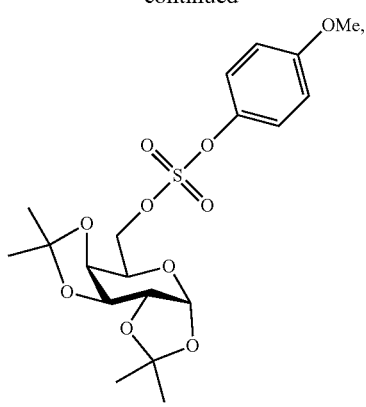

or a combination thereof.

Aspect 62. The method of aspect 60 or 61, wherein the sulfated product comprises

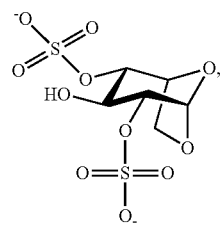

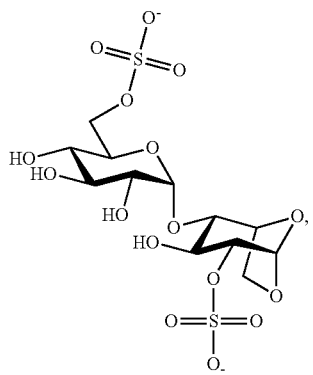

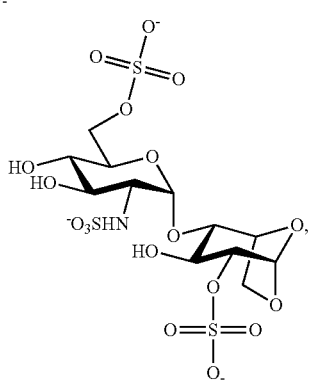

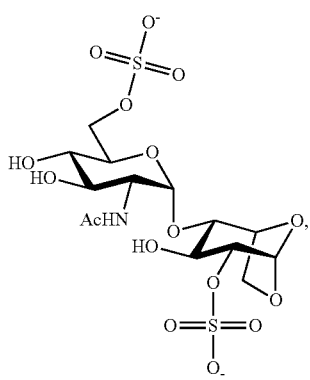

-continued

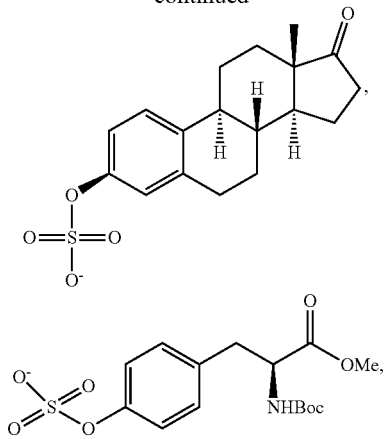

or a combination thereof.

Aspect 63. The method of any of aspects 60-62, wherein the solvent comprises a first solvent, methanol, and phosphate-buffered saline.

Aspect 64. The method of aspect 63, wherein the first solvent comprises acetonitrile, tetrahydrofuran, or dimethylformamide.

Aspect 65. The method of aspect 63, wherein the first solvent comprises acetonitrile.

Aspect 66. The method of any of aspects 63-65, wherein the phosphate-buffered saline comprises a pH of about 7.4.

Aspect 67. The method of any of aspects 60-66, wherein the catalyst comprises $Pd(OH)_2/C$ or $PtO_2/C$.

Aspect 68. The method of any of aspects 60-67, wherein the reducing agent comprises $H_2$ or ammonium formate.

Aspect 69. The method of aspect 67, wherein the reducing agent is $H_2$.

Aspect 70. The method of aspect 67, wherein the catalyst is $Pd(OH)_2/C$ and the reducing agent is ammonium formate.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

REFERENCES

References are cited herein throughout using the format of reference number(s) enclosed by parentheses corresponding to one or more of the following numbered references. For example, citation of references numbers 1 and 2 immediately herein below would be indicated in the disclosure as (1, 2).

1. Bowman, K. G. & Bertozzi, C. R. Carbohydrate sulfotransferases: mediators of extracellular communication. Chemistry & biology 6, R9-R22 (1999).
2. Chen, Y. et al. Tailored design and synthesis of heparan sulfate oligosaccharide analogues using sequential one-pot multienzyme systems. Angew. Chem. Int. Ed. 52, 11852-11856 (2013).
3. Desoky, A. Y. & Taylor, S. D. Multiple and regioselective introduction of protected sulfates into carbohydrates using sulfuryl imidazolium salts. The Journal of organic chemistry 74, 9406-9412 (2009).
4. Dong, J., Krasnova, L., Finn, M. & Sharpless, K. B. Sulfur (VI) fluoride exchange (SuFEx): another good reaction for click chemistry. Angew. Chem. Int. Ed. 53, 9430-9448 (2014).
5. Dong, J., Sharpless, K. B., Kwisnek, L., Oakdale, J. S. & Fokin, V. V. SuFEx-Based Synthesis of Polysulfates. Angew. Chem. Int. Ed. 53, 9466-9470 (2014).
6. Fang, W.-Y., Zha, G.-F., Zhao, C. & Qin, H.-L. Regioselective installation of fluorosulfate (—OSO 2 F) functionality into aromatic C (sp 2)-H bonds for the construction of para-amino-arylfluorosulfates. Chem. Commun. 55, 6273-6276 (2019).
7. Gao, B. et al. Bifluoride-catalysed sulfur (VI) fluoride exchange reaction for the synthesis of polysulfates and polysulfonates. Nat. Chem. 9, 1083-1088 (2017).
8. Gembus, V., Marsais, F. & Levacher, V. An efficient organocatalyzed interconversion of silyl ethers to tosylates using DBU and p-toluenesulfonyl fluoride. Synlett 2008, 1463-1466 (2008).
9. Gilles, P. et al. Synthesis of N-acyl sulfamates from fluorosulfates and amides. J. Org. Chem. 84, 1070-1078 (2018).
10. Guan, B.-T. et al. Biaryl construction through Kumada coupling with diaryl sulfates as one-by-one electrophiles under mild conditions. Org. Lett. 12, 396-399 (2010).
11. Herczeg, M. et al. Synthesis of disaccharide fragments of the AT-III binding domain of heparin and their sulfonatomethyl analogues. Carbohydr. Res. 346, 1827-1836 (2011).
12. Ingram, L. J. & Taylor, S. D. Introduction of 2, 2, 2-Trichloroethyl-Protected Sulfates into Monosaccharides with a Sulfuryl Imidazolium Salt and Application to the Synthesis of Sulfated Carbohydrates. Angew. Chem. Int. Ed. 45, 3503-3506 (2006).
13. Ingram, L. J., Desoky, A., Ali, A. M. & Taylor, S. D. O- and N-sulfations of carbohydrates using sulfuryl imidazolium salts. The Journal of organic chemistry 74, 6479-6485 (2009).
14. Joseph, A. A. et al. TMSOTf-Catalyzed silylation: streamlined regioselective one-pot protection and acetylation of carbohydrates. Eur. J. Org. Chem. 2012, 744-753 (2012).
15. Karmakar, A. et al. Tertiary-butoxycarbonyl (Boc)-A strategic group for N-protection/deprotection in the synthesis of various natural/unnatural N-unprotected amino-acid cyanomethyl esters. Tetrahedron Lett. 59, 4267-4271 (2018).
16. Karst, N. A., Islam, T. F. & Linhardt, R. J. Sulfo-protected hexosamine monosaccharides: Potentially versatile building blocks for glycosaminoglycan synthesis. Org. Lett. 5, 4839-4842 (2003).
17. Karst, N. A., Islam, T. F., Avci, F. Y. & Linhardt, R. J. Trifluoroethylsulfonate protected monosaccharides in glycosylation reactions. Tetrahedron Lett. 45, 6433-6437 (2004).
18. Lázár, L. et al. Synthesis of the non-reducing end trisaccharide of the antithrombin-binding domain of heparin and its bioisosteric sulfonic acid analogues. Tetrahedron 68, 7386-7399 (2012).
19. Lee, J.-C., Lu, X.-A., Kulkarni, S. S., Wen, Y.-S. & Hung, S.-C. Synthesis of heparin oligosaccharides. J. Am. Chem. Soc. 126, 476-477 (2004).
20. Lee, J.-C., Tai, C.-A. & Hung, S.-C. Sc (OTf) 3-catalyzed acetolysis of 1, 6-anhydro-β-hexopyranoses and solvent-free per-acetylation of hexoses. Tetrahedron Lett. 43, 851-855 (2002).
21. Li, Y. et al. A practical and benign synthesis of amines through Pd@ mpg-C3N4 catalyzed reduction of nitriles. Catal. Commun. 28, 9-12 (2012).
22. Liang, Q. et al. Palladium-catalyzed, ligand-free Suzuki reaction in water using aryl fluorosulfates. Org. Lett. 17, 1942-1945 (2015).
23. Liu, J. & Linhardt, R. J. Chemoenzymatic synthesis of heparan sulfate and heparin. Natural product reports 31, 1676-1685 (2014).
24. Liu, Y., Lien, I.-F. F., Ruttgaizer, S., Dove, P. & Taylor, S. D. Synthesis and protection of aryl sulfates using the 2, 2, 2-trichloroethyl moiety. Org. Lett. 6, 209-212 (2004).
25. Ma, C. et al. Nickel-Catalyzed Carboxylation of Aryl and Heteroaryl Fluorosulfates Using Carbon Dioxide. Org. Lett. 21, 2464-2467 (2019).
26. Matsushita, K., Sato, Y., Funamoto, S. & Tamura, J.-i. Side reactions with 2, 2, 2-trichloroethoxysulfates during the synthesis of glycans. Carbohydr. Res. 396, 14-24 (2014).
27. McLean, J. The thromboplastic action of cephalin. American Journal of Physiology-Legacy Content 41, 250-257 (1916).
28. Miethchen, R. & Fehring, V. Chirale Kronenether mit integriertem 1, 4-verbrückten d-Glucopyranose-Baustein. Synthesis 1998, 94-98 (1998).
29. Nielsen, M. K., Ugaz, C. R., Li, W. & Doyle, A. G. PyFluor: a low-cost, stable, and selective deoxyfluorination reagent. J. Am. Chem. Soc. 137, 9571-9574 (2015).
30. Oediger, H., Moeller, F. & Eiter, K. Bicyclic amidines as reagents in organic syntheses. Synthesis 1972, 591-598 (1972).
31. Ortiz-Cervantes, C., Iyañez, I. & Garcia, J. J. Facile preparation of ruthenium nanoparticles with activity in hydrogenation of aliphatic and aromatic nitriles to amines. J. Phys. Org. Chem. 25, 902-907 (2012).
32. Penney, C. L. & Perlin, A. S. A method for the sulfation of sugars, employing a stable, aryl sulfate intermediate. Carbohydr. Res. 93, 241-246 (1981).

33. Proud, A. D., Prodger, J. C. & Flitsch, S. L. Development of a protecting group for sulfate esters. Tetrahedron Lett. 38, 7243-7246 (1997).
34. Ratzka, A., Vogel, H., Kliebenstein, D. J., Mitchell-Olds, T. & Kroymann, J. Disarming the mustard oil bomb. Proc. Natl. Acad. Sci. U.S.A. 99, 11223-11228 (2002).
35. Saad, F., Comparot, J., Brahmi, R., Bensitel, M. & Pirault-Roy, L. Influence of acid-base properties of the support on the catalytic performances of Pt-based catalysts in a gas-phase hydrogenation of acetonitrile. Appl. Catal. A-Gen. 544, 1-9 (2017).
36. Sasisekharan, R., Shriver, Z., Venkataraman, G. & Narayanasami, U. Roles of heparan-sulphate glycosaminoglycans in cancer. Nature Reviews Cancer 2, 521-528 (2002).
37. Simpson, L. S. & Widlanski, T. S. A comprehensive approach to the synthesis of sulfate esters. J. Am. Chem. Soc. 128, 1605-1610 (2006).
38. Takada, K. et al. Schulzeines A-C, new α-glucosidase inhibitors from the marine sponge Penares schulzei. J. Am. Chem. Soc. 126, 187-193 (2004).
39. Tiruchinapally, G., Yin, Z., El-Dakdouki, M., Wang, Z. & Huang, X. Divergent heparin oligosaccharide synthesis with preinstalled sulfate esters. Chemistry-A European Journal 17, 10106-10112 (2011).
40. Tully, S. E. et al. A chondroitin sulfate small molecule that stimulates neuronal growth. J. Am. Chem. Soc. 126, 7736-7737 (2004).
41. Winkler, J. D., Isaacs, A., Holderbaum, L., Tatard, V. & Dahmane, N. Design and synthesis of inhibitors of Hedgehog signaling based on the alkaloid cyclopamine. Org. Lett. 11, 2824-2827 (2009).
42. Xia, M.-j., Yao, W., Meng, X.-b., Lou, Q.-h. & Li, Z.-j. Co2 (CO) 6-propargyl cation mediates glycosylation reaction by using thioglycoside. Tetrahedron Lett. 58, 2389-2392 (2017).
43. Xu, Y. et al. Chemoenzymatic synthesis of homogeneous ultralow molecular weight heparins. Science 334, 498-501 (2011).
44. Yang, C., Flynn, J. P. & Niu, J. Facile Synthesis of Sequence-Regulated Synthetic Polymers Using Orthogonal SuFEx and CuAAC Click Reactions. Angew. Chem. Int. Ed. 57, 16194-16199 (2018).
45. Zhang, X. et al. Chemoenzymatic synthesis of heparan sulfate and heparin oligosaccharides and NMR analysis: paving the way to a diverse library for glycobiologists. Chemical science 8, 7932-7940 (2017).
46. Zulueta, M. M. L. et al. α-Glycosylation by D-glucosamine-derived donors: synthesis of heparosan and heparin analogues that interact with mycobacterial heparin-binding hemagglutinin. J. Am. Chem. Soc. 134, 8988-8995 (2012).

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Materials and Methods

Chemicals were purchased from Alfa Aesar, Sigma-Aldrich, Acros, Fisher Scientific, or TCI chemical companies and used as received. Deuterated solvents were purchased from either Cambridge Isotope Laboratories, Inc. or Acros. Sulfuryl fluoride (Vikane) was purchased from SynQuest Lab. Inc. The organic solvents such as acetonitrile (MeCN), tetrahydrofuran (THF), dichloromethane (DCM), and dimethylformamide (DMF) were purchased from Fisher Scientific and used after the purification of a dry solvent system (Pure Process Technology). Thin layer chromatography was performed on Merck TLC plates (silica gel 60 $F_{254}$) and were visualized by UV irradiation (254 nm) and by charring with sulfuric acid in ethanol. Silica gel chromatography was carried out using an automated flash chromatography (Biotage). The reaction Schlenk bottles were flame dried.

$^1$H NMR, $^{13}$C NMR, $^{19}$F NMR, $^{31}$P NMR, DOSY, NOESY, and HSQC measurements were conducted in $CDCl_3$, $D_2O$, or $CD_3OD$ using a Varian Gemini-600 (600 MHz) or Varian Inova-500 (500 MHz) NMR spectrometer. Chemical shifts are in ppm calibrated using the resonances of the carbon and the residual proton of the deuterated solvent. GC measurements were carried out on a Shimadzu GCMS system (QP2010S) equipped with Chiral GTA and Dex-CB column when using helium as a carrier gas. High-resolution mass spectrometry was performed on a JEOL AccuTOF DART Micromass LCT ESI-MS and an Agilent 6220 Time-of-Flight LC/MS instruments.

Example 2: Procedure A, Stepwise Installation of Sulfate Diesters Via SuFEx

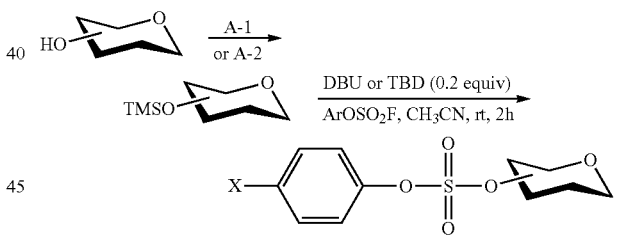

(A-1) Silylation by TMSCl: In a flask, the hydroxyl-exposed substrate (1 mmol of OH group, 1 eq) was dissolved in pyridine (10 mL). After cooling down to 0° C., chloro(trimethyl)silane (TMSCl, 1.2 mmol, 1.2 eq) was added under the protection of $N_2$. The mixture was warmed to room temperature and stirred for 2-24 h. The solution was diluted with 20 mL of ethyl acetate and washed by water three times. The organic layer was dried over $Na_2SO_4$ and concentrated under reduced pressure. The residue was purified by column chromatography to give the TMS-protected product.

(A-2) Silylation by HMDS: A stirred solution of the hydroxyl-exposed substrate (2.19 mmol) in dry acetonitrile (7.30 mL) was added hexamethyldisilazane (HMDS, 2.19 mmol, 1.0 equivalent per free hydroxyl) at room temperature under the protection of nitrogen. The resulting mixture was allowed to stir for 3 h until the TLC showed a full conversion of the starting materials. The whole reaction mixture was diluted with DCM and concentrated for automated flash chromatography. The product was used directly in the next SuFEx coupling reaction without further characterization.

(A-3) SuFEx reaction: The TMS-protected substrate (0.3 mmol of O-TMS, 1 eq) and aryl fluorosulfate (0.33 mmol, 1.1 eq) were dissolved in anhydrous acetonitrile (1 mL). Catalyst (DBU or TBD, 0.06 mmol, 0.2 eq) was added under a positive nitrogen flow. The flask was sealed and stirred at RT for 2 h. The solvent was removed immediately, and the residue was purified by column chromatography to give the sulfate diester-protected product.

Example 3: Procedure B, One-Pot Installation of Sulfate Diesters Via SuFEx

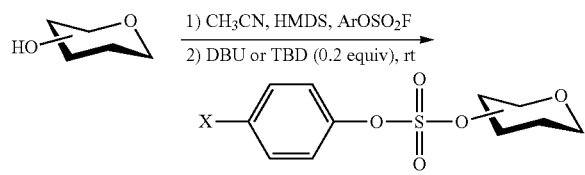

A stirred solution of the hydroxyl-exposed substrate (6.34 mmol) and aryl fluorosulfate (7.02 mmol, 1.1 equivalent per hydroxyl) in dry acetonitrile (21.13 mL) was added hexamethyldisilazane (HMDS, 3.80 mmol, 0.6 equivalent per free hydroxyl) at room temperature under nitrogen atmosphere. 10 min later, DBU or TBD (0.63 mmol, 0.1 equivalent per TMS ether unless otherwise noted) was added at the same temperature. When TLC showed no TMS ether intermediate left in the reaction mixture, the reaction was diluted with acetone and concentrated directly under reduced pressure for purification. When TBS ether substrate was involved, the reaction mixture was diluted with EA and successively washed with phosphate buffer, washed with brine, and dried over anhydrous $Na_2SO_4$. After filtration, the filtrate was concentrated under reduced pressure and purified by automated flash chromatography. Note: Aqueous solution washing can help avoid the removal of TBS group by the residue of strong organic base.

Example 4: Procedure C, Deprotection of Sulfate Diester Via Hydrolysis

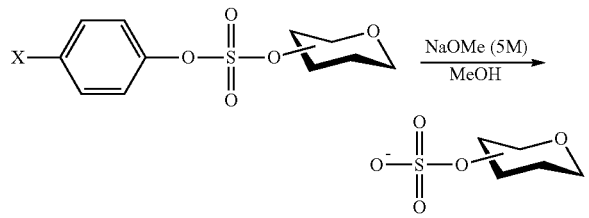

Sulfate diester masked reactant (125 μmol, 1 eq) was dissolved in 0.2 mL of acetonitrile in a flask. NaOMe solution was prepared by dissolving NaOMe powder (12.5 mmol, 100 eq) in 2.3 mL of methanol. Upon vigorously stirring, NaOMe solution was added in the mixture. After 1~2 h, the solution was neutralized by adding DOWEX 50WX8 resin until pH=8.0. The resin was removed by filtration. The filtrate was concentrated and purified by column chromatography to give the sulfated product.

Example 5: Procedure D, Deprotection of Sulfate Diester Via Hydrogenolysis

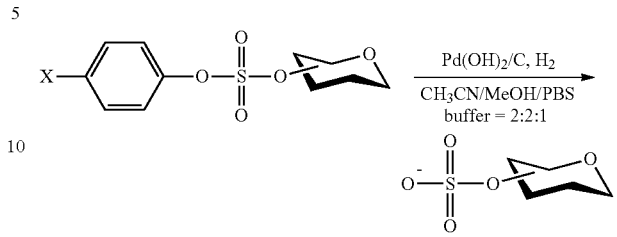

Sulfate diester masked reactant (200 μmol, 1 eq) and 20% $Pd(OH)_2$ on carbon (1 mmol, 5 eq) was dispersed in the mixture of MeCN/MeOH/PBS buffer (v/v/v, 2/2/1, 10 mL, pH=7.4). The solution was equipped with a hydrogen balloon and stirred at room temperature for 2 h. The mixture was filtered through celite and the filtrate was concentrated under reduced pressure. The residue was sequentially purified by column chromatography and passed through a column of Amberlite™ IR-120 Na ion-exchange resin to give the sulfated product. Acetonitrile is a good solvent to improve the solubility of the reactant in a polar environment but can be replaced by other polar solvents such as THF, DMF etc.

Example 6: Synthesis and Characterization of Model Compounds

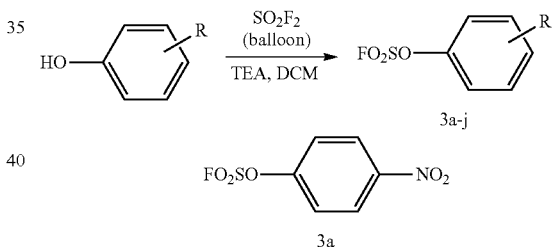

A 25 mL single-neck round-bottom flask was charged with 4-nitrophenol (g, mmol, 1 eq), dichloromethane (mL), and triethylamine (mg, mmol, 1.5 eq) and was then sealed with a septum. The atmosphere above the solution was removed with gentle vacuum, and $SO_2F_2$ gas (sulfuryl fluoride, Vikane) was introduced by a needle from a balloon filled with the gas. The reaction mixture was vigorously stirred at room temperature overnight. The solvent was evaporated, and the residual was purified by column chromatography using hexane/EA (10/1, v/v) as eluent to afford 3a as a colorless oil (95% yield). $^1H$ NMR (500 MHz, $CDCl_3$) δ 8.43-8.37 (m, 2H), 7.60-7.52 (m, 2H); $^{19}F$ NMR (470 MHz, Chloroform-d) δ 39.49.

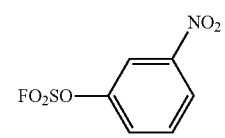

Compound 3b was isolated as a colorless oil in 99% yield. $^1$H NMR (400 MHz, CDCl$_3$) δ 8.38-8.30 (m, 1H), 8.26-8.25 (m, 1H), 7.79-7.68 (m, 2H); $^{19}$F NMR (376 MHz, CDCl$_3$) δ 39.03 (d, J=4.6 Hz); $^{13}$C NMR (126 MHz, CDCl$_3$) δ 149.79, 149.27, 131.54, 127.30, 123.82, 117.13; HRMS (DART) ([M+H]$^+$ Calcd. For C$_6$H$_5$NO$_5$SF: 221.9867, found 221.9860.

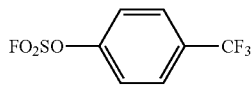
3c

Compound 3c was isolated as a colorless oil in 85% yield. $^1$H NMR (500 MHz, CDCl$_3$) δ/ppm: 7.78 (d, J=8.4 Hz, 2H), 7.49 (d, J=8.4 Hz, 2H). $^{19}$F NMR (470 MHz, CDCl$_3$) δ/ppm: 38.62, −62.74. Spectral data matched those previously reported.

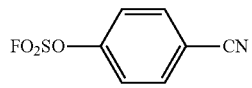
3d

Compound 3d was isolated as a white crystal in 96% yield. $^1$H NMR (500 MHz, CDCl$_3$) δ/ppm: 7.83 (d, J=8.3 Hz, 2H), 7.50 (d, J=8.4 Hz, 2H). $^{19}$F NMR (470 MHz, CDCl$_3$) δ/ppm: 39.39. Spectral data matched those previously reported.

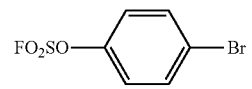
3e

Compound 3e was isolated as a colorless oil in 96% yield. $^1$H NMR (500 MHz, CDCl$_3$) δ 7.61 (d, J=7.8 Hz, 2H), 7.24 (d, J=8.5 Hz, 2H). $^{19}$F NMR (470 MHz, CDCl$_3$) δ 37.78. Spectral data matched those previously reported.

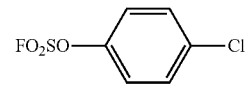
3f

Compound 3f was isolated as a colorless oil in 91% yield. $^1$H NMR (500 MHz, CDCl$_3$) δ 7.46 (d, J=8.4 Hz, 2H), 7.30 (d, J=8.5 Hz, 2H). $^{19}$F NMR (564 MHz, CDCl$_3$) δ 37.66. Spectral data matched those previously reported.

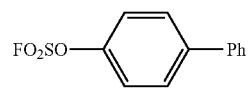
3g

Compound 3g was isolated as a white crystal in 99% yield. $^1$H NMR (600 MHz, CDCl$_3$) δ 7.67 (d, J=8.7 Hz, 2H), 7.56 (d, J=7.0 Hz, 2H), 7.47 (t, J=7.5 Hz, 2H), 7.44-7.37 (m, 3H). $^{19}$F NMR (564 MHz, CDCl$_3$) δ 37.61. Spectral data matched those previously reported.

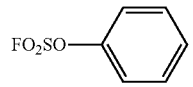
3h

Compound 3h was isolated as a colorless oil in 82% yield. $^1$H NMR (500 MHz, CDCl$_3$) δ 7.49 (t, J=8.1 Hz, 2H), 7.42 (t, J=6.7 Hz, 1H), 7.35 (d, J=7.3 Hz, 2H). $^{19}$F NMR (470 MHz, CDCl$_3$) δ 37.54. Spectral data matched those previously reported.

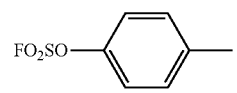
3i

Compound 3i was isolated as a colorless oil in 60% yield. $^1$H NMR (500 MHz, CDCl$_3$) δ 7.26 (d, J=8.5 Hz, 1H), 7.22 (d, J=8.4 Hz, 1H), 2.39 (s, 1H). $^{19}$F NMR (470 MHz, CDCl$_3$) δ 37.03. Spectral data matched those previously reported.

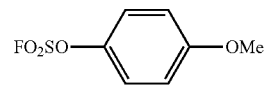
3j

Compound 3j was isolated as a colorless oil in 98% yield. $^1$H NMR (500 MHz, CDCl$_3$) δ 7.23 (d, J=9.2 Hz, 2H), 6.92 (d, J=9.3 Hz, 2H), 3.79 (s, 3H). $^{19}$F NMR (470 MHz, CDCl$_3$) δ 36.26. Spectral data matched those previously reported.

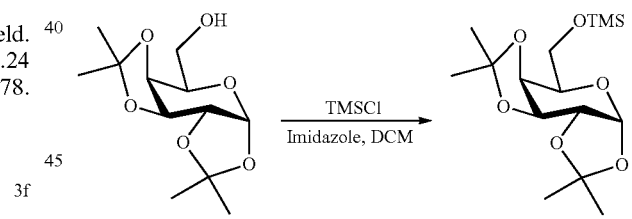

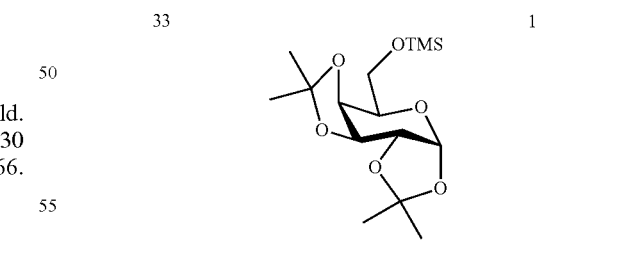

In a 500 mL round-bottom flask, 1,2:3,4-Di-O-isopropylidene-α-D-galactopyranose (5.4 g, 20.75 mmol) and imidazole (2.82 g, 41.49 mmol) were dissolved in 200 mL of DCM. After cooling down to 0° C., chloro(trimethyl)silane (2.70 g, 24.90 mmol, 3.16 mL) was added and the mixture was stirred overnight. Water (100 mL) was added to the solution for extraction. The organic layer was dried over Na$_2$SO$_4$ and concentrated under reduced pressure. The crude product was purified by column chromatography using hexane/ethyl acetate (10:1) as eluent, yielding the product as a colorless oil (95% of yield). $^1$H NMR (500 MHz, CDCl$_3$) δ 5.52 (d, J=5.0 Hz, 1H), 4.60 (dd, J=8.0, 2.4 Hz, 1H), 4.30 (dd, J=7.8, 2.3 Hz, 2H), 3.83 (t, J=6.3 Hz, 1H), 3.78 (dd, J=10.0, 7.3 Hz, 1H), 3.71 (dd, J=10.1, 6.1 Hz, 1H), 1.53 (s, 3H), 1.44 (s, 3H), 1.35 (s, 3H), 1.33 (s, 3H), 0.13 (s, 9H).

Hz, 1H), 1.49 (s, 3H), 1.45 (s, 3H), 1.35-1.32 (m, 6H). $^{13}$C NMR (151 MHz, CDCl$_3$) δ 154.32, 146.38, 125.59, 122.44, 110.03, 109.13, 96.14, 73.62, 70.63, 70.58, 70.19, 65.79, 25.93, 25.90, 24.84, 24.37. HRMS (DART) ([M+NH$_4$]+) Calcd. For C$_{18}$H$_{27}$N$_2$O$_{11}$S: 479.1336, found 479.1333.

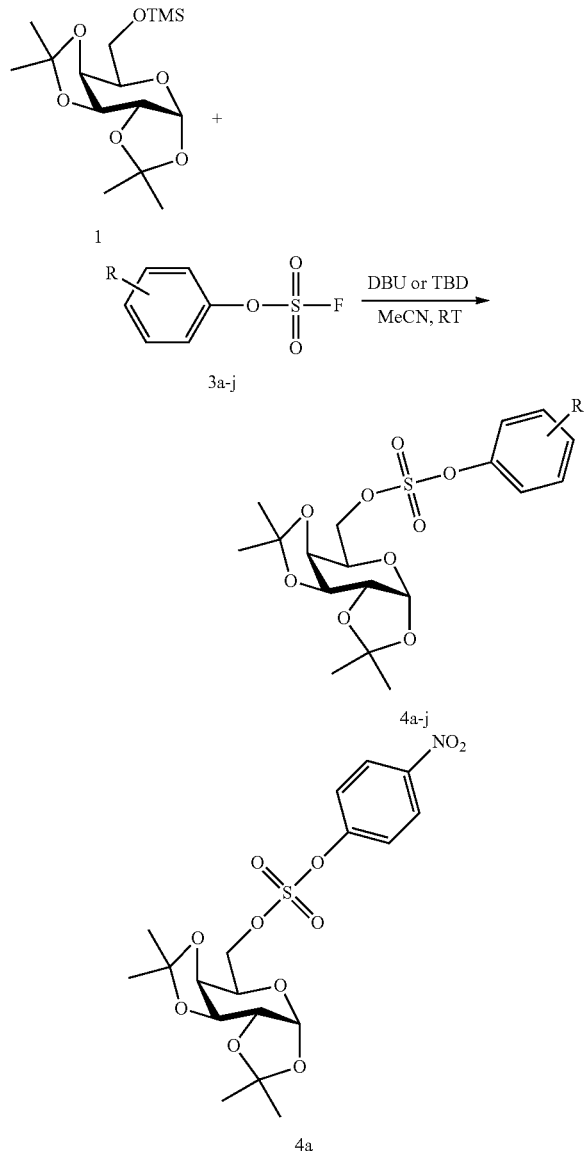

Compound 1 (101.5 mg, 0.3 mmol) was reacted with 3a (74 mg, 0.33 mmol) following General Procedure A-3. The product was further purified by silica gel chromatography (DCM-hexane/ethyl acetate 3:1) to obtain 4b as a colorless liquid (129 mg, 92%). $[α]_D^{20}$=−36.26 (c 1.00 in CHCl$_3$). $^1$H NMR (600 MHz, CDCl$_3$) δ 8.30 (t, J=2.3 Hz, 1H), 8.21 (ddd, J=8.3, 2.1, 1.0 Hz, 1H), 7.76 (ddd, J=8.3, 2.4, 1.0 Hz, 1H), 7.62 (t, J=8.2 Hz, 1H), 5.56 (d, J=5.0 Hz, 1H), 4.66 (dd, J=7.8, 2.6 Hz, 1H), 4.62 (dd, J=4.5, 2.7 Hz, 1H), 4.59 (dd, J=7.2, 5.4 Hz, 1H), 4.36 (dd, J=5.0, 2.6 Hz, 1H), 4.26 (dd, J=7.8, 2.0 Hz, 1H), 4.19 (ddd, J=7.0, 4.5, 2.0 Hz, 1H), 1.48 (s, 3H), 1.46 (s, 3H), 1.34 (s, 3H), 1.32 (s, 3H). $^{13}$C NMR (151 MHz, CDCl$_3$) δ 150.27, 148.96, 130.53, 128.00, 122.29, 117.54, 110.07, 109.07, 96.20, 73.50, 70.69, 70.61, 70.16, 65.72, 25.90, 25.86, 24.81, 24.39. HRMS (DART) ([M+NH$_4$]$^+$) Calcd. For C$_{18}$H$_{27}$N$_2$O$_{11}$S: 479.1336, found 479.1318.

In a 10 mL flask, 1 (100 mg, 0.3 mmol, 1 eq) and 3a (75 mg, 0.33 mmol) were dissolved in anhydrous acetonitrile (1 mL). DBU (9.4 mg, 9.2 µL, 0.06 mmol) was added under a positive nitrogen flow. The flask was sealed and stirred at RT for 2 h. The solvent was removed immediately, and the crude product was purified by column chromatography using Hexane/Ethyl acetate (7:1) as eluent. The product 4a was obtained as a white powder in 94% yield. $[α]_D^{20}$=−32.53 (c 1.00 in CHCl$_3$). $^1$H NMR (600 MHz, CDCl$_3$) δ 8.30 (d, J=9.1 Hz, 2H), 7.59 (d, J=9.1 Hz, 2H), 5.53 (d, J=4.9 Hz, 1H), 4.66 (dd, J=7.8, 2.6 Hz, 1H), 4.61 (dd, J=10.9, 4.0 Hz, 1H), 4.57 (dd, J=10.9, 7.7 Hz, 1H), 4.36 (dd, J=5.0, 2.6 Hz, 1H), 4.25 (dd, J=7.8, 2.0 Hz, 1H), 4.18 (ddd, J=7.7, 4.0, 2.0

Compounds 1 (101.5 mg, 0.3 mmol) and 3c (82 mg, 0.33 mmol) were reacted following General Procedure A-3. The product was further purified by silica gel chromatography (hexane/ethyl acetate 8:1) to obtain 4c as a white powder (134 mg, 91%). $[α]_D^{20}$=−35.39 (c 1.00 in CHCl$_3$). $^1$H NMR (500 MHz, CDCl$_3$) δ 7.69 (d, J=8.4 Hz, 2H), 7.52 (d, J=8.4 Hz, 2H), 5.54 (d, J=4.9 Hz, 1H), 4.65 (dd, J=7.9, 2.6 Hz, 1H), 4.59 (dd, J=10.9, 4.2 Hz, 1H), 4.54 (dd, J=10.8, 7.4 Hz, 1H), 4.36 (dd, J=5.0, 2.6 Hz, 1H), 4.25 (dd, J=7.8, 2.1 Hz, 1H), 4.17 (ddd, J=7.2, 4.3, 2.1 Hz, 1H), 1.49 (s, 3H), 1.45 (s, 3H), 1.34 (s, 6H). $^{13}$C NMR (151 MHz, CDCl$_3$) δ 152.49, 127.29, 127.26, 121.98, 109.97, 109.10, 96.15, 73.09, 70.62, 70.57, 70.23, 65.76, 25.90, 25.88, 24.84, 24.35. 19F NMR (470 MHz, CDCl$_3$) δ -62.47. HRMS (DART) ([M+H]$^+$) Calcd. For C$_{19}$H$_{24}$F$_3$O$_9$S: 485.1093, found 485.1082.

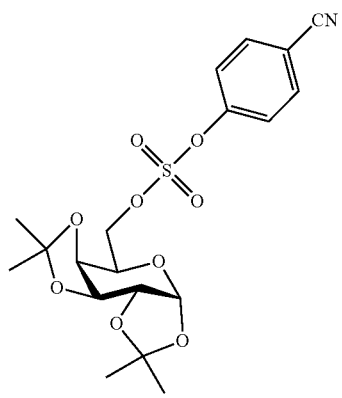

4d

Compounds 1 (99.5 mg, 0.3 mmol) and 3d (66.2 mg, 0.33 mmol) were reacted following General Procedure A-3. The product was further purified by silica gel chromatography (hexane/ethyl acetate 8:1) to obtain 4d as a white powder (125 mg, 95%). [α]$_D{}^{20}$=-28.33 (c 1.00 in CHCl$_3$). $^1$H NMR (600 MHz, CDCl$_3$) δ 7.73 (d, J=8.6 Hz, 2H), 7.53 (d, J=8.6 Hz, 2H), 5.53 (d, J=5.0 Hz, 1H), 4.65 (dd, J=7.9, 2.5 Hz, 1H), 4.60 (dd, J=10.9, 4.1 Hz, 1H), 4.55 (dd, J=10.8, 7.6 Hz, 1H), 4.36 (dd, J=4.9, 2.6 Hz, 1H), 4.24 (dd, J=7.8, 2.0 Hz, 1H), 4.17 (ddd, J=7.7, 4.1, 2.0 Hz, 1H), 1.49 (s, 2H), 1.45 (s, 2H), 1.34 (s, 4H). $^{13}$C NMR (151 MHz, CDCl$_3$) δ 153.06, 134.09, 122.61, 117.67, 111.51, 110.01, 109.13, 96.13, 73.47, 70.62, 70.58, 70.20, 65.78, 25.93, 25.90, 24.85, 24.37. HRMS (DART) ([M+H]$^+$) Calcd. For C$_{19}$H$_{24}$NO$_9$S: 442.1172, found 442.1167.

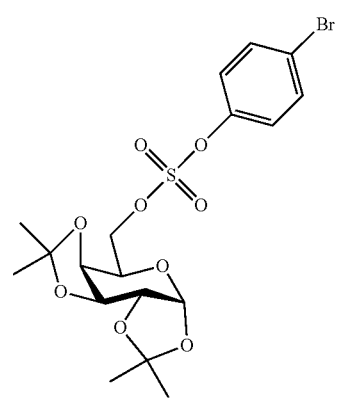

4e

Compounds 1 (101.7 mg, 0.3 mmol) and 3e (85.8 mg, 0.33 mmol) were reacted following General Procedure A-3. The product was further purified by silica gel chromatography (hexane/ethyl acetate 6:1) to obtain 4e as a white powder (140.8 mg, 93%). [α]$_D{}^{20}$=-37.66 (c 1.00 in CHCl$_3$). $^1$H NMR (500 MHz, CDCl$_3$) δ 7.52 (d, J=8.9 Hz, 2H), 7.28 (d, J=9.0 Hz, 2H), 5.54 (d, J=4.9 Hz, 1H), 4.65 (dd, J=7.9, 2.6 Hz, 1H), 4.57 (dd, J=10.7, 4.5 Hz, 1H), 4.51 (dd, J=10.7, 7.4 Hz, 1H), 4.35 (dd, J=4.9, 2.6 Hz, 1H), 4.25 (dd, J=7.8, 2.0 Hz, 1H), 4.17 (ddd, J=6.9, 4.5, 2.0 Hz, 1H), 1.50 (s, 3H), 1.45 (s, 3H), 1.34 (s, 3H), 1.33 (s, 3H). $^{13}$C NMR (126 MHz, CDCl$_3$) δ 149.29, 132.94, 123.32, 120.84, 109.93, 109.09, 96.16, 72.82, 70.64, 70.57, 70.27, 65.76, 25.94, 25.91, 24.88, 24.39. HRMS (DART) ([M+H]$^+$) Calcd. For C$_{18}$H$_{24}$BrO$_9$S: 495.0324, found 495.0308.

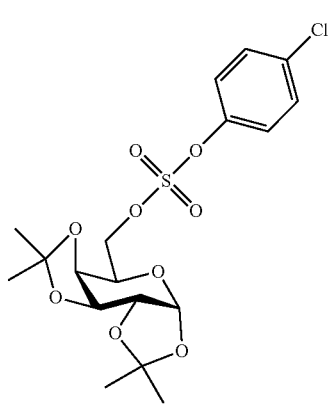

4f

Compounds 1 (100.2 mg, 0.3 mmol) and 3f (69.8 mg, 0.33 mmol) were reacted following General Procedure A-3. The product was further purified by silica gel chromatography (hexane/ethyl acetate 6:1) to obtain 4f as a white powder (117.5 mg, 86%). [α]$_D{}^{20}$=-36.86 (c 1.00 in CHCl$_3$). 1H NMR (600 MHz, CDCl$_3$) δ 7.37 (d, J=9.0 Hz, 1H), 7.34 (d, J=8.7 Hz, 1H), 5.54 (d, J=4.9 Hz, 1H), 4.65 (dd, J=7.9, 2.5 Hz, 1H), 4.57 (dd, J=10.7, 4.5 Hz, 1H), 4.51 (dd, J=10.8, 7.4 Hz, 1H), 4.36 (dd, J=5.0, 2.6 Hz, 1H), 4.25 (dd, J=7.8, 2.0 Hz, 1H), 4.17 (ddd, J=7.0, 4.4, 1.9 Hz, 1H), 1.50 (s, 2H), 1.45 (s, 2H), 1.34 (s, 2H), 1.34 (s, 2H). $^{13}$C NMR (151 MHz, CDCl$_3$) δ 148.69, 133.08, 129.93, 122.96, 109.93, 109.09, 96.15, 72.79, 70.62, 70.56, 70.25, 65.74, 25.93, 25.90, 24.87, 24.38. HRMS (DART) ([M+NH$_4$]$^+$) Calcd. For C$_{18}$H$_{24}$ClO$_9$S: 451.0830, found 451.0826.

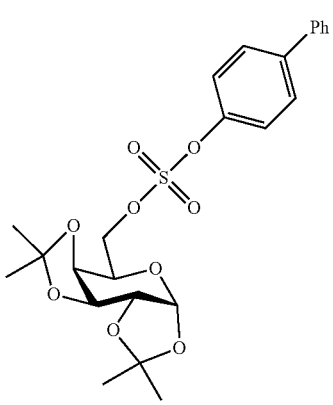

4g

Compounds 1 (101.3 mg, 0.3 mmol) and 3 g (84.6 mg, 0.33 mmol) were reacted following General Procedure A-3. The product was further purified by silica gel chromatography (hexane/ethyl acetate 8:1) to obtain 4 g as a white powder (113.9 mg, 76%). $[\alpha]_D^{20}=-35.13$ (c 1.00 in $CHCl_3$). $^1$H NMR (600 MHz, $CDCl_3$) δ 7.59 (d, J=8.6 Hz, 2H), 7.54 (d, J=7.1 Hz, 2H), 7.47-7.42 (m, 4H), 7.37 (t, J=7.3 Hz, 1H), 5.56 (d, J=4.9 Hz, 1H), 4.65 (dd, J=7.9, 2.5 Hz, 1H), 4.60 (dd, J=10.6, 4.8 Hz, 1H), 4.54 (dd, J=10.7, 7.3 Hz, 1H), 4.35 (dd, J=5.0, 2.5 Hz, 1H), 4.27 (dd, J=7.9, 2.0 Hz, 1H), 4.20 (ddd, J=7.0, 4.8, 2.0 Hz, 1H), 1.51 (s, 3H), 1.46 (s, 3H), 1.34 (s, 3H), 1.33 (s, 3H). $^{13}$C NMR (151 MHz, $CDCl_3$) δ 149.69, 140.63, 139.82, 128.55, 127.72, 127.16, 121.70, 109.91, 109.09, 96.18, 72.49, 70.63, 70.57, 70.31, 65.77, 25.97, 25.93, 24.90, 24.41. HRMS (DART) ([M+H]$^+$) Calcd. For $C_{24}H_{29}O_9S$: 493.1532, found 493.1525.

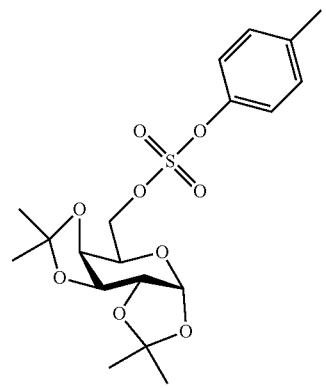

4i

Compounds 1 (102.4 mg, 0.3 mmol) and 3i (64.8 mg, 0.33 mmol) were reacted following General Procedure A-3. The product was further purified by silica gel chromatography (hexane/ethyl acetate 6:1) to obtain 4i as a white solid (38.7 mg, 29%). $[\alpha]_D^{20}=-49.73$ (c 1.00 in $CHCl_3$). $^1$H NMR (600 MHz, $CDCl_3$) δ 7.25 (d, J=8.5 Hz, 2H), 7.18 (d, J=8.5 Hz, 2H), 5.54 (d, J=4.9 Hz, 1H), 4.64 (dd, J=7.9, 2.6 Hz, 1H), 4.56 (dd, J=10.6, 4.9 Hz, 1H), 4.49 (dd, J=10.6, 7.2 Hz, 1H), 4.35 (dd, J=5.0, 2.5 Hz, 1H), 4.26 (dd, J=7.9, 2.0 Hz, 1H), 4.17 (ddd, J=7.1, 5.0, 2.0 Hz, 1H), 2.35 (s, 3H), 1.51 (s, 3H), 1.46 (s, 3H), 1.34 (s, 3H), 1.33 (s, 3H). $^{13}$C NMR (151 MHz, $CDCl_3$) δ 148.20, 137.30, 130.31, 121.13, 109.85, 109.05, 96.16, 72.20, 70.60, 70.53, 70.31, 65.71, 25.95, 25.91, 24.90, 24.38, 20.87. HRMS (DART) ([M+H]$^+$) Calcd. For $C_{19}H_{27}O_9S$: 431.1376, found 431.1367.

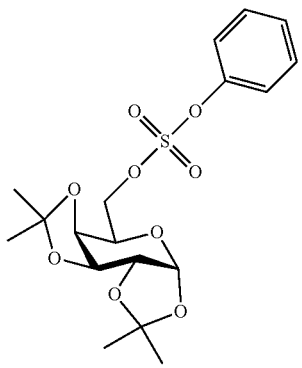

4h

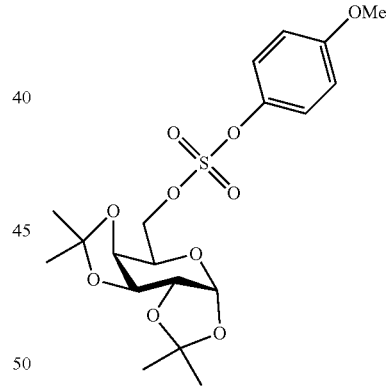

4j

Compounds 1 (102.4 mg, 0.3 mmol) and 3 h (59.7 mg, 0.33 mmol) were reacted following General Procedure A-3. The product was further purified by silica gel chromatography (hexane/ethyl acetate 6:1) to obtain 4h as a colorless liquid (55.5 mg, 43%). $[\alpha]_D^{20}=-51.99$ (c 1.00 in $CHCl_3$). $^1$H NMR (600 MHz, $CDCl_3$) δ 7.43-7.39 (m, 2H), 7.37 (d, J=7.5 Hz, 2H), 7.32 (t, J=7.1 Hz, 1H), 5.55 (d, J=5.0 Hz, 1H), 4.64 (dd, J=7.9, 2.5 Hz, 1H), 4.57 (dd, J=10.6, 4.9 Hz, 1H), 4.51 (dd, J=10.6, 7.2 Hz, 1H), 4.35 (dd, J=5.0, 2.5 Hz, 1H), 4.26 (dd, J=7.9, 2.0 Hz, 1H), 4.18 (ddd, J=7.0, 4.9, 2.0 Hz, 1H), 1.51 (s, 3H), 1.46 (s, 3H), 1.34 (s, 3H), 1.33 (s, 3H). $^{13}$C NMR (151 MHz, $CDCl_3$) δ 150.33, 129.86, 127.38, 121.41, 109.88, 109.07, 96.16, 72.33, 70.61, 70.53, 70.30, 65.72, 25.95, 25.91, 24.89, 24.38. HRMS (DART) ([M+NH$_4$]$^+$) Calcd. For $C_{18}H_{24}NO_9S$: 434.1485, found 434.1478.

Compounds 1 (102.4 mg, 0.3 mmol) and 3j (67.6 mg, 0.33 mmol) were reacted following General Procedure A-3. The product was further purified by silica gel chromatography (hexane/ethyl acetate 8:1) to obtain 4j as a white solid (41.5 mg, 31%). $[\alpha]_D^{20}=-35.46$ (c 1.00 in $CHCl_3$). $^1$H NMR (600 MHz, $CDCl_3$) δ 7.29 (d, J=9.1 Hz, 1H), 6.88 (d, J=9.2 Hz, 1H), 5.55 (d, J=4.9 Hz, 0H), 4.64 (dd, J=7.8, 2.6 Hz, 1H), 4.55 (dd, J=10.6, 4.8 Hz, 1H), 4.49 (dd, J=10.6, 7.3 Hz, 1H), 4.35 (dd, J=5.0, 2.5 Hz, 1H), 4.26 (dd, J=7.8, 2.0 Hz, 1H), 4.17 (ddd, J=7.0, 4.8, 2.0 Hz, 1H), 3.80 (s, 2H), 1.51 (s, 2H), 1.46 (s, 2H), 1.34 (s, 2H), 1.33 (s, 2H). $^{13}$C NMR (151 MHz, $CDCl_3$) δ 158.44, 143.79, 122.54, 114.70, 109.85, 109.06, 96.16, 72.29, 70.61, 70.55, 70.30, 65.74, 55.62, 25.95, 25.91, 24.90, 24.39. HRMS (DART) ([M+H]$^+$) Calcd. For $C_{19}H_{27}O_{10}S$: 447.1325, found 447.1312.

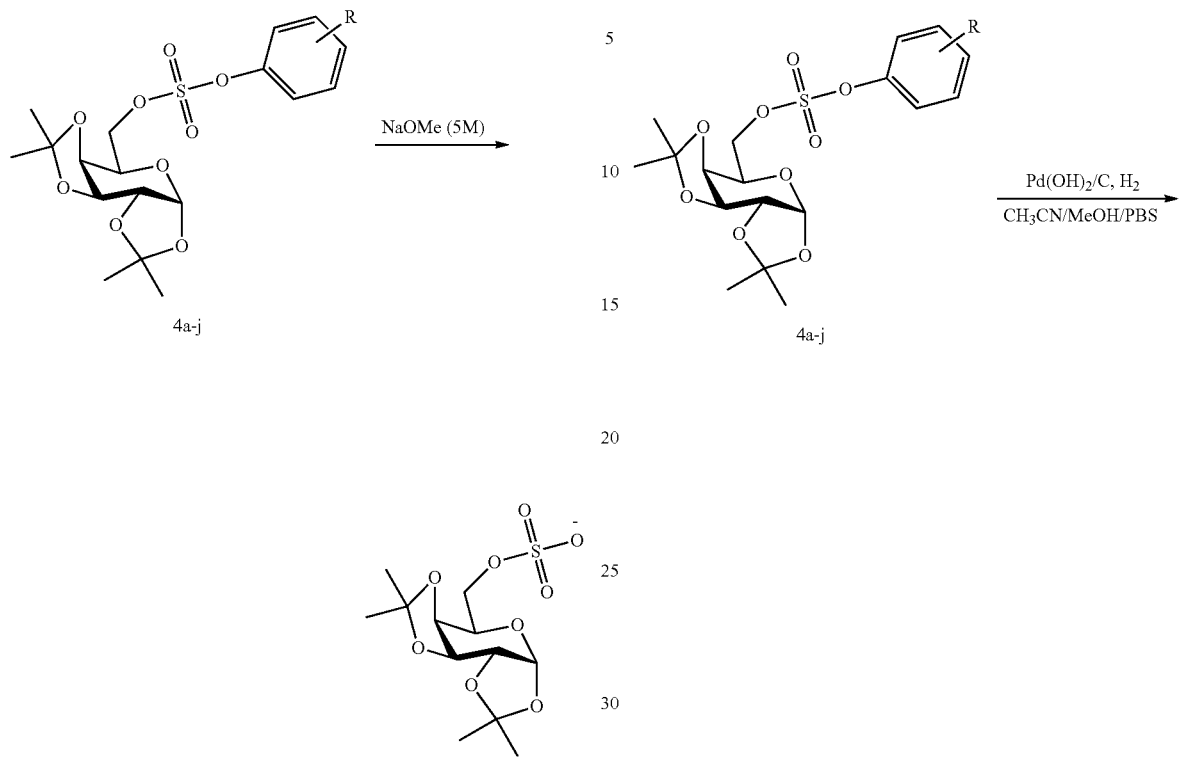

In a 10 mL vial, 4a (55.18 mg, 125 μmol) was dissolved in 0.2 mL of acetonitrile. NaOMe solution was prepared by dissolving NaOMe powder (675.2 mg, 12.5 mmol) in 2.3 mL of methanol. Upon vigorously stirring, NaOMe solution was added in the vial. After 1 h, the solution was neutralized by adding DOWEX 50WX8 resin until pH=8.0. The resin was removed by filtration. The filtrate was concentrated and purified by column chromatography using DCM/methanol (5:1) as eluent. The product 5 was obtained as a white solid in 92% yield. To monitor the kinetics of reaction, methanol-$d_4$ was used as solvent. The aliquots were obtained, diluted with a fixed volume of MeOD and neutralized with DOWEX 50WX8 resin directly for $^1$H NMR test. The progress of the reaction was monitored at 5 min, 10 min, 15 min, 20 min, 25 min, 30 min, 40 min, 60 min. The preparation of 5 from 4b-j by hydrolysis was carried out by the same procedure to give different yields as shown in Table 1 in the main text. $[\alpha]_D^{20}$=−40.39 (c 1.00 in MeOH). $^1$H NMR (500 MHz, CD$_3$OD) δ 5.47 (d, J=4.9 Hz, 1H), 4.64 (dd, J=8.0, 2.4 Hz, 1H), 4.35 (dd, J=5.0, 2.4 Hz, 1H), 4.32 (dd, J=7.8, 1.6 Hz, 1H), 4.20-4.10 (m, 2H), 4.06 (dd, J=9.9, 6.3 Hz, 1H), 1.51 (s, 3H), 1.41 (s, 3H), 1.34 (s, 3H), 1.33 (s, 3H). $^{13}$C NMR (151 MHz, CD$_3$OD) δ 109.06, 108.58, 96.26, 70.89, 70.59, 70.49, 66.41, 66.40, 24.91, 24.89, 23.79, 23.14. HRMS (ESI) ([M−H]$^−$) Calcd. For C$_{12}$H$_{19}$O$_9$S: 339.0755, found 339.0760.

In a 10 mL vial, 4a (93.2 mg, 200 μmol) and 20% Pd(OH)$_2$ on carbon (535.2 mg) was dispersed in the mixture of MeCN/MeOH/PBS buffer (v/v/v=2/2/1, 10 mL, pH=7.4). The solution was equipped with a hydrogen balloon and stirred at room temperature for 2 h. The mixture was filtered through celite. The filtrate was concentrated and purified by column chromatography using DCM/methanol (5:1) as eluent, and further passed through a column of Amberlite™ IR-120 Na ion-exchange resin. The product 5 was obtained as a white solid in 96% yield. The preparation of 5 from 4b-j by hydrogenolysis was carried out by the same procedure to give comparably high yields as shown in Table 1. The spectral data is consistent with that by hydrolysis.

TABLE 1

Optimization of O-Sulfation and Deprotection[a]

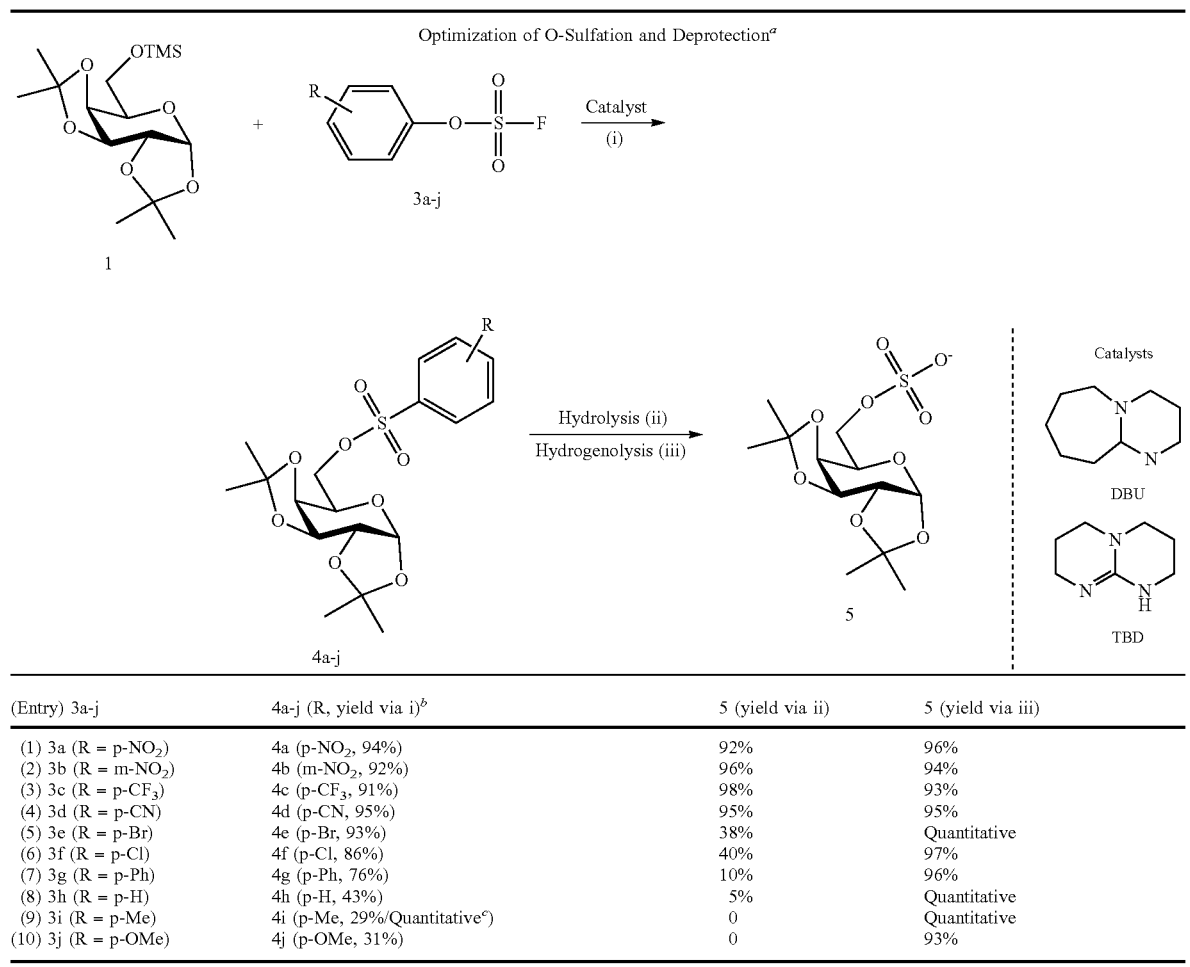

| (Entry) 3a-j | 4a-j (R, yield via i)[b] | 5 (yield via ii) | 5 (yield via iii) |
|---|---|---|---|
| (1) 3a (R = p-NO$_2$) | 4a (p-NO$_2$, 94%) | 92% | 96% |
| (2) 3b (R = m-NO$_2$) | 4b (m-NO$_2$, 92%) | 96% | 94% |
| (3) 3c (R = p-CF$_3$) | 4c (p-CF$_3$, 91%) | 98% | 93% |
| (4) 3d (R = p-CN) | 4d (p-CN, 95%) | 95% | 95% |
| (5) 3e (R = p-Br) | 4e (p-Br, 93%) | 38% | Quantitative |
| (6) 3f (R = p-Cl) | 4f (p-Cl, 86%) | 40% | 97% |
| (7) 3g (R = p-Ph) | 4g (p-Ph, 76%) | 10% | 96% |
| (8) 3h (R = p-H) | 4h (p-H, 43%) | 5% | Quantitative |
| (9) 3i (R = p-Me) | 4i (p-Me, 29%/Quantitative[c]) | 0 | Quantitative |
| (10) 3j (R = p-OMe) | 4j (p-OMe, 31%) | 0 | 93% |

[a]Reaction conditions: (i) DBU in acetonitrile for 2 h at room temperature; (ii) 5 M sodium methoxide in methanol for 1 h at room temperature; (iii) Pd(OH)$_2$/C and H$_2$ CH$_3$CN/MeOH/PBS buffer=2:2:1 for 2 h at room temperature.
[b]Isolated yield when DBU was used as catalyst.
[c]When TBD was used as catalyst.

Example 7: GC-MS Detection for Hydrogenolysis

PtO$_2$/H$_2$ Condition

Figure 20:
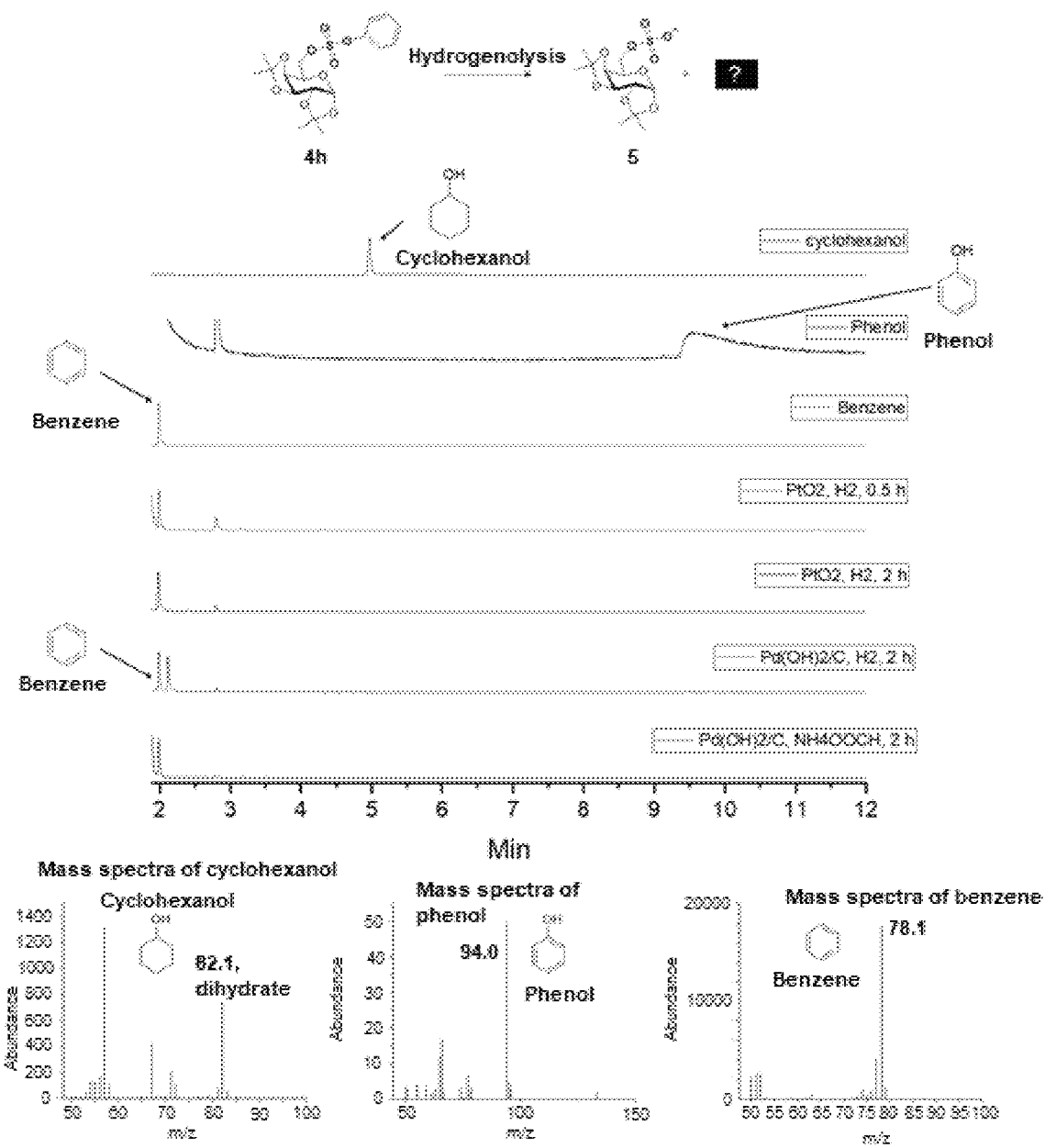
FIG. 20 shows GC-MS analysis of the hydrogenolysis of compound 4h (top) including GC traces of standards and hydrogenolysis reactions (middle), and mass spectra of cyclohexanol, phenol, and benzene (bottom). Top: Reaction scheme. Middle: from top to bottom, GC traces of the hydrogenolysis reactions under following conditions: $PtO_2/H_2$, 0.5 h; $PtO_2/H_2$, 2 h; $Pd(OH)_2/C/H_2$, 2h; $Pd(OH)_2/C/NH_4OOCH$, 2h. A byproduct, trimethylamine, was formed from the hydrogenation of acetonitrile by $Pd(OH)_2/C/H_2$. Bottom: GC-MS spectra of cyclohexanol, phenol, and benzene. By comparing to the standard GC traces of cyclohexanol, phenol, and benzene, it was observed that, besides the sulfated carbohydrate, benzene was also generated in the hydrogenolysis process of 4h while no other byproducts were observed. This product profile did not change when the reaction time was extended to two hours. Switching the catalyst from platinum oxide to palladium hydroxide also did not change the reaction outcome. Furthermore, various hydride sources including $H_2$ and ammonium formate can all be used for the hydrogenolysis of the sulfate diester.

To a stirred suspension of 4h (33.5 mg, 0.08 mmol) in a mixed solvent (4.02 mL, ethanol/H2O=9:1) was added potassium carbonate (33.5 mg, 0.24 mmol) and platinum oxide (167.5 mg, 0.74 mmol) at room temperature. The reaction bottle was charged with a gentle vacuum, followed by the filling of the hydrogen gas through a syringe attached balloon. The resulting reaction mixture was allowed to stir at room temperature. 0.5 h later, a small portion of the reaction mixture was taken and filtered for GC-MS analysis. 2 h later, another portion of the reaction mixture was abstracted, filtered and used for GC-MS analysis (FIG. 20).

Pd(OH)$_2$/H$_2$ Condition

Figure 21:
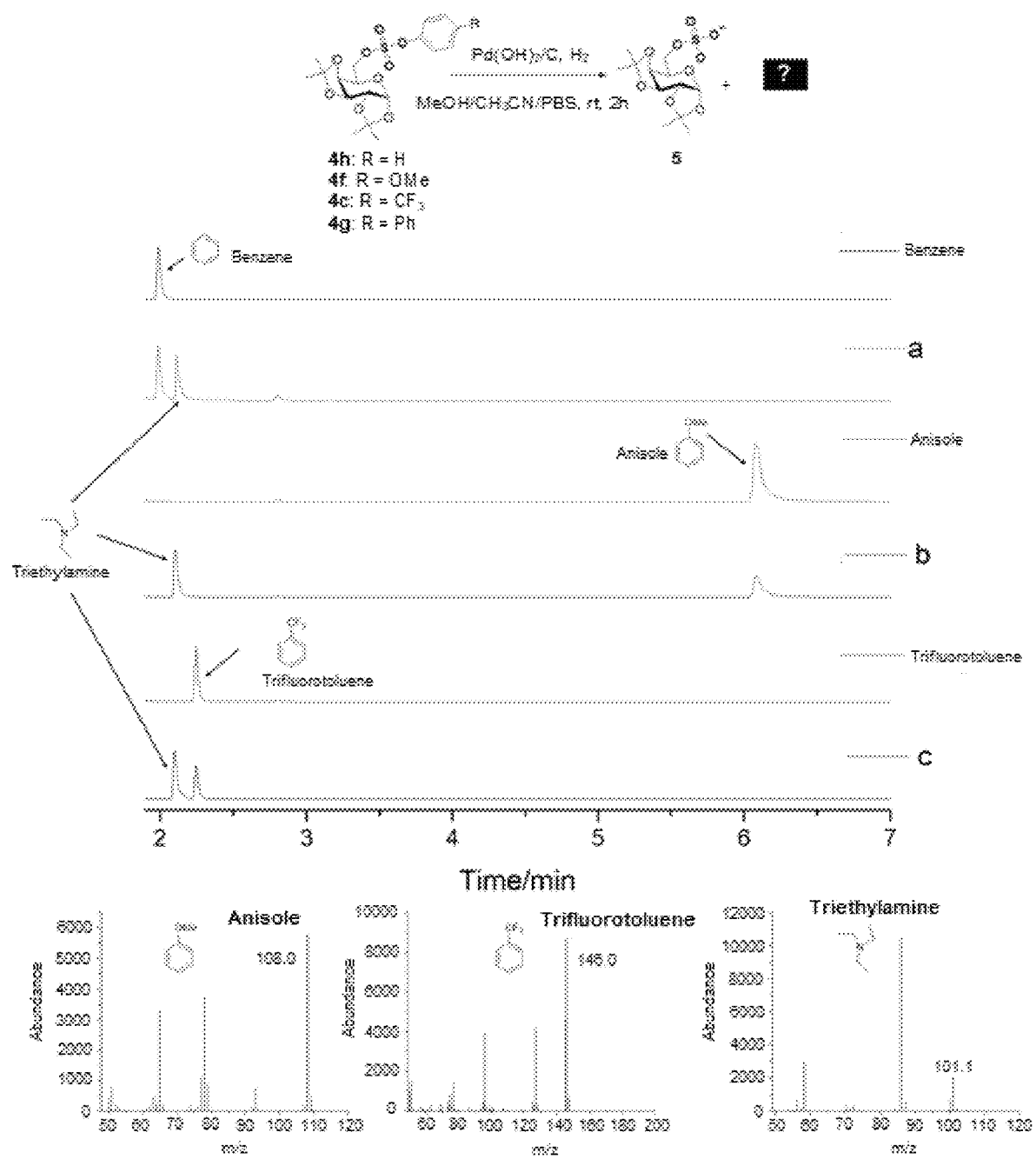
FIG. 21 shows GC-MS analysis of the hydrogenolysis of sulfate esters with various substitutions (top) including GC traces of standards and hydrogenolysis reactions (middle), and mass spectra of anisole, trifluorotoluene, and triethylamine (bottom). Top: reaction scheme. Middle: from top to bottom: standard GC trace of benzene, the hydrogenolysis of 4h, standard GC trace of anisole, the hydrogenolysis of 4f, standard GC trace of trifluorotoluene, and the hydrogenolysis of 4c. A byproduct, trimethylamine, was formed from the hydrogenation of acetonitrile by $Pd(OH)_2/C/H_2$. Bottom: GC-MS spectra of anisole, trifluorotoluene, and triethylamine

The test was conducted following General Procedure D. 2 h later, a portion of the reaction mixture was taken for GC-MS analysis (FIG. 21).

Pd(OH)$_2$/NH$_4$OOCH Condition

Figure 22:
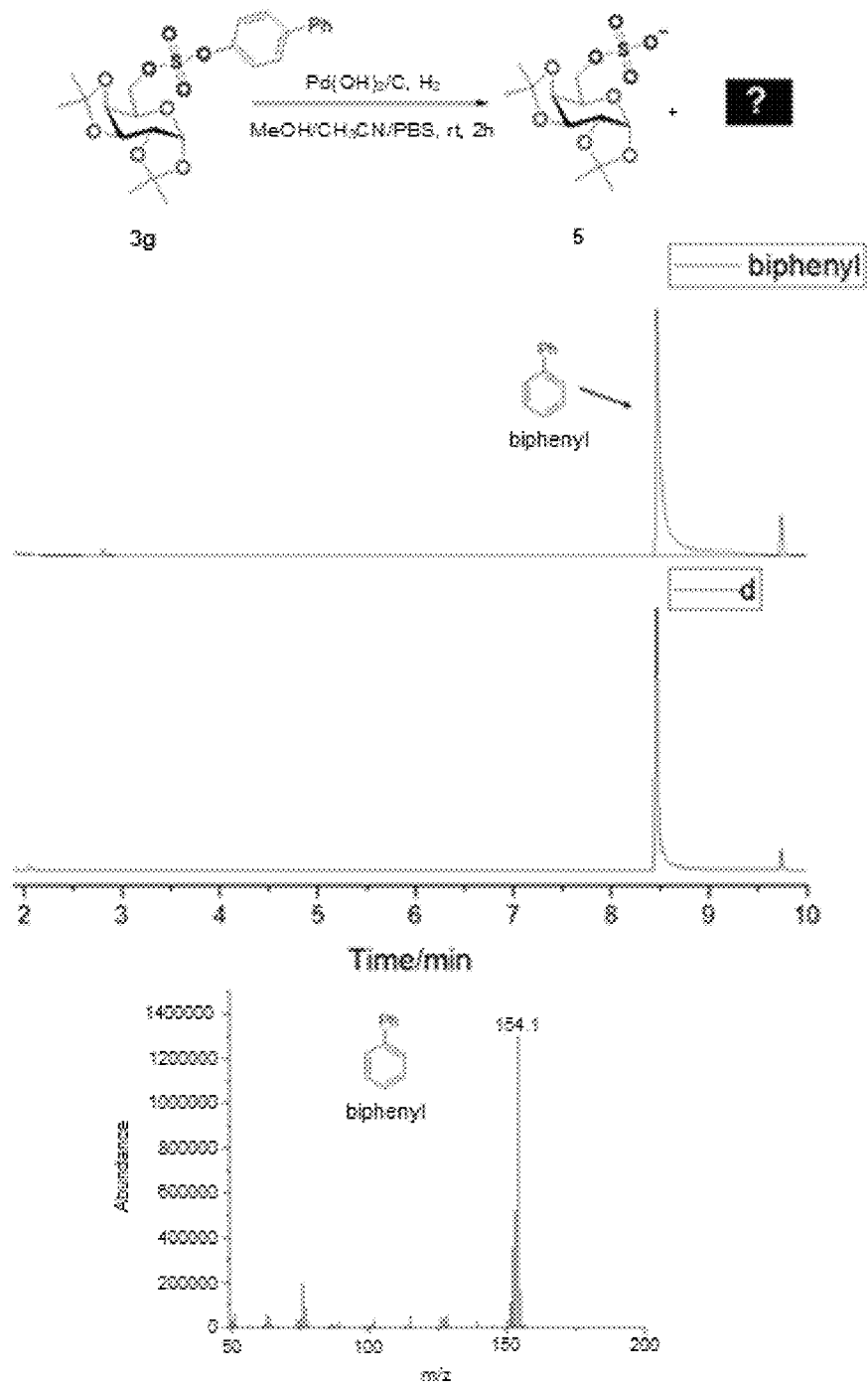
FIG. 22 shows GC-MS analysis of the hydrogenolysis of compound 4g (top) including a standard GC trace of biphenyl and the hydrogenolysis of 4g (middle) and a mass spectrum of biphenyl (bottom).

A stirred solution of 4h (33.3 mg, 0.08 mmol) in the mixed solvent (4.0 mL, MeOH/THF=1:1) was added ammonium formate (30.3 mg, 0.48 mmol) and Pd(OH)$_2$ on activated carbon (20% Pd, wet, 166.5 mg, 5 g per gram of substrate) at room temperature. 2 h later, a small portion of the reaction mixture was taken and filtered for GC-MS analysis (FIG. 22).

Example 8: Silylation Reactions Using HMDS and TMSCl

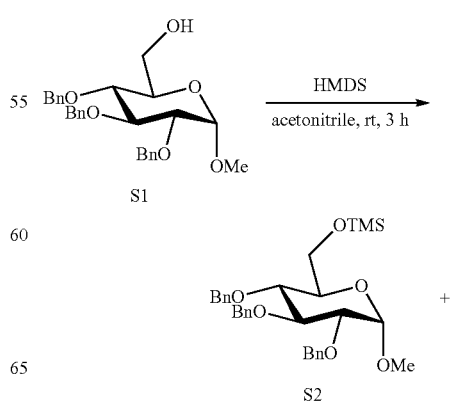

-continued

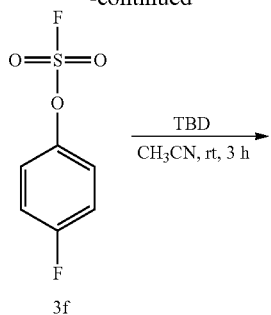

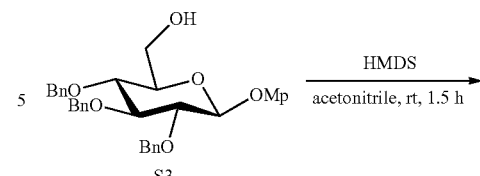

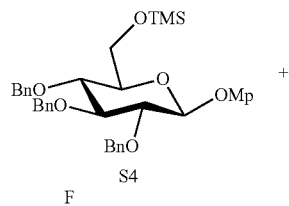

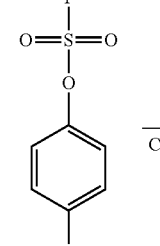

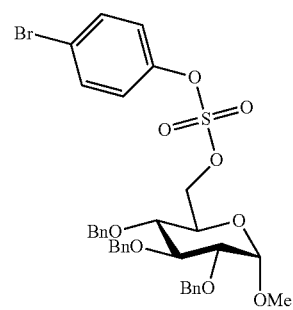

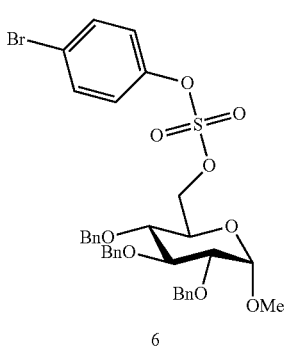

Compound S1 (1.02 g, 2.19 mmol) was converted to trimethylsilyl ether S2 (1.13 g, 96%) following General Procedure A-2. S2 was used directly in the next step without further characterization.

Compound S2 (1.13 g, 2.10 mmol) coupled with fluoride sulfate 3f (588.0 mg, 2.31 mmol) in the presence of TBD (58.4 mg, 0.42 mmol) providing compound 6 (1.02 g, 70%) according to General Procedure A-3. $[\alpha]_D^{20}$=+62.9 (c 1.00, CHCl$_3$); $^1$H NMR (500 MHz, CDCl$_3$) δ 7.47-7.42 (m, 2H), 7.40-7.26 (m, 13H), 7.26-7.22 (m, 2H), 7.18-7.11 (m, 2H), 5.00 (d, J=10.9 Hz, 1H), 4.90 (d, J=11.0 Hz, 1H), 4.84-4.76 (m, 2H), 4.65 (d, J=12.1 Hz, 1H), 4.55 (dd, J=7.3, 3.7 Hz, 2H), 4.50 (dd, J=10.5, 2.1 Hz, 1H), 4.45 (dd, J=10.5, 4.8 Hz, 1H), 4.01 (t, J=9.2 Hz, 1H), 3.87 (ddd, J=10.2, 4.8, 2.0 Hz, 1H), 3.53-3.47 (m, 1H), 3.44 (m, 1H), 3.35 (s, 3H); $^{13}$C NMR (126 MHz, CDC$_{l3}$) δ 149.28, 138.59, 138.04, 137.73, 133.08, 128.72, 128.70, 128.59, 128.29, 128.24, 128.20, 128.13, 128.04, 127.86, 123.16, 120.94, 98.30, 81.89, 79.83, 76.85, 75.89, 75.22, 73.65, 73.04, 68.49, 55.65; HRMS (ESI) m/z [M+Na]$^+$ calcd for C$_{34}$H$_{35}$BrO$_9$SNa 721.1077, found 721.1095.

Compound S3 (3.14 g, 5.64 mmol) was converted to trimethylsilyl ether S4 (3.22 g, 91%) following General Procedure A-2. S4 was used directly in the next step without further characterization.

Compound S4 (1.62 g, 2.58 mmol) coupled with fluoride sulfate 3f (722.8 mg, 2.83 mmol) in the presence of TBD (71.7 mg, 0.52 mmol) providing compound 6 (1.58 g, 78%) according to General Procedure A-3. $[\alpha]_D^{20}$=−16.3 (c 1.01, CHCl$_3$); $^1$H NMR (500 MHz, CDCl$_3$) δ 7.37-7.27 (m, 11H), 7.27-7.20 (m, 4H), 7.14-7.08 (m, 2H), 6.99-6.91 (m, 2H), 6.85-6.79 (m, 2H), 5.04 (d, J=10.9 Hz, 1H), 4.98 (d, J=11.0 Hz, 1H), 4.94 (d, J=7.6 Hz, 1H), 4.90 (d, J=11.0 Hz, 1H), 4.83 (d, J=3.6 Hz, 1H), 4.81 (d, J=3.6 Hz, 1H), 4.61-4.55 (m, 2H), 4.41 (dd, J=10.5, 5.7 Hz, 1H), 3.77 (s, 3H), 3.74 (d, J=8.8 Hz, 1H), 3.72-3.67 (m, 2H), 3.55 (dd, J=9.9, 8.6 Hz, 1H); $^{13}$C NMR (126 MHz, CDCl$_3$) δ 155.55, 150.94, 149.07, 138.14, 137.95, 137.23, 132.90, 128.66, 128.51, 128.45, 128.25, 128.21, 127.89, 127.82, 127.79, 123.18, 120.82, 118.00, 114.74, 102.16, 84.28, 81.71, 76.30, 75.75, 75.16, 75.09, 72.50, 72.36, 55.66; HRMS (ESI) m/z [M+Na]+ calcd for $C_{40}H_{39}BrO_{10}SNa$ 813.1340, found 813.1357.

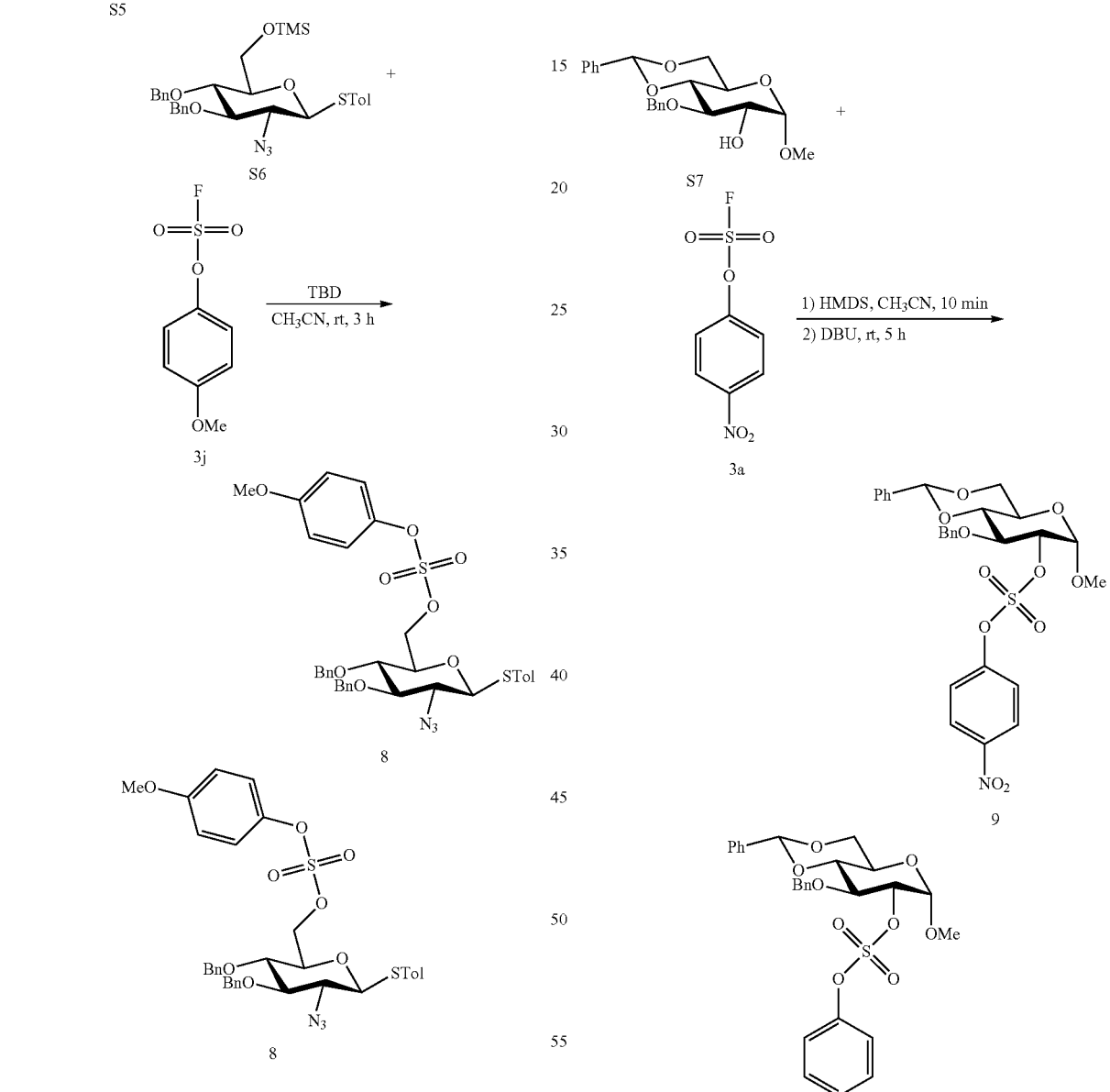

Compound S5 (1.44 g, 2.93 mmol) was converted to trimethylsilyl ether S6 (1.37 g, 83%) following General Procedure A-2. S6 was used directly in the next step without further characterization.

Compound S6 (219.2 mg, 0.39 mmol) coupled with fluoride sulfate 3f (89.7 mg, 0.44 mmol) in the presence of TBD (18.6 mg, 0.13 mmol) providing compound 8 (189.3 mg, 72%) according to General Procedure A-3. $[\alpha]_D^{20}$=−23.2 (c 1.00, CHCl$_3$); $^1$H NMR (600 MHz, CDCl$_3$) δ 7.47-7.42 (m, 2H), 7.38-7.27 (m, 8H), 7.26 (m, 2H), 7.14-7.08 (m, 2H), 6.88-6.82 (m, 2H), 4.90 (d, J=10.6 Hz, 1H), 4.85 (d, J=3.9 Hz, 1H), 4.83 (d, J=3.6 Hz, 1H), 4.59 (dd, J=10.6, 1.9 Hz, 1H), 4.56 (d, J=10.9 Hz, 1H), 4.46 (dd, J=10.6, 4.8 Hz, 1H), 4.38 (d, J=10.1 Hz, 1H), 3.74 (s, 3H), 3.60-3.56 (m, 1H), 3.52 (t, J=9.1 Hz, 1H), 3.44 (dd, J=9.9, 8.9 Hz, 1H), 3.29 (dd, J=10.2, 9.3 Hz, 1H), 2.34 (s, 3H); 13C NMR (151 MHz, CDCl$_3$) δ 158.53, 143.70, 139.08, 137.30, 137.10, 134.27, 129.93, 128.69, 128.58, 128.28, 128.17, 128.15, 128.03, 126.54, 122.50, 114.86, 86.16, 84.91, 76.44, 76.39, 75.95, 75.23, 71.67, 64.73, 55.60, 21.17; HRMS (ESI) m/z [M+Na]+ calcd for $C_{34}H_{35}O_8N_3S_2Na$ 700.1758, found 700.1752.

Compound S7 (358.1 mg, 0.96 mmol) was converted to trimethylsilyl ether in situ by HMDS (108.6 mg, 140.4 μL, 0.67 mmol) and coupled with fluoride sulfate 3a (360.2 mg, 1.63 mmol) via the following addition of DBU (22.0 mg, 0.14 mmol) to provide sulfoglucofuranose 9 (424.4 mg, 77%) according to the General Procedure B. $[\alpha]_D^{20}=+53.1$ (c 1.01, CHCl$_3$); $^1$H NMR (500 MHz, CDCl$_3$) δ 8.04-7.98 (m, 2H), 7.49-7.44 (m, 2H), 7.42-7.39 (m, 2H), 7.38-7.37 (m, 3H), 7.29-7.22 (m, 5H), 5.59 (s, 1H), 5.16 (d, J=3.7 Hz, 1H), 4.94 (d, J=11.2 Hz, 1H), 4.71 (dd, J=9.5, 3.7 Hz, 1H), 4.63 (d, J=11.2 Hz, 1H), 4.33 (dd, J=10.3, 4.8 Hz, 1H), 4.15 (t, J=9.4 Hz, 1H), 3.90 (td, J=9.8, 4.7 Hz, 1H), 3.82-3.69 (m, 2H), 3.43 (s, 3H); $^{13}$C NMR (126 MHz, CDCl$_3$) δ 154.37, 146.31, 137.67, 137.04, 129.31, 128.53, 128.47, 128.10, 128.04, 126.13, 125.61, 121.95, 101.71, 97.48, 82.71, 82.38, 75.51, 75.29, 68.89, 62.33, 55.81; HRMS (ESI) m/z [M+H]$^+$ calcd for O$_{27}$H$_{28}$O$_{11}$NS 574.1378, found 574.1351.

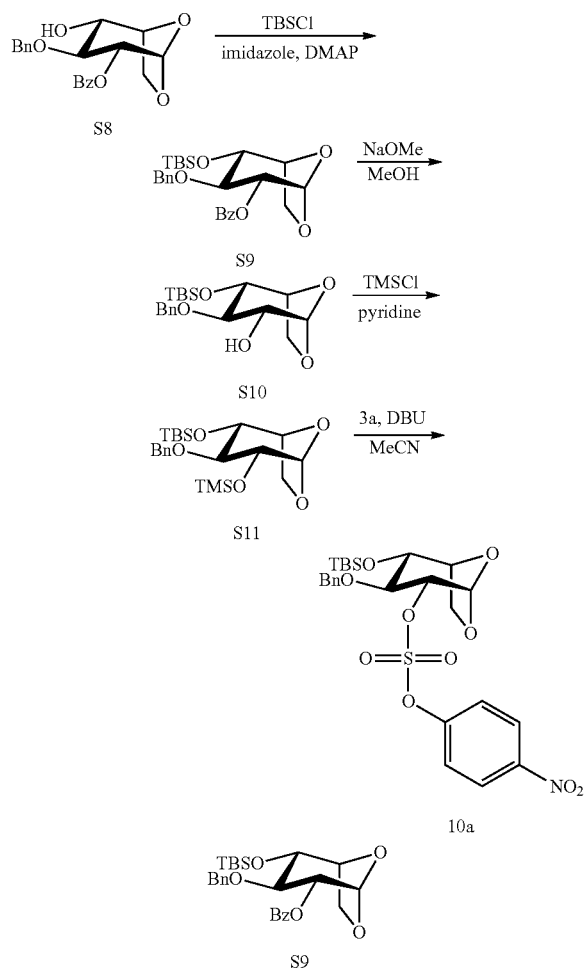

In a 500 mL round-bottom flask, S8 (1.03 g, 2.89 mmol), imidazole (295.2 mg, 4.34 mmol), 4-Dimethylaminopyridine (423.7 mg, 3.47 mmol) and tert-butyldimethylchlorosilane (522.8 mg, 3.47 mmol) were dissolved in 28 mL of MeCN. The mixture was stirred at 90° C. for 5 days. The solvent was removed under reduced pressure and the residue was diluted with ethyl acetate (30 mL). Water (50 mL) was added to the solution for extraction. The organic layer was dried over Na$_2$SO$_4$ and concentrated under reduced pressure. The crude product was purified by column chromatography using hexane/ethyl acetate (10:1) as eluent, yielding the S9 as a colorless oil (840 mg, 62%). $[\alpha]_D^{20}=+120.70$ (c 1.00 in CHCl$_3$). $^1$H NMR (600 MHz, CDCl$_3$) δ 7.99 (dd, J=8.4, 1.3 Hz, 2H), 7.56 (tt, J=7.3, 1.3 Hz, 1H), 7.42 (dd, J=8.3, 7.4 Hz, 2H), 7.22-7.12 (m, 5H), 5.51 (d, J=1.8 Hz, 1H), 5.03 (dd, J=8.4, 1.9 Hz, 1H), 4.75 (d, J=11.3 Hz, 1H), 4.70 (d, J=11.3 Hz, 1H), 4.35 (t, J=4.7 Hz, 1H), 4.22 (dd, J=7.5, 0.8 Hz, 1H), 4.01 (ddd, J=7.8, 4.4, 1.1 Hz, 1H), 3.85 (t, J=8.1 Hz, 1H), 3.75 (ddd, J=7.6, 5.1, 1.2 Hz, 1H), 0.92 (s, 9H), 0.11 (s, 6H). $^{13}$C NMR (151 MHz, CDCl$_3$) δ 165.78, 138.06, 133.23, 129.84, 129.53, 128.36, 128.21, 127.71, 127.52, 99.37, 80.70, 76.72, 75.83, 75.14, 72.62, 65.15, 25.71, 18.60, 17.85, 11.18. HRMS (ESI) ([M+NH$_4$]$^+$) Calcd. For C$_{26}$H$_{35}$O$_6$Si: 471.2203, found 471.2199.

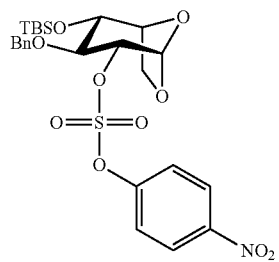

S9 (488 mg, 1.04 mmol) was dissolved in methanol (5 mL), followed by the addition of NaOMe-methanol solution (231 μL, 1.04 mmol, 25% purity). The mixture was stirred for 1 h and neutralized by DOWEX 50WX8 resin. After filtration, the filtrate was concentrated under the reduced pressure. General Procedure A-1 was employed to prepare the above crude product. The product was further purified by silica gel chromatography hexane/ethyl acetate (10:1) to obtain S11 (265.6 mg, 61%). S11 (100 mg, 0.3 mmol) and 3a (55.5 mg, 0.33 mmol) were reacted following General Procedure A-3. The product was further purified by silica gel chromatography hexane/ethyl acetate (10:1) to obtain 10b as a colorless liquid (102.9 mg, 80%). $^1$H NMR (600 MHz, CDCl$_3$) δ 8.09 (d, J=9.0 Hz, 2H), 7.42 (d, J=9.0 Hz, 2H), 7.43-7.25 (m, 5H), 5.68 (d, J=1.7 Hz, 1H), 4.81 (d, J=10.9 Hz, 1H), 4.69-4.63 (m, 2H), 4.35 (t, J=4.7 Hz, 1H), 4.21 (d, J=7.7 Hz, 1H), 3.99 (dd, J=7.8, 4.4 Hz, 1H), 3.80-3.76 (m, 1H), 3.74 (t, J=8.0 Hz, 1H), 0.89 (s, 9H), 0.10 (s, 3H), 0.09 (s, 3H); $^{13}$C NMR (151 MHz, CDCl$_3$) δ 154.22, 146.41, 137.53, 128.62, 128.41, 127.66, 127.47, 125.83, 125.77, 125.68, 122.20, 122.05, 98.53, 98.41, 86.72, 86.64, 80.30, 80.17, 75.91, 75.82, 73.14, 73.00, 65.59, 25.80, 25.77, 17.94; HRMS (ESI) ([M+H]$^+$) Calcd. For C$_{25}$H$_{34}$O$_{10}$SiNS: 568.1667, found 518.1626.

One-Pot Synthesis for Compounds 10a

Compound S10 (330.6 mg, 0.90 mmol) was converted to trimethylsilyl ether in situ by HMDS (101.9 mg, 131.7 μL, 0.63 mmol) and coupled with fluoride sulfate 3a (302.0 mg, 1.63 mmol) via the following addition of DBU (22.0 mg, 0.14 mmol) to provide sulfoglucopyranose 10a (437.8 mg, 86%) according to General Procedure D. Note: The whole reaction mixture was washed by aqueous solution.

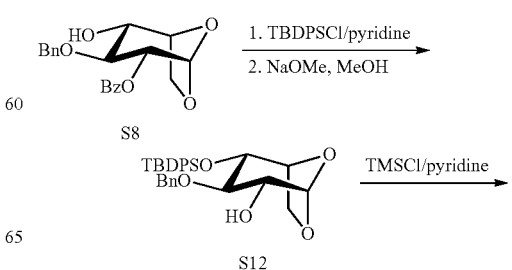

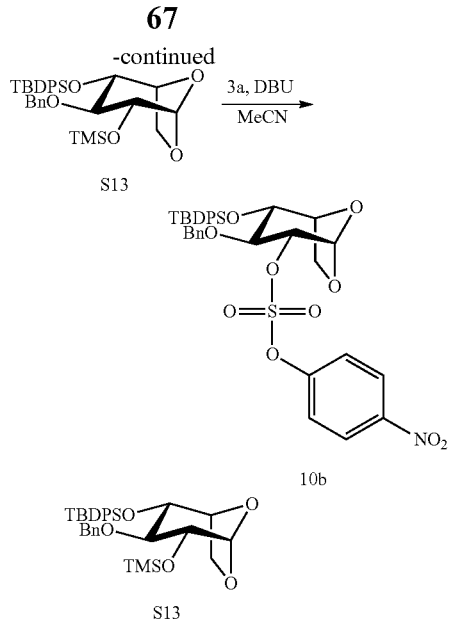

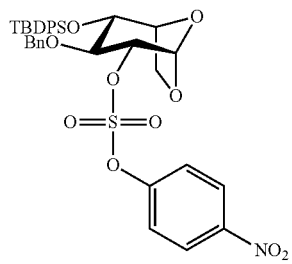

To a solution of compound S8 (437.5 mg, 1.23 mmol) in mixed dry solvent DMF/THF (9 mL/4.5 mL) was consecutively added imidazole (167.2 mg, 2.46 mmol), tert-Butyl (chloro)diphenylsilane (474.9 mg, 2.46 mmol) at rt. 80 h later, the reaction was concentrated directly under reduced pressure, purified directly for the usage in next step. Above product (731.6 mg, 1.23 mmol) was dissolved in mixed solvent DCM/MeOH (13.3 mL/13.3 mL), followed by the addition of NaOMe (225.9 mg, 4.18 mmol) at room temperature. 22 h later, the reaction was neutralized with H-form resin to pH=7, concentrated, purified on silica gel column, providing compound S12 (603.5 mg, 89%). S12 (403 mg, 0.82 mmol) was directly used to prepare S13 following General Procedure A-1. The product was further purified by silica gel chromatography (hexane/ethyl acetate 10:1) to obtain S13 as a colorless liquid (361.5 mg, 78%). $[\alpha]_D^{20}$=+89.38 (c 1.00 in CHCl$_3$). $^1$H NMR (500 MHz, CDCl$_3$) δ 7.67 (d, J=6.4 Hz, 2H), 7.61 (d, J=6.6 Hz, 2H), 7.42 (t, J=7.4 Hz, 1H), 7.37 (t, J=7.5 Hz, 1H), 7.35-7.26 (m, 7H), 7.22 (t, J=7.6 Hz, 2H), 5.08 (d, J=1.8 Hz, 1H), 4.93 (d, J=11.0 Hz, 1H), 4.82 (d, J=11.0 Hz, 1H), 4.25 (d, J=7.5 Hz, 1H), 4.02 (dd, J=7.9, 4.3 Hz, 1H), 3.78 (t, J=4.7 Hz, 1H), 3.70 (t, J=7.8 Hz, 1H), 3.62 (dd, J=7.8, 1.8 Hz, 1H), 3.54 (dd, J=7.3, 5.3 Hz, 1H), 1.04 (s, 9H), 0.13 (s, 9H). HRMS (ESI) ([M+NH4]$^+$) Calcd. For C$_{32}$H$_{46}$NO$_5$Si$_2$: 580.2915, found 580.2906.

Compound 10b was prepared following General Procedure A-1 from S13 (104 mg, 0.18 mmol). The product was further purified by silica gel chromatography (hexane/ethyl acetate 12:1) to obtain 10b as a colorless liquid (95.9 mg, 75%). $[\alpha]_D^{20}$=+74.48 (c 2.00 in CHCl$_3$). $^1$H NMR (600 MHz, CDCl$_3$) δ 8.16-8.10 (m, 2H), 7.70-7.65 (m, 2H), 7.64-7.60 (m, 2H), 7.47-7.38 (m, 4H), 7.36 (t, J=7.4 Hz, 2H), 7.32-7.24 (m, 5H), 7.20 (dd, J=7.1, 2.5 Hz, 2H), 5.58 (d, J=1.7 Hz, 1H), 4.87 (d, J=10.6 Hz, 1H), 4.76 (d, J=10.6 Hz, 1H), 4.62 (dd, J=8.1, 1.8 Hz, 1H), 4.28 (dd, J=7.6, 0.8 Hz, 1H), 4.14 (ddd, J=7.9, 4.4, 1.1 Hz, 1H), 3.92 (t, J=7.9 Hz, 1H), 3.85 (t, J=4.6 Hz, 1H), 3.59 (dd, J=7.8, 5.0 Hz, 1H), 1.08 (s, 9H). $^{13}$C NMR (151 MHz, CDCl$_3$) δ 154.06, 146.30, 137.29, 135.78, 135.74, 133.43, 131.97, 130.44, 130.13, 128.32, 128.13, 127.85, 127.83, 127.68, 125.62, 122.00, 98.22, 86.76, 80.35, 75.61, 74.71, 73.39, 65.46, 26.95, 19.16. HRMS (ESI) ([M+NH$_4$]$^+$) Calcd. For O$_{35}$H$_{41}$N$_2$O$_{10}$SSi: 709.2251, found 709.2242.

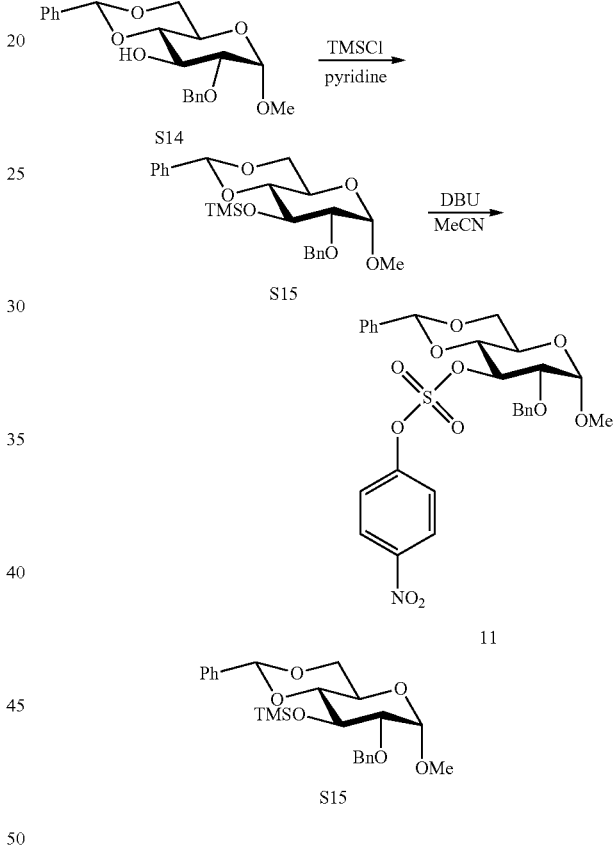

S15 was prepared following General Procedure A-1 was followed with S14 (1.32 g, 3.55 mmol). S14 was obtained according to the literature 15. The product was purified by silica gel chromatography (hexane/ethyl acetate 6:1) to obtain S15 (1.53 g, 97%). $[\alpha]_D^{20}$=−4.67 (c 1.00 in CHCl$_3$). $^1$H NMR (600 MHz, CDCl$_3$) δ 7.48 (dd, J=7.5, 1.9 Hz, 2H), 7.41-7.31 (m, 7H), 7.30 (t, J=7.1 Hz, 1H), 5.49 (s, 1H), 4.84 (d, J=12.3 Hz, 1H), 4.64 (d, J=12.3 Hz, 1H), 4.52 (d, J=3.7 Hz, 1H), 4.23 (dd, J=10.1, 4.8 Hz, 1H), 4.12 (t, J=9.0 Hz, 1H), 3.77 (ddd, J=10.6, 9.8, 4.8 Hz, 1H), 3.67 (t, J=10.3 Hz, 1H), 3.43-3.39 (m, 2H), 3.38 (s, 3H), 0.14 (s, 9H). $^{13}$C NMR (151 MHz, CDCl$_3$) δ 138.30, 137.39, 128.88, 128.42, 128.16, 128.12, 127.89, 126.14, 101.63, 99.44, 82.07, 79.74, 73.91, 71.70, 69.03, 62.23, 55.30, 0.54. HRMS (DART) ([M+NH$_4$]$^+$) Calcd. For C$_{24}$H$_{33}$O$_6$Si: 445.2046, found 445.2035.

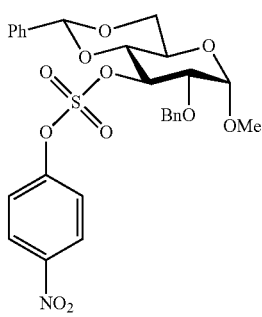

11

Compound 11 was prepared following General Procedure A-3 from S15 (100 mg, 0.27 mmol) and 4 h of reaction time. The product was purified by silica gel chromatography (hexane/ethyl acetate 8:1) to obtain 11 (84.7 mg, 55%). $[\alpha]_D^{20}$=−15.46 (c 1.00 in CHCl$_3$). $^1$H NMR (500 MHz, CDCl$_3$) δ 7.87 (d, J=9.2 Hz, 2H), 7.42-7.30 (m, 10H), 7.24 (d, J=9.3 Hz, 2H), 5.43 (s, 1H), 5.23 (t, J=9.4 Hz, 1H), 4.81 (d, J=12.1 Hz, 1H), 4.65 (d, J=1.5 Hz, 1H), 4.63 (d, J=7.0 Hz, 1H), 4.29 (dd, J=10.4, 4.8 Hz, 1H), 3.89 (td, J=9.9, 4.9 Hz, 1H), 3.76-3.65 (m, 3H), 3.40 (s, 3H). $^{13}$C NMR (151 MHz, CDCl$_3$) δ 154.43, 145.62, 137.05, 136.34, 129.59, 128.61, 128.36, 128.21, 126.27, 125.15, 121.30, 102.15, 98.77, 84.17, 78.78, 73.57, 68.82, 62.28, 55.65. HRMS (ESI) ([M+NH$_4$]$^+$) Calcd. For C$_{27}$H$_{31}$N$_2$O$_{11}$S: 591.1649, found 591.1641.

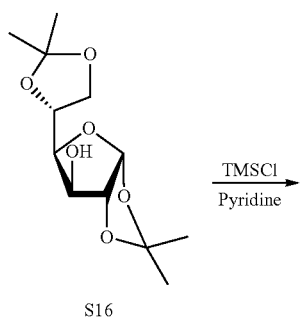

S16

TMSCl / Pyridine →

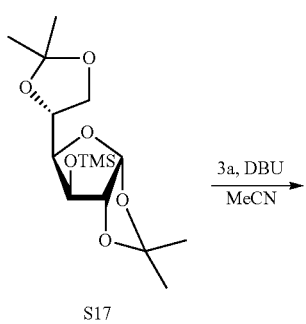

S17

3a, DBU / MeCN →

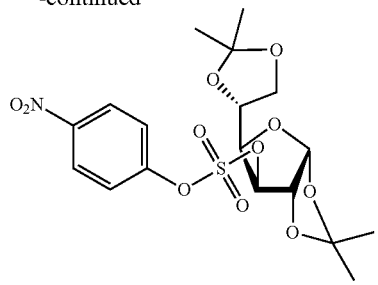

12

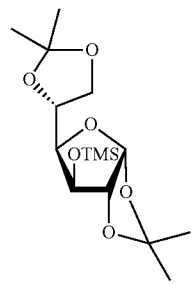

S17

S17 was prepared following General Procedure A-1 from S16 (300 mg, 1.15 mmol). The product was purified by silica gel chromatography (hexane/ethyl acetate 10:1) to obtain S17 (358.1 mg, 93%). $[\alpha]_D^{20}$=−18.60 (c 1.00 in CHCl$_3$). $^1$H NMR (500 MHz, CDCl$_3$) δ 5.90 (d, J=3.6 Hz, 1H), 4.35 (d, J=3.6 Hz, 1H), 4.25-4.15 (m, 3H), 4.08 (dd, J=8.5, 6.2 Hz, 1H), 4.05 (dd, J=7.8, 2.7 Hz, 1H), 3.97 (dd, J=8.5, 6.1 Hz, 1H), 1.50 (s, 3H), 1.41 (s, 3H), 1.33 (s, 3H), 1.31 (s, 3H), 0.17 (s, 9H). $^{13}$C NMR (151 MHz, CDCl$_3$) δ 111.76, 108.82, 105.32, 85.58, 81.85, 75.25, 72.38, 67.42, 26.88, 26.74, 26.31, 25.34, −0.15. HRMS (DART) ([M+H]$^+$) Calcd. For C$_{15}$H$_{29}$O$_6$Si: 333.1733, found 333.1727.

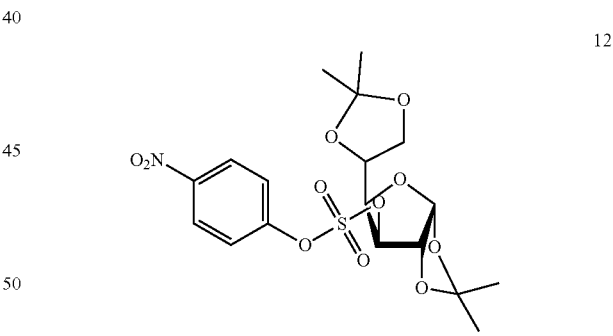

12

Compound 12 was prepared following General Procedure A-3 from S17 (100 mg, 0.3 mmol). The product was purified by silica gel chromatography (hexane/ethyl acetate 10:1) to obtain 12 (118.0 mg, 94%). $[\alpha]_D^{20}$=−89.44 (c 1.00 in CHCl$_3$). $^1$H NMR (600 MHz, CDCl$_3$) δ 8.31 (d, J=9.2 Hz, 2H), 7.59 (d, J=9.2 Hz, 2H), 5.96 (d, J=3.7 Hz, 1H), 5.19 (d, J=2.6 Hz, 1H), 4.94 (d, J=3.7 Hz, 1H), 4.22 (ddd, J=9.6, 5.9, 4.0 Hz, 1H), 4.18 (dd, J=8.8, 2.6 Hz, 1H), 4.12 (dd, J=8.9, 5.9 Hz, 1H), 4.05 (dd, J=8.9, 4.0 Hz, 1H), 1.53 (s, 3H), 1.42 (s, 3H), 1.34 (s, 3H), 1.27 (s, 3H). $^{13}$C NMR (151 MHz, CDCl$_3$) δ 154.26, 146.37, 125.63, 121.94, 112.93, 109.83, 104.81, 86.73, 82.53, 79.64, 71.45, 67.34, 26.94, 26.52, 26.20, 25.08. HRMS (ESI) ([M+H]$^+$) Calcd. For C$_{18}$H$_{23}$NO$_{11}$S: 462.1070, found 462.1064.

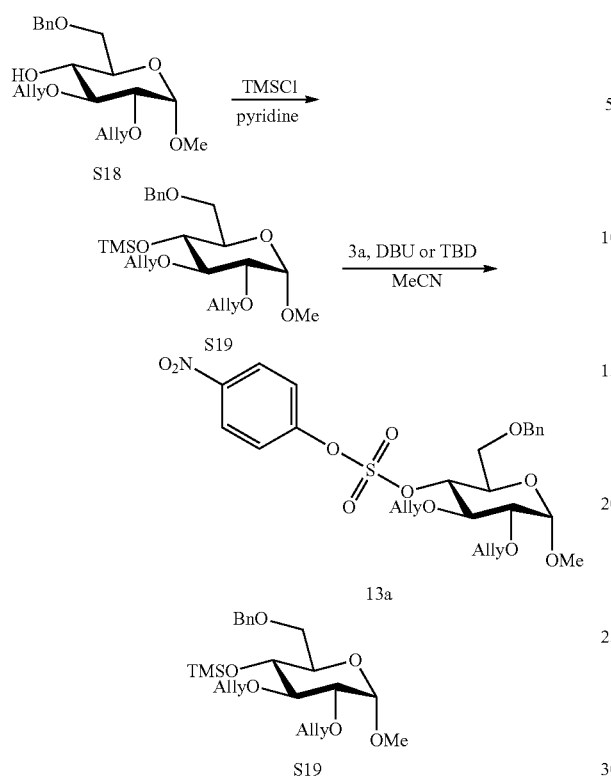

S19 was prepared following General Procedure A-1 from S18 (440 mg, 1.31 mmol). S18 was obtained according to the literature 16. The product was purified by silica gel chromatography (hexane/ethyl acetate 10:1) to obtain S19 (291.0 mg, 54%). $[\alpha]_D^{20}$=+68.59 (c 1.00 in CHCl$_3$). $^1$H NMR (600 MHz, CDCl$_3$) δ 7.37-7.25 (m, 5H), 6.00-5.85 (m, 2H), 5.26 (ddq, J=17.2, 6.8, 1.7 Hz, 2H), 5.15 (ddq, J=25.4, 10.5, 1.4 Hz, 2H), 4.78 (d, J=3.5 Hz, 1H), 4.60 (d, J=12.1 Hz, 1H), 4.56 (d, J=12.1 Hz, 1H), 4.39 (ddt, J=12.4, 5.5, 1.6 Hz, 1H), 4.21-4.10 (m, 3H), 3.70-3.59 (m, 4H), 3.56 (dd, J=9.5, 8.4 Hz, 1H), 3.41 (s, 4H), 0.09 (s, 9H). $^{13}$C NMR (151 MHz, CDCl$_3$) δ 138.07, 135.32, 134.87, 128.30, 127.66, 127.55, 117.57, 116.13, 98.11, 81.20, 79.97, 74.18, 73.46, 72.46, 71.16, 70.88, 68.92, 54.99, 0.49. HRMS (ESI) ([M+NH4]$^+$) Calcd. For O$_{23}$H$_{40}$NO$_6$Si: 454.2625, found 454.2624.

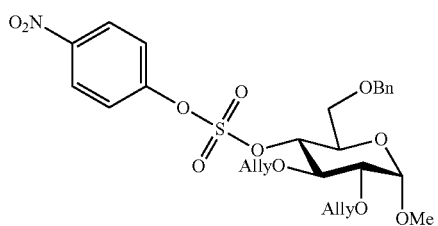

Compound 13a was prepared following General Procedure A-3 from S19 (100 mg, 0.25 mmol). DBU or TBD was used as the catalyst. The product was purified by silica gel chromatography (hexane/ethyl acetate 8:1) to obtain 13a (DBU: 62.5 mg, 49%; TBD: 5.1 mg, 4%). $[\alpha]_D^{20}$=+71.72 (c 0.25 in CHCl$_3$). $^1$H NMR (500 MHz, CDCl$_3$) δ 8.24 (d, J=9.2 Hz, 2H), 7.41 (d, J=9.2 Hz, 2H), 7.36-7.22 (m, 5H), 5.96-5.83 (m, 2H), 5.29 (dq, J=17.2, 1.5 Hz, 1H), 5.26-5.19 (m, 2H), 5.11 (dq, J=10.4, 1.4 Hz, 1H), 4.97 (dd, J=10.1, 9.2 Hz, 1H), 4.81 (d, J=3.5 Hz, 1H), 4.60-4.48 (m, 2H), 4.37 (ddt, J=12.0, 5.8, 1.4 Hz, 1H), 4.25-4.10 (m, 3H), 3.96-3.87 (m, 2H), 3.76-3.65 (m, 2H), 3.51 (dd, J=9.6, 3.6 Hz, 1H), 3.45 (s, 3H). $^{13}$C NMR (151 MHz, CDCl$_3$) δ 154.23, 146.21, 137.53, 134.29, 134.22, 128.35, 127.79, 127.76, 125.61, 122.00, 118.33, 117.31, 97.98, 82.82, 79.33, 77.98, 74.32, 73.76, 72.73, 68.09, 67.88, 55.64. HRMS (ESI) ([M+NH$_4$]$^+$) Calcd. For C$_{26}$H$_{35}$N$_2$O$_{11}$S: 583.1962, found 583.1956.

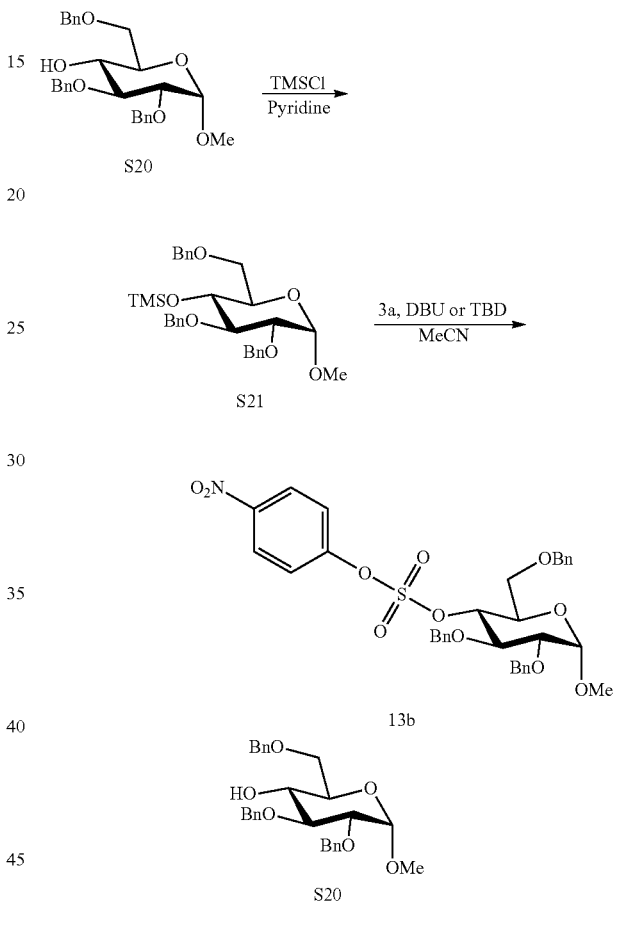

S20 was prepared according to a protocol that was previously reported. $^1$H NMR (600 MHz, CDCl$_3$) δ 7.42-7.26 (m, 15H), 5.00 (d, J=11.4 Hz, 1H), 4.75 (dd, J=20.0, 11.8 Hz, 2H), 4.66 (d, J=12.1 Hz, 1H), 4.63 (d, J=3.5 Hz, 1H), 4.59 (d, J=12.2 Hz, 1H), 4.54 (d, J=12.2 Hz, 1H), 3.78 (t, J=9.2 Hz, 1H), 3.73-3.65 (m, 3H), 3.59 (t, J=9.1 Hz, 1H), 3.53 (dd, J=9.6, 3.5 Hz, 1H), 3.38 (s, 3H), 2.32 (d, J=2.4 Hz, 1H). Spectral data matched those previously reported.

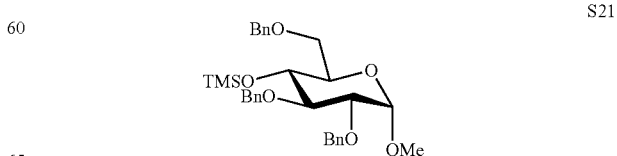

S21 was prepared following General Procedure A-1 from S20 (300 mg, 1.15 mmol). The product was purified by silica gel chromatography (hexane/ethyl acetate 10:1) to obtain S21 (358.1 mg, 93%). (566.5 mg, 60%). [α]$_D^{20}$=+33.46 (c 0.50 in CHCl$_3$). $^1$H NMR (500 MHz, CDCl$_3$) δ 7.39-7.22 (m, 15H), 5.01 (d, J=11.3 Hz, 1H), 4.72 (dd, J=20.1, 11.7 Hz, 2H), 4.63-4.51 (m, 4H), 3.78-3.59 (m, 5H), 3.51 (dd, J=9.4, 3.6 Hz, 1H), 3.38 (s, 3H), 0.04 (s, 9H). $^{13}$C NMR (151 MHz, CDCl$_3$) δ 139.14, 138.14, 138.04, 128.38, 128.30, 128.14, 127.83, 127.66, 127.55, 127.22, 127.11, 98.00, 81.89, 80.23, 75.21, 73.46, 73.28, 71.13, 70.93, 68.92, 55.07, 0.52. HRMS (ESI) ([M+NH4]$^+$) Calcd. For C$_{31}$H$_{44}$NO$_6$Si: 554.2938, found 554.2934.

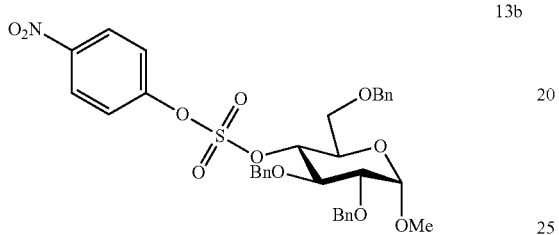

13b

Compound 13b was prepared following General Procedure A-3 in two batches: S21 (60 mg, 0.11 mmol), DBU (3.4 mg, 0.022 μmol); S21 (100 mg, 00.19 mmol), TBD (5.2 mg, 0.037 μmol). The product was purified by silica gel chromatography (hexane/ethyl acetate 6:1) to obtain 13b (DBU: 40.2 mg, 54%; TBD: 6.6 mg, 5%). [α]$_D^{20}$=+10.398 (c 1.00 in CHCl$_3$)$^1$H NMR (500 MHz, CDCl$_3$) δ 8.12 (d, J=9.2 Hz, 2H), 7.35-7.21 (m, 17H), 5.03 (t, J=9.6 Hz, 1H), 4.95 (d, J=10.5 Hz, 1H), 4.77 (d, J=12.1 Hz, 1H), 4.70 (d, J=10.5 Hz, 1H), 4.64-4.58 (m, 2H), 4.55 (d, J=11.6 Hz, 1H), 4.51 (d, J=11.7 Hz, 1H), 4.08 (t, J=9.3 Hz, 1H), 3.95 (d, J=10.0 Hz, 1H), 3.77-3.67 (m, 2H), 3.62 (dd, J=9.6, 3.6 Hz, 1H), 3.40 (s, 3H). $^{13}$C NMR (126 MHz, CDCl$_3$) δ 154.08, 146.09, 137.80, 137.55, 137.53, 128.57, 128.35, 128.25, 128.18, 128.15, 127.83, 127.76, 127.69, 127.62, 125.45, 121.82, 97.90, 82.84, 79.72, 78.39, 75.35, 73.77, 73.61, 68.11, 67.90, 55.71.

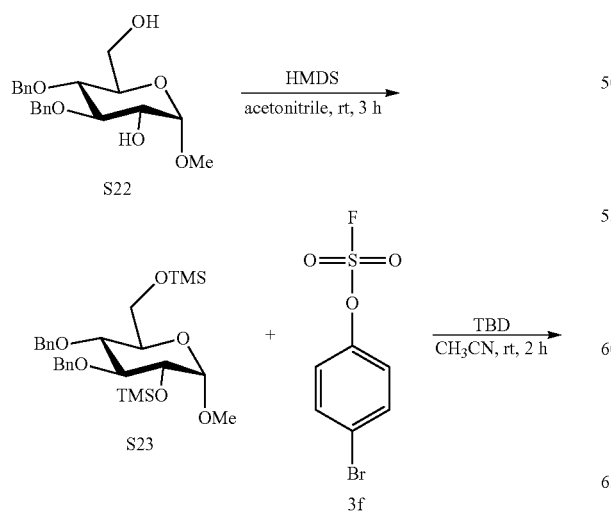

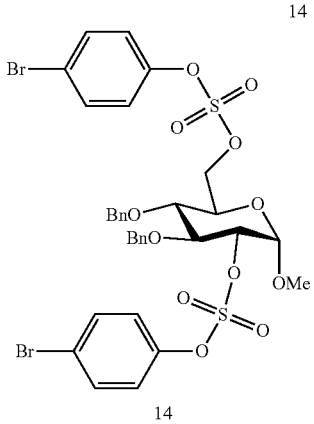

14

14

Compound S22 (104.1 mg, 0.28 mmol) was converted to trimethylsilyl ether S23 (137.4 mg, 95%) following General Procedure A-2. S23 was used directly in the next step without further characterization.

Compound S23 (105.8 mg, 0.20 mmol) coupled with fluoride sulfate 3f (110.7 mg, 0.44 mmol) in the presence of TBD (8.4 mg, 0.06 mmol) providing compound 14 (125.2 mg, 73%) according to General Procedure A-3. [α]$_D^{20}$=+ 51.6 (c 1.00, CHCl$_3$); $^1$H NMR (600 MHz, CDCl$_3$) δ 7.53-7.46 (m, 2H), 7.40-7.36 (m, 2H), 7.36-7.27 (m, 8H), 7.25-7.22 (m, 2H), 7.22-7.17 (m, 2H), 7.17-7.14 (m, 2H), 5.04 (d, J=3.6 Hz, 1H), 4.89 (d, J=11.0 Hz, 1H), 4.83 (d, J=10.8 Hz, 1H), 4.77 (d, J=10.8 Hz, 1H), 4.65 (dd, J=9.8, 3.6 Hz, 1H), 4.57 (d, J=11.0 Hz, 1H), 4.50 (dd, J=10.7, 2.0 Hz, 1H), 4.45 (dd, J=10.7, 4.8 Hz, 1H), 4.11 (dd, J=9.7, 8.7 Hz, 1H), 3.93 (ddd, J=10.1, 4.9, 1.9 Hz, 1H), 3.56 (dd, J=10.2, 8.7 Hz, 1H), 3.36 (s, 3H); $^{13}$C NMR (151 MHz, CDCl$_3$) δ 149.30, 149.21, 137.40, 137.16, 133.21, 133.14, 128.83, 128.67, 128.46, 128.29, 128.18, 128.09, 123.10, 123.04, 121.13, 121.08, 96.78, 82.64, 79.18, 77.02, 75.99, 75.53, 72.29, 68.54, 55.88; HRMS (ESI) m/z [M+NH4]$^+$ calcd for C$_{33}$H$_{36}$O$_{12}$Br$_2$S$_2$N 860.0040, found 860.0006.

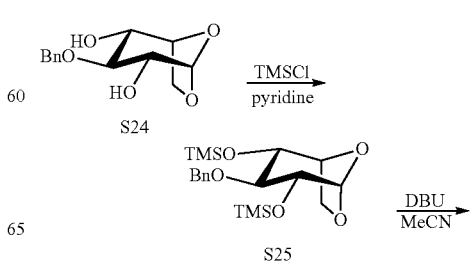

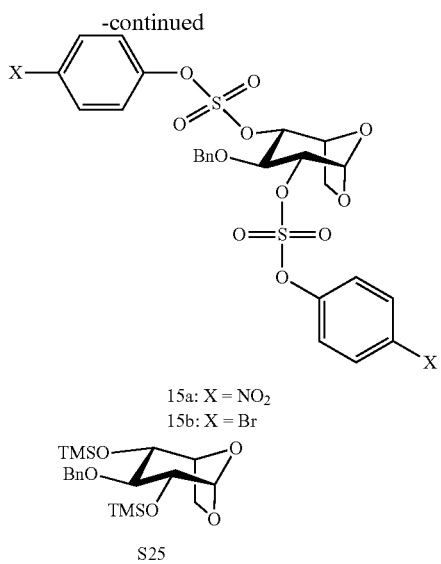

15a: X = NO₂
15b: X = Br

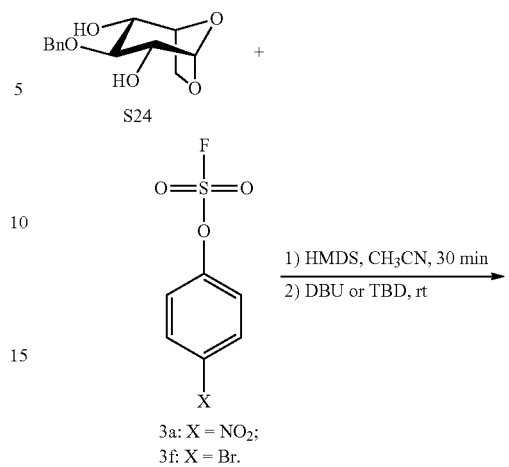

1) HMDS, CH₃CN, 30 min
2) DBU or TBD, rt

3a: X = NO₂;
3f: X = Br.

S17 was prepared following General Procedure A-1 from S24 (200 mg, 0.79 mmol). S24 was prepared according to a previously published procedure. The product was purified by silica gel chromatography (hexane/ethyl acetate 10:1) to obtain S25 (313.8 mg, quantitative). ¹H NMR (500 MHz, CDCl₃) δ 7.37-7.22 (m, 5H), 5.16 (d, J=1.8 Hz, 1H), 4.82-4.74 (m, 2H), 4.23 (t, J=4.7 Hz, 1H), 4.15 (dd, J=7.6, 0.8 Hz, 1H), 3.84 (ddd, J=8.0, 4.3, 1.1 Hz, 1H), 3.71 (ddd, J=7.6, 5.1, 1.1 Hz, 1H), 3.63 (dd, J=7.8, 1.8 Hz, 1H), 3.50 (t, J=7.9 Hz, 1H), 0.14 (s, 9H), 0.11 (s, 9H).

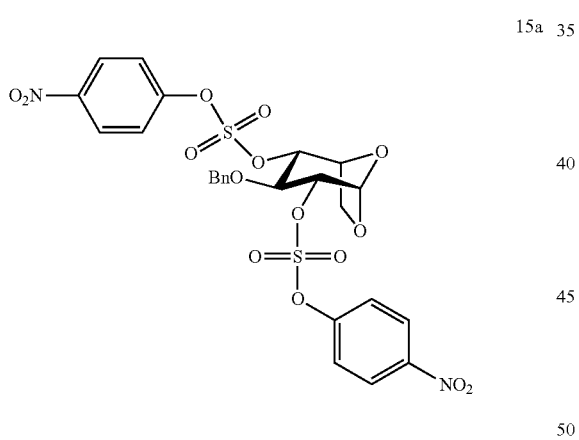

15a

Compound 15a was prepared following General Procedure A-3 in two batches: S25 (100 mg, 0.25 mmol), DBU (15.4 mg, 0.022 mmol); S25 (85 mg, 0.21 mmol), TBD (11.9 mg, 0.086 mmol). The product was purified by silica gel chromatography (hexane/ethyl acetate 8:1-4:1) to obtain 15a (DBU: 117 mg, 71%; TBD: 100 mg, 71%). $[\alpha]_D^{20}$=+10.20 (c 1.00 in CHCl₃). ¹H NMR (600 MHz, CDCl₃) δ 8.18 (d, J=9.0 Hz, 2H), 8.06 (d, J=9.2 Hz, 2H), 7.46 (d, J=9.2 Hz, 2H), 7.35 (d, J=9.2 Hz, 2H), 7.29-7.16 (m, 5H), 5.75 (d, J=1.7 Hz, 1H), 5.01 (t, J=4.6 Hz, 1H), 4.97 (ddd, J=8.3, 4.3, 1.2 Hz, 1H), 4.80-4.74 (m, 2H), 4.65 (d, J=10.9 Hz, 1H), 4.22 (dd, J=8.7, 0.7 Hz, 1H), 4.03 (t, J=8.1 Hz, 1H), 3.94 (ddd, J=8.7, 4.9, 1.3 Hz, 1H). ¹³C NMR (151 MHz, CDCl₃) δ 153.81, 153.59, 146.50, 146.41, 136.12, 128.56, 128.37, 127.34, 127.32, 125.74, 125.72, 121.97, 121.61, 98.37, 85.72, 81.97, 76.10, 75.40, 72.56, 65.85. HRMS (ESI) ([M+NH4]⁺) Calcd. For $C_{25}H_{26}N_3O_{15}S_2$: 672.0805, found 672.0787.

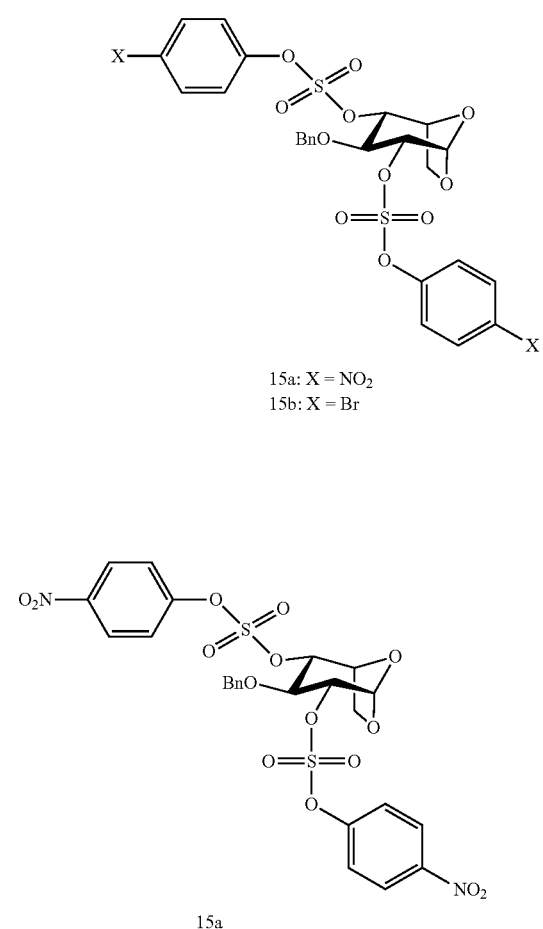

15a: X = NO₂
15b: X = Br

15a

Compound S24 (204.6 mg, 0.81 mmol) was converted to trimethylsilyl ether in situ by HMDS (144.0 mg, 186.0 μL, 0.89 mmol) and coupled with fluoride sulfate 3a (425.6 mg, 1.92 mmol) via the following addition of DBU (24.5 mg, 0.16 mmol) to provide sulfoidopyranose 15a (360.2 mg, 68%) in 5 h according to the General Procedure B.

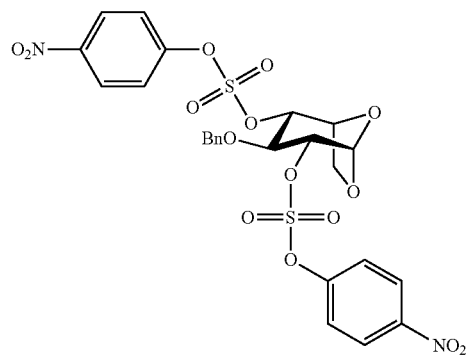

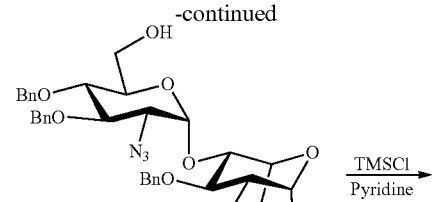

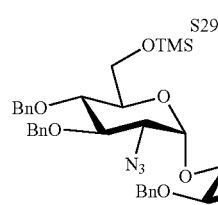

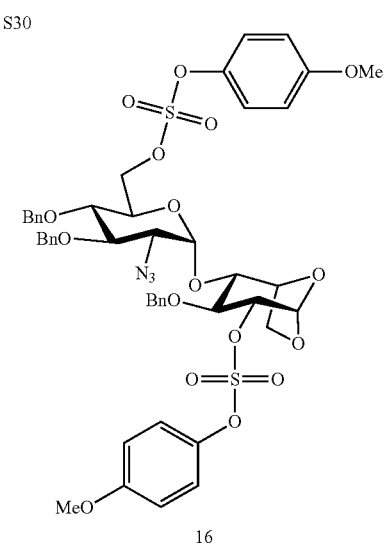

Compound S24 (1.60 g, 6.34 mmol) was converted to trimethylsilyl ether in situ by HMDS (1.13 g, 1.45 mL, 6.98 mmol) and coupled with fluoride sulfate 3f (3.40 g, 13.32 mmol) via the following addition of TBD (176.6 mg, 1.27 mmol) to provide sulfoidopyranose 15b (4.32 g, 94%) in 13 h according to the General Procedure B. $[\alpha]_D^{20}$=+7.8 (c 1.01, CHCl$_3$); $^1$H NMR (500 MHz, CDCl$_3$) δ 7.46-7.41 (m, 2H), 7.39-7.34 (m, 2H), 7.32-7.28 (m, 3H), 2.24-7.23 (m, 2H), 7.21-7.17 (m, 2H), 7.14-7.09 (m, 2H), 5.69 (d, J=1.8 Hz, 1H), 4.93-4.87 (m, 2H), 4.74 (d, J=10.8 Hz, 1H), 4.71 (dd, J=7.9, 1.8 Hz, 1H), 4.66 (d, J=10.7 Hz, 1H), 4.15 (d, J=8.5 Hz, 1H), 4.00-3.94 (m, 1H), 3.88-3.85 (m, 1H); $^{13}$C NMR (126 MHz, CDCl$_3$) δ 149.15, 148.96, 136.48, 133.30, 133.26, 128.65, 128.64, 128.61, 128.38, 128.08, 123.17, 122.90, 121.41, 121.38, 98.62, 85.42, 81.80, 76.25, 75.56, 72.73, 65.90; HRMS (ESI) m/z [M+NH$_4$]$^+$ calcd for C$_{25}$H$_{26}$O$_{11}$NBr$_2$S$_2$ 737.9309, found 737.9297.

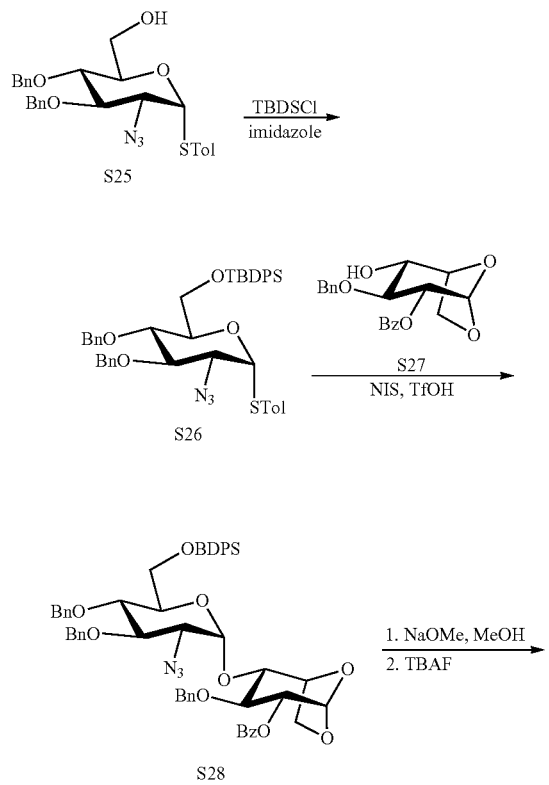

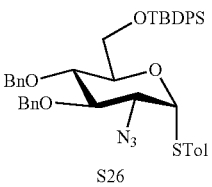

In a 25 mL flask, S25 (200 mg, 406.8 μmol) and imidazole (55.4 mg, 813.7 μmol) was dissolved in 5 mL of DMF, as followed by the addition of tert-butyl(chloro)diphenylsilane (TBDPSCl, 134.2 mg, 488.2 μmol, 125 μL) under the protection of N$_2$. After stirred for 6 h, ethyl acetate (10 mL) was added to dilute the solution. The mixture was washed by water (5 mL) 3 times. The organic layer was concentrated and purified by column chromatography using (hexane/ethyl acetate 20:1) as eluent, yielding the S26 as a colorless liquid (276 mg, 93%). $[\alpha]_D^{20}$=−98.31 (c 0.20 in CHCl$_3$). $^1$H NMR (500 MHz, CDCl$_3$) δ 7.79 (dd, J=8.0, 1.5 Hz, 2H), 7.70 (dd, J=8.0, 1.4 Hz, 2H), 7.53 (d, J=8.2 Hz, 2H), 7.46-7.27 (m, 14H), 7.18-7.12 (m, 2H), 7.03 (d, J=7.6 Hz, 2H), 4.87-4.83 (m, 3H), 4.69 (d, J=10.8 Hz, 1H), 4.37 (d, J=10.1 Hz, 1H), 4.00 (dd, J=11.4, 1.8 Hz, 1H), 3.93 (dd, J=11.4, 3.2 Hz, 1H), 3.76 (t, J=9.5 Hz, 1H), 3.53 (t, J=9.3 Hz, 1H), 3.38-3.30 (m, 2H), 2.31 (s, 3H), 1.08 (s, 9H). $^{13}$C NMR (151 MHz, CDCl$_3$) δ 138.60, 137.91, 137.54, 135.84, 135.60, 134.22, 133.30, 132.77, 129.78, 129.73, 129.70, 128.58, 128.47, 128.39, 128.10, 127.81, 127.79, 127.72, 127.70, 127.11, 85.98, 85.29, 80.09, 77.11, 76.06, 75.05, 64.76, 62.25, 26.82, 21.15, 19.26. HRMS (ESI) ([M+NH$_4$]$^+$) Calcd. For C$_{43}$H$_{51}$N$_4$O$_4$SSi: 747.3400, found 747.3386.

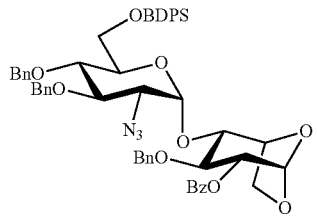

S27 was prepared according to a previously published procedure. A mixture of S26 (267.0 mg, 365.8 μmol) and S27 (156.4 mg, 438.9 μmol) was co-evaporated with toluene (3×2 mL) in a Schlenk tube (10 mL) and placed under vacuum for 1 h. Under N$_2$ protection, the reactants were dissolved in dry DCM (7 mL), followed by the addition of freshly dried 4 Å molecular sieves (700 mg). The mixture was stirred at room temperature for 0.5 h, and then cooled to −48° C. (acetonitrile/dry ice bath). N-Iodosuccinimide (118.5 mg, 526.7 μmol) and trifluoromethanesulfonic acid (TfOH, 11.0 mg, 73.2 μmol, 6.4 μL) were added to the reaction flask. The solution was warmed up by removing the acetonitrile/dry ice bath and stirred for 2 h. Et$_3$N (1 mL) was added to quench the reaction. The whole mixture was filtered through celite and the filtrate was sequentially washed with aqueous Na$_2$S$_2$O$_3$ (10%, 10 mL) and brine. The organic layer was dried over anhydrous MgSO$_4$ and concentrated. The crude product was purified by column chromatography (hexane/EA=15:1-10:1 v/v) to get S28 (270 mg, 77%). [α]$_D^{20}$+90.64 (c 0.50 in CHCl$_3$). $^1$H NMR (500 MHz, CDCl$_3$) δ 8.04 (d, J=7.0 Hz, 2H), 7.67 (dt, J=8.2, 1.4 Hz, 4H), 7.58 (t, J=7.5 Hz, 1H), 7.47-7.27 (m, 18H), 7.25-7.18 (m, 3H), 7.14 (dd, J=6.3, 3.3 Hz, 2H), 5.50 (d, J=1.8 Hz, 1H), 5.27 (d, J=3.8 Hz, 1H), 5.06 (dd, J=8.0, 1.9 Hz, 1H), 4.96-4.88 (m, 3H), 4.85 (d, J=10.5 Hz, 1H), 4.76 (d, J=10.8 Hz, 1H), 4.61 (d, J=10.5 Hz, 1H), 4.57 (t, J=4.6 Hz, 1H), 4.12 (d, J=7.7 Hz, 1H), 4.05 (t, J=8.1 Hz, 1H), 4.02-3.95 (m, 2H), 3.90-3.81 (m, 2H), 3.72-3.61 (m, 3H), 3.40 (dd, J=10.3, 3.8 Hz, 1H), 1.06 (s, 9H). $^{13}$C NMR (101 MHz, CDCl$_3$) δ 165.72, 137.92, 137.64, 137.44, 135.75, 135.61, 133.36, 133.13, 132.82, 129.86, 129.82, 129.78, 129.41, 128.57, 128.44, 128.36, 128.14, 128.08, 128.06, 127.88, 127.77, 127.72, 127.69, 99.63, 99.22, 79.92, 79.33, 78.85, 78.24, 77.20, 75.60, 75.46, 74.96, 74.20, 72.79, 65.66, 63.59, 62.51, 26.78, 19.19. HRMS (ESI) ([M+NH4]$^+$) Calcd. For C$_{56}$H$_{63}$N$_4$O$_{10}$Si: 979.4313, found 979.4293.

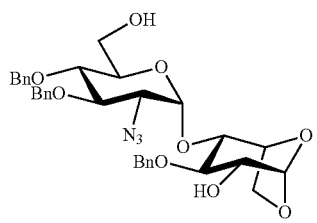

S28 (258.3 mg, 268.5 μmol) was dissolved in the mixture of THF/methanol (v/v, 3 mL/3 mL), followed by the addition of NaOMe-methanol solution (299.34 μL, 1.34 mmol, 25% purity). The mixture was stirred for 1 h and neutralized by DOWEX 50WX8 resin. After filtration, the filtrate was concentrated under the reduced pressure. The crude product was directly dissolved in THF (5 mL). To the solution was added tetrabutylammonium fluoride (TBAF, 1 M, 1.34 mL) and the mixture was stirred overnight. The solvent was removed under reduced pressure, and the residue was purified by silica column chromatography (ethyl acetate/hexane=1/2~1/0, v/v) to give the S29 (154.6 mg, 93%). [α]$_D^{20}$=+12.66 (c 0.10 in CHCl$_3$). $^1$H NMR (500 MHz, CDCl$_3$) δ 7.43-7.27 (m, 15H), 5.31-5.26 (m, 2H), 4.94-4.88 (m, 4H), 4.87 (d, J=10.7 Hz, 1H), 4.66 (d, J=10.8 Hz, 1H), 4.50 (t, J=4.7 Hz, 1H), 4.04 (d, J=7.8 Hz, 1H), 3.95 (dt, J=10.4, 4.2 Hz, 1H), 3.88 (dd, J=8.0, 4.3 Hz, 1H), 3.76 (ddt, J=17.0, 9.1, 3.9 Hz, 3H), 3.68-3.57 (m, 4H), 3.33 (dd, J=10.4, 3.8 Hz, 1H), 1.92 (d, J=8.6 Hz, 1H), 1.66 (t, J=6.6 Hz, 1H). $^{13}$C NMR (101 MHz, CDCl$_3$) δ 138.27, 137.61, 137.43, 128.65, 128.52, 128.22, 128.13, 128.03, 128.01, 127.95, 127.85, 101.52, 99.42, 83.40, 79.63, 78.11, 77.79, 75.84, 75.44, 75.39, 74.83, 74.17, 72.02, 65.41, 63.41, 61.42. HRMS (ESI) ([M+NH4]$^+$) Calcd. For C$_{33}$H$_{41}$N$_4$O$_9$: 637.2874, found 637.2858.

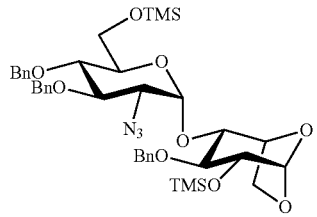

S17 was prepared following General Procedure A-1 from S29 (148.5 mg, 0.24 mmol). The product was purified by silica gel chromatography (hexane/ethyl acetate 6:1) to obtain S29 (150 mg, 82%). [α]$_D^{20}$=+31.99 (c 0.40 in CHCl$_3$). $^1$H NMR (500 MHz, CDCl$_3$) δ 7.41-7.26 (m, 15H), 5.18 (d, J=4.0 Hz, 1H), 5.18 (d, J=1.7 Hz, 1H), 4.93 (d, J=10.7 Hz, 1H), 4.88 (s, 2H), 4.84 (dd, J=10.8, 8.2 Hz, 2H), 4.65-4.59 (m, 2H), 4.10 (d, J=7.4 Hz, 1H), 3.93 (dd, J=10.3, 8.0 Hz, 1H), 3.85-3.80 (m, 1H), 3.76-3.65 (m, 5H), 3.59-3.50 (m, 2H), 3.35 (dd, J=10.3, 3.8 Hz, 1H), 0.17 (s, 9H), 0.09 (s, 9H). $^{13}$C NMR (101 MHz, CDCl$_3$) δ 138.56, 137.67, 128.58, 128.49, 128.30, 128.08, 127.98, 127.75, 127.51, 102.10, 99.73, 82.33, 79.97, 79.40, 78.12, 76.45, 75.55, 75.47, 75.23, 74.24, 72.63, 65.76, 63.58, 61.41, 0.34, −0.50. HRMS (ESI) ([M+NH4]$^+$) Calcd. For C$_{39}$H$_{57}$N$_4$O$_9$Si$_2$: 781.3664, found 781.3657.

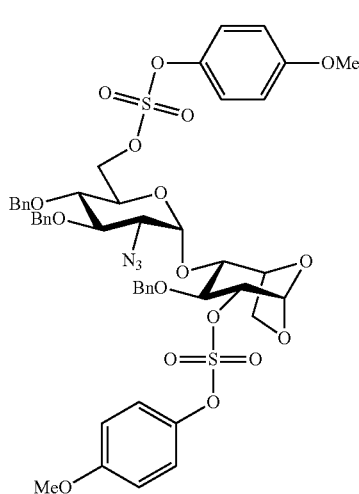

16

Compound 16 was prepared following General Procedure A-3 was followed in two batches: S22 (50 mg, 0.065 mmol), DBU (3.99 mg, 0.026 mmol); S22 (1.32 g, 1.73 mmol), TBD (49.0 mg, 0.35 mmol). The product was purified by silica gel chromatography (hexane/ethyl acetate 4:1~2:1) to obtain 16 (DBU: 29%; TBD: 67%). $[\alpha]_D^{20}$=+44.65 (c 1.00 in CHCl$_3$). $^1$H NMR (600 MHz, CDCl$_3$) δ 7.41-7.26 (m, 17H), 7.17 (d, J=9.1 Hz, 2H), 6.85 (d, J=9.2 Hz, 2H), 6.81 (d, J=9.2 Hz, 2H), 5.59 (d, J=1.7 Hz, 1H), 5.22 (d, J=3.8 Hz, 1H), 4.94-4.87 (m, 3H), 4.85 (d, J=10.2 Hz, 1H), 4.79 (d, J=10.2 Hz, 1H), 4.66-4.61 (m, 1H), 4.57 (d, J=10.8 Hz, 1H), 4.49-4.43 (m, 2H), 4.35 (dd, J=10.7, 6.0 Hz, 1H), 4.09-4.05 (m, 1H), 3.96-3.87 (m, 3H), 3.81 (ddd, J=10.2, 6.0, 1.8 Hz, 1H), 3.78 (s, 3H), 3.76 (s, 3H), 3.74 (dd, J=7.8, 4.8 Hz, 1H), 3.46 (dd, J=10.2, 8.7 Hz, 1H), 3.40 (dd, J=10.3, 3.7 Hz, 1H). $^{13}$C NMR (151 MHz, CDCl$_3$) δ 158.59, 158.55, 143.61, 143.48, 137.41, 137.18, 136.76, 128.81, 128.61, 128.52, 128.44, 128.23, 128.21, 128.07, 128.01, 127.92, 122.47, 122.21, 114.83, 114.77, 99.40, 98.46, 85.67, 79.87, 79.06, 78.79, 77.17, 75.63, 75.49, 75.43, 74.02, 71.80, 69.95, 65.79, 63.24, 55.66, 55.60. HRMS (ESI) ([M+NH4]$^+$) Calcd. For C$_{47}$H$_{53}$N$_4$O$_{17}$S$_2$: 1009.2847, found 1009.2816.

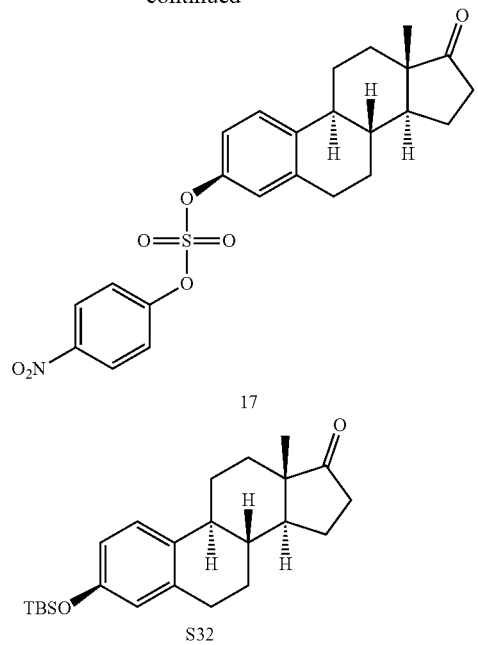

In a 25 mL flask, estrone S31 (0.5 g, 1.85 mmol) and imidazole (188.9 mg, 2.77 mmol) was dissolved in DCM/DMF (5 mL/2 mL). After cooling down to 0° C., tert-butyldimethylsilane chloride (278.7 mg, 1.85 mmol) was added under an N$_2$ atmosphere. After stirring overnight, water (10 mL) was added to the solution, which was further extracted by ethyl acetate (20 mL). The organic layer was concentrated and purified by column chromatography using hexane/ethyl acetate (10:1) as eluent, yielding the S32 as a white powder (606 mg, 85%). $^1$H NMR (500 MHz, CDCl$_3$) δ 7.12 (d, J=8.5 Hz, 1H), 6.62 (dd, J=8.5, 2.7 Hz, 1H), 6.57 (d, J=2.6 Hz, 1H), 2.86 (dd, J=10.3, 6.3 Hz, 2H), 2.50 (dd, J=19.0, 8.7 Hz, 1H), 2.42-2.32 (m, 1H), 2.24 (td, J=10.8, 4.4 Hz, 1H), 2.14 (dt, J=18.6, 8.8 Hz, 1H), 2.09-1.91 (m, 3H), 1.68-1.37 (m, 6H), 0.98 (s, 9H), 0.91 (s, 3H), 0.19 (s, 6H). Spectral data matched those previously reported.

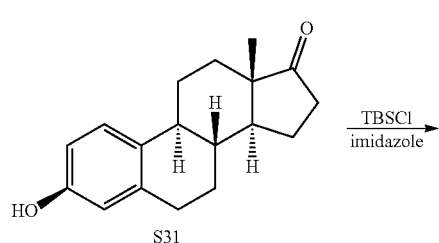

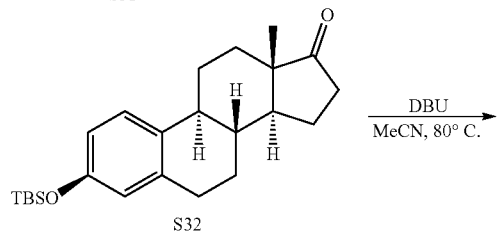

In a 25 mL flask, S32 (500 mg, 1.30 mmol) and 3a (316.2 mg, 1.43 mmol) were dissolved in acetonitrile (10 mL). DBU (39.6 mg, 0.26 mmol) was added to the solution under N$_2$ atmosphere. The mixture was heated to 80° C. and stirred for 2 h. The solvent was removed rapidly under reduced pressure, and the residue was purified by column chromatography using hexane/ethyl acetate (10/1~5/1) as eluent. The product 17 was obtained as a white powder (546 mg, 89%). ¹H NMR (500 MHz, CDCl₃) δ 8.33 (d, J=9.2 Hz, 2H), 7.51 (d, J=9.2 Hz, 2H), 7.34 (d, J=8.6 Hz, 1H), 7.07 (d, J=8.8 Hz, 1H), 7.04 (s, 1H), 2.93 (dd, J=9.2, 4.3 Hz, 2H), 2.52 (ddd, J=18.9, 8.7, 2.2 Hz, 1H), 2.45-2.36 (m, 1H), 2.30 (td, J=10.6, 3.7 Hz, 1H), 2.16 (dtd, J=18.6, 8.9, 2.3 Hz, 1H), 2.11-1.93 (m, 3H), 1.70-1.41 (m, 6H), 0.92 (d, J=1.9 Hz, 3H). ¹³C NMR (126 MHz, CDCl₃) δ 220.31, 154.32, 148.20, 146.44, 139.97, 139.26, 127.16, 125.80, 121.88, 120.80, 117.86, 50.39, 47.85, 44.11, 37.81, 35.79, 31.49, 29.42, 26.10, 25.72, 21.56, 13.80. HRMS (DART) ([M+H]⁺) Calcd. For $O_{24}H_{26}NO_7S$: 472.1430, found 472.1406.

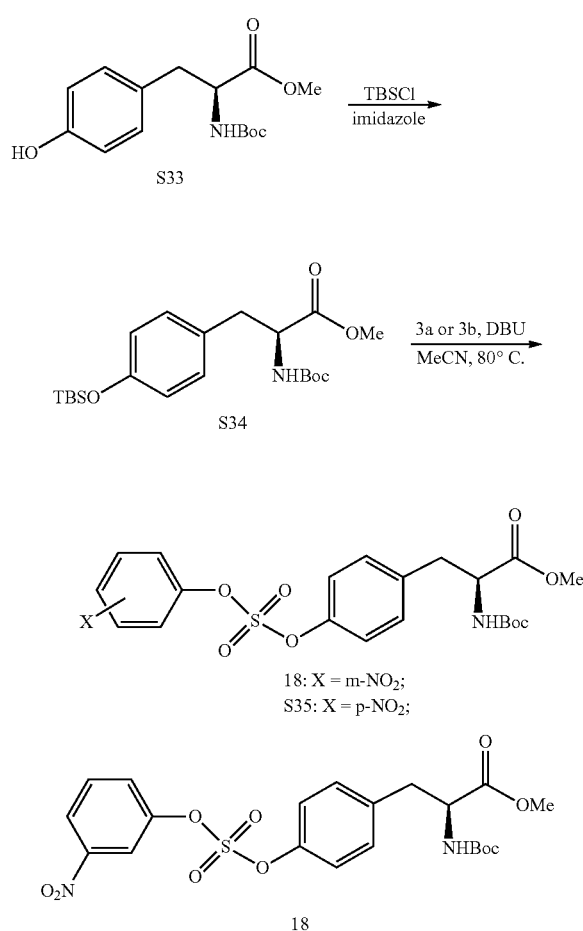

Compound 18 was prepared from S33 (0.5 g, 1.22 mmol) following the same procedure for the synthesis of 17. S33 was prepared according to a previously published procedure. The product was purified by silica gel chromatography (hexane/ethyl acetate 4:1-1:1) to obtain 18 (0.57 g, 94%). ¹H NMR (500 MHz, CDCl₃) δ 8.28-8.20 (m, 1H), 8.15 (s, 1H), 7.65 (d, J=5.6 Hz, 2H), 7.28 (d, J=8.7 Hz, 2H), 7.23 (d, J=8.7 Hz, 2H), 5.03 (d, J=8.1 Hz, 1H), 4.61 (q, J=6.8 Hz, 1H), 3.73 (s, 3H), 3.19 (dd, J=14.0, 5.7 Hz, 1H), 3.06 (dd, J=14.0, 6.4 Hz, 1H), 1.41 (s, 9H). ¹³C NMR (151 MHz, CDCl₃) δ 171.89, 154.96, 150.24, 149.17, 148.96, 136.54, 131.13, 130.90, 127.39, 122.52, 120.97, 116.95, 80.18, 54.24, 52.39, 37.85, 28.25. HRMS (ESI) ([M+Na]⁺) Calcd. For $C_{21}H_{24}N_2O_{10}SNa$: 519.1040, found 519.1045.

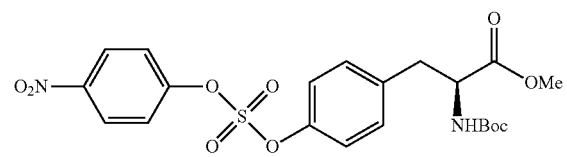

In a 25 mL flask, S32 (500 mg, 1.30 mmol) and 3a (316.2 mg, 1.43 mmol) were dissolved in acetonitrile (10 mL). DBU (39.6 mg, 0.26 mmol) was added to the solution under N₂ atmosphere. The mixture was heated to 80° C. and stirred for 2 h. The solvent was removed rapidly under reduced pressure, and the residue was purified by column chromatography using hexane/ethyl acetate (10/1-5/1) as eluent. The product 17 was obtained as a white powder (546 mg, 89%). ¹H NMR (500 MHz, CDCl₃) δ 8.33 (d, J=9.2 Hz, 2H), 7.51 (d, J=9.2 Hz, 2H), 7.34 (d, J=8.6 Hz, 1H), 7.07 (d, J=8.8 Hz, 1H), 7.04 (s, 1H), 2.93 (dd, J=9.2, 4.3 Hz, 2H), 2.52 (ddd, J=18.9, 8.7, 2.2 Hz, 1H), 2.45-2.36 (m, 1H), 2.30 (td, J=10.6, 3.7 Hz, 1H), 2.16 (dtd, J=18.6, 8.9, 2.3 Hz, 1H), 2.11-1.93 (m, 3H), 1.70-1.41 (m, 6H), 0.92 (d, J=1.9 Hz, 3H). ¹³C NMR (126 MHz, CDCl₃) δ 220.31, 154.32, 148.20, 146.44, 139.97, 139.26, 127.16, 125.80, 121.88, 120.80, 117.86, 50.39, 47.85, 44.11, 37.81, 35.79, 31.49, 29.42, 26.10, 25.72, 21.56, 13.80. HRMS (DART) ([M+H]⁺) Calcd. For $O_{24}H_{26}NO_7S$: 472.1430, found 472.1406.

Example 9: Compatibility Tests for Compounds S35 and 18

Condition a (Benzylamine+Et₃N)

To a solution of compound S35 (23.9 mg, 0.05 mmol) in DMF (0.5 mL) were subsequently added benzylamine (10.3 mg, 10.5 μL, 0.10 mmol) and Et₃N (4.9 mg, 6.7 μL, 0.05 mmol) at room temperature. The resulting mixture was allowed to stir at the same temperature for 24 h. The reaction was diluted with EA, washed by water, brine, dried over Na₂SO₄, filtered, and concentrated under reduced pressure. The residue was purified on a silica gel column on Biotage, providing recovered compound S35 (22.0 mg, 92% recovery).

Condition b (Benzyamine+DIPEA)

To a solution of compound S35 (19.5 mg, 0.04 mmol) in DMF (0.5 mL) was subsequently added benzylamine (8.4 mg, 8.6 μL, 0.08 mmol) and DIPEA (5.1 mg, 6.8 μL, 0.04 mmol) at room temperature. The resulting mixture was allowed to stir at the same temperature for 24 h. The reaction was diluted with EA, washed by water, brine, dried over Na₂SO₄, filtered, and concentrated under reduced pressure. The residue was purified on a silica gel column on Biotage, providing recovered compound S35 (16.7 mg, 86% recovery).

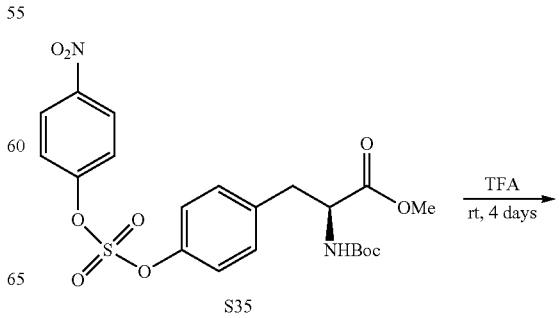

85

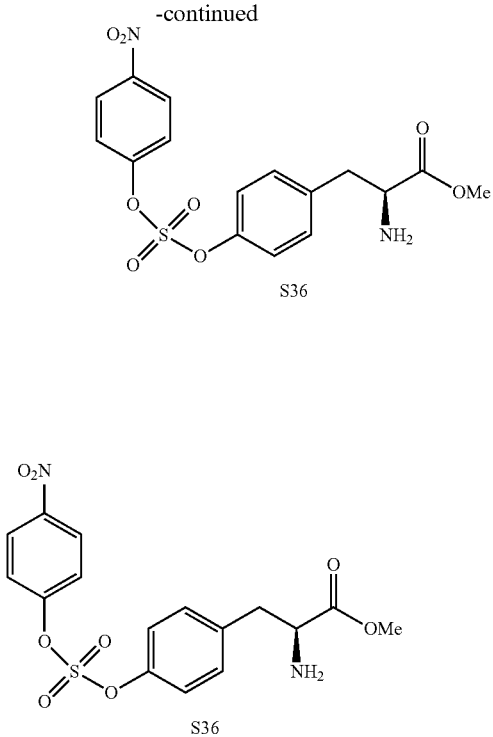

Condition c (Trifluoroacetic Acid)

To 20 mL vial equipped with compound S35 (18.8 mg, 0.04 mmol) and a stirring bar was added trifluoroacetic acid (TFA, 740.0 mg, 0.5 mL, 6.49 mmol) at room temperature. The resulting mixture was allowed to stir at the same temperature for 4 days. The reaction was diluted with EA, carefully washed by sat. aq. NaHCO$_3$, brine, dried over Na$_2$SO$_4$, filtered, and concentrated under reduced pressure. The residue was purified on a silica gel column on Biotage, providing de-Boc product S36 (14.0 mg, quantitative). $^1$H NMR (400 MHz, CDCl$_3$) δ 8.37-8.28 (m, 2H), 7.55-7.43 (m, 2H), 7.35-7.19 (m, 5H), 3.72 (s, 1H), 3.10 (dd, J=13.7, 5.3 Hz, 1H), 2.90 (dd, J=13.7, 7.8 Hz, 1H), 1.50 (broad, 2H).

Condition d (Piperidine)

To a vial equipped with compound S35 (36.8 mg, 0.07 mmol) and a stirring bar was added 20% piperidine in DMF (0.5 mL) at room temperature. The resulting mixture was allowed to stir at the same temperature for 1 h. The reaction was diluted with EA, washed by water, brine, dried over Na$_2$SO$_4$, filtered, and concentrated under reduced pressure. The residue was purified on a silica gel column on Biotage, providing recovered compound S36 (19.8 mg, 54% recovery).

Condition e (Piperidine)

Figure 12:
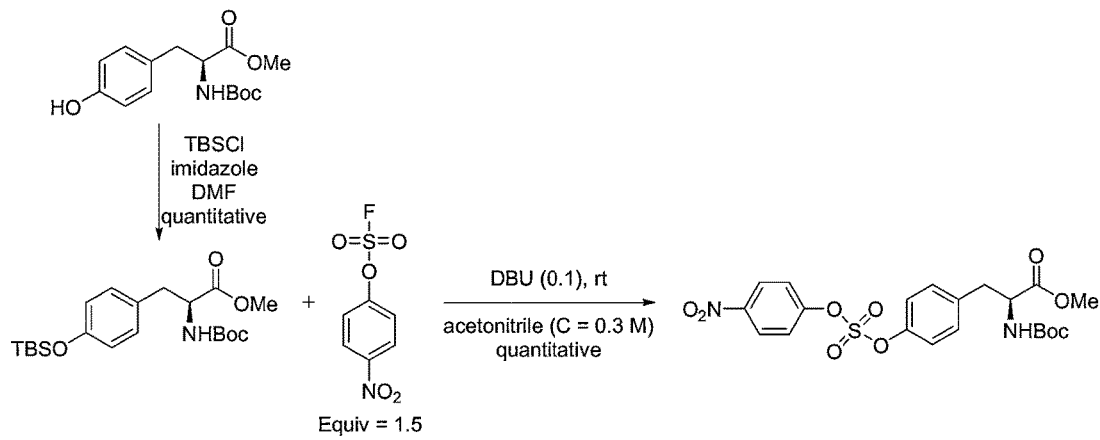
FIG. 12 shows incorporation of a sulfate diester on tyrosine and robustness tests for various experimental conditions.
Figure 12:
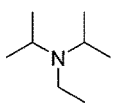
Figure 13:
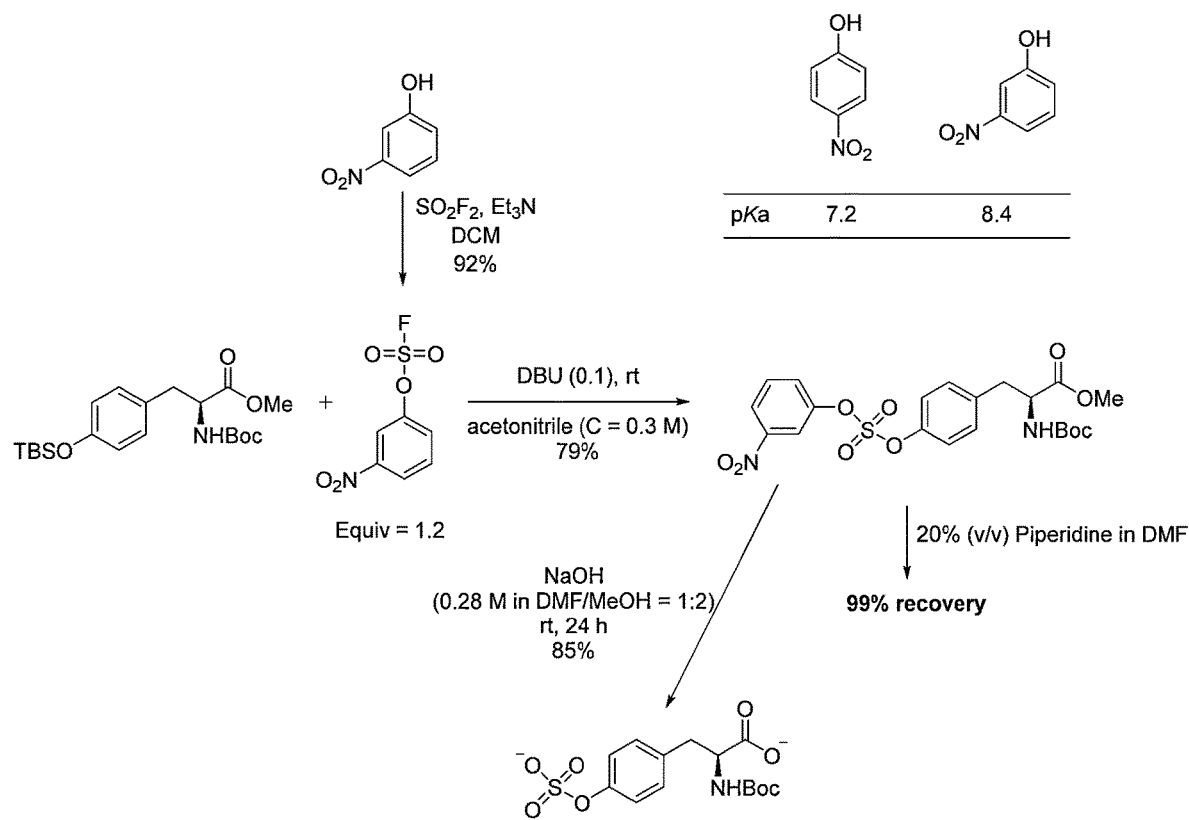
FIG. 13 shows tuning of the stability of tyrosine sulfate diesters to be compatible with piperidine.
Figure 14:
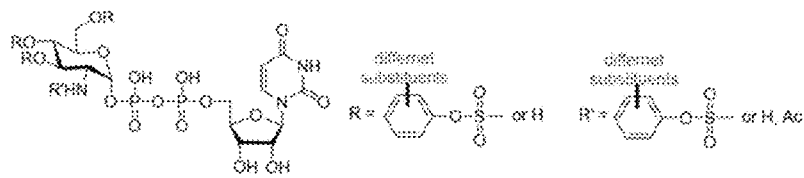
FIG. 14 shows several applications of reaction products as disclosed herein, including, but not limited to, using a UDP sugar with a masked sulfate for enzymatic synthesis, photocaging for drug delivery of sugar-containing anticancer drugs, and synthesis of sulfated polysaccharides.
Figure 14:
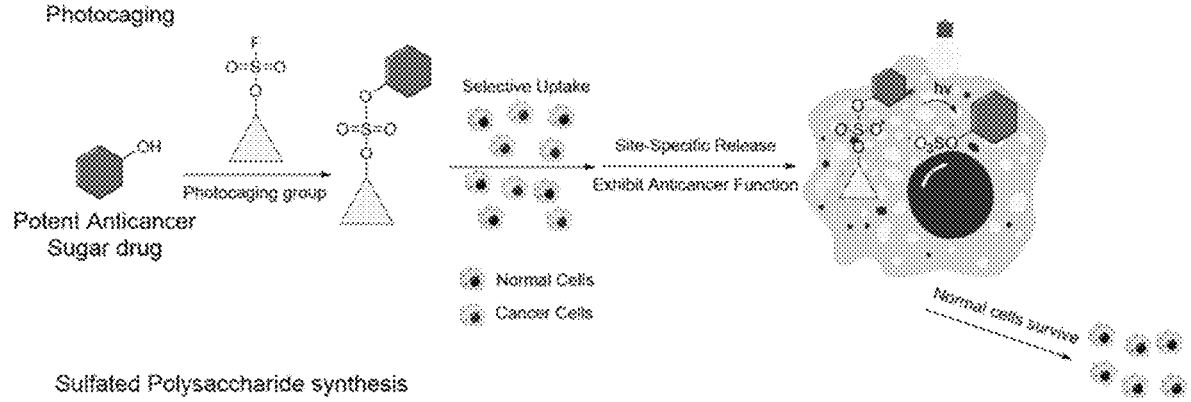
Figure 14:
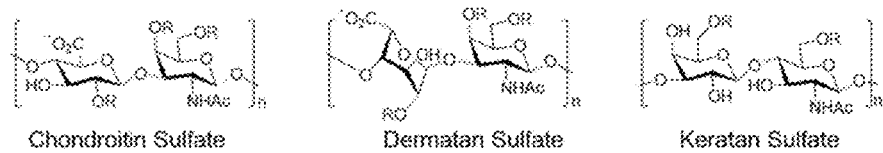
Figure 14:
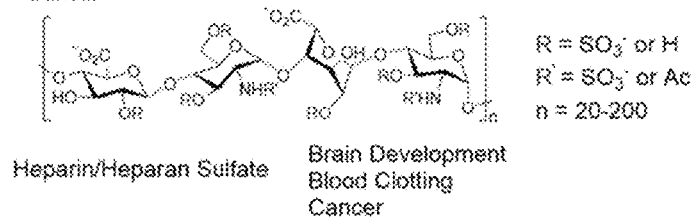
Figure 15D:
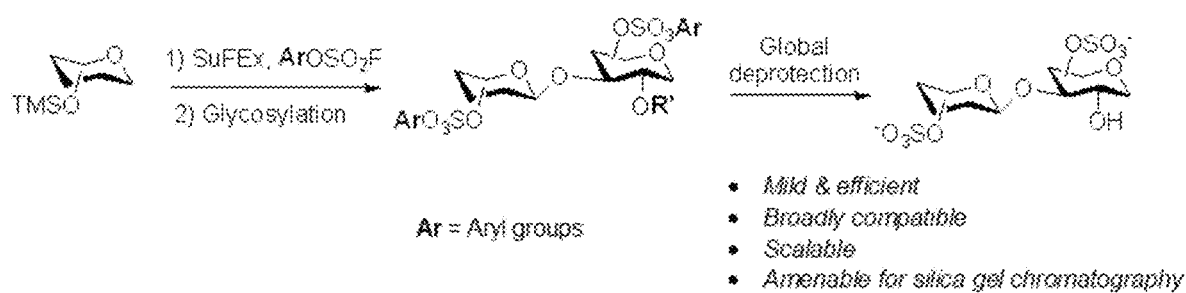

To a vial equipped with compound 18 (37.0 mg, 0.07 mmol) and a stirring bar was added 20% piperidine in DMF (0.5 mL) at room temperature. The resulting mixture was allowed to stir at the same temperature for 1 h. The reaction was diluted with EA, washed by water (three times), brine, dried over Na$_2$SO$_4$, filtered, and concentrated under reduced pressure. The residue was purified on a silica gel column on Biotage, providing recovered compound S35 (36.8 mg, quantitative recovery; see also FIGS. 12-13).

86

Example 10: O-Acetylation Reactions

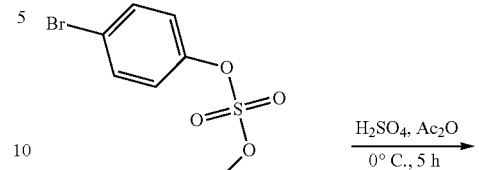

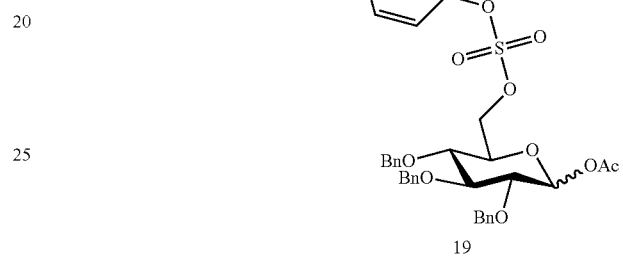

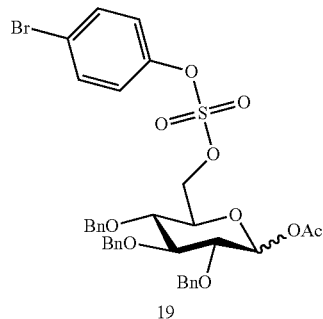

To a solution of compound 6 (181.6 mg, 0.26 mmol) in acetic anhydride (865.3 μL) was added sulfuric acid (5.1 mg, 2.8 μL, dissolved in 203.8 μL acetic anhydride) dropwise at 0° C. under a nitrogen atmosphere. The resulting mixture was allowed to stir at the same temperature for 2 hours until the NMR detection showed no residue of the starting material. The whole reaction mixture was diluted with EA, washed by sat. aq. NaHCO$_3$, brine and dried over anhydrous Na$_2$SO$_4$, filtered. The filtrate was concentrated under reduced pressure for the purification on Biotage to provide a α/β=11.1:1.0 mixture of compound 19 (159.9 mg, 85%). Major α isomer: $^1$H NMR (600 MHz, CDCl$_3$) δ 7.51-7.44 (m, 2H), 7.36-7.27 (m, 13H), 7.26-7.22 (m, 2H), 7.18-7.13 (m, 2H), 6.27 (d, J=3.5 Hz, 1H), 4.99 (d, J=10.9 Hz, 1H), 4.91 (d, J=10.7 Hz, 1H), 4.81 (d, J=10.9 Hz, 1H), 4.68 (d, J=11.4 Hz, 1H), 4.64 (d, J=11.4 Hz, 1H), 4.58 (d, J=10.8 Hz, 1H), 4.51-4.50 (t, J=3.0 Hz, 2H), 4.02-3.93 (m, 2H), 3.62 (dd, J=9.6, 3.6 Hz, 1H), 3.54 (dd, J=10.2, 8.9 Hz, 1H), 2.13 (s, 3H); $^{13}$C NMR (151 MHz, CDCl$_3$) δ 169.16, 149.13, 138.25, 137.28, 137.27, 137.21, 133.01, 132.93, 128.64, 128.56, 128.49, 128.46, 128.21, 128.14, 128.12, 128.08, 127.81, 127.79, 127.78, 127.76, 89.40, 89.39, 81.34, 78.58, 75.90, 75.66, 75.39, 73.34, 72.17, 70.74, 20.99; HRMS (ESI) m/z [M+Na]$^+$ calcd for C$_{35}$H$_{35}$O$_{10}$BrSNa 749.1027, found 749.1029.

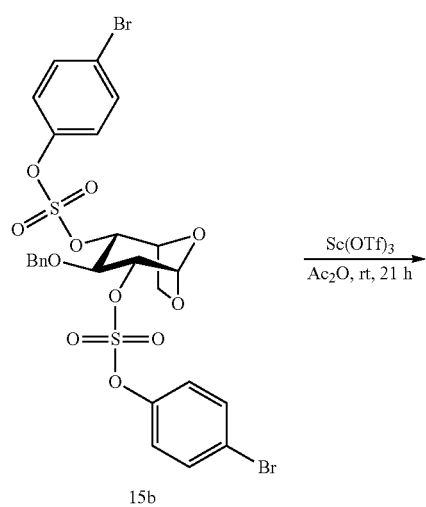

15b

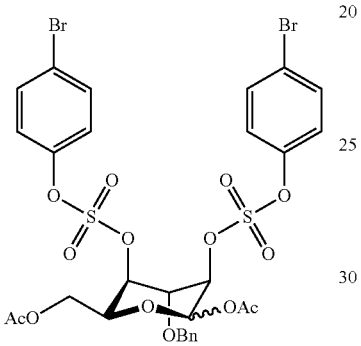

20

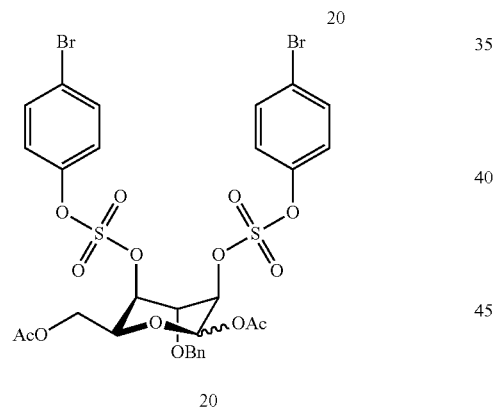

20

To a solution of compound 15b (1.30 g) in Ac₂O (30.0 mL) was added scandium (III) triflate (Sc(OTf)₃, 578.7 mg, 1.18 mmol) at room temperature under a nitrogen atmosphere. 21 h later, the whole reaction mixture was diluted with EA, carefully washed by sat. aq. NaHCO₃ twice (a great deal of CO₂ was released), then washed by brine, dried over anhydrous Na₂SO₄, and filtered. The filtrate was concentrated under reduced pressure for the purification on Biotage to provide a α/β=0.9:1.0 mixture of compound 25 (159.9 mg, 85%). $^1$H NMR (500 MHz, CDCl₃) δ 7.51-7.45 (m, 8H), 7.39-7.28 (m, 10H), 7.16-7.11 (m, 4H), 7.11-7.05 (m, 4H), 6.27 (s, 1H), 6.08 (d, J=1.5 Hz, 1H), 4.82 (m, 1H), 4.74 (m, 2H), 4.71-4.70 (m, 1H), 4.69 (s, 1H), 4.68 (d, J=2.9 Hz, 1H) 4.63-4.59 (m, 1H), 4.44-4.41 (m, 1H), 4.31 (t, J=2.9 Hz, 1H), 4.29-4.17 (m, 5H), 2.12 (s, 3H), 2.10 (s, 3H), 2.07 (s, 3H), 2.06 (s, 3H).

Example 11: Removal of Protecting Groups

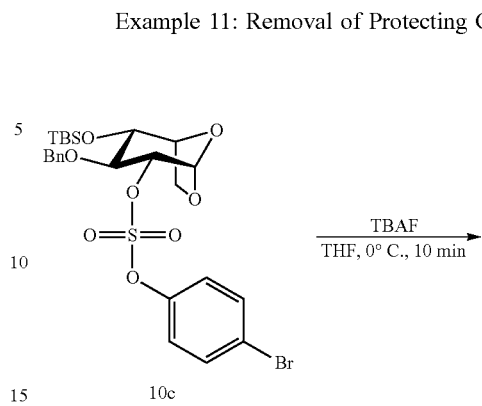

10c

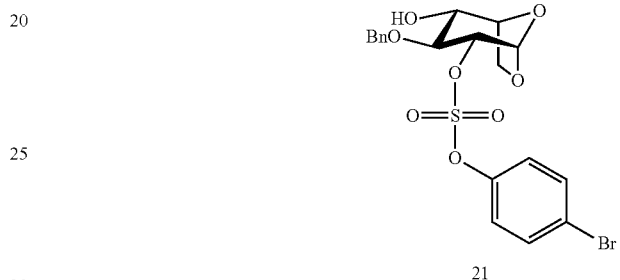

21

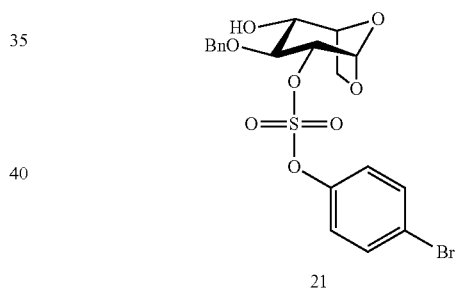

21

To a solution of compound 10c (3.47 g, 5.77 mmol) in tetrahydrofuran (THF, 57.7 mL) was added tetrabutylammonium fluoride (TBAF, 1 M solution in THF, 6.34 mL, 6.34 mmol) at 0° C. 10 min later, TLC showed full consumption of the starting material. The whole reaction mixture was diluted with EA, washed by aq. NH₄Cl, brine, dried over anhydrous Na₂SO₄, filtered, and concentrated under reduced pressure. The filtrate was purified on a silica gel column on Biotage to provide compound 23 (2.40 g, 85%). $[α]_D^{20}$=+22.0 (c 1.01, CHCl₃); $^1$H NMR (500 MHz, CDCl₃) δ 7.49-7.44 (m, 2H), 7.38-7.33 (m, 2H), 7.34-7.29 (m, 3H), 7.28-7.21 (m, 2H), 5.64 (d, J=1.7 Hz, 1H), 4.82 (d, J=11.5 Hz, 1H), 4.65 (dd, J=8.1, 1.7 Hz, 1H), 4.62 (d, J=11.5 Hz, 1H), 4.45 (t, J=4.6 Hz, 1H), 4.11 (d, J=7.9 Hz, 1H), 3.92 (ddd, J=8.1, 4.4, 1.1 Hz, 1H), 3.76 (ddd, J=8.0, 4.9, 1.1 Hz, 1H), 3.71 (t, J=8.1 Hz, 1H), 2.13 (s, 1H); $^{13}$C NMR (126 MHz, CDCl₃) δ 149.29, 137.75, 133.20, 128.88, 128.41, 128.10, 123.28, 121.20, 98.67, 86.18, 80.00, 75.26, 75.16, 71.74, 65.70; HRMS (DART) m/z [M+NH₄]⁺ calcd for C₁₉H₂₃O₈NSBr 504.0322, found 504.0318.

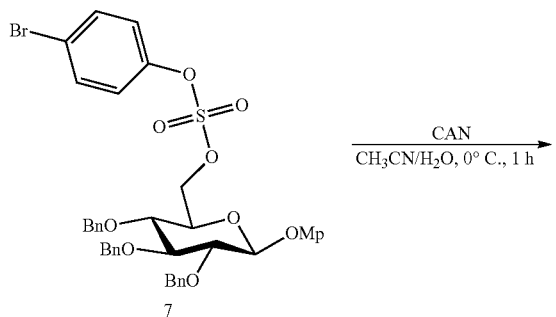

To a suspension of compound 7 (2.31 g, 2.92 mmol) in CH₃CN/H₂O (40.9 mL/17.5 mL) was added ceric ammonium nitrate (CAN, 3.85 g, 17.51 mmol) at 0° C. 1 h later, TLC indicated no starting material left. The whole reaction mixture was poured into ice-water mixture, extracted with DCM twice. The combined organic layer was washed by sat. aq. NaHCO₃, brine, dried over anhydrous Na₂SO₄, and filtered. The filtrate was purified on silica gel column to provide lactol 22 (1.84 g, 92%) which was used directly in the following step without further characterization. $^1$H NMR (500 MHz, CDCl₃) δ 7.48-7.44 (m, 2H), 7.40-7.24 (m, 20H), 7.20-7.15 (m, 2H), 5.17 (d, J=3.5 Hz, 1H), 5.01-4.97 (m, 1H), 4.94-4.89 (m, 2H), 4.88-4.84 (m, 1H), 4.79 m, 1H), 4.70 (d, J=11.7 Hz, 1H), 4.61-4.57 (m, 2H), 4.55-4.52 (m, 2H), 4.20-4.11 (m, 2H), 4.01 (t, J=9.2 Hz, 1H), 3.57-3.48 (m, 2H); HRMS (DART) m/z [M+NH₄]⁺ calcd for C₃₃H₃₇O₉BrSN 702.1367, found 702.1365.

To a solution of compound 8 (100.6 mg) in DCM (1.60 mL) was added m-CPBA (26.7 mg, 0.16 mmol) at −78° C. under a nitrogen atmosphere. 2 h later, the whole reaction mixture was moved to stir for another 3 h at 0° C. The whole reaction mixture was then diluted with EA, washed by aq. Na₂S₂O₃, sat. aq. NaHCO₃, brine and dried over anhydrous Na₂SO₄, filtered. The filtrate was concentrated under reduced pressure for the purification on Biotage to provide a 1.1:1.0 diastereomeric mixture of compound 23 (159.9 mg, 85%). $^1$H NMR (600 MHz, CDCl₃) δ 7.55 (d, J=7.9 Hz, 2H), 7.51 (d, J=7.9 Hz, 2H), 7.39-7.30 (m, 14H), 7.27-7.24 (m, 3H), 7.19-7.17 (m, 2H), 6.95-6.87 (m, 1H), 4.94 (d, J=10.7 Hz, 1H), 4.90 (d, J=10.8 Hz, 1H), 4.87-4.78 (m, 1H), 4.60 (dd, J=10.9, 1.8 Hz, 1H), 4.55 (dd, J=11.0, 4.8 Hz, 1H), 4.42 (dd, J=10.8, 5.0 Hz, 1H), 4.33 (dd, J=10.8, 1.9 Hz, 1H), 4.27 (dd, J=10.8, 5.5 Hz, 1H), 4.17 (d, J=9.8 Hz, 1H), 3.89 (t, J=9.8 Hz, 1H), 3.80-3.74 (m, 7H), 3.67-3.60 (m, 3H), 3.55-3.39 (m, 1H), 2.42 (s, 3H), 2.38 (s, 3H); $^{13}$C NMR (151 MHz, CDCl₃) δ 158.72, 158.68, 143.73, 143.67, 142.51, 142.23, 137.23, 137.17, 136.95, 136.92, 136.54, 135.47, 130.06, 129.87, 128.83, 128.79, 128.71, 128.69, 128.51, 128.49, 128.33, 128.31, 128.28, 128.26, 128.24, 128.20, 128.17, 125.52, 125.49, 124.54, 122.54, 122.48, 115.05, 115.03, 94.28, 91.40, 84.95, 84.74, 77.28, 76.32, 76.12, 76.06, 75.97, 75.35, 71.33, 71.30, 60.75, 59.82, 55.78, 55.77, 21.58, 21.57; HRMS (DART) m/z [M+H]⁺ calcd for C₃₄H₃₆O₉S₂N₃ 694.1887, found 694.1906.

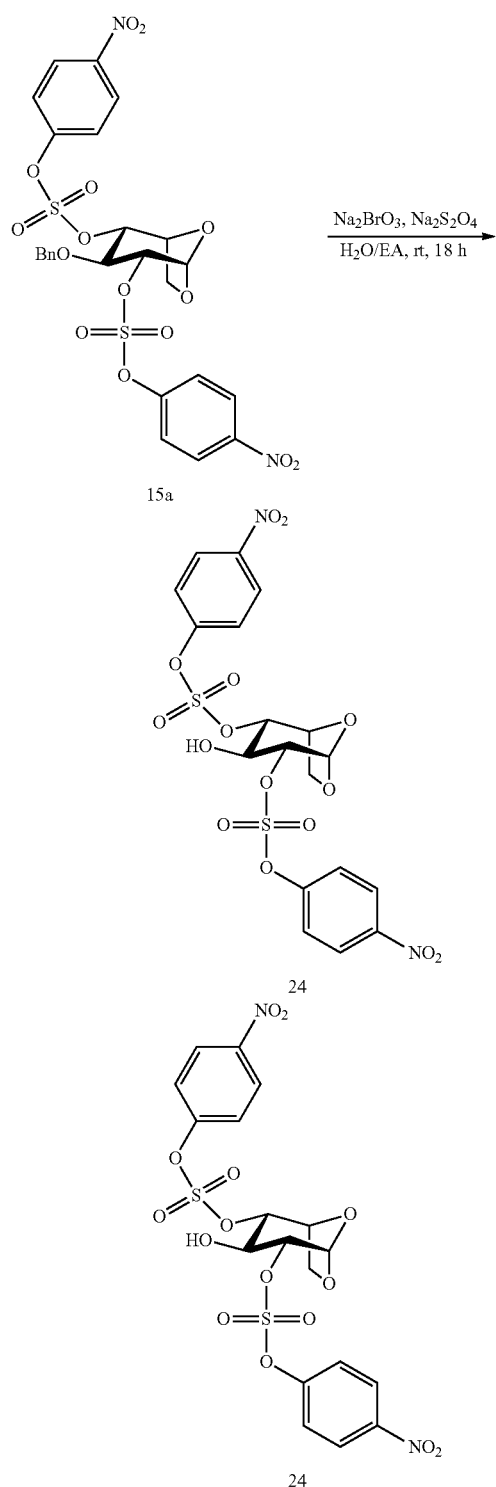

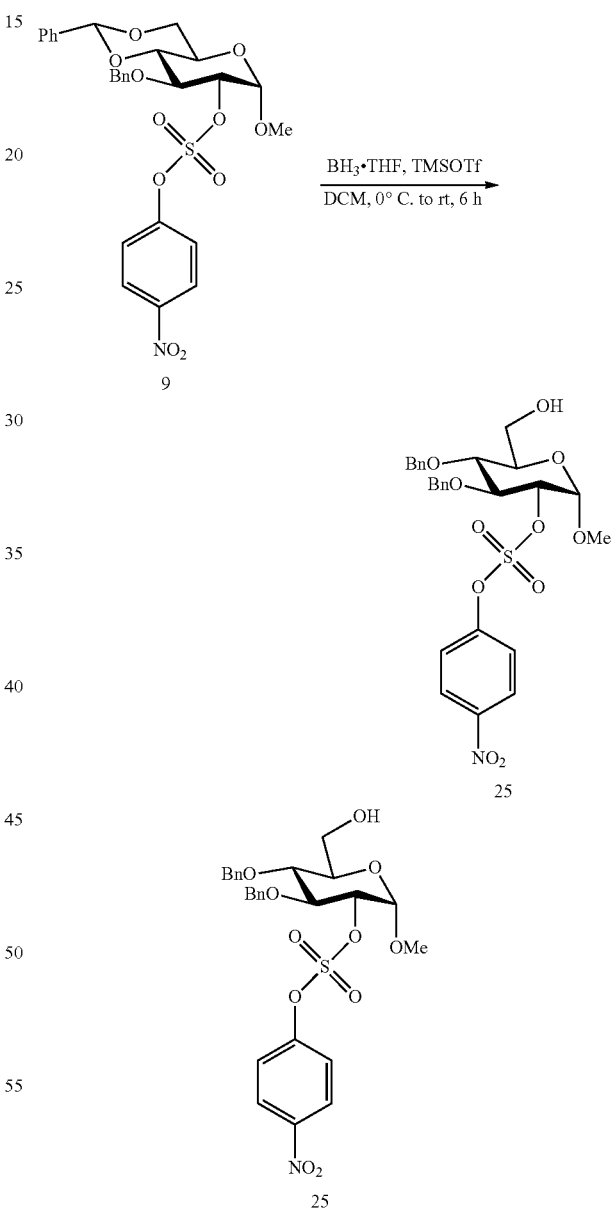

To a solution of compound 15a (360.2 mg, 0.55 mmol) in EA (7.0 mL) was added sodium bromate (Na$_2$BrO$_3$, 747.3 mg, 4.95 mmol, dissolved in 10.8 mL H$_2$O). An aqueous solution of sodium dithionite (Na$_2$S$_2$O$_4$, 766.5 mg, 4.40 mmol, dissolved in 18.7 mL H$_2$O) was added dropwise via an injection pump in 18 min at room temperature. The resulting reaction mixture was allowed to stir for 18 h. TLC showed a full conversion of the starting material. The reaction was diluted with EA, washed with aq. Na$_2$S$_2$O$_3$ four times, washed with brine, dried over anhydrous Na$_2$SO$_4$, filtered, and concentrated under reduced pressure. The filtrate was purified by a silica gel column on Biotage to provide compound 24 (310.0 mg, quantitative). $[\alpha]_D^{20}$=+ 14.4 (c 1.00, acetone); $^1$H NMR (600 MHz, acetone-d$_6$) δ 8.43-8.37 (m, 4H), 7.83-7.74 (m, 4H), 5.79 (d, J=1.8 Hz, 1H), 5.08-4.99 (m, 2H), 4.29-4.26 (m, 2H), 3.93 (ddd, J=8.7, 4.6, 1.5 Hz, 1H), 2.83 (s, 1H); $^{13}$C NMR (151 MHz, acetone-d$_6$) δ 155.15, 155.12, 147.64, 147.61, 126.68, 126.64, 123.49, 123.39, 99.44, 87.65, 84.17, 73.60, 69.40, 66.57; HRMS (ESI) m/z [M+Na]$^+$ calcd for C$_{18}$H$_{16}$O$_{15}$N$_2$S$_2$Na 586.9884, found 586.9870.

To a solution of compound 9 (215.5 mg, 0.38 mmol) in DCM (3.8 mL) was added borane tetrahydrofuran complex solution (BH3.THF, 1 M in THF, 2.3 mL, 2.3 mmol) and trimethylsilyl trifluoromethanesulfonate (TMSOTf, 25.1 mg, 21.7 μL, 0.11 mmol) subsequently at 0° C. under a nitrogen atmosphere. The resulting mixture was moved to stir at room temperature. 6 h later, TLC showed complete conversion of the starting material. Triethylamine (22.8 mg, 31.4 µL, 0.23 mmol) was added to quench the reaction. The whole mixture was concentrated under reduced pressure and co-evaporated twice with methanol. The residue was directly purified with silica gel column on Biotage to provide compound 25 (215.0 mg, 99%). $[\alpha]_D^{20}$=+59.6 (c 0.54, CHCl$_3$); $^1$H NMR (500 MHz, CDCl$_3$) δ 8.09-8.01 (m, 2H), 7.48-7.39 (m, 2H), 7.36-7.26 (m, 10H), 5.11 (d, J=3.6 Hz, 1H), 4.88 (d, J=2.0 Hz, 1H), 4.86 (d, J=2.0 Hz, 1H), 4.75 (d, J=11.0 Hz, 1H), 4.71-4.65 (m, 2H), 4.15-4.07 (m, 1H), 3.83 (ddd, J=11.9, 5.2, 1.6 Hz, 1H), 3.78-3.67 (m, 4H), 3.38 (s, 3H), 1.62 (dd, J=7.9, 5.1 Hz, 1H); $^{13}$C NMR (101 MHz, CDCl$_3$) δ 154.31, 146.32, 137.65, 128.74, 128.62, 128.30, 128.18, 128.10, 127.71, 125.70, 121.89, 96.70, 83.52, 79.07, 77.65, 75.80, 75.45, 71.02, 61.38, 55.57; HRMS (DART) m/z [M+NH$_4$]$^+$ calcd for C$_{27}$H$_{33}$O$_{11}$N$_2$S 593.1800, found 593.1785.

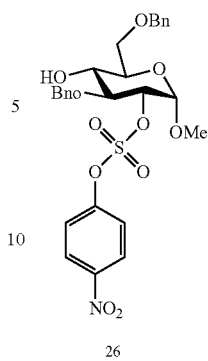

26

To a solution of compound 9 (391.5 mg, 2.46 mmol) in DCM (7.0 mL) was added triethylsilane (Et$_3$SiH, 400.4 mg, 550.0 µL, 3.44 mmol) and trifluoroacetic acid (TFA, 389.1 mg, 262.9 µL, 3.41 mmol) at 0° C. under a nitrogen atmosphere. The resulting mixture was allowed to stir at the same temperature for 4 h. TLC showed complete conversion of the starting material. The whole reaction mixture was diluted with EA, washed with sat. aq. NaHCO$_3$, washed with brine, dried over anhydrous Na$_2$SO$_4$, filtered, and concentrated under reduced pressure. The filtrate was purified with silica gel column on Biotage to provide compound 26 (374.6 mg, 95%). $[\alpha]_D^{20}$=+56.4 (c 1.01, CHCl$_3$); $^1$H NMR (500 MHz, CDCl$_3$) δ 8.14-8.06 (m, 2H), 7.48-7.42 (m, 2H), 7.38-7.26 (m, 10H), 5.10 (d, J=3.6 Hz, 1H), 4.79-4.71 (m, 2H), 4.69 (dd, J=9.7, 3.6 Hz, 1H), 4.61 (d, J=12.1 Hz, 1H), 4.55 (d, J=12.1 Hz, 1H), 3.92 (dd, J=9.7, 7.9 Hz, 1H), 3.82-3.72 (m, 3H), 3.71-3.65 (m, 1H), 3.39 (s, 3H); $^{13}$C NMR (126 MHz, CDCl$_3$) δ 154.35, 146.35, 137.86, 137.71, 128.73, 128.66, 128.24, 128.08, 127.93, 127.89, 125.69, 121.96, 96.76, 83.30, 78.76, 75.60, 73.93, 72.32, 69.71, 69.51, 55.62.

Example 12: Azido Reduction

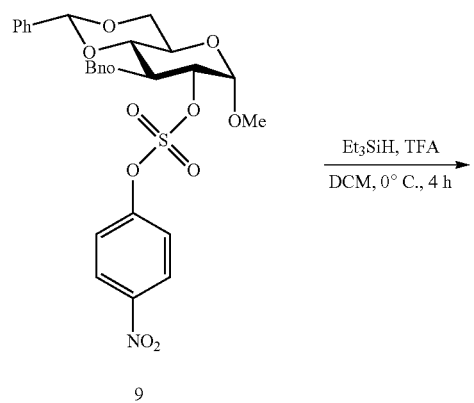

9

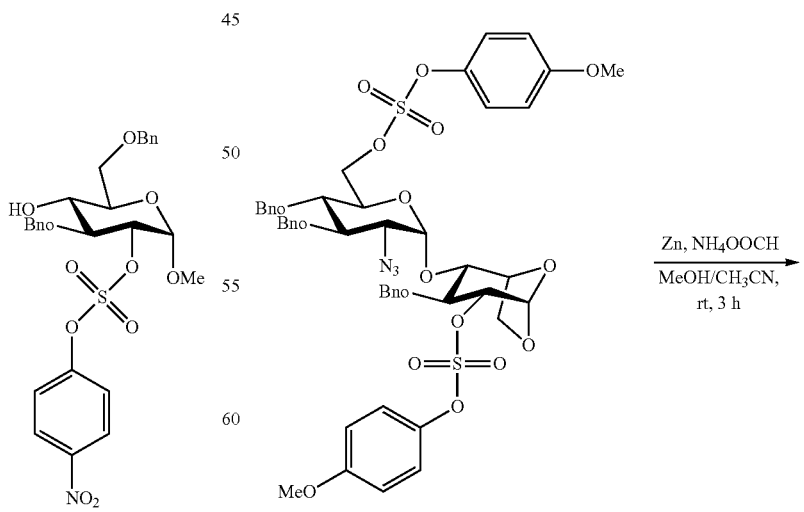

95
-continued

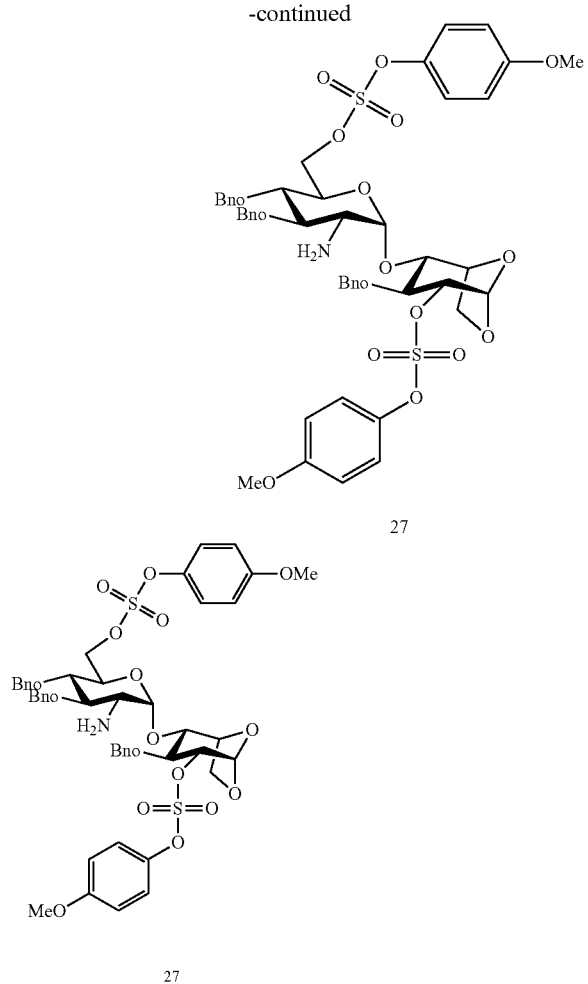

27

27

96
Example 13: N-Sulfation

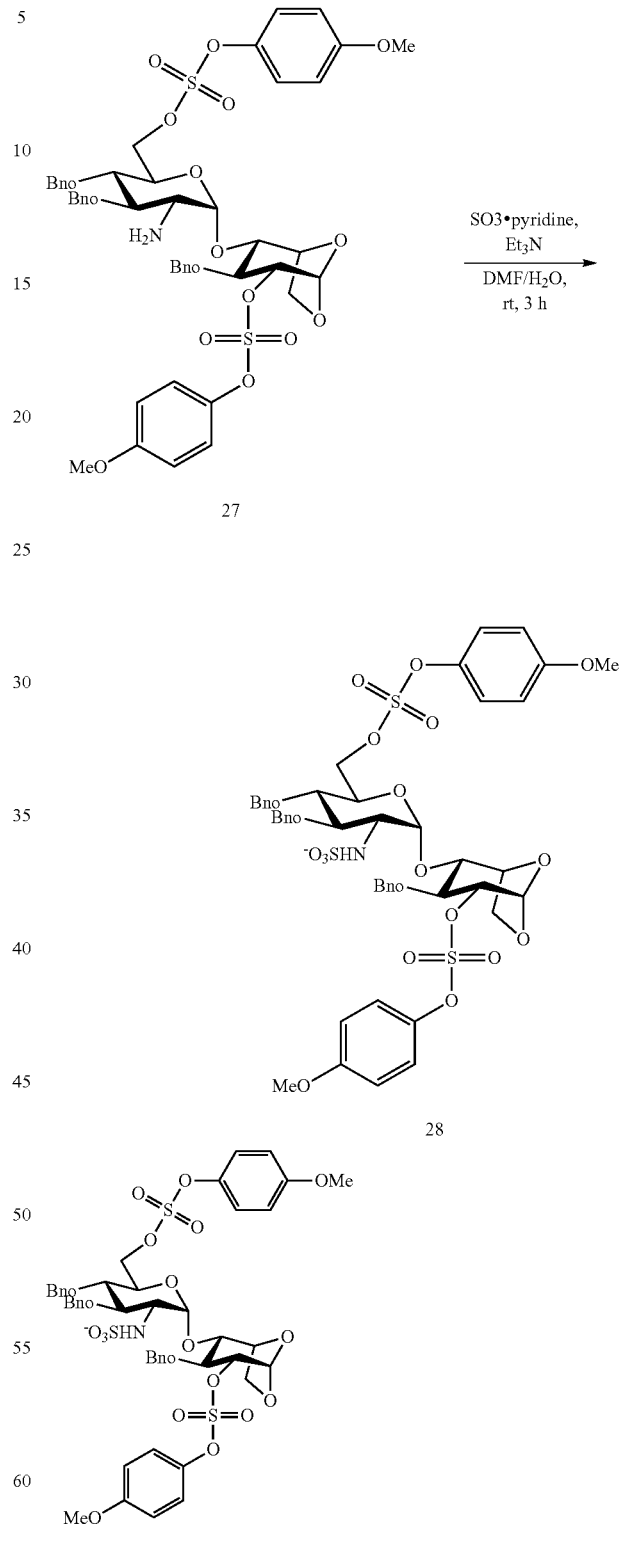

To a solution of disaccharide 16 (789.5 mg, 0.80 mmol) in MeOH/CH$_3$CN (17.8 mL/3.0 mL) were consecutively added ammonium formate (NH$_4$OOCH, 1.99 g, 31.6 mmol) and zinc powder (Zn, 520.4 mg, 7.96 mmol) at rt. The resulting mixture was allowed to stir at the same temperature for 3 h. The reaction mixture was filtered, diluted with EA, washed with sat. aq. NaHCO$_3$, washed with brine, dried over anhydrous Na$_2$SO$_4$, and filtered. The filtrate was concentrated under reduced pressure for the purification with a silica gel column on Biotage to provide product 27 (401.4 mg, 78%). $[\alpha]_D^{20}$=+42.6 (c 1.02, CHCl$_3$); $^1$H NMR (500 MHz, CDCl$_3$) δ 7.40-7.23 (m, 17H), 7.21-7.12 (m, 2H), 6.90-6.84 (m, 2H), 6.84-6.77 (m, 2H), 5.58 (d, J=1.7 Hz, 1H), 5.04 (d, J=3.6 Hz, 1H), 4.94 (d, J=11.3 Hz, 1H), 4.88 (d, J=10.9 Hz, 1H), 4.77 (d, J=10.5 Hz, 1H), 4.73 (d, J=11.2 Hz, 1H), 4.68-4.61 (m, 2H), 4.57 (d, J=10.9 Hz, 1H), 4.53 (t, J=4.6 Hz, 1H), 4.47 (dd, J=10.5, 1.8 Hz, 1H), 4.34 (dd, J=10.5, 6.5 Hz, 1H), 4.00 (d, J=7.9 Hz, 1H), 3.86 (dd, J=8.3, 4.1 Hz, 1H), 3.84-3.79 (m, 2H), 3.78 (s, 3H), 3.76 (s, 3H), 3.75-3.69 (m, 1H), 3.49 (t, J=9.4 Hz, 1H), 3.36 (t, J=9.4 Hz, 1H), 2.78 (dd, J=10.1, 3.7 Hz, 1H), 1.38 (broad, 2H; NH2); $^{13}$C NMR (151 MHz, CDCl$_3$) δ 158.73, 158.71, 143.76, 143.66, 138.09, 137.48, 137.18, 128.93, 128.78, 128.60, 128.56, 128.40, 128.27, 128.24, 128.13, 128.04, 122.62, 122.43, 114.96, 114.92, 102.03, 98.55, 86.02, 83.34, 79.72, 78.80, 77.85, 75.90, 75.45, 75.38, 74.17, 72.50, 70.60, 65.83, 56.01, 55.81, 55.75; HRMS (ESI) m/z [M+H]$^+$ calcd for O$_{47}$H$_{52}$O$_{17}$S$_2$N 966.2671, found 966.2398.

To a solution of amine S2 (251.3 mg, 0.26 mmol) in DMF/MeOH (1.6 mL/4.9 mL) were consecutively added Et$_3$N (1.83 g, 18.05 mmol, 2.52 mL) and sulfur trioxide pyridine complex (414.0 mg, 2.60 mmol) at room temperature. 3 h later, aqueous solution of NaHCO$_3$ (874.2 mg, 10.41 mmol, 404.7 µL, dissolved in 4.9 mL H$_2$O) was added the reaction. The resulting mixture was allowed to stir for another 30 min, filtered through a pad of Celite, and concentrated. The residue was purified on a silica gel column with DCM/MeOH=10:1 as eluent on Biotage to provide N-Sulfated compound 28 (199.0 mg, 72%). $^1$H NMR (500 MHz, CD$_3$OD) δ 7.48-7.43 (m, 2H), 7.42-7.36 (m, 2H), 7.35-7.15 (m, 15H), 6.95-6.90 (m, 2H), 6.85-6.80 (m, 2H), 5.54 (d, J=1.7 Hz, 1H), 5.51 (d, J=3.5 Hz, 1H), 4.98 (d, J=11.0 Hz, 1H), 4.90 (d, J=11.2 Hz, 1H), 4.85 (d, J=11.0 Hz, 1H), 4.69 (d, J=7.3 Hz, 1H), 4.67 (d, J=7.1 Hz, 1H), 4.62-4.56 (m, 2H), 4.54 (d, J=11.1 Hz, 1H), 4.50 (dd, J=10.6, 1.8 Hz, 1H), 4.39 (dd, J=10.6, 7.0 Hz, 1H), 4.07 (ddd, J=8.3, 4.2, 1.1 Hz, 1H), 3.93 (d, J=8.1 Hz, 1H), 3.90-3.82 (m, 2H), 3.76 (s, 3H), 3.74 (s, 3H), 3.61-3.57 (m, 1H), 3.54-3.51 (m, 2H), 3.43 (dd, J=10.2, 8.4 Hz, 1H); $^{13}$C NMR (126 MHz, CD$_3$OD) δ 160.27, 160.16, 145.13, 145.01, 139.89, 139.25, 139.14, 129.70, 129.58, 129.54, 129.42, 129.37, 129.28, 129.24, 129.02, 128.70, 128.69, 128.64, 123.66, 123.63, 115.93, 115.79, 100.28, 99.67, 87.18, 81.14, 80.87, 78.59, 78.45, 76.09, 76.06, 75.70, 75.08, 74.24, 71.41, 66.63, 59.50, 56.26, 56.14; HRMS (ESI) m/z [M−H]$^-$ calcd for C$_{47}$H$_{50}$O$_{20}$S$_3$N 1044.2094, found 1044.2010.

Example 14: Glycosylation with Trichloroacetimidate (Schmidt) Donor

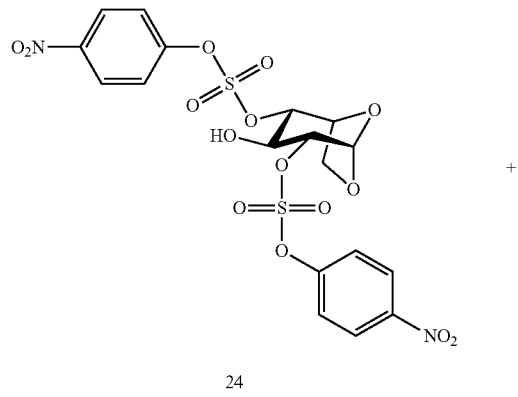

24

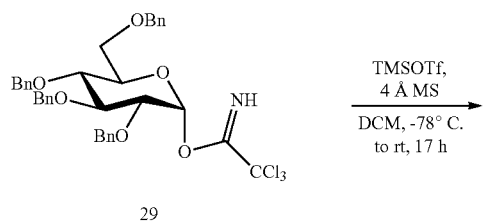

29

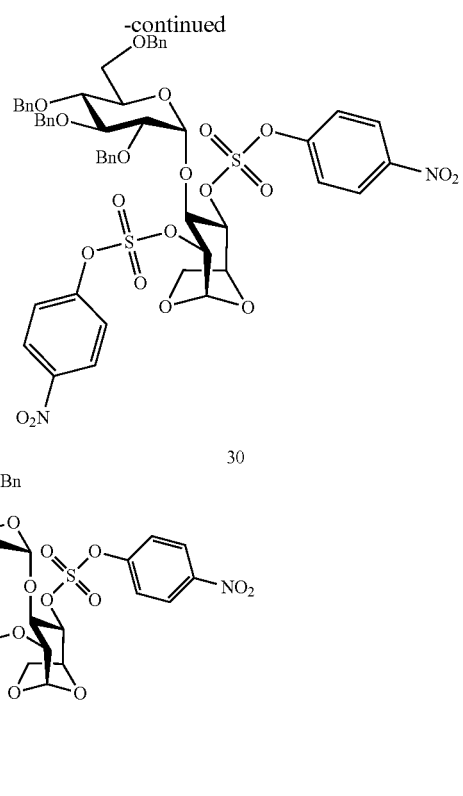

30

A mixture of acceptor 24 (102.9 mg, 0.18 mmol) and Schmidt donor 29 (153.5 mg, 0.22 mmol) was azeotropically dried with toluene three times. To a solution of above mixture in DCM (2.0 mL) was added freshly activated 4 Å MS (200 mg, 100 mg per 1 mL solvent) under a nitrogen atmosphere. The resulting mixture was allowed to stir at room temperature for 30 min. Then the reaction was cooled down to −78° C., followed by the addition of TMSOTf (4.6 mg, 4.0 µL, 0.02 mmol). The reaction was allowed to stir at the same temperature for 2 h, then was moved to stir at room temperature for another 15 h. Et$_3$N (3.6 mg, 0.04 mmol, 5.0 µL) was added to quench the reaction. The whole reaction mixture was filtered through a pad of Celite, diluted with EA, washed with phosphate buffer, washed with brine, dried over anhydrous Na$_2$SO$_4$, and filtered. The filtrate was concentrated under reduced pressure for the purification on Biotage to provide compound 30 (129.0 mg, 65%). [α]$_D^{20}$=+22.0 (c 1.01, CHCl$_3$); $^1$H NMR (600 MHz, CDCl$_3$) δ 8.27-8.20 (m, 2H), 7.98-7.93 (m, 2H), 7.49-7.44 (m, 2H), 7.43-7.39 (m, 2H), 7.35-7.23 (m, 16H), 7.22-7.20 (m, 2H), 7.12-7.05 (m, 2H), 5.82 (d, J=1.8 Hz, 1H), 5.37 (d, J=3.6 Hz, 1H), 5.16 (ddd, J=8.0, 4.5, 1.1 Hz, 1H), 4.98 (t, J=4.7 Hz, 1H), 4.80 (dd, J=8.0, 1.8 Hz, 1H), 4.78-4.72 (m, 3H), 4.69-4.58 (m, 3H), 4.46 (dd, J=11.2, 5.0 Hz, 2H), 4.38 (t, J=7.9 Hz, 1H), 4.17 (d, J=8.5 Hz, 1H), 4.03 (dt, J=10.1, 2.7 Hz, 1H), 3.93-3.86 (m, 2H), 3.79 (dd, J=10.9, 3.2 Hz, 1H), 3.74-3.67 (m, 2H), 3.61 (dd, J=9.9, 3.7 Hz, 1H); $^{13}$C NMR (151 MHz, CDCl$_3$) δ 153.49, 153.46, 146.84, 146.72, 138.56, 138.15, 137.95, 137.71, 128.60, 128.57, 128.52, 128.44, 128.26, 128.19, 128.08, 128.06, 127.95, 127.77, 127.72, 126.09, 125.78, 122.64, 122.13, 122.08, 98.41, 97.31, 84.78, 83.35, 81.55, 79.35, 75.71, 75.29, 73.68, 73.66, 72.48, 72.08, 71.54, 68.09, 65.77; HRMS (ESI) m/z [M+Na]+ calcd for $C_{52}H_{50}O_{20}N_2S_2Na$ 1109.2291, found 1109.2271.

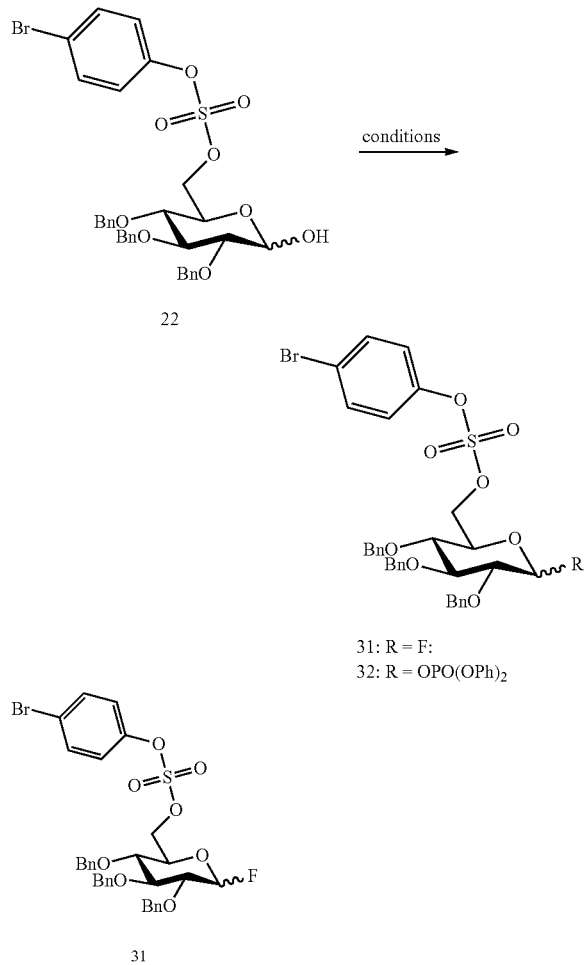

31: R = F:
32: R = OPO(OPh)$_2$

To a solution of above lactol 22 (596.4 mg, 0.87 mmol) in DCM (13.4 mL) was added (diethylamino)sulfur trifluoride (DAST, 1.40 g, 1.15 mL, 8.70 mmol) at −42° C. under a nitrogen atmosphere. The whole reaction mixture was moved to stir at 0° C. for 1.5 h. The reaction mixture was cooled down back to −42° C. and sat. aq. NaHCO$_3$ was added slowly to quench the reaction. The mixture was poured into a two-layer funnel with EA/sat. aq. NaHCO$_3$. The organic layer was washed with sat. aq. NaHCO$_3$ twice, washed with brine, dried over anhydrous Na$_2$SO$_4$, and filtered. The filtrate was concentrated under reduced pressure for the purification on Biotage to provide α/β=1.0:2.6 mixture of fluoride donor 31 (374.0 mg, 63%). Pure β-isomer was isolated: $[α]_D^{20}$=+25.5 (c 0.68, CHCl$_3$); $^1$H NMR (500 MHz, CDCl$_3$) δ 7.52-7.46 (m, 2H), 7.38-7.26 (m, 12H), 5.29 (ddd, J=52.6, 6.3, 0.9 Hz, 1H), 4.90-4.85 (m, 2H), 4.82 (d, J=11.1 Hz, 1H), 4.76 (d, J=11.1 Hz, 1H), 4.69 (d, J=11.2 Hz, 1H), 4.61-4.53 (m, 2H), 4.47 (dd, J=10.6, 4.8 Hz, 1H), 3.80-3.74 (m, 1H), 3.73-3.70 (m, 1H), 3.67-3.53 (m, 2H); $^{13}$C NMR (126 MHz, CDCl$_3$) δ 149.31, 137.99, 137.46, 137.30, 133.20, 133.16, 128.81, 128.69, 128.65, 128.42, 128.31, 128.29, 128.27, 128.05, 127.96, 123.38, 121.13, 109.25 (d, J=218.5 Hz), 83.20 (d, J=9.6 Hz), 80.90 (d, J=22.9 Hz), 75.58, 75.26, 75.19, 74.41 (d, J=2.1 Hz), 72.55 (d, J=5.1 Hz), 72.09; $^{19}$F NMR (470 MHz, CDCl$_3$) δ −136.41 (dd, J=52.7, 10.8 Hz); HRMS (ESI) m/z [M+Na]+ calcd for $C_{33}H_{32}O_8BrFSNa$ 709.0878, found 709.0892.

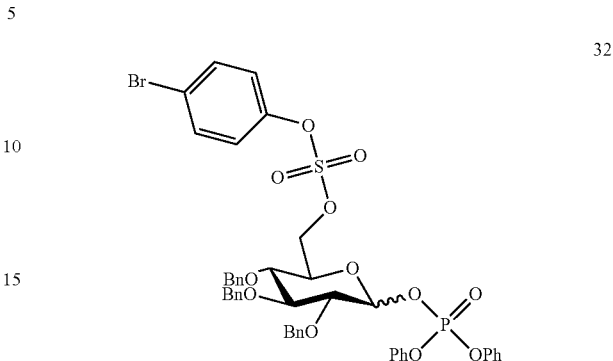

Lactol 22 (136.2 mg, 0.20 mmol) was azeotropically dried with toluene twice. To a solution of above compound in DCM (2.0 mL) was consecutively added diphenyl chlorophosphate (94.0 mg, 0.40 mmol) and 4-(dimethylamino)pyridine (DMAP, 63.4 mg, 0.52 mmol) at −18° C. The resulting mixture was allowed to stir at 0° C. for 3 h. The reaction was then diluted with EA, washed with sat. aq. NaHCO$_3$ twice, washed with brine, dried over anhydrous Na$_2$SO$_4$, and filtered. The filtrate was concentrated under reduced pressure for the purification on Biotage to provide α/β=4.5:1.0 mixture of phosphate donor 32 (81.9 mg, 45%).

32α: $[α]_D^{20}$=+49.2 (c 0.85, CHCl$_3$); $^1$H NMR (500 MHz, CDCl$_3$) δ 7.51-7.43 (m, 2H), 7.39-7.28 (m, 15H), 7.28-7.21 (m, 8H), 7.20-7.15 (m, 2H), 7.13-7.08 (m, 2H), 5.98 (dd, J=6.7, 3.2 Hz, 1H), 4.95 (d, J=11.0 Hz, 1H), 4.89 (d, J=10.8 Hz, 1H), 4.79 (d, J=11.0 Hz, 1H), 4.75 (d, J=11.4 Hz, 1H), 4.65 (d, J=11.4 Hz, 1H), 4.55 (d, J=10.8 Hz, 1H), 4.40 (dd, J=10.7, 3.8 Hz, 1H), 4.18 (dd, J=10.7, 1.9 Hz, 1H), 3.93 (t, J=9.3 Hz, 1H), 3.88 (ddd, J=10.2, 3.8, 1.9 Hz, 1H), 3.59 (dt, J=9.6, 3.3 Hz, 1H), 3.52 (dd, J=10.3, 9.0 Hz, 1H); $^{13}$C NMR (126 MHz, CDCl$_3$) δ 150.57 (d, J=7.7 Hz), 150.45 (d, J=7.1 Hz), 149.22, 133.18, 130.01, 129.82, 128.78, 128.67, 128.64, 128.36, 128.24, 128.03, 127.99, 125.70 (d, J=7.5 Hz), 123.16, 120.56 (d, J=4.7 Hz), 120.24 (d, J=4.8 Hz), 96.37 (d, J=6.2 Hz), 80.85, 78.96 (d, J=7.3 Hz), 75.85, 75.72, 75.54, 73.38, 71.72, 70.79; $^{31}$P NMR (202 MHz, CDCl$_3$) δ −13.22; HRMS (ESI) m/z [M+Na]+ calcd for $C_{45}H_{42}O_{12}BrPSNa$ 939.1210, found 939.1231.

32β: $[α]_D^{20}$=+5.8 (c 1.02, CHCl$_3$); $^1$H NMR (500 MHz, CDCl$_3$) δ 7.43-7.37 (m, 2H), 7.36-7.09 (m, 27H), 5.45 (t, J=7.2 Hz, 1H), 4.88 (d, J=7.0 Hz, 1H), 4.86 (d, J=6.9 Hz, 1H), 4.77 (d, J=11.0 Hz, 1H), 4.71 (d, J=10.9 Hz, 1H), 4.64 (d, J=11.0 Hz, 1H), 4.57 (d, J=10.9 Hz, 1H), 4.54 (dd, J=10.6, 1.9 Hz, 1H), 4.48 (dd, J=10.7, 4.0 Hz, 1H), 3.75-3.69 (m, 2H), 3.65-3.55 (m, 2H); $^{13}$C NMR (151 MHz, CDCl$_3$) δ 150.47 (d, J=7.4 Hz), 150.41 (d, J=6.9 Hz), 149.16, 138.00, 137.54, 137.29, 133.21, 130.00, 129.96, 128.80, 128.61, 128.50, 128.40, 128.28, 128.09, 127.98, 127.87, 125.79, 125.70, 99.53 (d, J=6.5 Hz), 84.04 (d, J=2.3 Hz), 81.41 (d, J=9.0 Hz), 75.82, 75.70, 75.32, 75.04, 73.31, 71.74; $^{31}$P NMR (202 MHz, CDCl$_3$) δ −13.41; HRMS (ESI) m/z [M+NH$_4$]+ calcd for $C_{45}H_{46}O_{12}NBrPS$ 934.1656, found 934.1646.

Example 15: Glycosylation with a Bromide Donor

Bromide Donor Preparation

To a solution of compound 19 (52.7 mg, 0.07 mmol) in DCM (724.3 µL) was added hydrogen bromide solution 33% wt in acetic acid (HBr/AcOH, 108.9 µL) at 0° C. under a nitrogen atmosphere. 1 h later, the reaction was quenched by dropwise addition of sat. aq. NaHCO₃ at the same temperature. The whole reaction mixture was poured into a two-layer separatory funnel with EA/sat. aq. NaHCO₃, washed with sat. aq. NaHCO₃ twice, washed with brine, dried over anhydrous Na₂SO₄, and filtered. The filtrate was concentrated under reduced pressure for direct usage in the next step.

Glycosylation

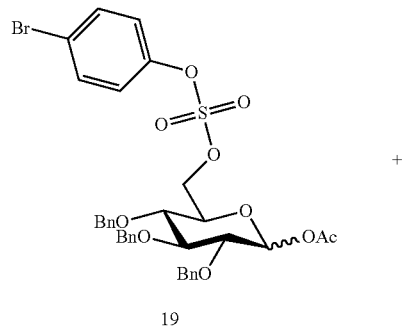

19

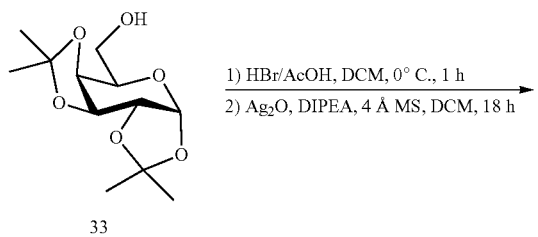

33

1) HBr/AcOH, DCM, 0° C., 1 h
2) Ag₂O, DIPEA, 4 Å MS, DCM, 18 h

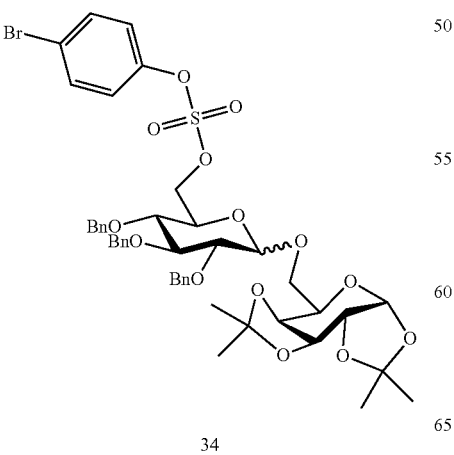

34

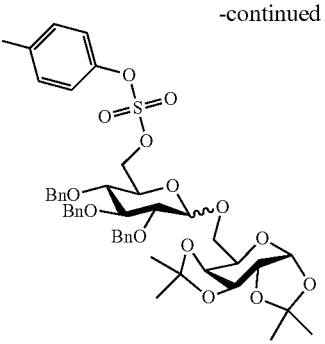

34

A mixture of above newly prepared bromide donor and acceptor 33 (25.8 mg, 0.10 mmol) was azeotropically dried over toluene three times. To a solution of above mixture in DCM (2.1 mL) was added freshly activated 4 Å MS (210 mg, 100 mg per mL of solvent). After being stirred for 30 min, the whole reaction was cooled down to 0° C., followed by consecutive addition of N,N-diisopropylethylamine (DIPEA, 14.0 mg, 18.9 µL, 0.12 mmol). The resulting mixture was allowed to warm up to rt slowly. 18 h later, TLC showed full conversion of the bromide donor. The reaction was filtered through a pad of Celite, concentrated directly under reduced pressure for the purification with a silica gel column on Biotage to solely provide only a product 34a (55.9 mg, 83%). 34a: $[\alpha]_D^{20}$=+3.6 (c 1.02, CHCl₃); $^1$H NMR (400 MHz, CDCl₃) δ 7.50-7.42 (m, 2H), 7.39-7.22 (m, 15H), 7.20-7.13 (m, 2H), 5.50 (d, J=5.0 Hz, 1H), 4.92-4.86 (m, 2H), 4.79 (d, J=10.7 Hz, 1H), 4.72 (s, 2H), 4.65-4.50 (m, 4H), 4.35-4.25 (m, 2H), 4.06-3.98 (m, 3H), 3.86-3.70 (m, 2H), 3.55-3.44 (m, 2H), 1.52 (s, 3H), 1.45 (s, 3H), 1.32 (s, 3H), 1.31 (s, 3H); $^{13}$C NMR (126 MHz, CDCl₃) δ 149.36, 138.75, 138.18, 137.97, 133.07, 128.65, 128.64, 128.62, 128.54, 128.07, 128.05, 128.03, 128.01, 127.77, 123.23, 123.21, 120.88, 109.52, 108.82, 97.31, 96.45, 81.76, 79.79, 76.73, 75.73, 74.99, 73.03, 72.84, 71.17, 70.85, 70.78, 70.71, 68.50, 67.70, 66.44, 26.27, 26.21, 25.09, 24.74; HRMS (ESI) m/z [M+NH₄]⁺ calcd for C₄₅H₅₅O₁₄BrSN 944.2521, found 944.2512.

Example 16: Glycosylation with a Fluoride Donor

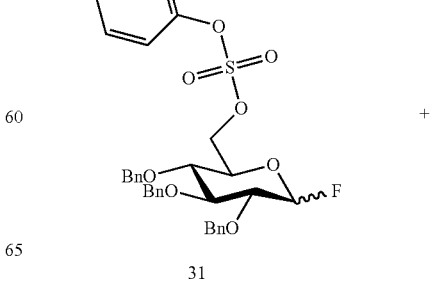

31

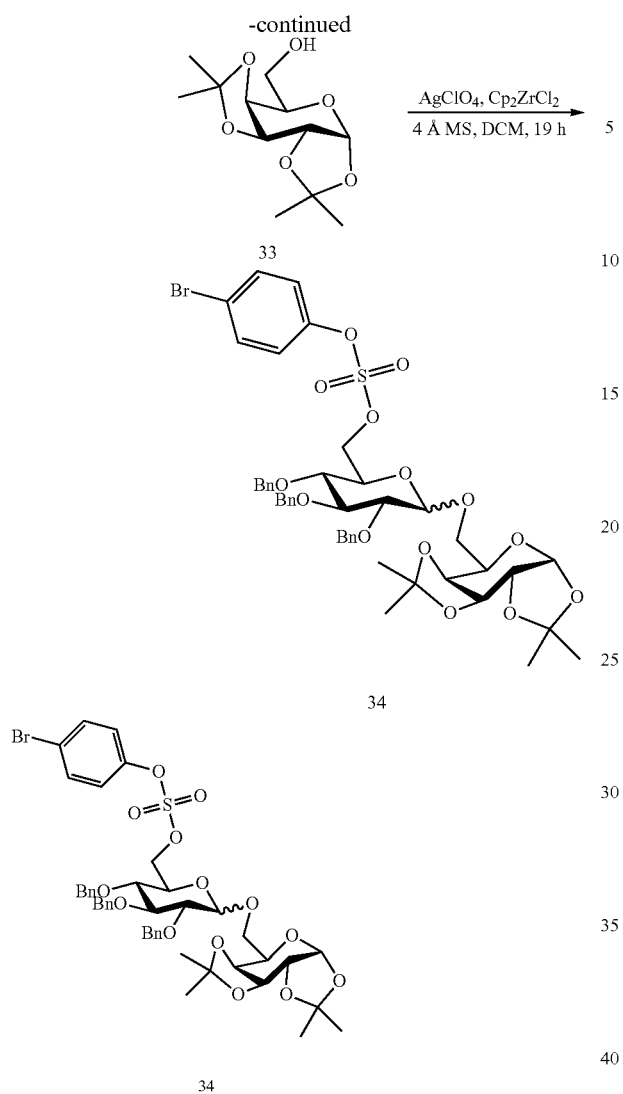

34

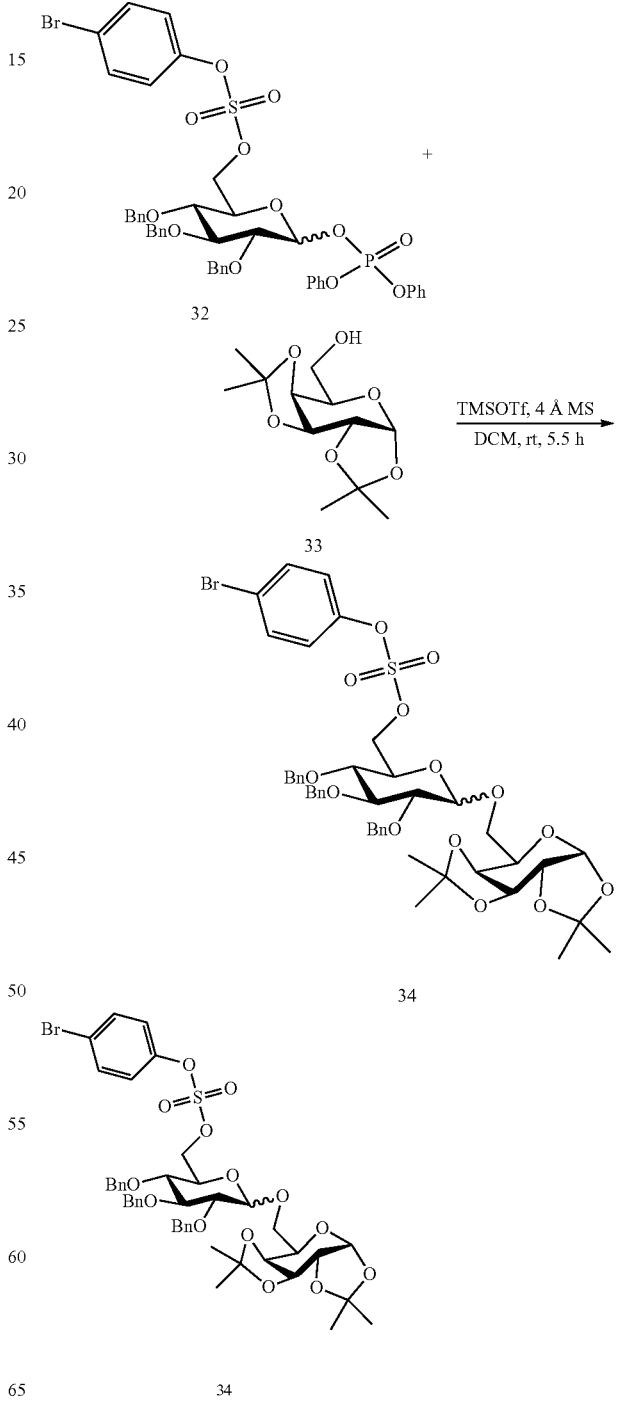

CDCl$_3$) δ 149.42, 138.55, 138.50, 137.58, 133.16, 128.80, 128.76, 128.55, 128.42, 128.30, 127.97, 127.83, 127.78, 123.35, 121.01, 109.67, 108.76, 104.39, 96.54, 84.33, 81.46, 77.36, 76.57, 75.79, 75.24, 74.55, 72.77, 72.52, 71.50, 70.93, 70.62, 70.05, 67.50, 26.23, 26.15, 25.13, 24.60; HRMS (ESI) m/z [M+NH$_4$]$^+$ calcd for C$_{45}$H$_{55}$O$_{14}$BrSN 944.2521, found 944.2503.

Example 17: Glycosylation with a Phosphate Donor

A mixture of fluoride donor 31 (154.3 mg, 0.22 mmol) and galactose acceptor 33 (70.1 mg, 0.27 mmol) was azeotropically dried over toluene three times. To above mixture in DCM (6.6 mL) was added freshly activated 4 Å MS (660 mg, 100 mg per mL of solvent) and zirconocene dichloride (Cp$_2$ZrCl$_2$, 98.4 mg, 0.34 mmol) at room temperature under the atmosphere of nitrogen. After stirring for 30 min, silver perchlorate (AgClO$_4$, 93.1 mg, 0.45 mmol) was added to the reaction. The whole reaction mixture was allowed to stir at the same temperature for another 19 h. The whole reaction mixture was filtered through a pad of Celite, concentrated directly for purification with a silica gel column on Biotage to provide α/β=6.3:1.0 mixture of product 34 (152.7 mg, 73%). 34β: [α]$_D^{20}$=−4.3 (c 0.49, CHCl$_3$); $^1$H NMR (500 MHz, CDCl$_3$) δ 7.53-7.48 (m, 2H), 7.42-7.40 (m, 2H), 7.35-7.26 (m, 11H), 7.24-7.21 (m, 4H), 5.57 (d, J=5.0 Hz, 1H), 5.05 (d, J=11.1 Hz, 1H), 4.98 (d, J=11.0 Hz, 1H), 4.87 (d, J=11.0 Hz, 1H), 4.77 (d, J=11.0 Hz, 1H), 4.71 (d, J=11.1 Hz, 1H), 4.61 (dd, J=7.9, 2.4 Hz, 1H), 4.57 (dd, J=10.5, 1.8 Hz, 1H), 4.54 (d, J=10.9 Hz, 1H), 4.50 (d, J=7.8 Hz, 1H), 4.43 (dd, J=10.5, 5.2 Hz, 1H), 4.32 (dd, J=5.0, 2.4 Hz, 1H), 4.22 (dd, J=8.0, 1.6 Hz, 1H), 4.11-4.03 (m, 2H), 3.75-3.63 (m, 2H), 3.61-3.55 (m, 1H), 3.48-3.41 (m, 2H), 1.50 (s, 3H), 1.45 (s, 3H), 1.33 (s, 3H), 1.31 (s, 3H); $^{13}$C NMR (126 MHz, A mixture of phosphate donor 32 (55.2 mg, 0.06 mmol) and acceptor 33 (18.7 mg, 0.07 mmol) was azeotropically dried over toluene three times. To a solution of above mixture in DCM (1.8 mL) was added freshly activated 4 Å MS (180 mg, 100 mg per mL of solvent). After being stirred for 30 min, the whole reaction was cooled down to −42° C., followed by the addition of TMSOTf (14.7 mg, 12.7 μL, 0.07 mmol). 2 h later, the reaction was moved to stir at 0° C. for another 3.5 h until NMR showed no residue of the phosphate donor left. The reaction was quenched with Et$_3$N (6.1 mg, 8.4 μL, 0.06 mmol) and filtered through a pad of Celite, diluted with EA, washed with sat. aq. NaHCO$_3$, washed with brine, dried over anhydrous Na$_2$SO$_4$, and filtered. The filtrate was concentrated under reduced pressure for the purification with a silica gel column on Biotage to provide α/β=3.3:1.0 mixture of product 34 (51.6 mg, 92%).

Example 18: Glycosylation with a Bromide Donor to Produce a Disaccharide

Bromide Donor Preparation

To a solution of compound 19 (94.1 mg, 0.13 mmol) in DCM (1.1 mL) was added hydrogen bromide solution 33% wt in acetic acid (HBr/AcOH, 194.5 μL) at 0° C. under a nitrogen atmosphere. 1.5 h later, the reaction was quenched by dropwise addition of sat. aq. NaHCO$_3$ at the same temperature. The whole reaction mixture was poured into a two-layer separatory funnel with EA/sat. aq. NaHCO$_3$, washed with sat. aq. NaHCO$_3$ twice, washed with brine, dried over anhydrous Na$_2$SO$_4$, and filtered. The filtrate was concentrated under reduced pressure for direct use in the next step.

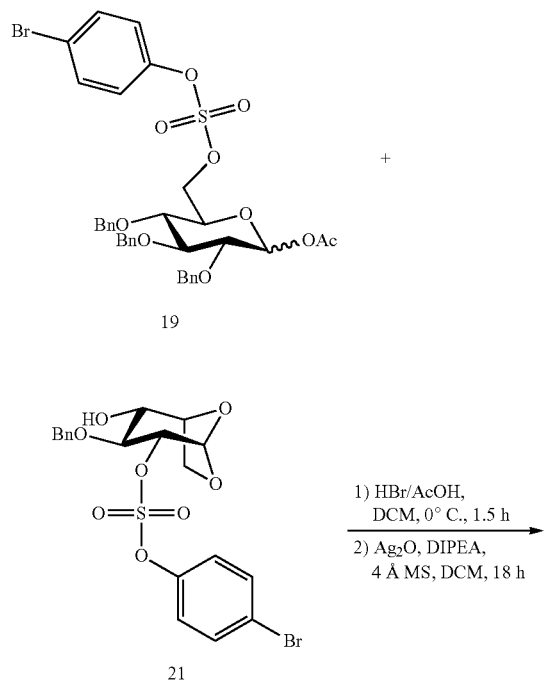

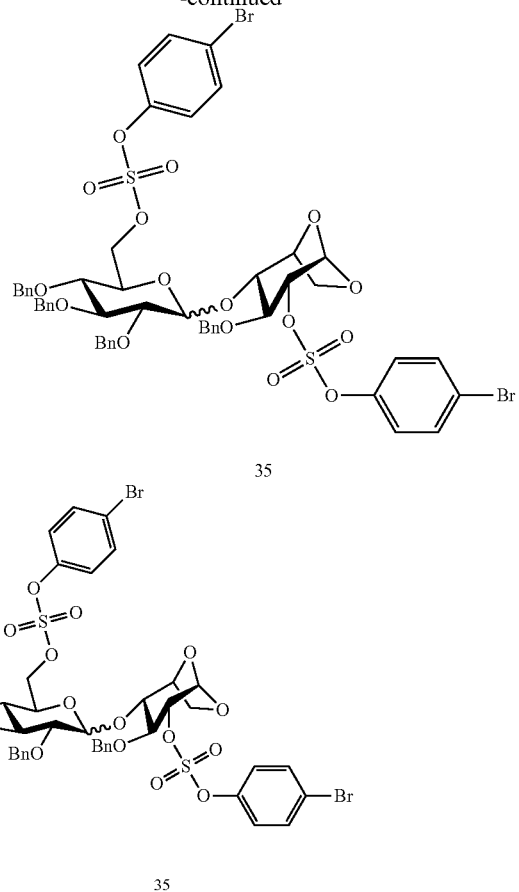

35

35

Glycosylation

A mixture of above newly prepared bromide donor and acceptor 21 (80.0 mg, 0.16 mmol) was azeotropically dried over toluene three times. To a solution of above mixture in DCM (2.6 mL) was added freshly activated 4 Å MS (260 mg, 100 mg per mL of solvent). This solution was stirred for 30 min, followed by consecutive addition of DIPEA (25.1 mg, 33.7 μL, 0.19 mmol) at room temperature. The resulting mixture was allowed to stir at the same temperature for 18 h. The reaction was filtered through a pad of Celite, concentrated directly under reduced pressure for the purification with a silica gel column on Biotage to provide product 34a (53.0 mg, 36%) and 34β (22.6 mg, 15%).

35a: $[α]_D^{20}$=+40.8 (c 0.33, CHCl$_3$); $^1$H NMR (500 MHz, CDCl$_3$) δ 7.50-7.45 (m, 2H), 7.41-7.37 (m, 2H), 7.36-7.29 (m, 8H), 7.28-7.23 (m, 10H), 7.22-7.19 (m, 2H), 7.19-7.15 (m, 2H), 7.13-7.08 (m, 2H), 5.61 (d, J=1.7 Hz, 1H), 5.00 (dd, J=11.1, 1.9 Hz, 1H), 4.92 (d, J=11.0 Hz, 1H), 4.88 (d, J=3.7 Hz, 1H), 4.86 (d, J=10.9 Hz, 1H), 4.72 (d, J=11.2 Hz, 1H), 4.68-4.61 (m, 2H), 4.60-4.49 (m, 3H), 4.41 (dd, J=10.5, 1.8 Hz, 1H), 4.27 (dd, J=10.5, 6.6 Hz, 1H), 4.03 (d, J=7.9 Hz, 1H), 3.97 (dd, J=9.9, 8.8 Hz, 1H), 3.86-3.80 (m, 1H), 3.76 (ddd, J=10.2, 6.6, 1.8 Hz, 1H), 3.69 (dd, J=7.9, 5.0 Hz, 1H), 3.47 (dd, J=9.8, 3.7 Hz, 1H), 3.35 (dd, J=10.2, 8.8 Hz, 1H); $^{13}$C NMR (126 MHz, CDCl$_3$) δ 149.29, 149.10, 138.18, 137.79, 137.60, 137.27, 133.25, 133.12, 128.90, 128.74, 128.68, 128.65, 128.55, 128.47, 128.45, 128.41, 128.29, 128.21, 128.12, 128.09, 127.85, 127.77, 123.28, 123.04, 121.20, 121.10, 99.72, 98.42, 85.70, 81.94, 81.28, 79.12, 77.56, 77.36, 76.77, 75.92, 75.53, 75.11, 74.15, 73.65, 72.93, 70.01, 65.77; HRMS (ESI) m/z [M+NH$_4$]$^+$ calcd for C$_{52}$H$_{54}$O$_{16}$Br$_2$S$_2$N 1172.1225, found 1172.1197.

35β: [α]$_D^{20}$=+26.3 (c 0.53, CHCl$_3$); $^1$H NMR (600 MHz, CDCl$_3$) δ 7.47-7.40 (m, 2H), 7.37-7.23 (m, 22H), 7.26-7.23 (m, 2H), 7.19-7.15 (m, 2H), 7.11-7.02 (m, 2H), 5.63 (d, J=1.8 Hz, 1H), 4.93-4.80 (m, 6H), 4.73 (d, J=11.2 Hz, 1H), 4.66 (d, J=11.2 Hz, 1H), 4.61-4.56 (m, 2H), 4.52-4.47 (m, 3H), 4.38 (dd, J=10.7, 5.0 Hz, 1H), 4.15 (dd, J=8.2, 4.2 Hz, 1H), 3.97 (d, J=8.0 Hz, 1H), 3.79 (t, J=8.1 Hz, 1H), 3.68 (t, J=8.9 Hz, 1H), 3.60-3.49 (m, 3H), 3.40 (dd, J=9.2, 7.8 Hz, 1H); $^{13}$C NMR (151 MHz, CDCl$_3$) δ 149.12, 148.92, 137.84, 137.62, 137.54, 137.14, 133.10, 132.94, 128.67, 128.59, 128.52, 128.32, 128.28, 128.14, 128.02, 127.90, 127.88, 127.81, 127.71, 127.32, 123.14, 123.12, 122.87, 120.94, 120.91, 101.24, 98.40, 85.34, 84.55, 81.91, 77.65, 76.42, 75.75, 75.24, 75.14, 74.84, 73.00, 72.38, 72.20, 65.52; HRMS (ESI) m/z [M+Na]$^+$ calcd for C$_{52}$H$_{50}$O$_{16}$Br$_2$S$_2$Na 1175.0799, found 1175.0852.

Example 19: Glycosylation with a Thioglycoside

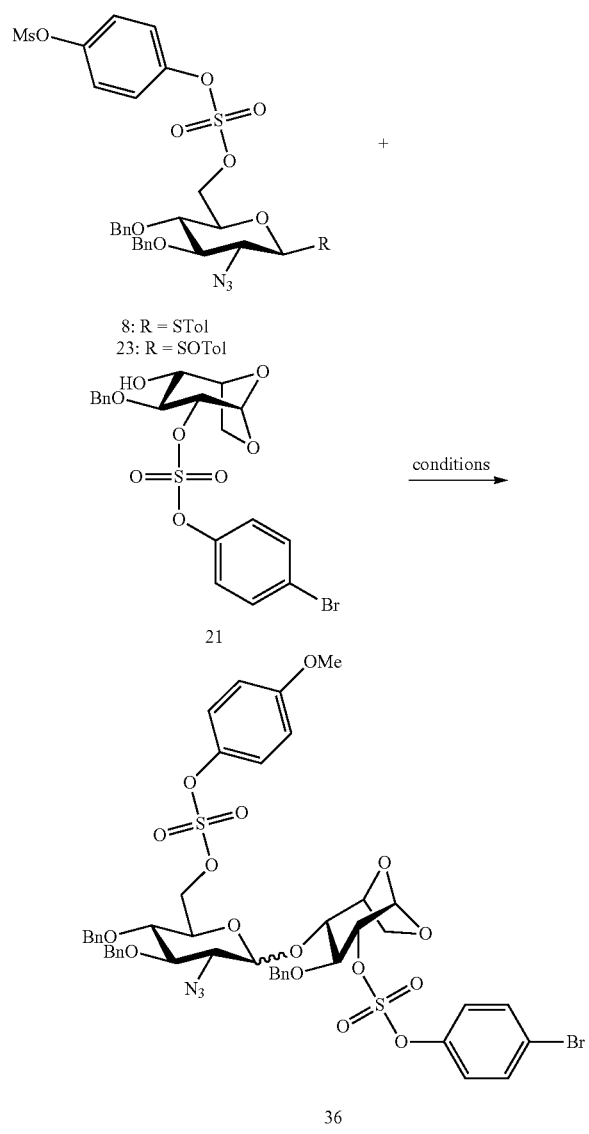

36

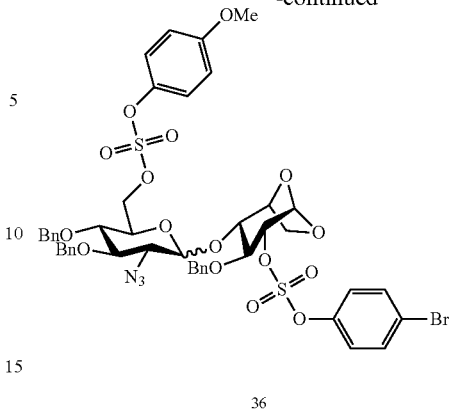

36

Glycosylation with thioglycoside 8. A mixture of thioglycoside 8 (165.2 mg, 0.24 mmol) and acceptor 21 (130.7 mg, 0.27 mmol) and was azeotropically dried with toluene three times. To a solution of above mixture in DCM (2.4 mL) was added freshly activated 4 Å MS (240 mg, 100 mg per 1 mL solvent) under a nitrogen atmosphere. The resulting mixture was allowed to stir at room temperature for 30 min. Then the reaction was cooled to −42° C., followed by the consecutive addition of N-iodosuccinimide (NIS, 109.7 mg, 0.49 mmol) and trifluoromethanesulfonic acid (TfOH, 7.3 mg, 4.3 μL, 0.05 mmol). The reaction was allowed to stir at the same temperature for 1.5 h, then Et$_3$N (14.5 mg, 20.0 μL, 0.14 mmol) was added to quench the reaction. The whole reaction mixture was filtered through a pad of Celite, diluted with EA, washed with a mixture of aq. Na$_2$S$_2$O$_3$ and sat. aq. NaHCO$_3$ (1:1) twice, washed with brine, dried over anhydrous Na$_2$SO$_4$, and filtered. The filtrate was concentrated under reduced pressure for the purification on Biotage to provide compound 36α (179.8 mg, 71%) and 36β (21.5 mg, 8%).

Example 20: Glycosylation with a Sulfoxide

Sulfoxide 23 (106.4 mg, 0.15 mmol) and was azeotropically dried with toluene three times. To a solution of sulfoxide 23 in DCM (3.1 mL) was consecutively added freshly activated 4 Å MS (460 mg) and 2,6-di-tert-butyl-4-methylpyridine (DTBMP, 78.7 mg, 0.38 mmol) under a nitrogen atmosphere. The resulting mixture was allowed to stir at room temperature for 30 min. Then the reaction was cooled down to −42° C., followed by the addition of trifluoromethanesulfonic anhydride (Tf$_2$O, 42.3 mg, 25.8 μL, 0.38 mmol). The reaction was kept stirring at the same temperature for another 40 min, then a solution of acceptor 21 (89.7 mg, 0.18 mmol) in DCM (1.5 mL) was added. 1 h later, TLC showed completed consumption of donor. Et$_3$N (15.5 mg, 21.4 μL, 0.15 mmol) was added to quench the reaction. The whole reaction mixture was filtered through a pad of Celite, concentrated directly under reduced pressure for the purification on Biotage to provide compound 36α (126.3 mg, 79%) and 36β (25.3 mg, 16%).

36α: [α]$_D^{20}$=+38.3 (c 0.98, CHCl$_3$); $^1$H NMR (500 MHz, CDCl$_3$) δ 7.45-7.40 (m, 2H), 7.40-7.26 (m, 15H), 7.24-7.19 (m, 2H), 7.19-7.13 (m, 2H), 6.88-6.83 (m, 2H), 5.61 (d, J=1.7 Hz, 1H), 5.21 (d, J=3.8 Hz, 1H), 4.94-4.85 (m, 5H), 4.76 (d, J=10.4 Hz, 1H), 4.66-4.62 (m, 1H), 4.57 (d, J=10.9 Hz, 1H), 4.51-4.43 (m, 2H), 4.34 (dd, J=10.7, 6.1 Hz, 1H), 4.06 (d, J=7.9 Hz, 1H), 3.96-3.86 (m, 3H), 3.81 (ddd, J=10.3, 6.1, 1.8 Hz, 1H), 3.78 (s, 3H), 3.74 (dd, J=8.0, 5.0

Hz, 1H), 3.46 (dd, J=10.2, 8.8 Hz, 1H), 3.42 (dd, J=10.3, 3.8 Hz, 1H); $^{13}$C NMR (126 MHz, CDCl3) δ 158.77, 149.24, 143.66, 137.48, 137.33, 136.92, 133.20, 128.96, 128.76, 128.74, 128.71, 128.68, 128.63, 128.60, 128.47, 128.38, 128.27, 128.23, 128.20, 128.14, 128.06, 123.29, 122.37, 121.23, 115.00, 99.60, 98.49, 86.18, 80.06, 79.48, 78.79, 77.35, 75.80, 75.64, 75.59, 74.17, 71.98, 70.19, 65.97, 63.46, 55.82; HRMS (ESI) m/z [M+Na]$^+$ calcd for C$_{46}$H$_{46}$O$_{16}$N$_3$S$_2$Na 1062.1395, found 1062.1411.

36β: $[\alpha]_D^{20}$=+18.9 (c 0.80, CHCl$_3$); $^1$H NMR (600 MHz, CDCl$_3$) δ 7.41-7.30 (m, 10H), 7.29-7.21 (m, 7H), 7.19-7.16 (m, 2H), 7.15-7.11 (m, 2H), 6.85-6.78 (m, 2H), 5.67 (d, J=1.7 Hz, 1H), 4.95-4.78 (m, 5H), 4.67 (d, J=11.2 Hz, 1H), 4.63-4.55 (m, 3H), 4.44 (d, J=10.8 Hz, 1H), 4.38 (d, J=8.1 Hz, 1H), 4.37-4.32 (m, 1H), 4.21 (d, J=8.1 Hz, 1H), 4.16 (dd, J=8.1, 4.2 Hz, 1H), 3.86-3.83 (m, 2H), 3.73 (s, 3H), 3.52-3.49 (m, 2H), 3.47-3.42 (m, 1H), 3.34 (dd, J=9.7, 8.0 Hz, 1H); $^{13}$C NMR (151 MHz, CDCl$_3$) δ 158.52, 149.12, 143.48, 137.51, 137.34, 136.94, 133.04, 132.97, 128.80, 128.69, 128.66, 128.65, 128.57, 128.56, 128.53, 128.51, 128.44, 128.35, 128.33, 128.28, 128.25, 128.18, 128.16, 128.14, 128.11, 128.06, 128.04, 127.98, 127.98, 127.84, 127.83, 127.79, 127.70, 123.23, 123.14, 123.12, 122.38, 122.21, 122.17, 122.16, 120.96, 114.86, 114.84, 114.71, 100.20, 98.39, 85.42, 82.69, 77.93, 77.28, 76.25, 75.65, 75.23, 74.97, 73.21, 72.59, 71.34, 66.50, 65.68, 55.61.

Example 21: Hydrogenolysis and Hydrolysis Reactions

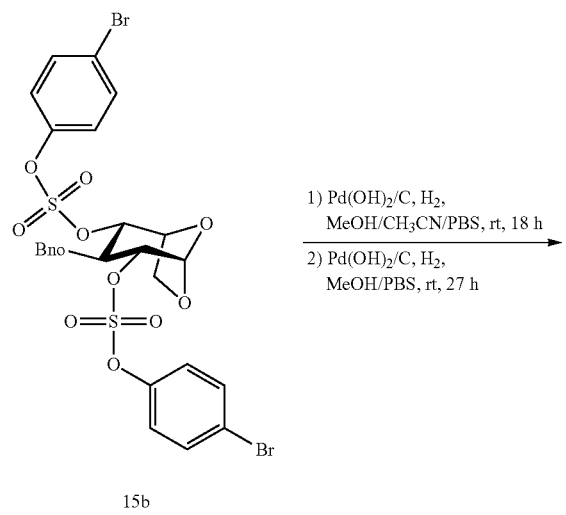

15b

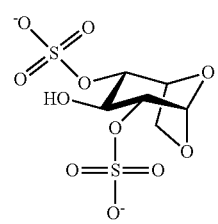

37

General Procedure D was employed to prepare compound 37 with minor modification. Compound 15b (3.17 g, 4.39 mmol) in MeOH/CH$_3$CN/PBS buffer (97.5 mL/97.5 mL/48.8 mL) was added 20% Pd(OH)$_2$ on activated carbon (15.9 g, 5 g per gram of substrate). The flask was charged with gentle vacuum, and then quickly filled with hydrogen gas via a syringe attached balloon. 18 h later, NMR showed complete removal of the sulfate diester masks with benzyl group left. The reaction mixture was filtered through a pad of Celite, washed by methanol, concentrated. The reaction residue was dissolved again in MeOH/PBS buffer (97.5 mL/48.8 mL), followed by the addition of 20% Pd(OH)$_2$ on activated carbon (15.9 g, 5 g per gram of substrate). Same procedure was applied to fill the reaction bottle with hydrogen gas. 27 h later, reaction mixture detection NMR showed no residual signal in aromatic zone. The whole reaction mixture was filtered again through a pad of Celite, concentrated. The residue was passed through a column of Amberlyst IR-120 (Na$_+$) resin using water as eluent, and then purified through a Sephadex LH-20 column eluted with methanol/water (1:1) to provide compound 37 along with residual $^1$H-NMR-inactive inorganic salts (e.g., sodium phosphate, sodium chloride, etc. Total mass: 4.13 g). The amount of 37 in the hydrogenolysis product was determined to be 1.53 g, giving the yield of 95% according to $^1$H-NMR quantification using β-Glycerophosphate disodium tetrahydrate as an internal standard. $^1$H NMR (600 MHz, D$_2$O) δ 5.86-5.71 (m, 1H), 5.03 (m, 1H), 4.57-4.45 (m, 1H), 4.37-4.19 (m, 2H), 3.89 (m, 2H); $^{13}$C NMR (151 MHz, D$_2$O) δ 99.16, 80.19, 76.98, 73.18, 69.72, 65.35; HRMS (ESI) m/z [M−H]$^-$ calcd for O$_6$H$_9$O$_{11}$S$_2$ 320.9592, found 320.9600.

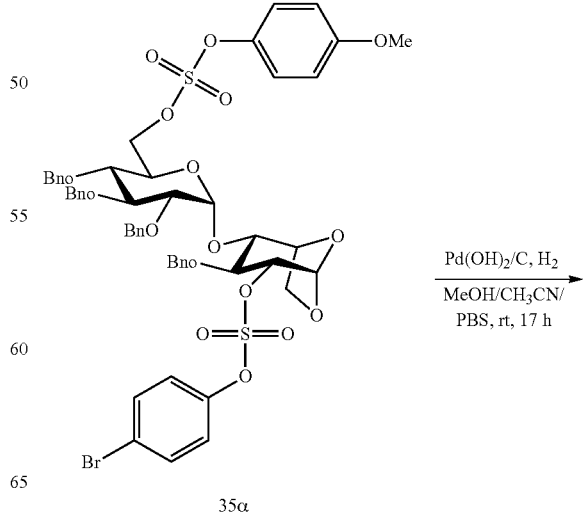

35α

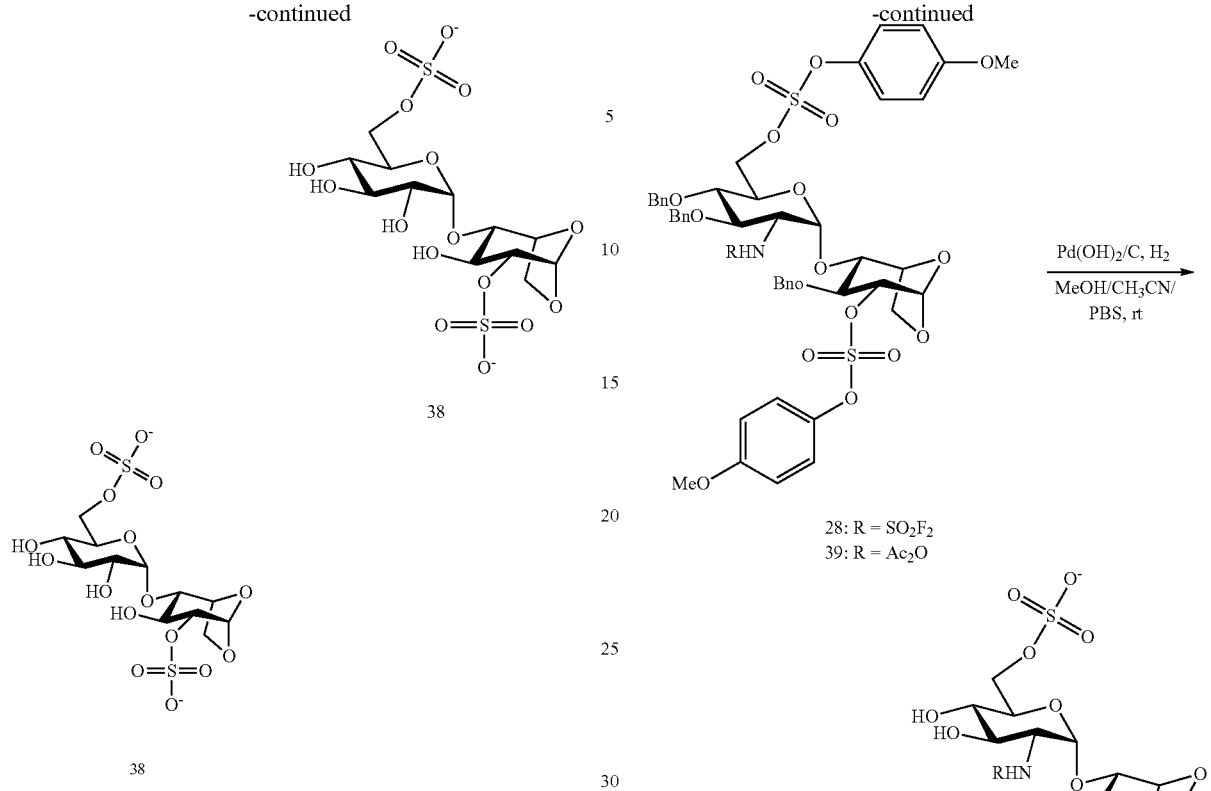

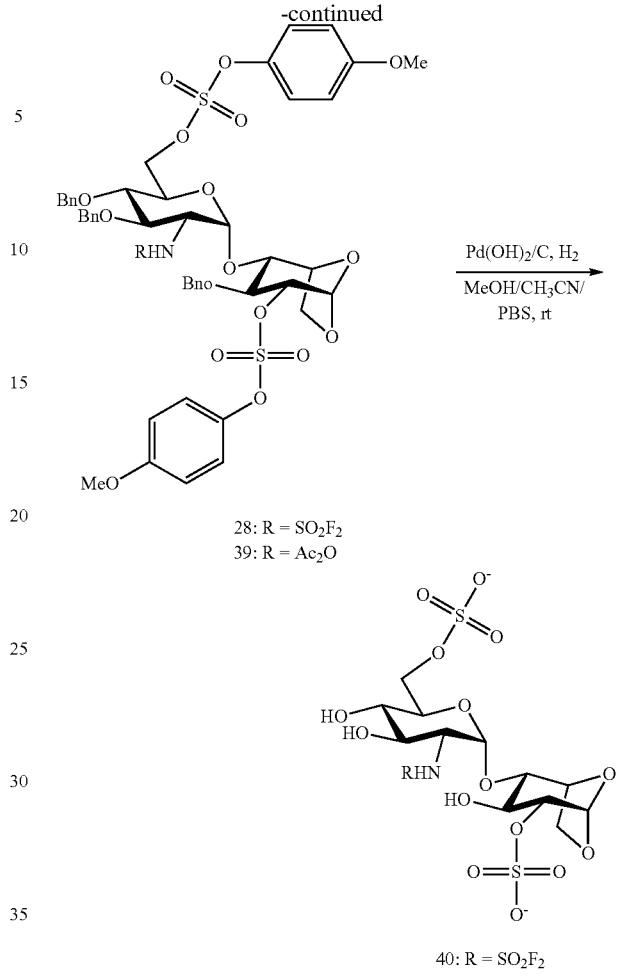

28: R = SO₂F₂
39: R = Ac₂O

40: R = SO₂F₂
41: R = Ac₂O

Compound 35a (54.2 mg, 0.05 mmol) was converted to trisulfated product 38 (24.5 mg, 99%) in 60 h following General Procedure D. Purification: Amberlyst IR-120 (Na+) resin column and Sephadex LH-20 column with MeOH as eluent as purification method. $^1$H NMR (600 MHz, CD$_3$OD) δ 5.58 (d, J=1.8 Hz, 1H), 5.07 (d, J=3.9 Hz, 1H), 4.86 (t, J=4.6 Hz, 1H), 4.31 (dd, J=10.9, 1.9 Hz, 1H), 4.11 (dd, J=8.3, 1.9 Hz, 1H), 4.05 (d, J=7.9 Hz, 1H), 4.01 (dd, J=10.9, 7.2 Hz, 1H), 3.85 (dd, J=7.8, 5.1 Hz, 1H), 3.82 (t, J=8.3 Hz, 1H), 3.74-3.67 (m, 2H), 3.64-3.59 (m, 1H), 3.44 (dd, J=9.9, 4.0 Hz, 1H), 3.25-3.20 (m, 1H); $^{13}$C NMR (126 MHz, CD$_3$OD) δ 102.44, 101.15, 82.95, 81.42, 75.55, 74.67, 73.43, 72.73, 72.55, 71.78, 68.61, 66.70; HRMS (ESI) m/z [M−2H+Na]$^−$ calcd for C$_{12}$H$_{18}$O$_{16}$S$_2$Na 504.9939, found 504.9939.

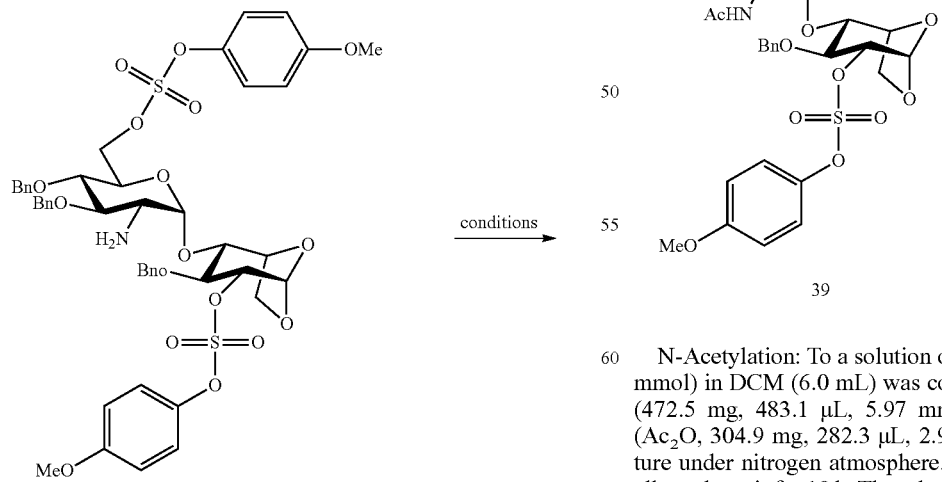

Figure 8:
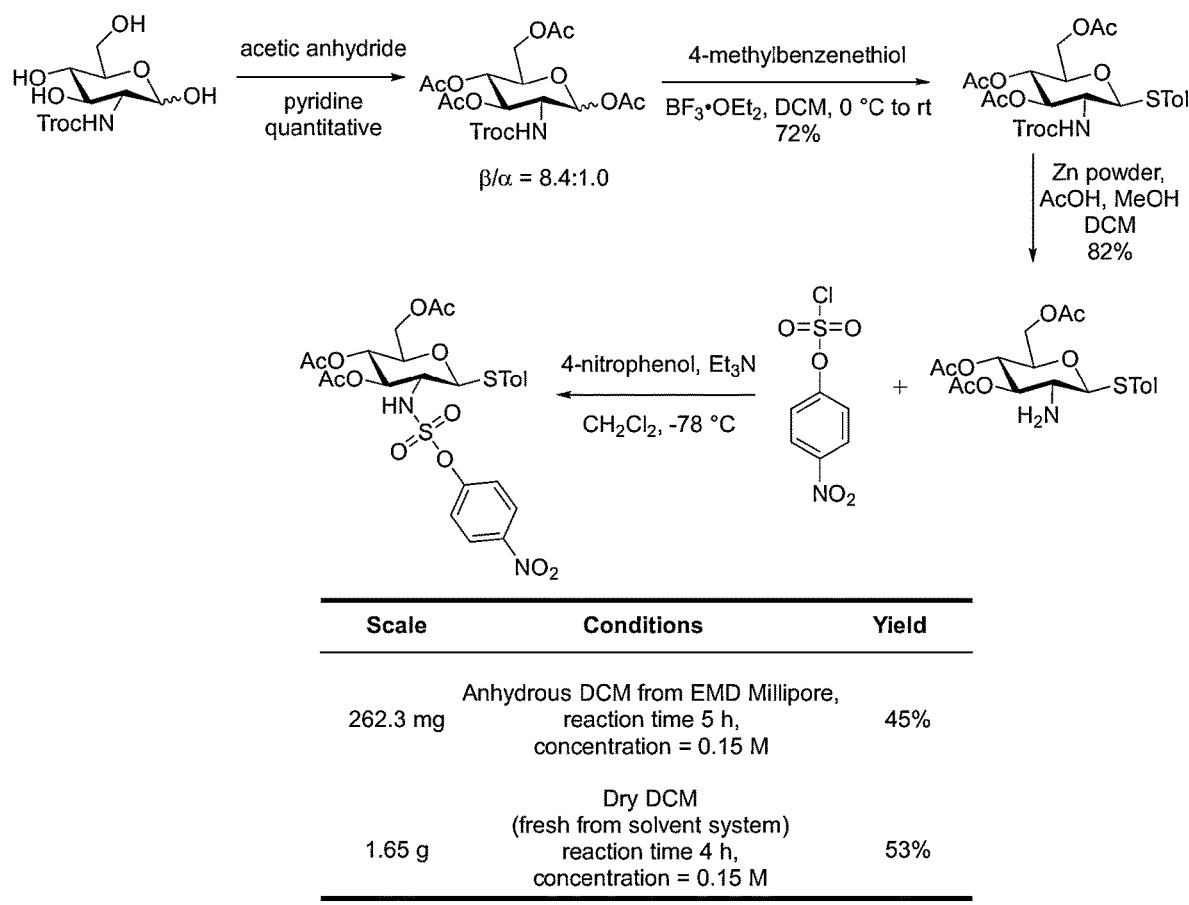
FIG. 8 shows gram scale N-sulfation using a chlorosulfate reagent.
Figure 9:
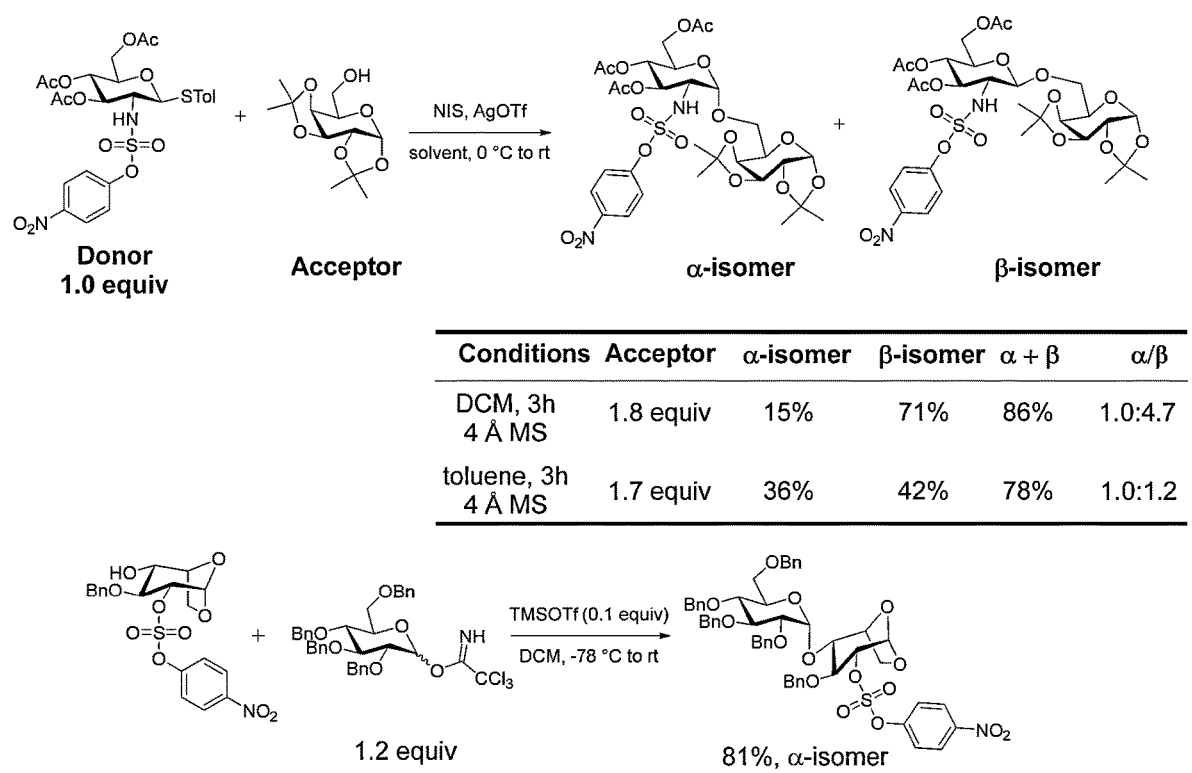
FIG. 9 shows that an aryl masked sulfate substrate can be used as a donor or acceptor in the disclosed reactions.
Figure 10:
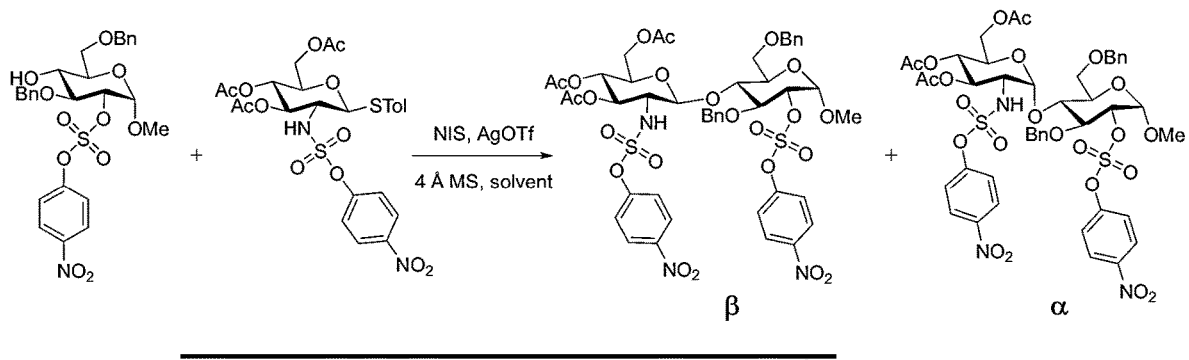
FIG. 10 shows a scheme according to one aspect of the present disclosure where masked sulfate groups are present on both the donor and acceptor.
Figure 10:
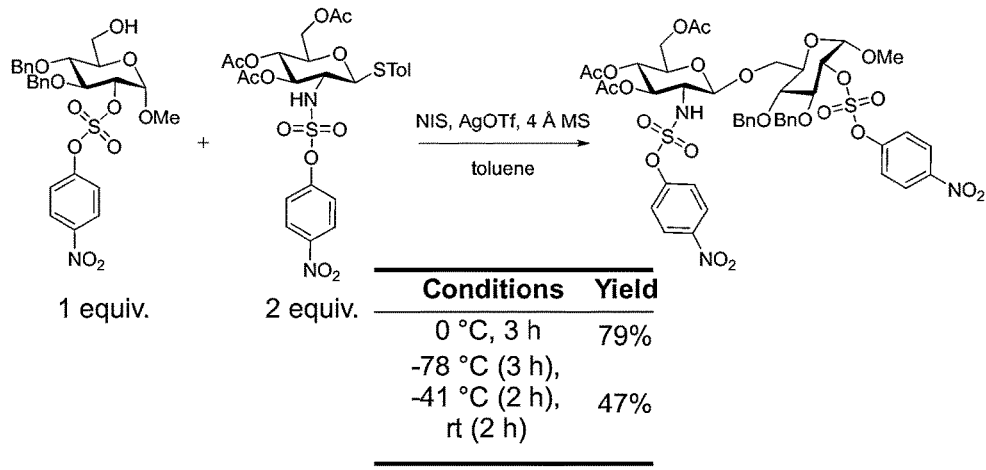
Figure 11:
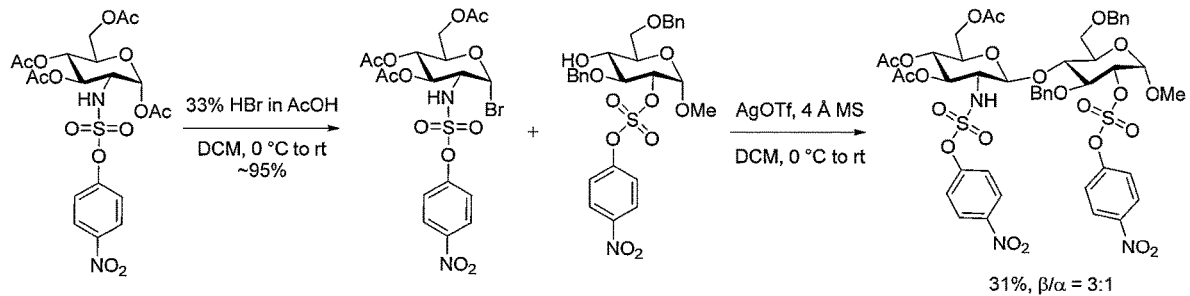
FIG. 11 shows that the disclosed reactions are compatible with bromide donors and can be followed by glycosylation.

N-Acetylation: To a solution of amine 27 (288.5 mg, 0.30 mmol) in DCM (6.0 mL) was consecutively added pyridine (472.5 mg, 483.1 μL, 5.97 mmol), and acetic anhydride (Ac₂O, 304.9 mg, 282.3 μL, 2.99 mmol) at room temperature under nitrogen atmosphere. The resulting mixture was allowed to stir for 10 h. Then the reaction was quenched with MeOH (237.3 mg, 300.0 μL, 7.41 mmol), diluted with EA, washed with sat. aq. NaHCO₃, brine, dried over anhydrous Na$_2$SO$_4$, filtered, and coevaporated with toluene twice to remove pyridine (see also FIG. 8). The residue was concentrated under reduced pressure for the purification with a silica gel column on Biotage to provide product 39 (234.7 mg, 78%). [α]$_D^{20}$=+61.3 (c 1.01, CHCl$_3$); $^1$H NMR (600 MHz, CDCl$_3$) δ 7.41-7.32 (m, 5H), 7.32-7.23 (m, 12H), 7.19-7.12 (m, 2H), 6.89-6.86 (d, J=8.8 Hz, 1H), 6.83-6.79 (m, 2H), 5.14 (d, J=9.1 Hz, 1H), 4.92 (d, J=3.7 Hz, 1H), 4.88 (d, J=10.9 Hz, 1H), 4.84-4.81 (m, 2H), 4.66-4.61 (m, 2H), 4.57 (d, J=10.9 Hz, 1H), 4.53 (t, J=4.5 Hz, 1H), 4.48-4.45 (m, 2H), 4.26-4.22 (m, 2H), 3.94 (d, J=8.0 Hz, 1H), 3.86 (dd, J=10.1, 7.3 Hz, 1H), 3.83-3.78 (m, 4H), 3.76-3.74 (m, 4H), 3.70 (dd, J=8.1, 5.1 Hz, 1H), 3.65 (dd, J=10.6, 8.8 Hz, 1H), 3.44 (t, J=9.4 Hz, 1H), 1.32 (s, 3H); $^{13}$C NMR (151 MHz, CDCl$_3$) δ 170.28, 158.77, 158.75, 143.70, 143.63, 137.83, 137.33, 137.03, 128.96, 128.88, 128.81, 128.65, 128.52, 128.47, 128.33, 128.23, 127.94, 122.56, 122.42, 114.97, 114.94, 100.06, 98.54, 85.78, 80.76, 79.98, 78.41, 75.50, 75.44, 75.22, 73.72, 72.35, 70.75, 65.67, 55.83, 55.76, 52.50, 22.72.

IR-120 (Na+) resin column, Sephadex LH-20 column with MeOH as eluent, and reversed column with MeOH/H$_2$O were used as purification method. $^1$H NMR (500 MHz, D$_2$O) δ 5.76 (t, J=1.5 Hz, 1H), 5.47 (d, J=3.8 Hz, 1H), 4.92 (t, J=4.5 Hz, 1H), 4.44-4.32 (m, 8H), 4.26-4.18 (m, 3H), 3.97-3.90 (m, 3H), 3.85 (ddd, J=8.9, 6.6, 1.9 Hz, 1H), 3.68 (ddd, J=10.3, 9.0, 1.1 Hz, 1H), 3.54 (ddd, J=10.2, 9.1, 1.1 Hz, 1H), 3.37 (ddd, J=10.4, 3.8, 1.1 Hz, 1H); $^{13}$C NMR (126 MHz, D$_2$O) δ 99.52, 99.49, 99.09, 80.26, 80.24, 80.14, 74.06, 71.17, 70.71, 69.79, 67.44, 65.40, 57.75; HRMS (ESI) m/z [M−2H+Na]$^−$ calcd for C$_{12}$H$_{19}$O$_{18}$NS$_3$Na 583.9667, found 583.9663.

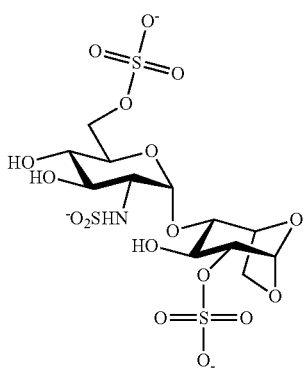

40

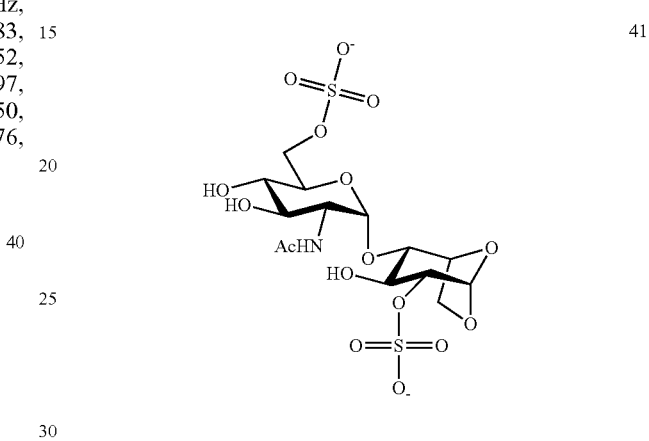

41

N-Sulfated compound 28 (229.1 mg, 0.21 mmol) was converted to trisulfated product 40 (135.0 mg, 83%) in 60 h following General Procedure D. Purification: Amberlyst Compound 39 (217.3 mg, 215.5 mmol) was converted to disulfated product 41 (110.0 mg, 90%) following General Procedure D in 23 h. $^1$H NMR (500 MHz, D$_2$O) δ 5.77 (d, J=1.8 Hz, 1H), 5.21 (d, J=3.8 Hz, 1H), 4.90 (t, J=4.0 Hz, 1H), 4.41 (dd, J=11.3, 2.0 Hz, 1H), 4.30-4.20 (m, 3H), 4.04 (dd, J=10.8, 3.8 Hz, 1H), 3.97-3.87 (m, 4H), 3.84 (dd, J=10.7, 9.0 Hz, 1H), 3.57 (dd, J=10.1, 9.1 Hz, 1H), 2.12 (s, 3H); $^{13}$C NMR (126 MHz, D$_2$O) δ 174.54, 99.27, 99.23, 99.12, 80.45, 79.86, 74.13, 70.93, 70.89, 70.60, 69.85, 67.43, 65.50, 53.60, 22.06; HRMS (ESI) m/z [M−2H+Na]$^−$ calcd for C$_{14}$H$_{21}$O$_{16}$NS$_2$Na 546.0205, found 546.0199.

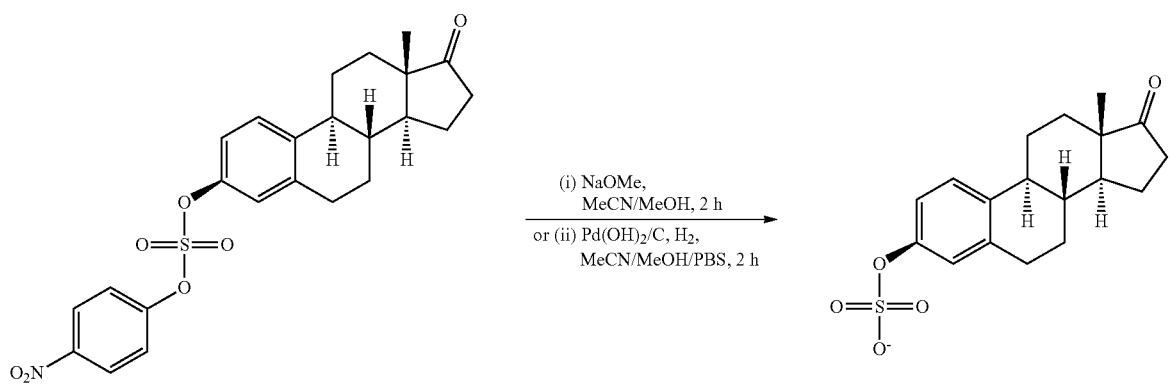

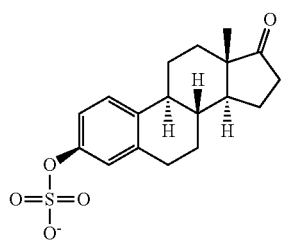

42

Hydrolysis of 17 (50 mg, 0.11 mmol) was conducted following General Procedure C. The product was purified by silica gel chromatography (dichloromethane/methanol 5:1) to obtain 35 (37.4 mg, 95%). Hydrogenolysis: Procedure D was followed with 17 (100 mg, 0.21 mmol). The product was purified by silica gel chromatography dichloromethane/methanol (5:1) to obtain 42 (69 mg, 87%). $[\alpha]_D^{20}$=+110.4 (c 1.00 in MeOH). $^1$H NMR (500 MHz, CD$_3$OD) δ 7.25 (d, J=8.6 Hz, 1H), 7.07-7.02 (m, 2H), 2.94-2.87 (m, 2H), 2.50 (dd, J=19.0, 8.5 Hz, 1H), 2.45-2.38 (m, 1H), 2.28 (td, J=10.5, 4.3 Hz, 1H), 2.20-2.00 (m, 3H), 1.96-1.87 (m, 1H), 1.73-1.39 (m, 6H), 0.93 (s, 3H). $^{13}$C NMR (126 MHz, CD$_3$OD) δ 222.30, 150.42, 137.33, 136.12, 125.54, 121.09, 118.41, 50.26, 47.87, 44.04, 38.24, 35.34, 31.40, 29.03, 26.17, 25.60, 21.10, 12.87. HRMS (ESI) ([M−H]$^-$) Calcd. for C$_{18}$H$_{21}$O$_5$S: 349.1115, found 349.1124.

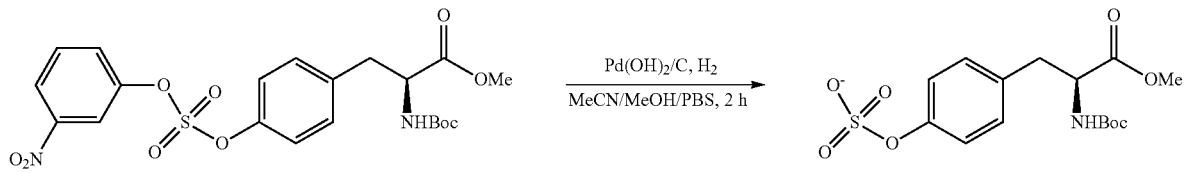

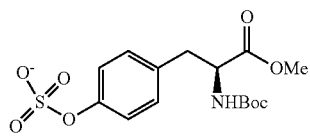

43

Hydrogenolysis of 18 (100 mg, 0.20 mmol) was performed following General Procedure D. The product was purified by silica gel chromatography (dichloromethane/methanol 5:1) to obtain 43 (73 mg, 91%). $[\alpha]_D^{20}=-0.4$ (c 1.00 in MeOH). $^1$H NMR (500 MHz, CD$_3$OD) δ 7.23 (d, J=8.6 Hz, 2H), 7.17 (d, J=8.6 Hz, 2H), 4.34 (dd, J=8.8, 5.6 Hz, 1H), 3.69 (s, 3H), 3.08 (dd, J=13.9, 5.6 Hz, 1H), 2.92 (dd, J=13.9, 8.8 Hz, 1H), 1.40 (s, 9H). $^{13}$C NMR (126 MHz, CD$_3$OD) δ 172.79, 156.42, 151.50, 133.42, 129.53, 121.06, 79.26, 55.16, 51.20, 36.49, 27.26. HRMS (ESI) ([M−H]$^-$) Calcd. for C$_{15}$H$_{20}$NO$_8$S: 374.0915, found 347.0924.

Example 22: Model Reaction Between TMS-Protected Substrate and Substituted Aryl Fluorosulfates The reaction between trimethylsilyl (TMS)-protected 1,2:3,4-di-O-isopropylidene-α-D-galactopyranose (1) and substituted aryl fluorosulfates was used as a model. Aryl fluorosulfates (3a-j) carrying variable substitutions ranging from strongly electron-withdrawing groups to electron-donating groups were readily prepared from corresponding phenols (Table 2).

TABLE 2

Preparation of Phenyl Fluorosulfates with Various Electron-Withdrawing and Electron-Donating Substitutions HO—[aryl]—R  →(SO$_2$F$_2$ (balloon), TEA, DCM)→  FO$_2$SO—[aryl]—R  3a-j

| Compound | 3a | 3b | 3c | 3d | 3e | 3f | 3g | 3h | 3i | 3j |
|---|---|---|---|---|---|---|---|---|---|---|
| Substituent | p-NO$_2$ | m-NO$_2$ | p-NO$_2$ | p-CF$_3$ | p-CN | p-Br | p-Cl | p-Ph | p-H | p-OMe |
| Yield | 95% | 99% | 85% | 96% | 96% | 91% | 99% | 82% | 60% | 98% |

Various catalysts were screened for the subsequent SuFEx reaction (Table 3) and it was found that the coupling of 1 with 3a-f carrying electron-withdrawing substitutions proceeded smoothly in the presence of 1,8-diazabicyclo[5.4.0]undec-7-ene (DBU) in two hours, providing 4a-f in excellent yields (Table 1, Entries 1-6).

TABLE 3

Screening Catalysts for the Model SuFEx Reaction

1 + Me—[aryl]—OSO$_2$F (3i) →(Base (0.2 equiv), rt, Acetonitrile (0.3M), 2 h)→ 4i

| Base | DBU | DBN | BTPP | BEMP | KHF$_2$ | MTBD | TBD |
|---|---|---|---|---|---|---|---|
| Structure Yield | 29% | 32% | 55% | 39% | NR | 47% | Quantitative |

Figure 4:
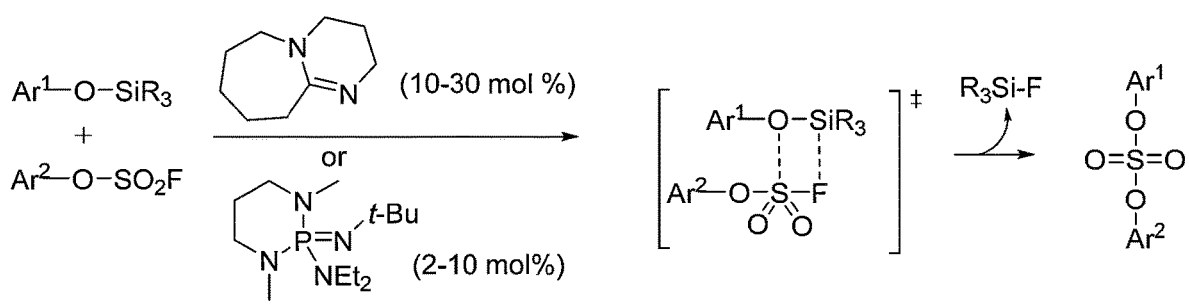
FIG. 4 shows a generic sulfur (VI) fluoride exchange reaction (SuFEx) according to one aspect of the present disclosure.

In contrast, the coupling of 1 with 3g-j carrying electron-neutral or electron-donating substitutions were sluggish, affording 4g-j in modest to low yields from 76% to 31% (Table 1, Entries 7-10). These results suggested that the rates of the SuFEx reaction between aryl fluorosulfates and glycosilylethers correlate with the electron deficiency of the aryl fluorosulfates, with stronger electron-withdrawing groups weakening the S—F bond in aryl fluorosulfates and rendering them more reactive to nucleophiles. Inspired by a previously published report, we switched to 1,5,7-triazabicyclo[4.4.0]dec-5-ene (TBD) as the catalyst and observed a significant improvement of the efficiency of the SuFEx reaction involving electron-rich aryl fluorosulfates (Table 1, Entry 9, Table 3, and FIG. 4).

Example 23: Deprotection Strategies

Figure 19:
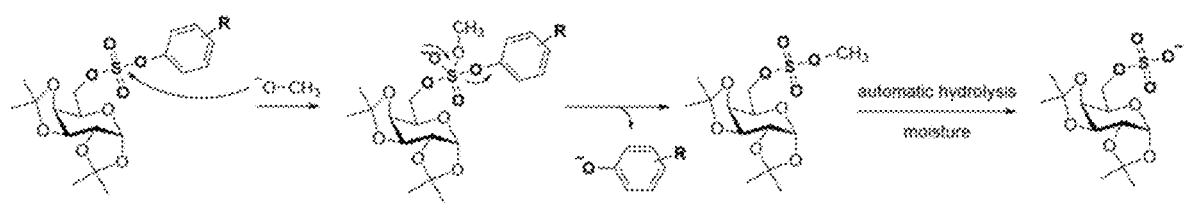
FIG. 19 shows a proposed mechanism of sulfate diester hydrolysis as disclosed herein.

We then sought to generate the desired 6-O-sulfated galactose (5) through the selective deprotection of the aryl groups in 4a-j. Previous studies have shown that, in alkyl aryl sulfate diesters, the rate difference of the S—O bond cleavage between an aryl sulfate monoester and an alkyl sulfate monoester is determined by the $pK_a$ differences between aliphatic and aromatic alcohol leaving groups. Consistently, we observed that 5 was efficiently generated as the sole product when 4a-d was treated with 5 M sodium methoxide in methanol at room temperature for one hour (Table 1, entries 1-4), as the corresponding phenols carrying strongly electron-withdrawing groups ($p-NO_2$, $p-CF_3$, and p-CN) are good leaving groups. The proposed mechanism of this reaction involved a glycosyl methyl sulfate diester intermediate, which subsequently underwent hydrolysis by reacting with the trace amount of water present in the methanolic solution of sodium methoxide (FIG. 19). In contrast, the yields of 5 from the hydrolysis of 4e-h carrying weak electron-withdrawing or electron-neutral groups dropped significantly, and no S—O bond fission was observed when 4i, j were subjected to the hydrolysis conditions, indicating that the corresponding electron-rich phenols have reduced ability to serve as leaving groups. These results also suggested that the stability difference of the variably substituted sulfate diesters against base can be used for selective deprotection in future studies.

While base-mediated hydrolysis can afford sulfated carbohydrates from glycosyl aryl sulfate diesters, concerns over undesired side reactions caused by strong base treatment prompted us to investigate alternative deprotection strategies. Perlin and Penny first reported hydrogenolysis of phenyl sulfate monoester using $PtO_2/H_2$ in modest yields. Inspired by this work, we studied the selective hydrogenolysis of the aryl sulfate monoester in glycosyl aryl sulfate diesters by $Pd(OH)_2/C/H_2$, and observed high deprotection efficiency in the methanol/water solution of phosphate salts. Notably, this condition is insensitive to the electronic properties of the aryl substitution, yielding the targeted 5 quantitatively from all substrates 4a-j in two hours at room temperature (Table 1). Gas chromatography-mass spectrometry (GC-MS) analysis of the hydrogenolysis reaction revealed a mechanism of oxidative insertion of palladium into the aryl C—O bond followed by the reductive elimination of arenes, as opposed to the previously proposed mechanism of hydrogenation of the aryl group followed by S—O bond fission to release cyclohexanol. Our observation that $H_2$ can be replaced by ammonium formate, a far less potent hydrogenation agent, without affecting the hydrogenolysis efficiency, further proved the oxidative insertion-reductive elimination mechanism.

Figure 23:
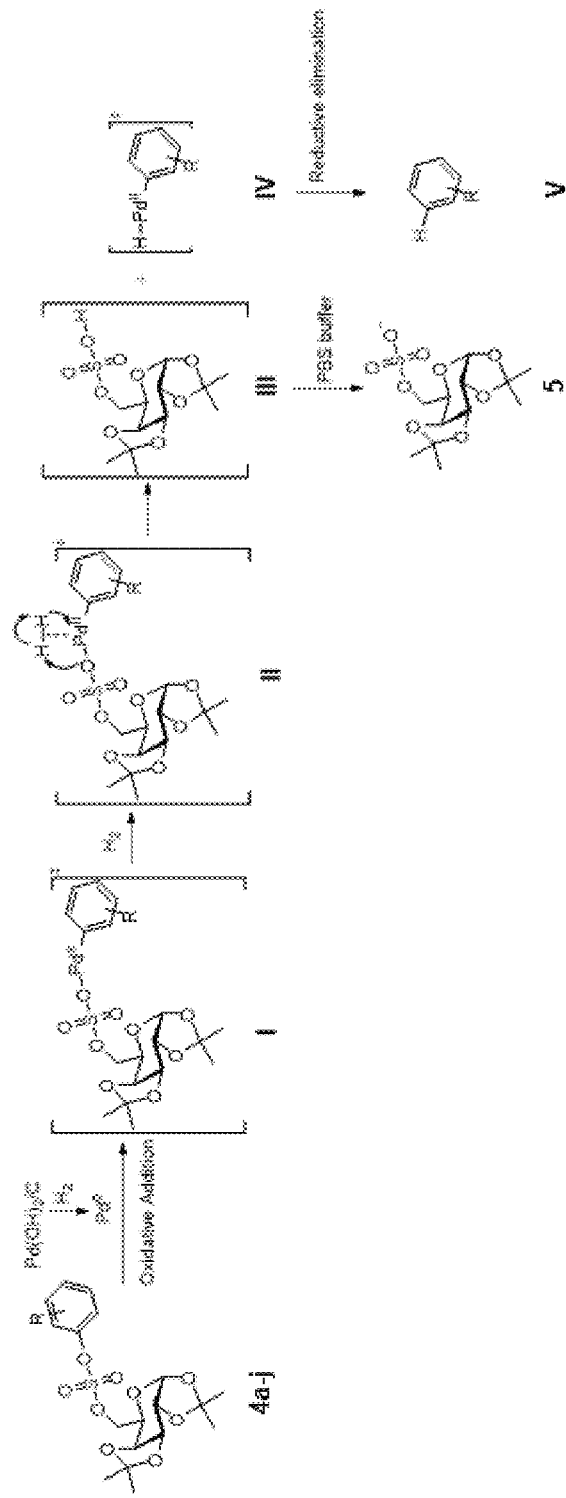
FIG. 23 shows a proposed mechanism of hydrogenolysis reactions as disclosed herein.

In hydrogenolysis, the catalyst palladium hydroxide on carbon is reduced to palladium (0) in situ. The oxidative addition of palladium(0) to the C—O bond of the aryl sulfate monoester generates I carrying a Pd(II) center. Subsequent coordination of $H_2$ to the Palladium center of the catalyst leads to II. The dissociation of galactosyl sulfuric acid II yields III and IV. The former is immediately quenched by PBS buffer to give O-sulfated galactose 5 while the latter undergoes reductive elimination of arene V and regenerates the palladium(0) catalyst (see FIG. 23).

Example 24: Adaptation of Strategy for Multiple Substrates

Figure 2:
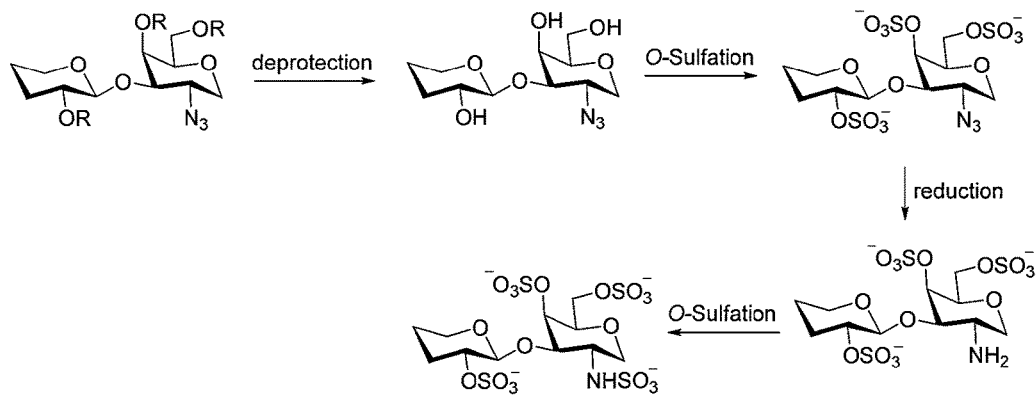
FIG. 2 shows stepwise O-sulfation and N-sulfation according to previously published procedures.
Figure 3:
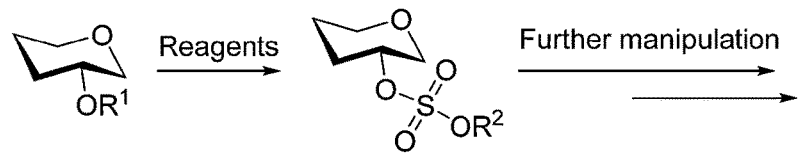
FIG. 3 shows various known reagents and schemes for O-sulfation using masked sulfate groups.
Figure 3:
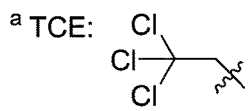
Figure 3:
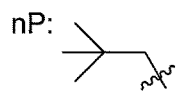
Figure 3:
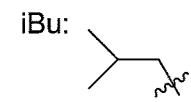

Our subsequent investigation focused on the feasibility of our strategy for a variety of substrates (FIG. 2). Initial attempts to install p-nitrophenyl sulfate diester onto the O-6 position of methyl 2,3,4-tris-O-benzyl-α-D-glucopyranoside by reacting with p-nitrophenyl fluorosulfate 3a generated an ether byproduct methyl 2,3,4-tris-O-benzyl-6-O-(para-nitrophenyl)-α-D-glucopyranoside inseparable from the targeted sulfate diester. We reasoned that the strong electron-withdrawing effect of the nitro and fluorosulfo substitutions made the aryl sulfate diester susceptible to the nucleophilic attack by the oxygen anion, and increasing the electron density of the phenyl group should alleviate this side reaction. Indeed, SuFEx using p-bromophenyl fluorosulfate 3e provided the desired sulfate diester 6 in 70% yield. Similarly, O-6 substitution using 3e successfully produced sulfate diesters 7 in 90% yield. In these reactions, it was also discovered that aryl fluorosulfates remained stable in the presence of silylethers before the introduction of organobase catalysts, making it possible for a one-pot procedure combining in situ silylation of the free hydroxyl and the subsequent SuFEx reaction. In addition to simplifying the operation, the one-pot procedure could also circumvent the challenge to isolate TMS silylethers that are often unstable on silica gel chromatography.

Figure 16:
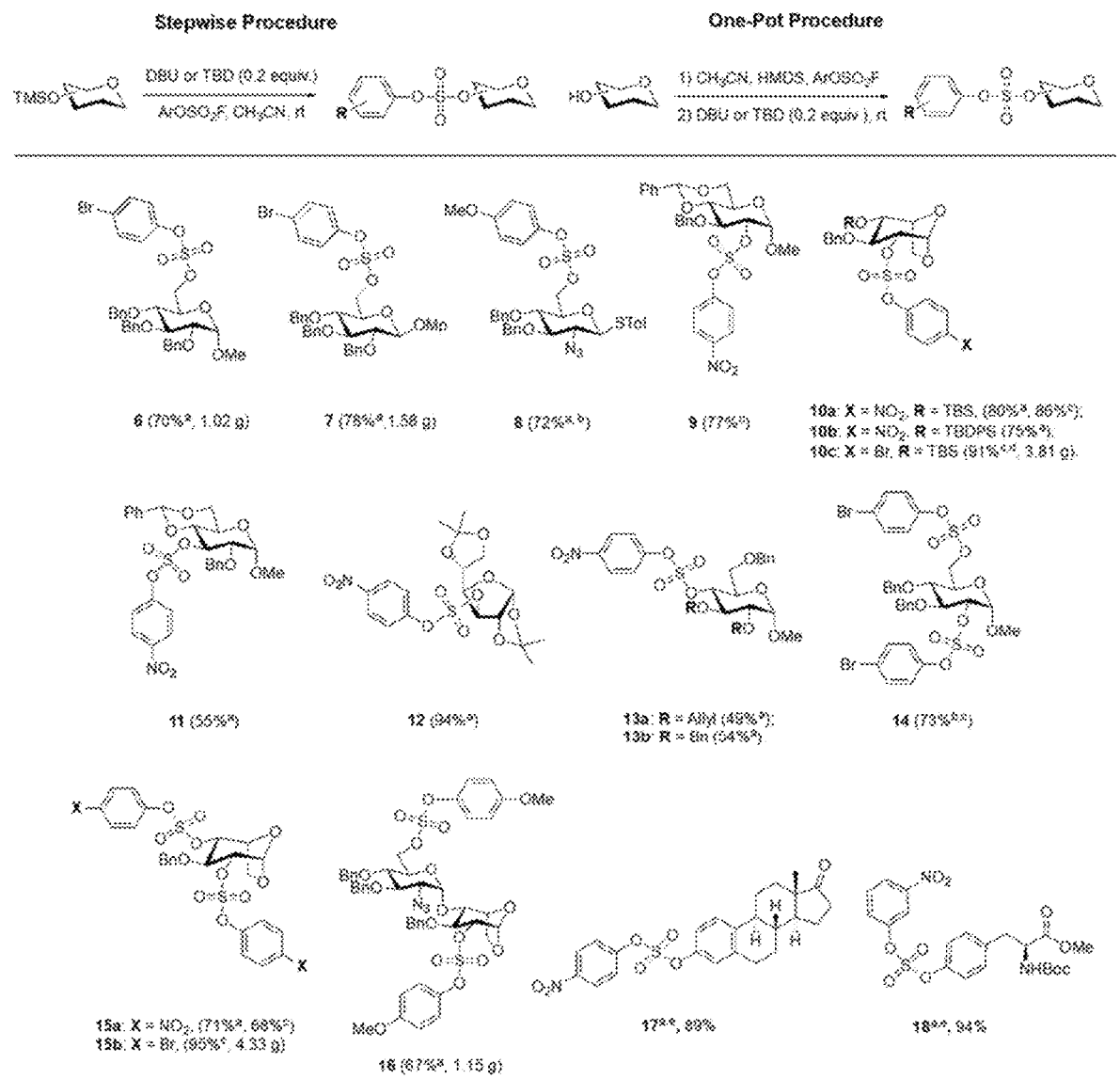
FIG. 16 shows examples of substrates that can be sulfated by the SuFEx strategy disclosed herein. Footnotes for reaction conditions are as follows: $^a$Isolated yield from stepwise reaction. $^b$0.3 equiv. of TBD was used. $^c$TBS was used as the 0-silyl protecting group. Bn: benzyl, Me: methyl, Mp: para-methoxyphenyl, Tol: tolyl, Boc: tert-butyloxycarbonyl.

Commercially available and inexpensive hexamethyldisilazane (HMDS) was found to enable in situ TMS silylation of carbohydrates in good yields. 32 Followed by the addition of DBU or TBD to initiate the SuFEx reaction, sulfate diesters 8 and 9 was isolated in 72% and 77% yields, respectively. No major difference in reaction efficiency was found between the stepwise and one-pot procedures, as shown in the preparation of 10a (FIG. 16). Other silylether protecting groups, such as tert-butyldimethylsilyl (TBS) in 10a and tert-butyldiphenylsilyl (TBDPS) in 10b, remained stable in the SuFEx reaction between TMS and aryl fluorosulfate under this reaction condition. Sulfate diesters at different positions like O-3 and O-4 of glucose were also successfully obtained, giving product 11, 12, 13a and 13b in 55%, 94%, 49%, and 54% yields, respectively. Furthermore, 14 and 15a, monosaccharides carrying two sulfate diesters were prepared successfully in 73% and 71% yields, respectively. The efficiency and scale of disubstitution could be further improved to 95% in multi-gram quantities when switching from 3a to 3e in the SuFEx reaction, again highlighting the versatility of our method in fine tuning aryl fluorosulfate reactivity by adjusting the aryl substitution. Disubstituted disaccharide 16 was also constructed in gram scale from the corresponding dual-TMS-protected substrate in 67% yield. p-Methoxyphenyl fluorosulfate 3j was found to enable the highest SuFEx efficiency for this substrate.

Besides carbohydrates, the SuFEx reaction was further applied to introduce sulfate diesters to non-carbohydrate substrates. The reaction between 3a and an O-3 TBS-silylated estrone afforded sulfate diester 17 in 89% yield. Similarly, a tyrosine disulfate diester 18 was prepared efficiently in 94% yield from 3b and a TBS-silylated tyrosine. It is noteworthy that all compounds mentioned above were prepared in readily scalable procedures and purified by silica gel chromatography. Taken together, these examples highlight the broad substrate scope of our method and its versatility in tuning the electronic properties of the aryl fluorosulfates to optimize their reactivities with a wide range of substrates.

Next, the compatibility of the sulfate diesters with frequently used reagents and reaction conditions in carbohydrate and peptide reactions was examined (Table 4).

TABLE 4
Compatibility of Aryl Sulfate Diesters
| Entry | Substrate | Conditions | Product | Yield |
|---|---|---|---|---|
| 1 | 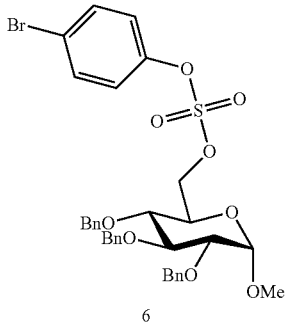 6 | H2SO4, Ac2O, 0° C., 5 h | 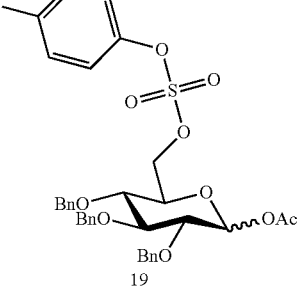 19 | 85% |
| 2 | 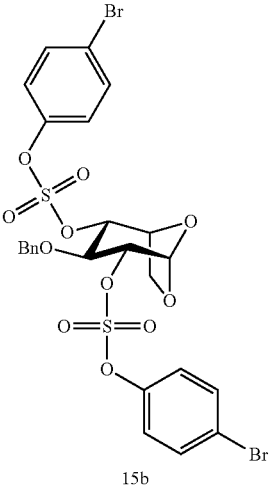 15b | Sc(OTf)$_3$, Ac$_2$O, rt, 21 h | 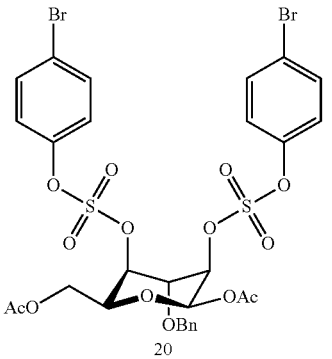 20 | 81% |
| 3 | 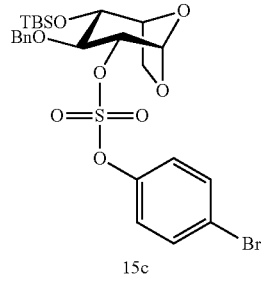 15c | TBAF, rt, 10 min | 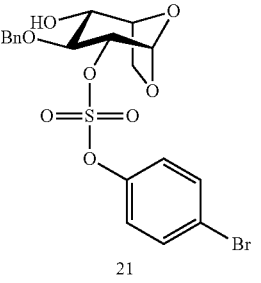 21 | 85% |
| 4 | 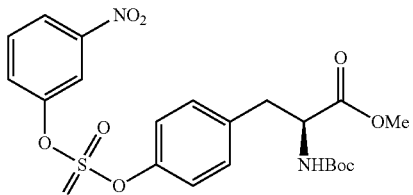 18 | 20% piperidine in DMF, rt, 2 h | 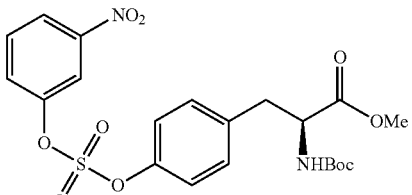 18 | Quantitative Recovery |

TABLE 4-continued

Compatibility of Aryl Sulfate Diesters

| Entry | Substrate | Conditions | Product | Yield |
| --- | --- | --- | --- | --- |
| 5 | 7 | CAN, 0° C., 1 h | 22 | 92% |
| 6 | 8 | m-CPBA, 0° C., 5 h | 23 | 79% |
| 7 | 15a | Na$_2$BrO$_3$, Na$_2$S$_2$O$_4$, rt, 18 h | 24 | Quamtitative |
| 8 | 9 | BH$_3$·THF, TMSOTf, 0° C. to rt, 6 h | 25 | Quantitative |

TABLE 4-continued

Compatibility of Aryl Sulfate Diesters

| Entry | Substrate | Conditions | Product | Yield |
|---|---|---|---|---|
| 9 | 9 | Et₃SiH, TFA, 0° C., 4 h | 26 | 95% |
| 10 | 16 | Zinc, NH₄OOCH, rt, 3 h | 27 | 78% |
| 11 | 27 | SO₃·pyridine, Et₃N, rt, 3 h | 28 | 72% |

First, the aryl sulfate diesters as the protected sulfate could overcome the acid sensitivity of the nonprotected sulfates and Brönsted and Lewis acid conditions were well tolerated (Table 4, Entries 1-2). The anomeric O-Me of 6 was converted to O—Ac in 19 by sulfuric acid over five hours in 75% yield. Disulfated 1,6-anhydroidose 15b was readily converted into a glycosyl donor precursor 20 in 81% yield by strong Lewis acid Scandium triflate. Mild basic conditions were tolerated (Table 5, Entries 3-4; see also FIGS. 7 and 9-11).

TABLE 5

Glycosylation with Sulfate Diester-Substituted Carbohydrate Substrates

| Entry | Donor | Acceptor | Product | Yield (β/α ratio) |
|---|---|---|---|---|
| 1 | 29 | 24 | 36 | 65%, α only[a] |
| 2 | 19: R = OAc; 31: R = F; 32: R = PO(OPh)₂ | 33 | 34 | 19 → 34: 83%, β only[b]; 31 → 34: 73%, α/β = 6.3:1.0[c] 32 → 34: 92%, α/β = 3.3:1.0[d] |

TABLE 5-continued
Glycosylation with Sulfate Diester-Substituted Carbohydrate Substrates
| Entry | Donor | Acceptor | Product | Yield (β/α ratio) |
|---|---|---|---|---|
| 3 | | | | 51% (α/β = 2.3:1.0)[e-g] |
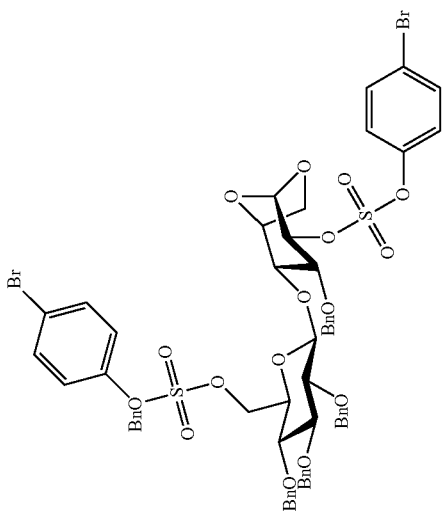

TABLE 5-continued

Glycosylation with Sulfate Diester-Substituted Carbohydrate Substrates

| Entry | Donor | Acceptor | Product | Yield (β/α ratio) |
|---|---|---|---|---|
| 4 | 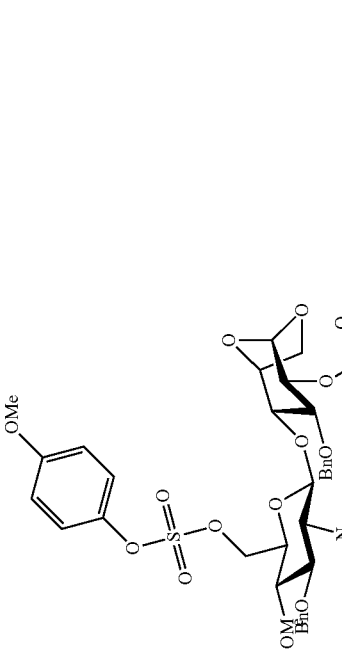<br>8: R = STol<br>23: R = SOTol | 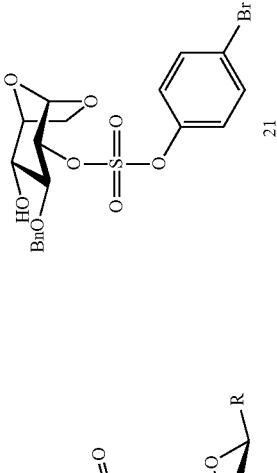<br>21 | 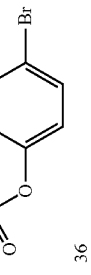<br>36 | 8 → 36: 79%<br>(α/β = 8.4:1.0)<sup>f</sup>;<br>23 → 36: 95%<br>(α/β = 5.0:1.0)<sup>f</sup> |

<sup>a</sup>TMSOTf, 4 Å MS, DCM
<sup>b</sup>1) HBr/AcOH, DCM, 0° C., 1 h; 2) Ag₂O, DIPEA, 4 Å MS.
<sup>c</sup>AgClO₄, Cp₂ZrCl₂, 4 Å MS, DCM.
<sup>d</sup>TMSOTf, 4 Å MS, DCM, rt, 5.5 h.
<sup>e</sup>NIS, AgOTf, 4 Å MS, DCM.
<sup>f</sup>Tf₂O, DTBP, 4 Å MS, DCM.
<sup>g</sup>α/β ratios were determined by ¹H NMR analysis of the purified material.

Removal of the TBS protecting group from 10c was quantitative by tetrabutylammonium fluoride (TBAF) treatment over ten minutes. Notably, TBAF compatibility was a challenge for the state-of-the-art TCE sulfate diesters, of which the undesired fluorination of the sulfated hydroxyl was a common side reaction. 7a While tyrosine p-nitrophenylsulfate diester demonstrated limited stability in 20% piperidine in DMF (Table 6), the m-nitrophenyl sulfate diester 18 is perfectly stable under the same condition with a quantitative recovery of the starting material after two hours.

ing in previous early stage sulfation strategies when both were modified by sulfate diesters. Our initial attempt to couple the bromide donor and the 1,6-anhydroidosyl acceptor 21 generated the disaccharide product 35 in 51% yield (Table 5, Entry 3). The yield of the disaccharide was improved to 77% when thiol donor 8 was employed (Table 5, Entry 4). However, while 8 demonstrated improved stability compared to corresponding TCE sulfate diesters and could be stored at 4° C. for up to a week, it nevertheless decomposed over long-term storage. The instability of 8 is likely resulted from the intramolecular nucleophilic attack of

TABLE 6

Robustness Screening for Tyrosine Sulfate Diester

[Structures of S35 and 18 shown; DIPEA: N,N-Diisopropyethylamine]

| Compound | Conditions | Stability |
|---|---|---|
| S35 | Benzylamine (2.0 equiv) + Et$_3$N (1.0 equiv) | 24 h, 92% recovery |
| S35 | Benzylamine (2.0 equiv) +DIPEA (1.0 equiv) | 24 h, 86% recovery |
| S35 | Trifluoroacetic acid | 4 days, de-Boc quantitative |
| S35 | 20% (v/v) Piperidine in DMF | 1 h, 54% recovery |
| 18 | 20% (v/v) Piperidine in DMF | 2 h, quantitative recovery |

Oxidative conditions were also well tolerated (Table 4, Entries 5-7). The anomeric p-methoxyphenyl group of 7 was removed to form 22 in 90% yield by cerium ammonium nitrate (CAN) in one hour. Oxidation of the thiol donor 8 by meta-chloroperoxybenzoic acid (m-CPBA) afforded sulfoxide 23 in 79% yield. Oxidative debenzylation of 15a by sodium bromate and sodium dithionite quantitatively yielded glycosyl acceptors 24. Reductive conditions were tolerated (Table 4, Entries 8-10). Acid-promoted reductive benzylidene opening of 9 exposed O-6 or O-4 positions as free hydroxyls to afford 25 and 26 in quantitative and 95% yields, respectively. Zinc-catalyzed azide reduction of 16 afforded the free amine 27 in 78% yield. Finally, the sulfate diesters are also compatible with late stage sulfation reagents (Table 4, Entry 11). N-Sulfation of 27 by SO$_3$.pyridine generated 28 in 72% yield over three hours. Overall, these results indicated excellent compatibilities of the aryl sulfate diesters with acidic, basic, oxidative, and reductive conditions commonly used in carbohydrate and peptide chemistries.

An early-stage sulfation strategy enables the monosaccharide building blocks carrying protected sulfates to serve as glysosyl donors and acceptors in glycosylation. We examined the glycosylation reactions of both donors and acceptors modified by glycosyl aryl sulfate diesters (Table 4). First, the disubstituted acceptor 24 were able to couple with imidate donor 29, successfully yielding disaccharide 30 in 65% yield (Table 5, Entry 1). Next, glycosylation of acceptor 33 using O-6 sulfate diester-substituted glucosyl donors including the fluoride donor (31), the bromide donor (in situ generated from 1-OAc glucopyranoside 19), and the phosphate donor (32) all proceeded efficiently, forming disaccharide 34 in excellent (73-92%) yields (Table 5, Entry 2). Because sulfate diester modifications could deactivate carbohydrate building blocks for glycosylation reaction, coupling the glycosyl donor and acceptor became challengthe O-6 sulfate diester by the anomeric thiol group. This challenge was overcome by switching to the sulfoxide donor 23, which can be stored indefinitely without any signs of decomposition. Moreover, glycosylation of 21 by 23 demonstrated high efficiency, affording 36 in 95% yield even when both the donor and the acceptor carry sulfate diester substitutions (Table 5, Entry 4).

As demonstrated in our study of the model compound, both hydrolysis and hydrogenolysis of sulfate diester can afford O-sulfated products. Because hydrogenolysis was expected to be milder and less prone to side reactions than hydrolysis, it became our method of choice for sulfate diester deprotection. Indeed, global deprotection of multigram amounts of 15b by Pd(OH)$_2$/C/H$_2$ successfully yielded O-2, O-4 disulfated idose 37 quantitatively (Table 6, Entry 1). Similarly, disulfate disaccharide 35 was generated by hydrogenolysis in quantitative yield (Table 6, Entry 2). Furthermore, our method has made the functional group manipulation at the late stage of synthesis easy and efficient. N-Sulfation and N-acetylation of 27 furnished a N-sulfoglucosamine residue in 28 and a N-acetylglucosamine residue in 39. Subsequent global deprotection of 28 and 39 provided trisulfated disaccharide 40 in 83% yield and disulfated disaccharide 41 in 90% yield (Table 6, Entry 3). Deprotection of non-carbohydrate sulfate diesters also proved to be efficient. Hydrogenolysis of 17 and 18 by Pd(OH)$_2$/C/H$_2$ exclusively furnished sulfoestrone 42 in 87% yield and sulfotyrosine 43 in 91% yield, respectively, without any desulfated byproduct being observed. The excellent selectivity of hydrogenolysis is attributed to the strong electron-withdrawing effect of the NO$_2$ group that weakens the C—O bond of the p- or m-NO$_2$-substituted phenyl sulfate monoester and makes it susceptible to oxidative insertion by palladium.

TABLE 6
O-Sulfated Compounds Generated after Deprotection
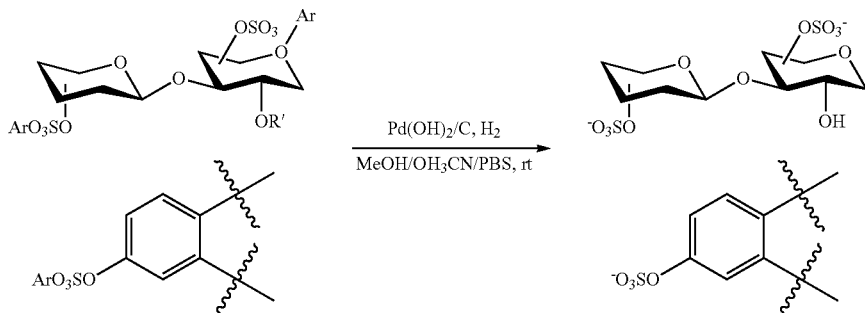
| Entry | Substrate | Product | Yield |
|---|---|---|---|
| 1 | 15b | 37 | Quantitative (1.60 g) |
| 2 | 35α | 38 | Quantitative |
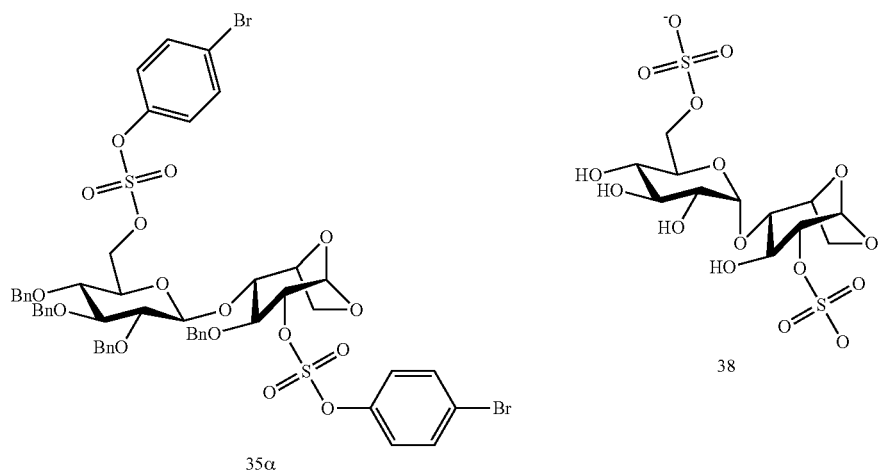

TABLE 6-continued
O-Sulfated Compounds Generated after Deprotection
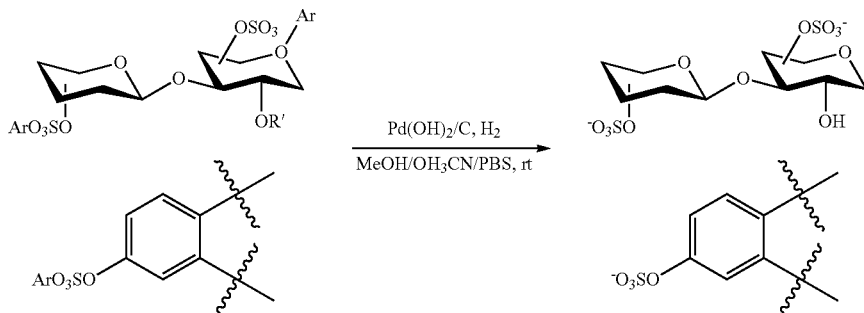
| Entry | Substrate | Product | Yield |
|---|---|---|---|
| 3 | 28: R = SO₃<br>39: R = Ac, | 40: R = SO₃<br>41: R = Ac, | 83%, 110.0 mg (40)<br>90%, 112.6 mg (41) |
| 4 | 17 | 42 | 87% |
| 5 | 18 | 43 | 91% |

Example 25: Optimization of Reaction Conditions Using a Model Reaction
Optimization of SuFEx Reaction between 1 and 3a
TABLE 7
Optimization of SuFEx Reaction between 1 and 3a
| 3a | DBU | [M] | Time (h) | T (° C.) | Yield (%) |
|---|---|---|---|---|---|
| 1.1 | 0.1 | 0.3 | 2 | rt | 89 |
| 1.1 | 0.1 | 0.3 | 1 | rt | 86 |
| 1.1 | 0.1 | 0.6 | 2 | rt | 88 |
| 2   | 0.1 | 0.3 | 2 | rt | 89 |
| 1.1 | 0.2 | 0.3 | 2 | rt | 94 |
| 2   | 0.2 | 0.3 | 2 | rt | 94 |
| 1.1 | 0.5 | 0.3 | 2 | rt | 89 |
Optimization of the Hydrolysis of 4a by NaOMe
TABLE 8
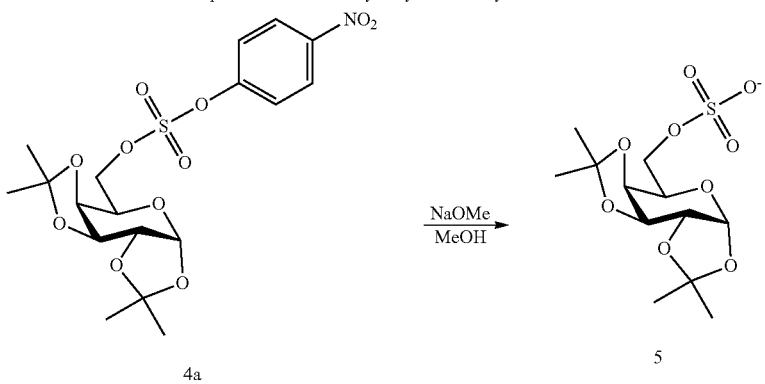
Optimization of the Hydrolysis of 4a by NaOMe
| 4a | NaOMe (eq) | [NaOMe] (M) | Time (h) | Yield (%) |
|---|---|---|---|---|
| 0.05 | 50  | 2.5 | 4 | 94 |
| 0.05 | 50  | 2.5 | 1 | 44 |
| 0.05 | 100 | 5   | 1 | 92 |

Figure 5:
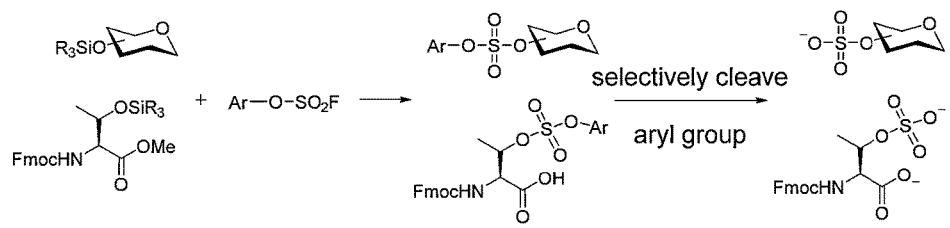
FIG. 5 shows a proposed scheme for O-sulfation on carbohydrates and peptides according to one aspect of the present disclosure.
Figure 5:
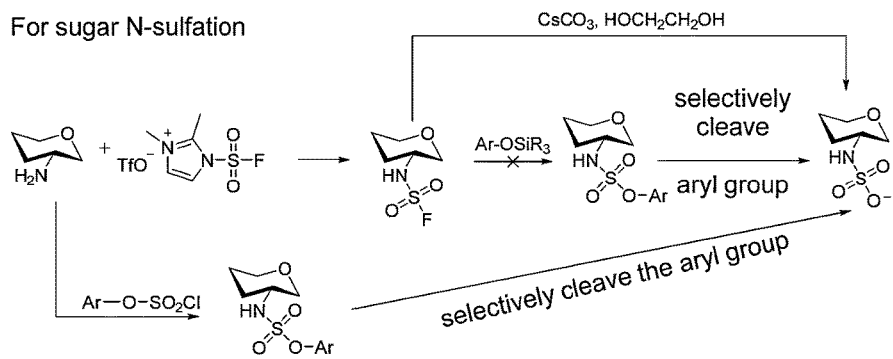
Figure 5:
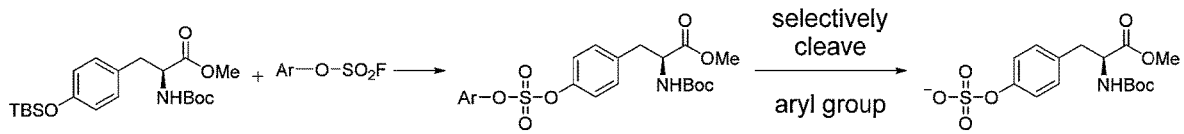
Figure 6:
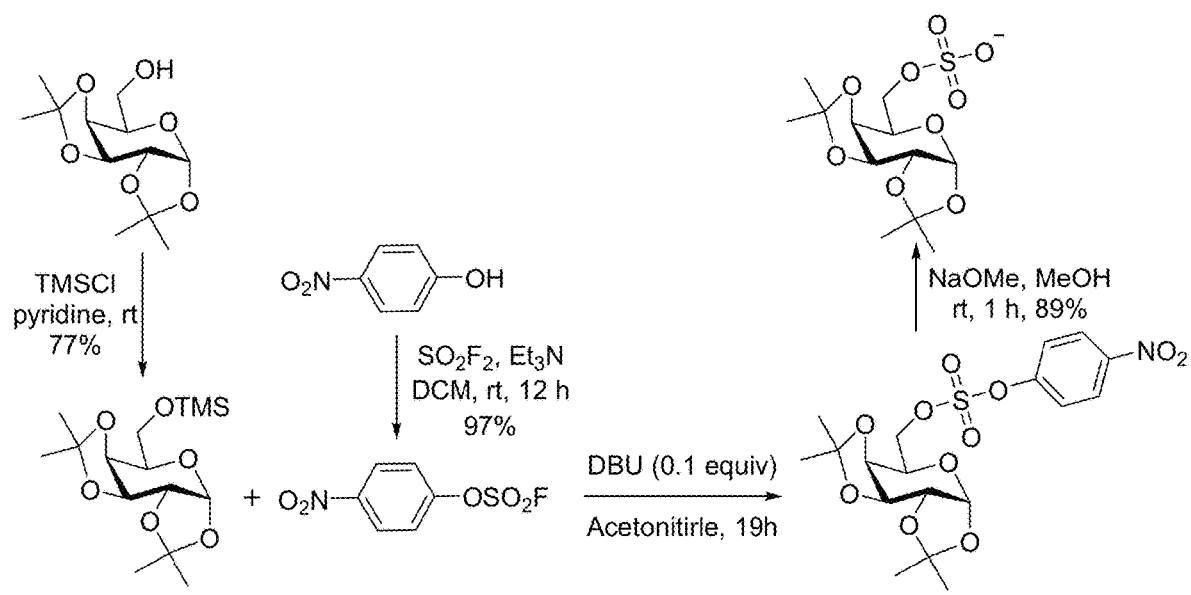
FIG. 6 shows a template reaction used as proof of principle for the disclosed reactions.
Figure 7:
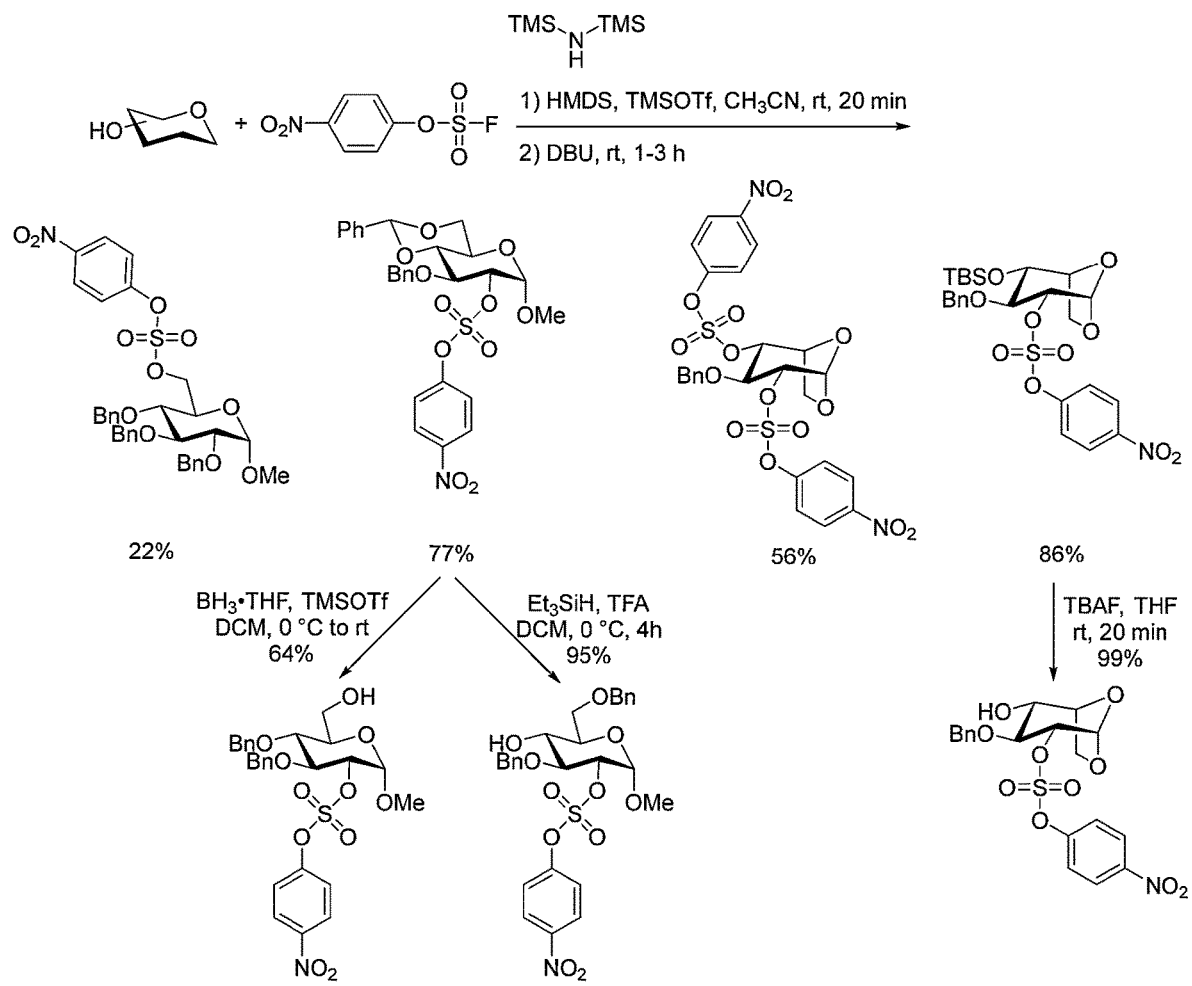
FIG. 7 shows a one-pot synthetic scheme according to one aspect of the present disclosure; this scheme can be followed by manipulation of protecting groups as desired.
Figure 18:
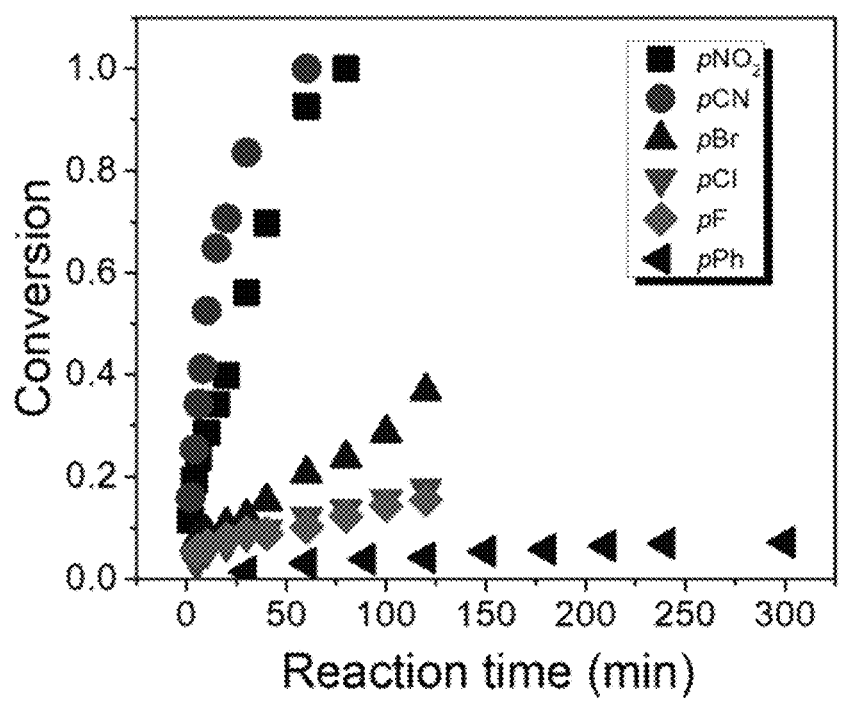
FIG. 18 shows the effect of phenyl substitutions on the kinetics of the hydrolysis of sulfate diesters.

In the presence of NaOMe, the nucleophilic attack of the methoxide anion towards the sulfur (VI) center generates I. The release of the phenolic anion leaving group provides II. The properties of the leaving groups varies from excellent to poor following the electron-withdrawing effect of the phenyl substituents, which is consistent with the trend shown in FIG. 18. Intermediate II is highly susceptible to moisture and further undergoes hydrolysis to give the sulfated compound 5. (See also FIGS. 5-6)

Optimization of the Hydrogenolysis of 4a

TABLE 9

Optimization of the Hydrogenolysis of 4a

| [M] (mM) | Pd(OH)$_2$/C | Solvent:PBS Buffer | Reaction Time (h) | Yield (%) |
|---|---|---|---|---|
| 30 | 5 eq | MeOH:PBS = 5:2 | 1 | 51 |
| 25 | 5 eq | MeOH:MeCN:PBS = 2:3:1 | 1 | 86 |
| 20 | 5 eq | MeOH:MeCN:PBS = 2:2:1 | 2 | 96 |

Figure 17:
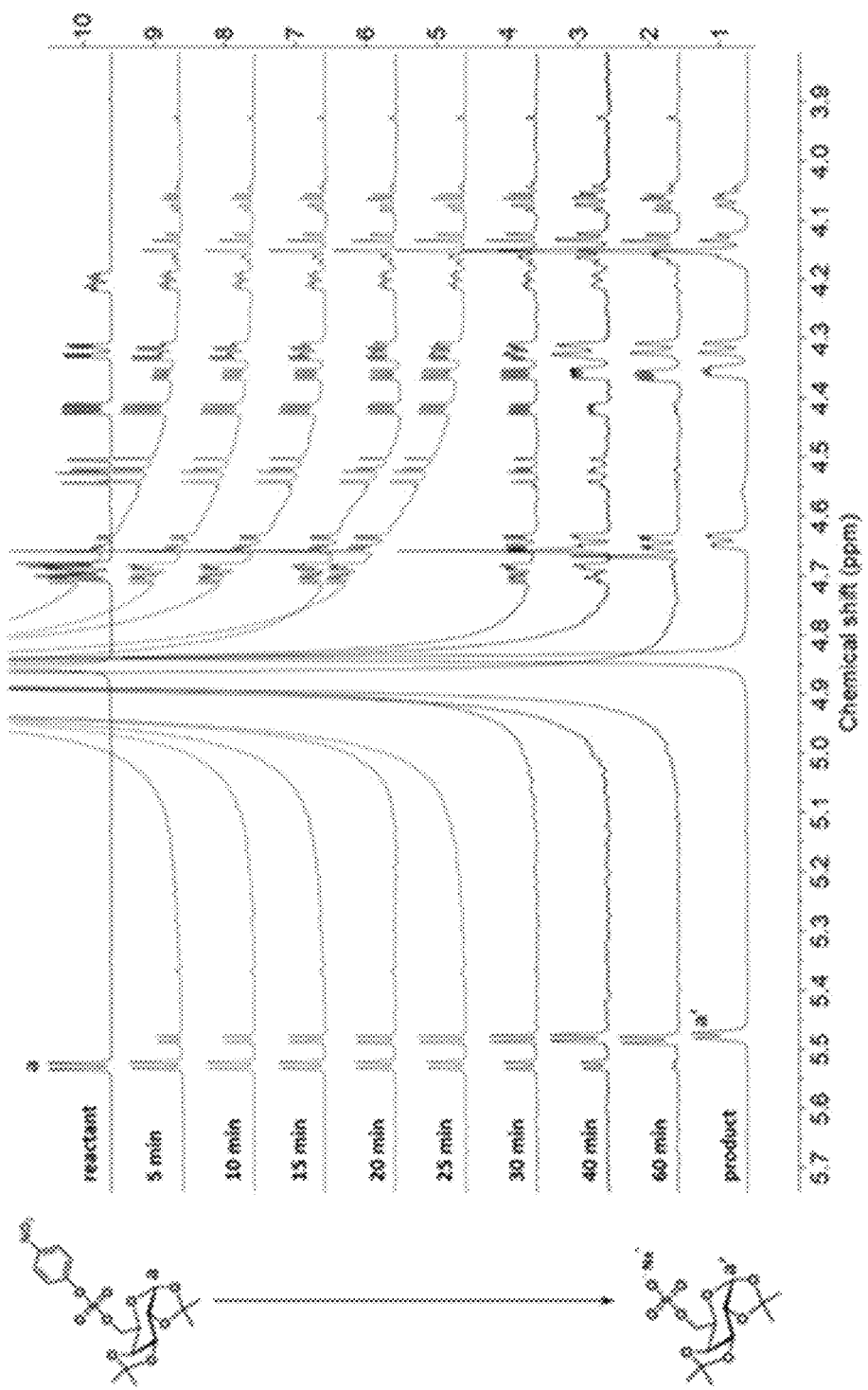
FIG. 17 shows $^1$H NMR monitoring of the kinetics of the hydrolysis of compound 4a (reaction at left) in $CD_3OD$.
Figure 24:
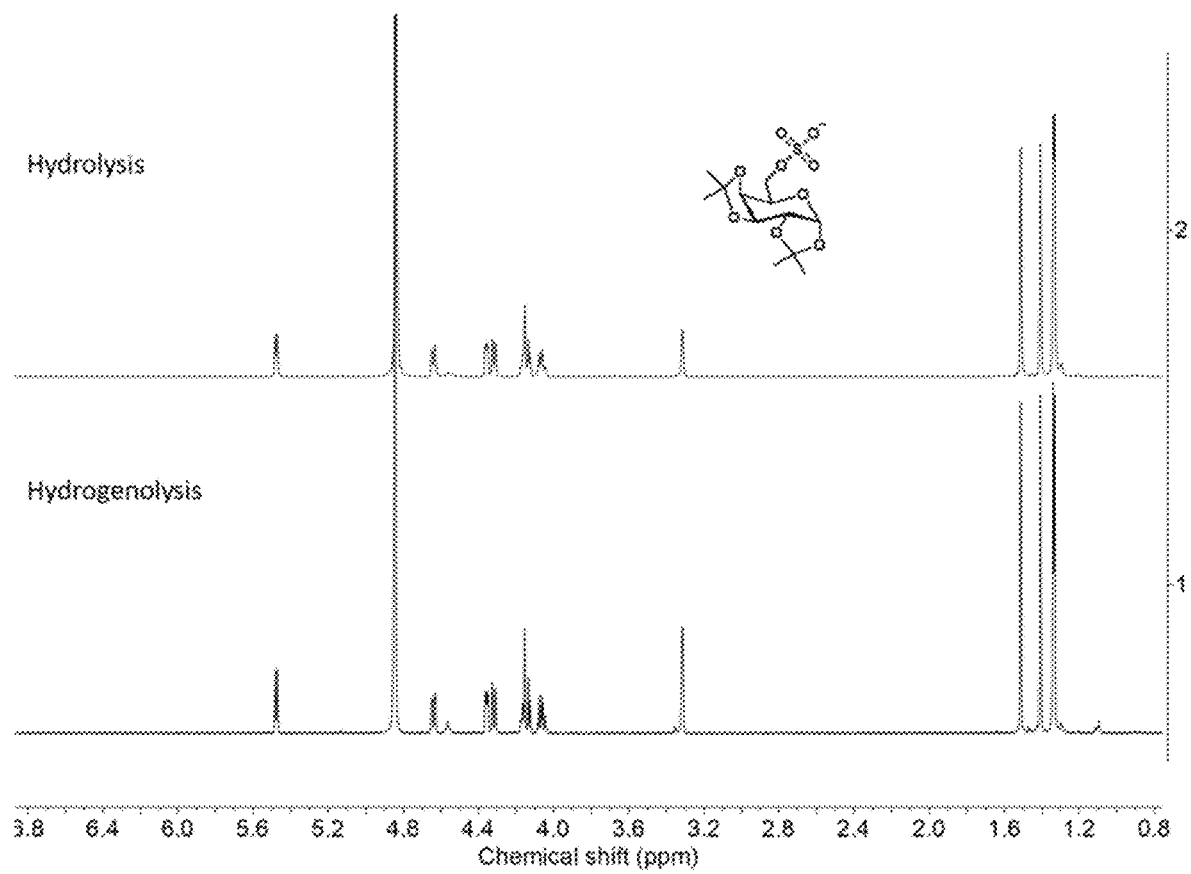
FIG. 24 shows $^1$H NMR spectra of compound 5 after the hydrolysis (top) and hydrogenolysis (bottom) processes disclosed herein.

In summary, a general approach for early-stage O-sulfation via SuFEx reaction was developed to achieve scalable synthesis and silica gel chromatography purification of a variety of carbohydrate and non-carbohydrate compounds carrying O-sulfation. The SuFEx coupling reaction between aryl fluorosulfates and glycosilylethers was optimized to achieve high reaction efficiency. Conditions allowing the selective deprotection of aryl sulfate monoester via both hydrolysis and hydrogenolysis pathways were investigated. The sulfate diesters demonstrated excellent compatibility with various commonly used conditions in carbohydrate and peptide chemistries. The established strategy herein provides a powerful tool to introduce sulfation in the synthesis of complex O-sulfated small molecules and macromolecules including carbohydrates, glycomimetic polymers, and peptides. $^1$H NMR spectra of hydrolysis and hydrogenolysis reactions of 4a can be seen in FIGS. 17 and 24.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A method for synthesis of masked sulfate diesters, the method comprising contacting a substrate having at least one hydroxyl group with an aryl fluorosulfate, a silylating reagent, and a base catalyst in a solvent to produce a product sulfate diester, and wherein the substrate comprises a sugar, a sugar comprising at least one protected hydroxyl group, a polysaccharide, a glycosaminoglycan, or a combination thereof.

2. The method of claim 1, wherein the substrate comprises

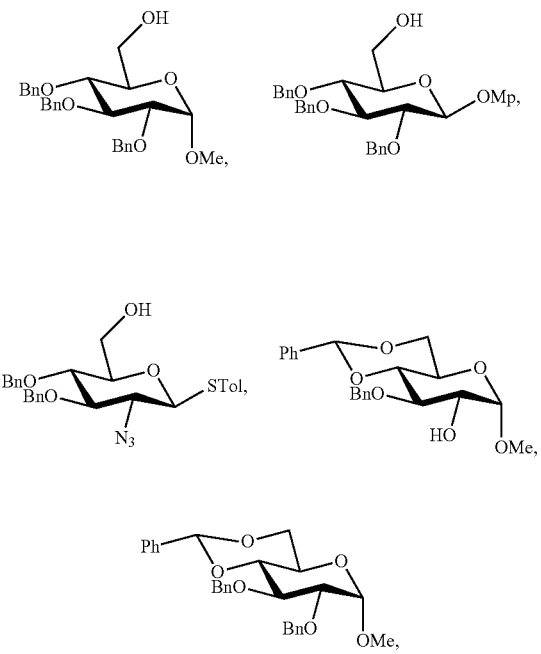

-continued

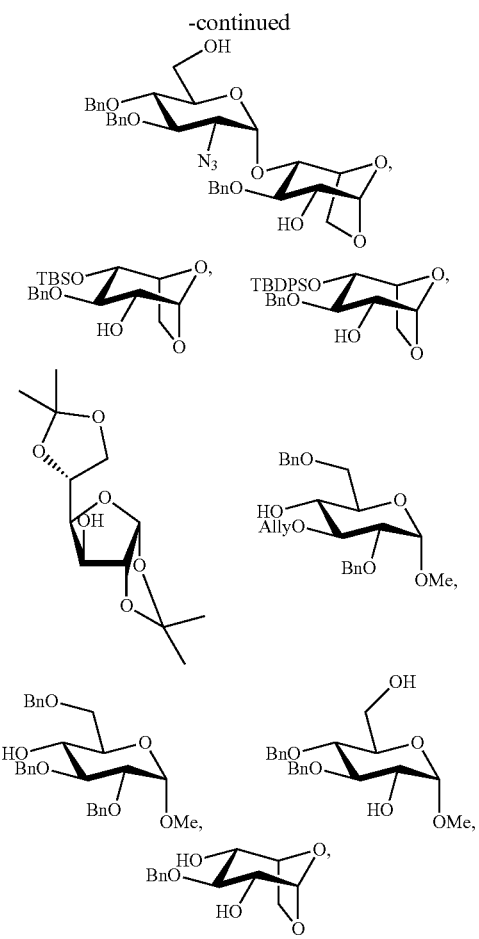

or a combination thereof.

3. The method of claim 1, wherein the silylating reagent comprises trimethylsilyl chloride (TMSCl), bis(trimethylsilyl)amine (HMDS), or a combination thereof.

4. The method of claim 1, wherein the aryl fluorosulfate comprises

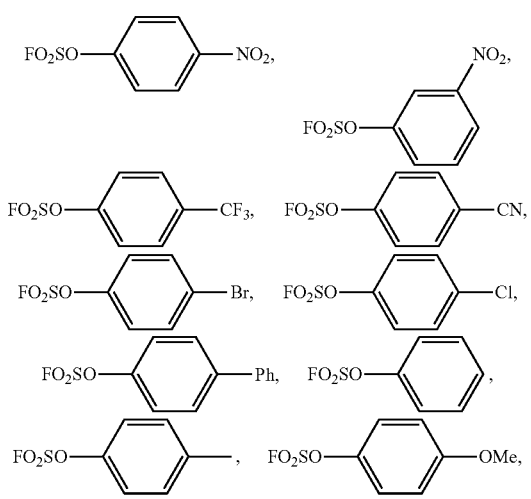

or a combination thereof.

5. The method of claim 1, wherein the base catalyst comprises 1,8-diazabicyclo[5.4.0]undec-7-ene (DBU), 1,5-diazabicyclo[4.3.0]non-5-ene (DBN), tert-butylamino-tri(pyrrolidino)phosphorane (BTPP), 2-tert-butylimino-2-diethylamino-1,3-dimethylperhydro-1,3,2-diazaphosphorine (BEMP), 7-methyl-1,5,7-triazabicyclo[4.4.0]dec-5-ene (MTBD), triazabicyclodecene (TBD), imidazole, or a combination thereof.

6. The method of claim 1, wherein the masked sulfate diester comprises from about 1 to about 3 sulfate diester linkages.

7. The method of claim 1, wherein the masked sulfate diester comprises

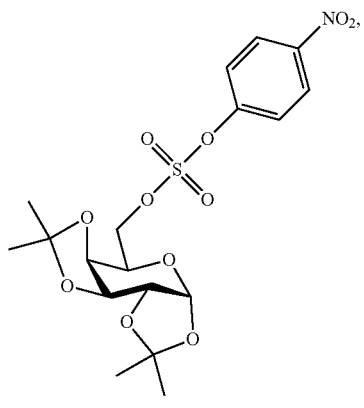

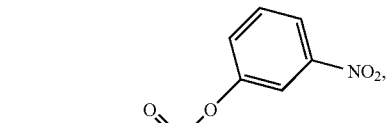

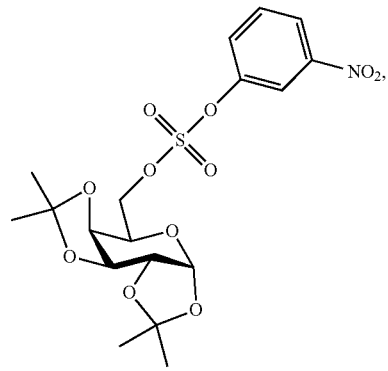

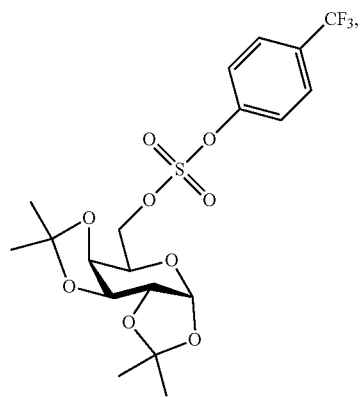

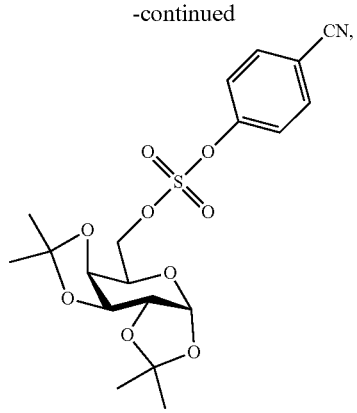
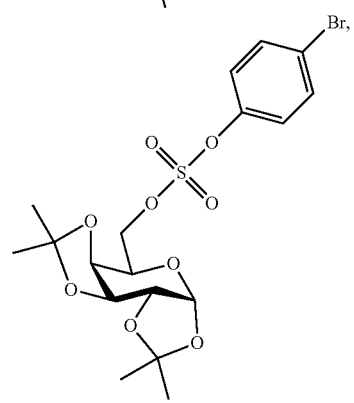
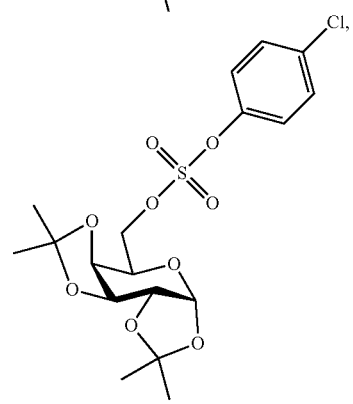
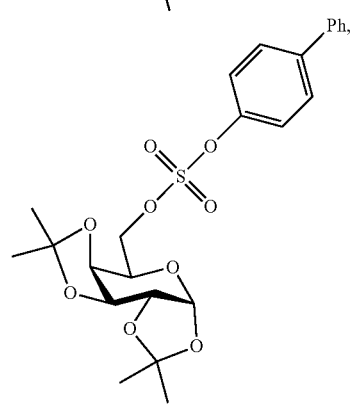
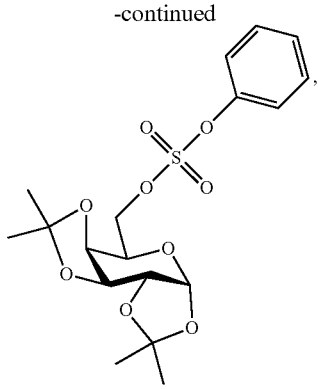
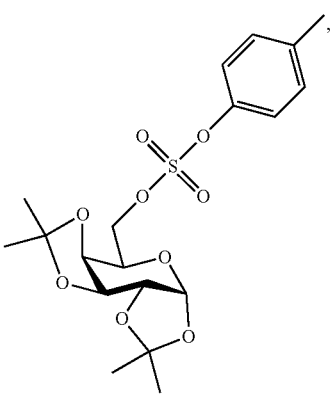
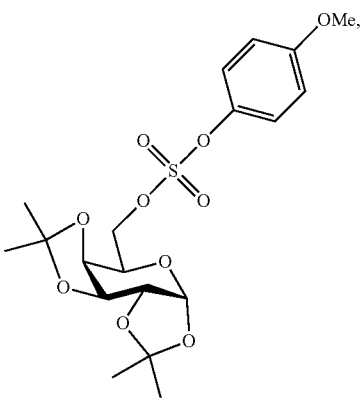
or a combination thereof.
8. The method of claim 1, wherein the substrate is first contacted with silylating reagent and then contacted with the aryl fluorosulfate and the catalyst.
9. The method of claim 1, wherein the substrate is contacted with the aryl fluorosulfate, catalyst, and the silylating reagent simultaneously.
* * * * *